United States Patent
Al-Awar et al.

(10) Patent No.: US 6,867,198 B2
(45) Date of Patent: Mar. 15, 2005

(54) AGENTS AND METHODS FOR THE TREATMENT OF PROLIFERATIVE DISEASES

(75) Inventors: Rima Salim Al-Awar, Raleigh, NC (US); Kyle Andrew Hecker, Indianapolis, IN (US); James Edward Ray, Indianapolis, IN (US); Jianping Huang, Carmel, IN (US); Sajan Joseph, Indianapolis, IN (US); Tiechao Li, Fishers, IN (US); Michael Paal, Hamburg (DE); Radhakrishnan Rathnachalam, Carmel, IN (US); Chuan Shih, Carmel, IN (US); Philip Parker Waid, Indianapolis, IN (US); Xun Zhou, Carmel, IN (US); Guoxin Zhu, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 137 days.

(21) Appl. No.: 10/130,493

(22) PCT Filed: Dec. 18, 2000

(86) PCT No.: PCT/US00/33273

§ 371 (c)(1),
(2), (4) Date: Dec. 2, 2002

(87) PCT Pub. No.: WO01/44247

PCT Pub. Date: Jun. 21, 2001

(65) Prior Publication Data

US 2003/0229026 A1 Dec. 11, 2003

Related U.S. Application Data

(60) Provisional application No. 60/171,087, filed on Dec. 16, 1999, and provisional application No. 60/171,220, filed on Dec. 16, 1999.

(51) Int. Cl.[7] ................. A61K 31/435; A61K 31/445

(52) U.S. Cl. ................. 514/44; 514/214; 514/392; 536/28.6; 536/24.31; 435/69.1; 530/350; 548/455; 548/430; 546/94; 540/479

(58) Field of Search ................. 514/44, 214, 392; 536/28.6, 24.31; 435/69.1; 530/350; 548/455, 430; 546/94; 540/479; 405/14

(56) References Cited

U.S. PATENT DOCUMENTS

| | | | |
|---|---|---|---|
| 5,545,636 A | * | 8/1996 | Heath et al. ............ 514/214.02 |
| 5,591,855 A | | 1/1997 | Hudkins et al. ............ 546/256 |
| 5,856,517 A | | 1/1999 | Keith et al. ................. 548/455 |

FOREIGN PATENT DOCUMENTS

WO    WO95/17182 A    6/1995

* cited by examiner

*Primary Examiner*—James O. Wilson
*Assistant Examiner*—Devesh Khare
(74) *Attorney, Agent, or Firm*—Tina M. Tucker; Kirby W. Lee

(57) ABSTRACT

The present invention provides selective kinase inhibitors of formula (I)

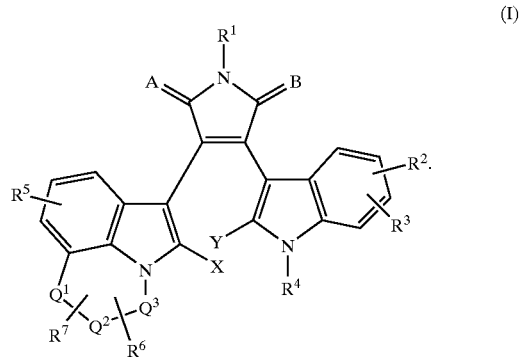

8 Claims, No Drawings

AGENTS AND METHODS FOR THE TREATMENT OF PROLIFERATIVE DISEASES

This application is a 371 of PCT/US00/33273, filed Dec. 18, 2000 which claims the benefit of Ser. No. 60/171,087, filed Dec. 16, 1999 and Ser. No. 60/171,220, filed Dec. 16, 1999.

Cancer is a heterogeneous group of diseases presenting in various forms in various tissues but having in common the characteristic of uncontrolled cell proliferation. For some time, cancer has been recognized as a disease of uncontrolled cell proliferation. Thus, the rapidly proliferating cell has been the target of cancer chemotherapy. The goal is to find agents that are more effective against cancer cells than against normal cells. As the basic science of the cell progressed, it was shown that certain anticancer agents were more effective against malignant cells at certain stages of the cell cycle than against cells at other stages of the cell cycle.

Attempts were made to develop treatment regimens that took advantage of these observations (SHACKNEY, S. E. et al Cell Kinetics. IN: Bruce Chabner (ed.), Pharmacologic Principles of Cancer Treatment; W. B. Saunder Company: Philadelphia, pp. 45–76, (1982)). Cell replication is now recognized to be controlled by the transient, sequential, highly-regulated expression of a series of cyclins which associate with specific cyclin-dependent kinases (CDK's) (TAULES, M., et al, J. Biol. Chem. 273, 33279–33286 (1998; FISHER, R. P. Current Opinion in Genetics & Develop. 7, 32–38 (1997); ARELLANO, M. et al., Int. J. Biochem. Cell Biol. 29, 559–573 (1997); and RAVITZ, M. J., et al. Adv. Cancer Res. 1997, 165–207 (1997)). These are serine/threonine protein kinases, which activate various enzymes and thereby initiate a cascade of phosphorylations allowing the cell to progress to the next stage of replication (COLLINS, et al., Proc. Natl. Acad. Sci. USA 94, 2776–2778 (1997); JACKS, T. et al., Science 280, 1035–1036 (1998)).

It has been found that cancerous cells often have mutated or missing components in the chain of proteins and enzymes, which control cell division. For example, the Rb protein, often called pRb, is a substrate for the cyclin-CDK's and is frequently missing or mutated in human tumors (KONSTANTINIDIS, A. K. et al, J. Biol. Chem. 273, 26506–26515 (1998); HARRINGTON, E. A., et al., Proc. Natl. Acad. Sci. USA 95, 11945–11950 (1998); YAMAMOTO, et al., Oncol. Rep. 5, 447–451 (1997); BARTEK, J., et al., Exp. Cell Res. 237, 1–6 (1997); SELLERS, et al., J. Clin. Oncol. 15, 3301–3312 (1997); HERWIG, S. et al., Eur. J. Biochem. 246, 581–601 (1997)).

In addition to the kinases, which can help to move the cell from one phase of division to the next, there are CDK inhibitors (CKIs) that block the actions of specific cyclin-CDK complexes. The CKIs halt cell cycle progression and cause cells to enter the quiescent Go phase. The CKIs of the INK4 group, including p15, p16, p18, and p19, block the cyclin-CDK4 and cyclin-CDK6 complexes.

Calmodulin is essential for cyclin-dependent kinase 4 (CDK4) activity and nuclear accumulation of cyclin D1-CDK4 during the $G_1$ phase (TAULES, M., et al, J. Biol. Chem. 273, 33279–33286 (1998)). CDKs and cyclins are important in transition(s) (FISHER, R. P. Current Opinion in Genetics & Develop. 7, 32–38 (1997)). CDK/cyclin complexes are regulated during the cell cycle (ARELLANO, M. et al., Int. J. Biochem. Cell Biol. 29, 559–573 (1997)). Cyclin-dependent kinase during the $G_1$ phase, and the cell cycle generally are regulated by TGF-β (RAVITZ, M. J., et al. Adv. Cancer Res. 1997, 165–207 (1997)).

The most frequent alteration in human malignant disease thus far recognized is the overexpression, mutation, and/or disregulation of cyclin D (IMOTO, M., et al., Exp. Cell Res. 236, 173–180 (1997); JUAN, G., et al., Cell Prolif. 29, 259–266 (1996); GONG, J. et al., Cell Prolif. 28, 337–346 (1995) et al., 1995). The cyclin D1 gene, CCND1, is amplified in about 20% of breast cancers and the protein, cyclin D1, is overexpressed in about 50% of breast cancers (BARNES, D. M. et al., Breast Cancer Res. Treat. 52, 1–15 (1998); KAMALATI, T., et al., Clin. Exp. Metastasis 16, 415–426 (1998); STEEG, P. S. et al. Breast Cancer Res. Treat. 52, 17–28 (1998); LANDBERG, G. et al., APMIS 105, 575–589 (1997); ALLE, et al., Clin. Cancer Res. 4, 847–854 (1998)). Overexpression of cyclin D1 has been reported in proliferative breast disease and in ductal carcinoma in situ, indicating that this change is important at the earliest stages of breast oncogenesis (ALLE, et al., Clin. Cancer Res. 4, 847–854 (1998); STEEG, et al., Breast Cancer Res. Treat. 52, 17–28 (1998)).

One researcher (KAMALATI, T., et al., Clin. Exp. Metastasis 16, 415–426 (1998) et al. (1998)) treated normal human epithelial cells so that they overexpressed cyclin D1. These transfected cells had reduced growth factor dependency, a shortened cell cycle time, thus providing the cells with a growth advantage. In 123 colorectal carcinoma specimens, those staining strongly for cyclin D1 corresponded to patients with a 5-year survival rate of 53.3% while those that were negative or weakly staining had 5-year survival rates of 96.2 and 78.8% (MEEDA, K., et al., Oncology 55, 145–151 (1998); PALMQVIST, R., et al., Europ. J. Cancer 34, 1575–1581 (1998)).

Amplification of CCND1 was found in 25% of dysplastic head-and-neck lesions, and 22% of head-and-neck carcinomas. Overexpression of cyclin D1 was found in 53% of head-and-neck carcinomas. This indicates that in this disease, like breast cancer, alterations in cyclin D1 occur at the very earliest stages of tumorigenesis (KYOMOTO, R., et al., Int. J. Cancer (Pred. Oncol.) 74, 576–581 (1997); PIGNATARO, L., et al., J. Clin. Oncol. 16, 3069–3077 (1998) et al., 1998). In a study of 218 specimens of esophageal squamous cell carcinoma, patients with cyclin D1-positive tumors had significantly worse survival than patients with cyclin D1-negative tumors (SARBIA, M. et al., Int. J. Cancer (Pred. Oncol. 84, 86–91 (1999)).

In eight human esophageal carcinoma cell lines, 7 (87.5%) and 6 (75%) cell lines had homozygous deletions of the p16 and p15 genes (KITAHARA, K. et al., J. Exp. Therap. Oncol. 1, 7–12 (1996)). All of the p16-negative cell lines express high levels of cyclin D1 and CDK4.

The Rustgi laboratory (MUELLER, A, et al., Cancer Res. 57, 5542–5549 (1997); NAKAGAWA, H, et al., Oncogene 14, 1185–1190 (1997)) developed a transgenic mouse which the Epstein-Barr virus ED-L2 promoter was linked to human cyclin D1 cDNA. The transgene protein localizes to squamous epithelium in the tongue and esophagus, resulting in a dysplastic phenotype associated with increased cell proliferation and indicating that cyclin D1 overexpression may be a tumor-initiating event. In a series of 84 specimens of soft-tissue sarcomas, there was no amplification of the CCND1 gene but there was overexpression of cyclin D1 in 29% of cases. The overexpression of cyclin D1 was significantly associated with worse overall survival (KIM, S. H., et al., Clin. Cancer Res. 4, 2377–2382 (1998); YAO, J., et al., Clin. Cancer Res. 4, 1065–1070 (1998)).

Another researcher (MARCHETTI, A., et al., Int. J. Cancer 75, 187–192 (1998)) found that abnormalities of cyclin D1 and/or Rb at the gene and/or expression level were present in more than 90% of a series of non-small cell lung cancer specimens, indicating that cyclin D1 and/or Rb alterations represent an important step in lung tumorigenesis. In 49 out of 50 pancreatic carcinomas (98%), the Rb/p16 pathway was abrogated exclusively through inactivation of the p16 gene (SCHUTTE, M., et al., Cancer Res. 57, 3126–3130 (1997)).

Mantle cell lymphoma is defined as a subentity of malignant lymphomas characterized by the chromosomal translocation t(11;14)(q13;q32) resulting in overexpression of cyclin D1 and, in addition, about 50% of these tumors have deletion of the p16 gene (DREYLING, M. H., et al., Cancer Res. 57, 4608–4614 (1997); TANIGUCHI, T., et al., Jpn. J. Cancer Res. 89, 159–166 (1998)).

In a series of 17 hepatoblastomas, 76% showed overexpression of cyclin D1 and 88% showed overexpression of CDK4 (KIM, H., et al., Cancer Lett. 131, 177–183 (1998)). There was a correlation between high level cyclin D1 expression and tumor recurrence. Alterations in the cyclin D1/CDK4/pRb pathway have also been associated with a high percentage of prostate carcinomas (HAN, E. K. H., et al., The Prostate 35, 95–101 (1998)), ovarian carcinomas (MASCIULLO, V., et al., Int. J. Cancer Pred. Oncol. 74, 390–395 (1997)) and osteosarcomas (WEI, G., et al., Int. J. Cancer 80, 199–204 (1999) et al., 1999).

Six distinct classes of small molecules from natural products have been identified as inhibitors of CDKs: the purine-based compound olomoucine and analogs, butyrolactone, flavopiridol, staurosporine and UCN-01, suramin and 9-hydroxyellipticine (CARLSON et al., Cancer Res. 56, 2973–2978 (1996); DE AZEVEDO, et al., Eur. J. Biochem. 243, 518–526 (1997); BRIDGES, A. J. Exp. Opin. Ther. Patents 5, 1245–1257 (1995); ORR, M. S., et al., REINHOLD, W., et al., J. Biol. Chem. 278, 3803–3807 (1998) et al., 1998; KAKEYA, H., et al., Cancer Res. 58, 704–710 (1998); HARPER, J. W. Cancer Surveys 29, 91–107 (1997); HARRINGTON, E. A., et al., Proc. Natl. Acad. Sci. USA 95, 11945–11950 (1998); GARRETT, M. D. et al., Current Opin. Genetics Develop. 9, 104–111 (1999); MGBONYEBI, O. P., et al., Cancer Res. 59, 1903–1910 (1999)). All of these molecules bind at the ATP-binding site of the enzyme and are competitive with ATP.

Olomoucine is an inhibitor of Cdc2, CDK2, CDK5 and MAP kinase in micromolar concentrations and has much weaker effects toward CDK4 and CDK6 (GARRETT, M. D. Current Opin. Genetics Develop. 9, 104–111 (1999)). Olomoucine has been reported to arrest several cell lines in $G_1$ and $G_2$ phases of the cell cycle and block known CDK-dependent cellular activities.

Flavopiridol, a novel synthetic flavone, potently inhibits several cyclin-dependent kinases including CDK1, CDK2, CDK4 and CDK7 (SEDLACEK, H. H., et al., Int. J. Cancer 65, 1143–1168 (1996); CZECH, J., et al., Int. J. Oncol. 6, 31–36 (1995); BIBLE, K. C. et al., Cancer Res. 56, 4856–4861 (1996); SCHRUMP, D. S., et al., Clin. Cancer Res. 4, 2885–2890 (1998); BRUSSELBACH, S., et al., Int. J. Cancer, 77, 146–152 (1998); JAGER, W., et al., Life Sciences 62, 1861–1873 (1998); SENDEROWICZ, A. M., et al., J. Clin. Oncol. 16, 2986–2999 (1998)). Exposure to flavopiridol can cause cells to arrest in both the $G_1$ and $G_2$ phases of the cell cycle, at concentrations similar to those required for cell growth inhibition (BIBLE, K. C. et al., Cancer Res. 56, 4856–4861 (1996); SCHRUMP, D. S., et al., Clin. Cancer Res. 4, 2885–2890 (1998)). Flavopiridol inhibits the CDK's in a manner competitive with ATP and noncompetitive with the substrate. Flavopiridol also inhibits other protein kinases such as protein kinase C, protein kinase A, and EGFR but at concentrations of 10 μM/L or greater. Flavopiridol is an active antitumor agent in several human tumor xenograft models including Colo-205 colon carcinoma, and DU-145 and LNCaP prostate carcinomas (SEDLACEK, H. H., et al., Int. J. Cancer 65, 1143–1168 (1996); CZECH, J., et al., Int. J. Oncol. 6, 31–36 (1995)). Flavopiridol has shown completed. Phase I clinical trial administered as a 72-hour continuous intravenous infusion every 2 weeks (SENDEROWICZ, A. M., et al., J. Clin. Oncol. 16, 2986–2999 (1998), and phase II trials are underway.

Much has already been published on the antineoplastic properties of certain compounds such as bisindolylmaleimides, indolocarbazoles, and derivations thereof. Staurosporine and UCN-01 are members of this broad molecular class (COLEMAN, K. G., et al., Ann. Reps. Med. Chem. 32, 171–179 (1997)). For example, U.S. Pat. No. 5,856,517 discloses substituted pyrroles, which are useful as antiproliferative agents in the treatment of cancer. U.S. Pat. No. 5,292,747 discloses substituted pyrroles useful in the prevention or control of oncological disorders. U.S. Pat. No. 5,721,245 discloses indolylpyrrolones useful in controlling oncological disorders. U.S. Pat. No. 5,438,050 (Godecke) discloses indolocarbazole derivatives useful in the prevention and treatment of cancer. U.S. Pat. No. 5,705,511 and U.S. Pat. No. 5,591,855 discloses fused pyrrolocarbazoles for the inhibition of growth associated with hyperproliferative states.

In addition to the kinases, which control the cell division cycle, there are over several hundred other kinases found in the human body. These kinases perform such diverse functions as growth factor and cytokine signal transduction, inflammatory mediators, biochemical routes controlling activity of nuclear transcription factors and apoptotic pathways. In treating proliferative diseases, it is particularly desirable to use a kinase inhibitor with a relatively narrow activity. Anti-cancer agents are generally given at high doses in order to kill as many cancerous cells as possible. With such high dosing, side effects due to broad kinase inhibition can become a serious problem. Accordingly, to treat proliferative diseases, it is desirable to use kinase inhibitors that are relatively selective for kinases controlling cell division.

The present invention provides compounds of Formula I

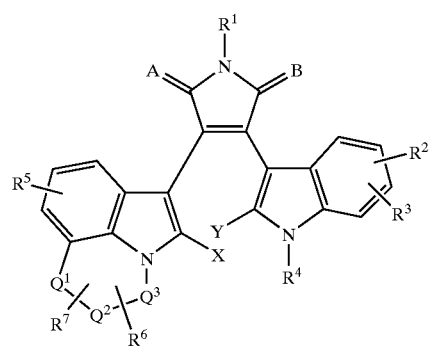

where:
A and B are independently O or S;
X and Y are both hydrogen or, taken together, form a bond;
$R^1$ is hydrogen or $C_1$–$C_4$ alkyl;
$R^2$ is optionally up to two substituents independently selected from the group consisting of halo, cyano, $C_1$–$C_6$ alkyl, substituted $C_1$–$C_6$ alkyl, $C_1$–$C_6$ alkenyl, substituted $C_1$–$C_6$ alkenyl, $C_1$–$C_6$ alkoxy, aryloxy, benzyloxy, $C_1$–$C_6$ alkylthio and arylthio;

$R^3$ is a substituent optionally selected from the group consisting of aryl, heteroaryl, —$CH_2$—NH-(1-deoxy-β-D-glucose), and —$(CH_2)_m$—Z;

$R^4$ is hydrogen, $C_1$–$C_4$ alkyl, substituted $C_1$–$C_4$ alkyl, —$(CH_2)_m$—Z, or 2-deoxy-α-D-ribofuranos-1-yl;

$R^5$ is optionally up to two substituents independently selected from the group consisting of halo, cyano, $C_1$–$C_6$ alkyl, substituted $C_1$–$C_6$ alkyl, $C_1$–$C_6$ alkenyl, substituted $C_1$–$C_6$ alkenyl, $C_1$–$C_6$ alkoxy, aryloxy, benzyloxy, $C_1$–$C_6$ alkylthio and arylthio;

$R^6$ is optionally up to three substituents selected from $C_1$–$C_4$ alkyl;

$R^7$ is a substituent optionally selected from ($C_1$–$C_6$ alkoxy)carbonyl or —$(CH_2)_m$—Z;

Z is halo, hydroxy, ($C_1$–$C_6$ alkyl)$_3$SiO—, (diphenyl)($C_1$–$C_6$ alkyl)SiO, carboxy, ($C_1$–$C_4$ alkoxy)carbonyl, or $NR^8R^9$;

$R^8$ is hydrogen, $C_1$–$C_6$ alkyl, or substituted $C_1$–$C_6$ alkyl, $C_1$–$C_6$ alkenyl, substituted $C_1$–$C_6$ alkenyl;

$R^9$ is hydrogen, $C_1$–$C_6$ alkyl, substituted $C_1$–$C_6$ alkyl, $C_1$–C6 alkenyl, substituted $C_1$–$C_6$ alkenyl, $C_1$–$C_6$ alkanoyl, substituted $C_1$–$C_6$ alkanoyl, tert-butoxycarbonyl, benzyloxycarbonyl, an amino acid residue, a protected amino acid residue, β-(pyridinyl)alaninyl, aryl, heteroaryl, arylcarbonyl, or heteroarylcarbonyl; or $R^8$ and $R^9$ taken together with the nitrogen to which they are attached form a saturated heterocycle optionally substituted with one or two hydroxy, amino, or $C_1$–$C_6$ alkyl groups;

$Q^1$ is O, $S(O)_n$ or —$(CH_2)_{1-3}$—;

$Q^2$ is a carbon-carbon single bond, a carbon-carbon double bond, —$NR^{10}$—, or —$NR^{10}$—$CHR^{11}$—;

$Q^3$ is —$(CH_2)_{1-3}$—;

$R^{10}$ is hydrogen, ($C_1$–$C_6$ alkyl)sulfonyl, arylsulfonyl, hetroarylsulfonyl, $C_1$–$C_6$ alkyl, substituted $C_1$–$C_6$ alkyl, ($C_1$–$C_5$ alkyl)carbonyl, substituted ($C_1$–$C_5$ alkyl)carbonyl, an amino acid residue, a protected amino acid residue, β-(pyridinyl)alaninyl, aryl, heteroaryl, arylcarbonyl, or heteroarylcarbonyl;

$R^{11}$ is hydrogen, $C_1$–$C_6$ alkyl, or substituted $C_1$–$C_6$ alkyl; or $R^{10}$ and $R^{11}$ taken together with the atoms to which they are attached form a 5- or 6-membered saturated heterocycle;

m is 0, 1, 2, 3, 4, or 5;

n is 0, 1, or 2; or a pharmaceutically acceptable salt thereof.

The invention also provides pharmaceutical formulations comprising a compound of Formula I in combination with at least one pharmaceutically acceptable excipient.

Furthermore, the invention provides a method for the inhibition of CDK4 in a mammal comprising administering to a mammal in need of such treatment an effective amount of a compound of Formula I.

The invention also provides a method for the treatment of cell proliferative disorders in mammals comprising administering to a mammal in need of such treatment an effective amount of a compound of Formula I.

The invention also provides the use of a compound of Formula I for the preparation of a medicament useful for the inhibition of CDK4.

The invention further provides the use of a compound of Formula I for the preparation of a medicament useful for the treatment of a cell proliferative disorder.

The following definitions are to set forth the meaning and scope of the various terms used herein. The general terms used herein have their usual meanings.

As used herein, the term "hyperproliferative state" refers to those cells whose unregulated and/or abnormal growth can lead to the development of an unwanted condition, for example, a cancerous condition or a psoriatic condition.

As used herein, the term "psoriatic condition" refers to disorders involving keratinocyte hyperproliferation, inflammatory cell infiltration, and cytokine alteration.

As used herein, the term "neoplasm" refers to an abnormal new growth of tissue that grows by cellular proliferation more rapidly than normal, continues to grow after the stimuli that initiated the new growth cease, shows partial or complete lack of structural organization and functional coordination with the normal tissue, and usually forms a distinct mass of tissue which may be either benign or malignant.

As used herein, the term "proliferative diseases" refers to diseases in which some tissue in a patient proliferates at a greater than normal rate. Proliferative diseases may be cancerous or non-cancerous. Non-cancerous proliferative diseases include epidermic and dermoid cysts, lipomas, adenomas, capillary and cutaneous hemangiomas, lymphangiomas, nevi lesions, teratomas, nephromas, myofibromatosis, osteoplastic tumors, other dysplastic masses and the like.

The types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, other dysplastic masses and the like.

The types of cancers which may be treated with the compositions of the present invention include, but are not limited to, Breast Carcinoma, Bladder Carcinoma, Brain Cancer, Colorectal Carcinoma, Esophageal Carcinoma, Gastric Carcinoma, Germ Cell Carcinoma e.g. Testicular Cancer, Gynecologic Carcinoma, Hepatocellular Carcinoma, Small Cell Lung Carcinoma, Non-small Cell Lung Carcinoma, Lymphomas, Hodgkin's Lymphoma, Non-Hodgkin's Lymphoma, Malignant Melanoma, Multiple Myeloma, Neurologic Carcinoma, Ovarian Carcinoma, Pancreatic Carcinoma, Prostate Carcinoma, Renal Cell Carcinoma, Ewings Sarcoma, Osteosarcoma, Soft Tissue Sarcoma, Pediatric Malignancies and the like.

The general chemical terms used herein have their usual meanings. For example, as used herein, the term "alkyl," alone or in combination, denotes a straight-chain or branched-chain $C_1$–$C_6$ alkyl group consisting of carbon and hydrogen atoms, examples of which are methyl, ethyl, propyl, isopropyl, butyl, sec-butyl, tert-butyl, and the like. The term "$C_1$–$C_6$ alkyl" also refers to $C_3$–$C_6$ cycloalkyl, including cyclopropyl, cyclobutyl, cyclopentyl, and cyclohexyl.

The term "alkenyl," alone or in combination, denotes a straight-chain or branched-chain $C_2$–$C_6$ alkenyl group consisting of carbon and hydrogen atoms and containing a carbon-carbon double bond, examples of which are ethylene, propylene, methylethylene, butylene, and the like.

The term "alkoxy," alone or in combination, denotes an alkyl group as defined earlier which is attached via an oxygen atom, such as, for example, methoxy, ethoxy, propoxy, isopropoxy, butoxy, tert-butoxy, and the like.

As used herein, the term "substituted $C_1$–$C_6$ alkyl" represents a straight or branched alkyl chain substituted with a carboxyl, ($C_1$–$C_6$ alkoxy)carbonyl, $C_1$–$C_6$ alkoxy, aryloxy, amino, ($C_1$–$C_6$ alkyl)amino, tetrahydrofuryl or up to one hydroxy moiety for each carbon atom on the alkyl chain.

As used herein, the term "aryl" represents a phenyl or naphthyl moiety optionally substituted with from one to three substituents selected from halo, $C_1$–$C_6$ alkyl, hydroxy, amino or $C_1$–$C_6$ alkoxy.

As used herein, the term "heteroaryl" means a stable one- or two-ring aromatic moiety that comprised of carbon atoms and 1–4 heteroatoms selected from O, S, and N. Examples of heteroaryl groups include pyrrolyl, furyl, thienyl, imidazolyl, pyridyl, pyrimidinyl, pyrazinyl, thiazolyl, triazinyl, phthalimido, indolyl, purinyl, benzothiazolyl, and the like. The heteroaryl moiety may be optionally substituted with one or two groups independently selected from amino, hydroxy, $C_{1-7}$ alkoxy, aryloxy, $C_{1-7}$ alkyl, aminoalkyl, haloalkyl and halogen.

As used herein, the term "saturated heterocycle" is taken to be a 4–9 membered ring containing nitrogen and optionally one other atom selected from oxygen, nitrogen, or sulfur.

As used herein, the term "halo" or "halogen" or "halide" represents fluorine, chlorine, bromine, or iodine. A haloalkyl is one such alkyl substituted with one or more halo atoms, preferably one to three halo atoms. However, all the hydrogen atoms in alkyl group may be replaced by halogens. As more halogens are added to an alkyl group, fluorine is preferred over the other halogens. An example of a haloalkyl is trifluoromethyl.

As used herein, an "amino acid residue" is taken to mean the product of an amino acid coupled to the compound of Formula I through the carboxylic acid moiety, forming an amide or ester bond, or through the α- or β-amino moiety, forming an amide or amine bond.

As used herein, a "protected amino acid residue" is taken to mean an amino acid residue where the amine or carboxylic acid moieties not participating in the bond to the compound nucleus are protected by suitable protecting groups. Such groups include tert-butyl, tert-butoxycarbonyl, benzyl, benzyloxycarbonyl, and the like.

As used herein, the term "pharmaceutically acceptable salt" includes acid and base addition salts. Such pharmaceutically acceptable salts include inorganic acid addition salts such as hydrochloride, sulfate, and phosphate, and organic acid addition salts such as acetate, maleate, fumarate, tartrate, and citrate. Examples of pharmaceutically acceptable basic salts include metal salts such as the alkali metal salts such as the sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable amine addition salts are salts with morpholine and piperidine. Examples of pharmaceutically acceptable amino acid addition salts include salts with lysine, glycine, and phenylalanine. Preferred salts include those with hydrochloric acid, trifluoroacetic acid, and methanesulfonic acid.

As used herein the term "amino acid" includes both naturally occurring and synthetic amino acids and includes both the D and L forms of the acids as well as the racemic form. More specifically, amino acids contain up to ten carbon atoms. They may contain an additional carboxyl group, and heteroatoms such as nitrogen and sulfur. Preferably the amino acids are α- and β-amino acids. The term α-amino acid refers to amino acids in which the amino group is attached to the carbon directly attached to the carboxyl group, which is the α-carbon. The term β-amino acid refers to amino acids in which the amino group is attached to a carbon two removed from the carboxyl group, which is the β-carbon. Some common α-amino acid residues are shown in Table I wherein the residues are given the name of the amino acids from which they are derived.

TABLE I

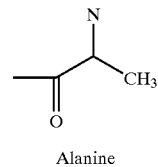

Alanine

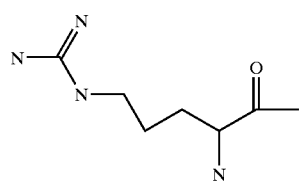

Arginine

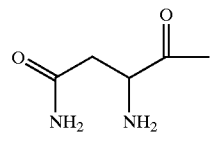

Asparagine

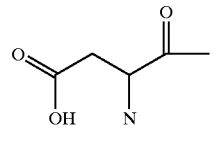

Asparamine

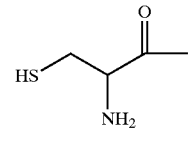

Cysteine

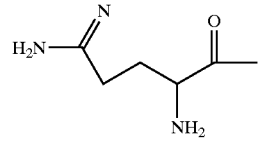

Glutamine

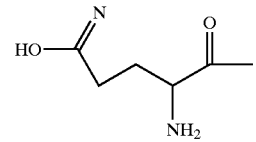

Glutamic Acid

TABLE I-continued
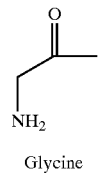
Glycine
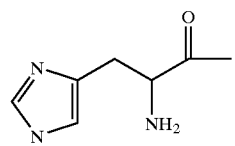
Histidine
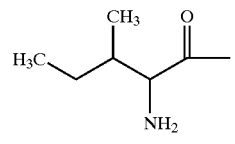
Isoleucine
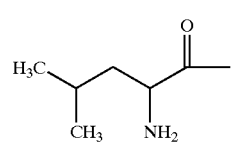
Leucine
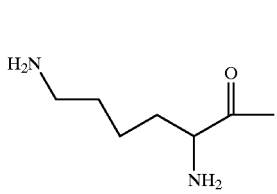
Lysine
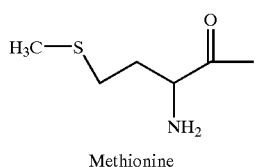
Methionine
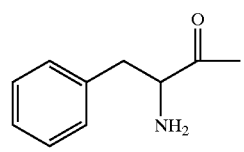
Phenylalanine
TABLE I-continued
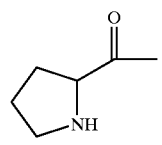
Proline
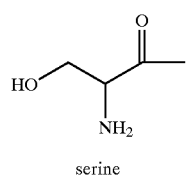
serine
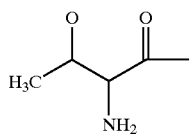
Threonine
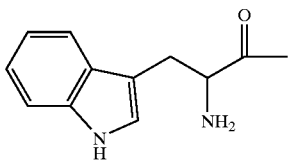
Tryptophan
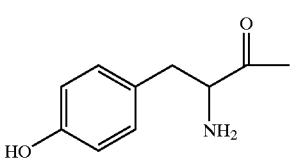
Tyrosine
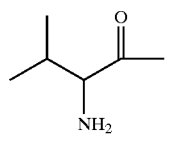
Valine Suitable β-amino acid residues can be the β-amino derivative of any suitable α-amino acid residue wherein the amino group is attached to the residue through the β-carbon rather than the α-carbon relative to the carboxyl group, for example, 3-aminopropionoic acid, 3-amino-3-phenylpropionoic acid, 3-aminobutyric acid and the like:

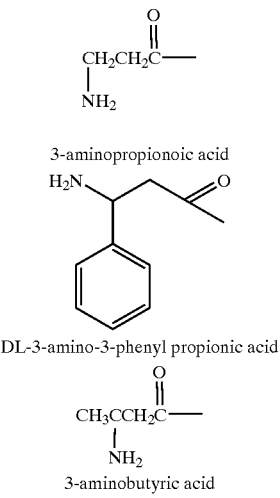

Although all of the compounds of Formula I are useful CDK4 inhibitors, certain compounds are preferred. The following paragraphs define preferred classes.

aa) A and B are both oxygen;
ab) X and Y, taken together, form a bond;
ac) $R^1$ is hydrogen;
ad) $R^2$ is one substituent selected from halo;
ae) $R^2$ is chloro;
af) $R^2$ is fluoro;
ag) $R^2$ is bromo;
ah) $R^2$ is two substituents independently selected from halo;
ai) $R^2$ is difluoro;
aj) $R^2$ is chloro, fluoro;
ak) $R^2$ is methoxy;
al) $R^3$ is heteroaryl;
am) $R^3$ is pyridin-3-yl;
an) $R^3$ is pyridin-4-yl;
ao) $R^3$ is —$(CH_2)_m$—Z;
ap) m is 0;
aq) m is 1, 2, or 3;
ar) m is 1;
as) Z is ($C_1$–$C_4$ alkoxy)carbonyl;
at) Z is methoxycarbonyl;
au) Z is hydroxy;
av) Z is $NR^8R^9$;
aw) $R^8$ and $R^9$ taken together with the nitrogen to which they are attached form an aziridinyl, pyrrolidinyl, 3-hydroxypyrrolidinyl, piperidinyl, piperazinyl, or diazepinyl;
ax) $R^4$ is hydrogen;
ay) $R^4$ is $C_1$–$C_4$ alkyl;
az) $R^4$ is methyl;
ba) $R^5$ is halogen;
bb) $R^6$ is geminal dimethyl;
bc) $R^7$ is —$(CH_2)_m$—Z;
bd) $R^7$ is hydroxymethyl;
be) $Q^2$ is a carbon-carbon single bond;
bf) $Q^2$ is —$NR^{10}$—;
bg) $Q^2$ is —$NR^{10}$—$CHR^{11}$—;
bh) $Q^1$, $Q^2$, and $Q^3$, taken together with the atoms to which they are attached, form a 6-membered, 7-membered and 8-membered ring;
bi) $Q^1$, $Q^2$, and $Q^3$, taken together with the atoms to which they are attached, form an unsubstituted ring;
bj) $Q^1$ is —$(CH_2)$—;
bk) $Q^1$ is —$(CH_2)_2$—;
bl) $Q^3$ is —$(CH_2)$—;
bm) $Q^3$ is —$(CH_2)_2$—;
bn) $Q^3$ is —$(CH_2)_3$—;
bo) $R^{10}$ is methanesulfonyl;
bp) $R^{10}$ is heteroarylsulfonyl;
bq) $R^{10}$ is $C_1$–$C_4$ alkyl;
br) $R^{10}$ is hydrogen.

The preceding paragraphs may be combined to define additional preferred classes of compounds.

The compounds of Formula I are useful for the treatment of disorders of mammals, and the preferred mammal is a human.

The skilled artisan will appreciate that the introduction of certain substituents will create asymmetry in the compounds of Formula I. The present invention contemplates all enantiomers and mixtures of enantiomers, including racemates. It is preferred that the compounds of the invention containing chiral centers are single enantiomers.

Variables $R^2$, $R^3$, $R^5$, $R^6$ and $R^7$ may optionally be selected from specified groups. A preferred embodiment of the invention are those compounds where no substituent is selected from said groups.

The carbazoles, compounds of Formula I where X and Y taken together form a bond, are prepared by oxidation of the corresponding maleimide, compounds of Formula I where X and Y are each hydrogen. This oxidative step is illustrated in Scheme I, where the ring designated "A" corresponds to the annulated rings of Formula I. The skilled artisan will appreciate that the transformations illustrated in the following schemes are not limited to the unsubstituted compounds represented. Substituents have been eliminated in the following schemes for the sake of clarity, and are not intended to limit the teaching of the schemes in any way.

SCHEME I

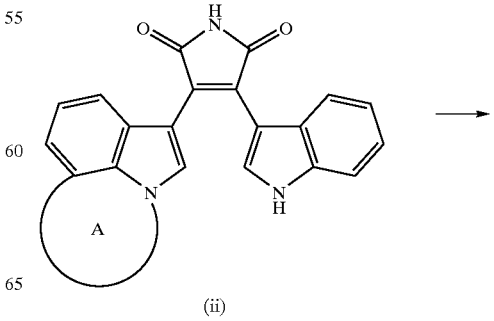

(ii)

-continued

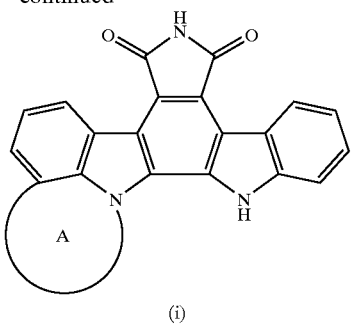

(i)

This transformation may be prepared by a number of methods. For example, the maleimide of formula (ii) in an appropriate solvent, such as acetic acid, may be treated with a palladium salt such as palladium dichloride, palladium bis(trifluoroacetate), or preferably palladium diacetate. The reaction is conducted at a temperature of about 60° C. to about reflux, and the mixture is stirred for 1–24 hours. The resulting carbazole of formula (i) is recovered by standard isolation techniques and may be purified by chromatography or recrystallization as necessary or desired.

Alternatively, a mixture of a maleimide of formula (ii) in a suitable solvent, such as benzene and an acid, such as para-toluenesulfonic acid monohydrate, and 2,3-dichloro-5,6-dicyano-1,4-benzoquinone (DDQ) is stirred at about reflux for 1–6 hours, after which the mixture is allowed to cool to about ambient temperature and stirred for an additional 1–24 hours. The resulting carbazole of formula (i) is isolated and purified by standard techniques.

Furthermore, a maleimide of formula (ii) and iodine in a suitable solvent, such as dioxane, may be reacted via irradiation by a medium-pressure mercury lamp. The reaction mixture is irradiated for about 10 minutes to about 24 hours. The resulting carbazole formula (i) may be isolated and purified by standard techniques.

The requisite maleimides of formula (ii) may be prepared from an appropriately substituted oxoacetic acid ester and an appropriately substituted acetamide as illustrated in Scheme II, where the ring designated "A" corresponds to the annulated rings of Formula I.

SCHEME II

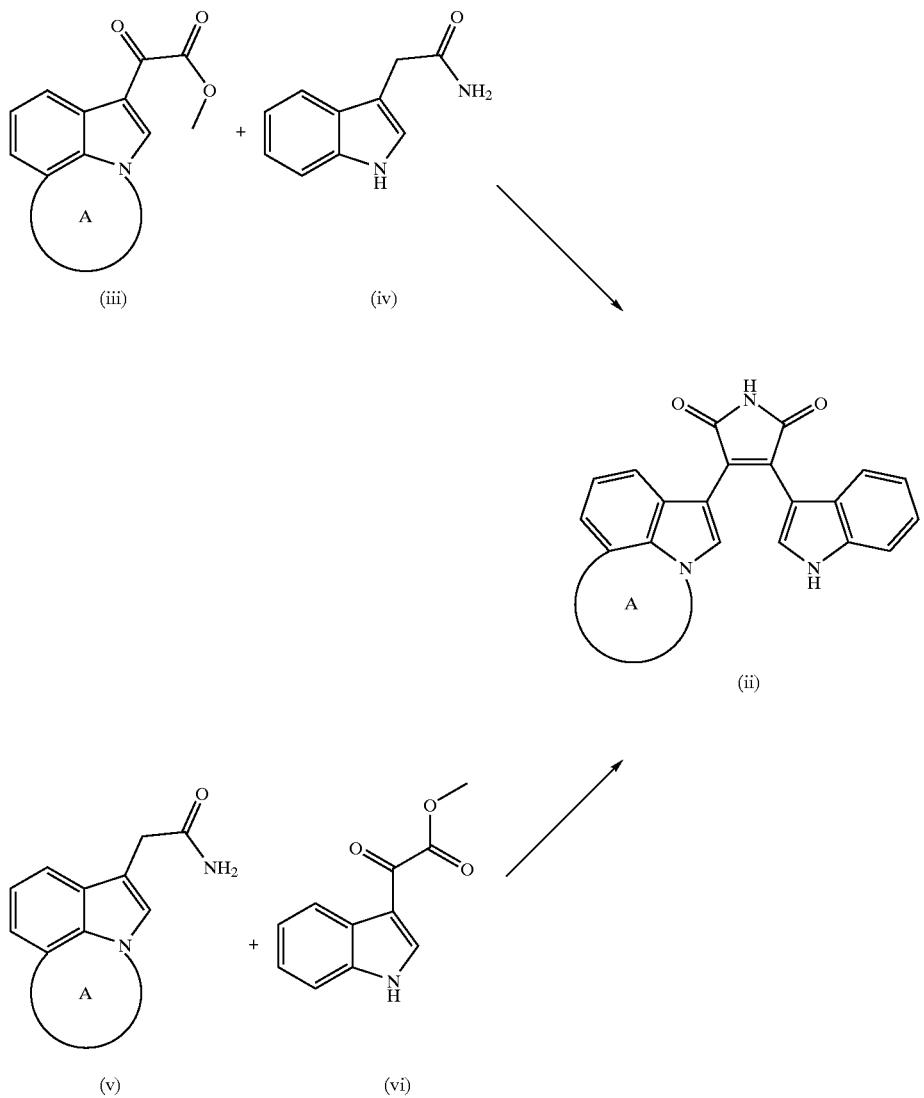

The oxoacetic acid esters of formula (iii) or (vi) are reacted with an acetamide of formula (iv) or (v), respectively, in a suitable solvent, such as tetrahydrofuran, in the presence of a suitable base, preferably potassium tert-butoxide. The condensation reaction is conducted at 0° C. or room temperature, and the reactants are stirred for 1–24 hours. The reaction mixture is treated with a suitable acid, such as hydrochloric acid, after which the mixture is stirred at about ambient temperature for 1–24 hours. The resulting maleimide (ii) may be isolated by standard techniques, and purified by crystallization or chromatography as necessary or desired.

The requisite indolylacetamides of formula (iv) are either commercially available or may be prepared from the corresponding oxoacetic acid of formula (vi) by reaction with ammonium hydroxide in a suitable solvent, such as tetrahydrofuran or diethyl ether. The reaction is conducted at about 0° C. for 1–12 hours, after which the reaction mixture is allowed to warm to about ambient temperature. The resulting ketoamide may be isolated by standard techniques and purified by crystallization or chromatography as necessary or desired. This ketoamide is then reduced by reaction with a metal catalyst, such as palladium, and sodium hypophosphite in a suitable solvent, such as tetrahydrofuran, dioxane, or dimethylformamide. The reaction is conducted under nitrogen at about reflux conditions for 1–12 hours. The resulting indolylacetamide of formula (iv) is isolated by standard techniques and may be purified by crystallization or chromatography as necessary or desired.

The indolyloxoacetic acid esters of formula (vi) are either commercially available or may be prepared by reacting an appropriately substituted indole with oxalyl chloride in an appropriate solvent, such as dichloromethane or diethyl ether. The addition is performed at a temperature of about 0° C., and the mixture is stirred for 1–24 hrs. The mixture is then cooled to about −78° C. and than a source of alkoxide, such as sodium methoxide, is added in an appropriate solvent, such as methanol. The resulting oxoacetic acid ester may be isolated by standard techniques and purified by crystallization or chromatography as necessary or desired.

The requisite indoles are either commercially available or may be prepared by methods well known in the art. Indole syntheses are described in Robinson, *The Fischer Indole Synthesis*, Wiley, N.Y. (1983); Hamel, et al., *Journal of Organic Chemistry*, 59, 6372 (1994); and Russell, et al., *Organic Preparations and Procedures International*, 17, 391 (1985).

The annulated-indole oxoacetic acid esters (iii) and annulated-indole acetamides (v) may be similarly prepared from the corresponding annulated-indoles of formula (vii):

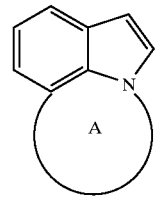

vii where the ring designated "A" corresponds to the annulated ring in Formula I. These annulated-indoles (vii), annulated-indole oxoacetic acid esters (iii), and annulated-indole acetamides (iv) are further embodiments of the present invention.

The requisite annulated-indoles are prepared by a variety of methods depending upon the specific structure of the ring system. Synthetic methodologies leading to the various annulated-indoles are illustrated in the following schemes and discussed in the following paragraphs. The preparations and examples further illustrate these basic routes as well modifications to these routes to prepare certain requisite substituted variants.

4,5-dihydropyrrolo[3,2,1-hi]indoles

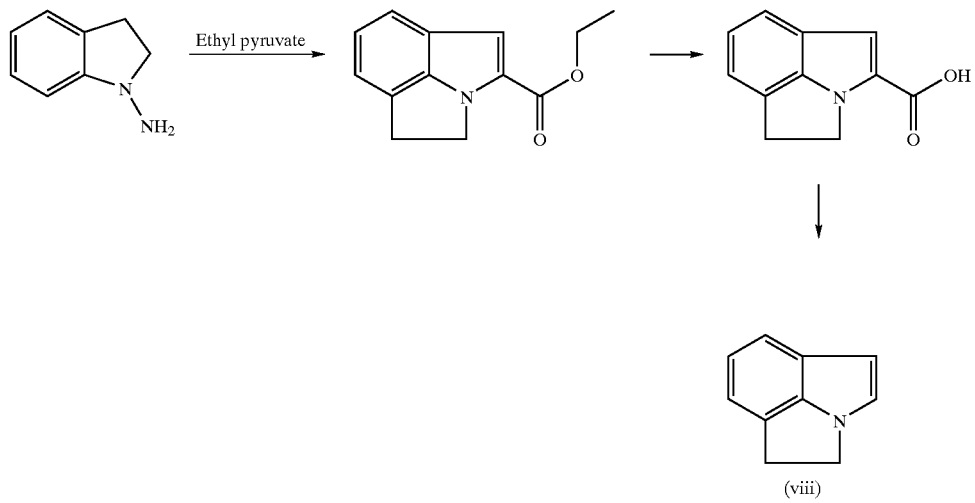

(viii)

An N-aminoindoline (Wijngaarden, et al., *J. Med. Chem.*, 36, 3693 (1993)) is treated with ethyl pyruvate in a suitable solvent, such as ethanol, at reflux. After about an hour, the imine from this reaction is dissolved in a suitable solvent, such as acetic acid, and is treated with an appropriate Lewis acid, such as boron trifluoride etherate, at reflux for about an hour. The resulting ethyl pyrroloindole-2-carboxylic acid is isolated by standard conditions. The ester is hydrolyzed to provide the corresponding carboxylic acid under standard conditions, and then is decarboxylated in the presence of copper (II) oxide in quinoline to provide compounds of formula (viii).

5,6-dihydro-4H-pyrrolo[3,2,1-ij]quinolines

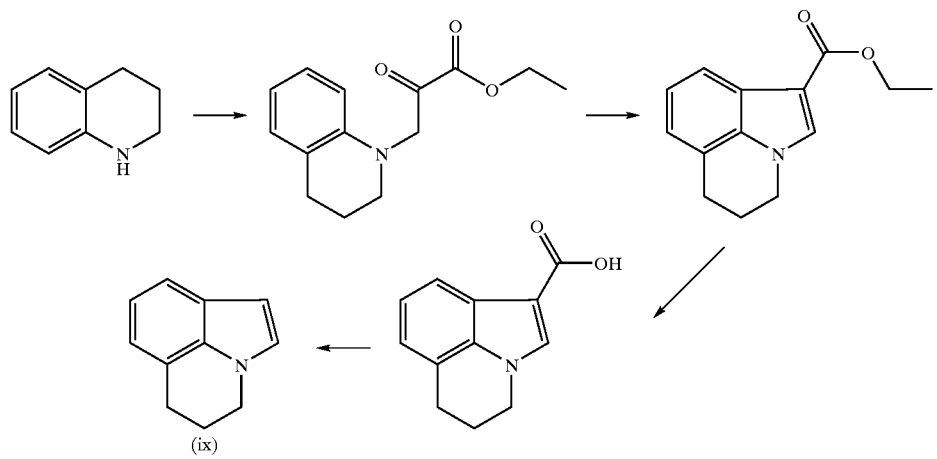

An appropriately substituted 1,2,3,4-tetrahydroquinoline is reacted with ethyl bromopyruvate in an appropriate solvent, such as dimethylformamide or tetrahydrofuran. The reaction mixture is stirred for 1–30 hours. The product from this reaction is isolated by standard techniques and is then reacted with an appropriate magnesium halide, typically magnesium chloride, and an appropriate alcohol such as methoxyethanol in an appropriate cosolvent, such as tetrahydrofuran or dimethylformamide. The skilled artisan will appreciate that the addition must be performed slowly and carefully, after which the resulting reaction mixture is stirred for 1–12 hours at about reflux. The resulting carboxylic acid ester is isolated by standard techniques. This ester is then hydrolyzed and decarboxylated under standard conditions to provide compounds of formula (ix).

3,4-Dihydro-5-thia-2a-aza-acenaphthalene and 3,4-Dihydro-5-oxo-2a-aza-acenaphthalene

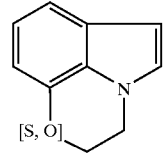
(x)

Compounds of formula (x) are prepared beginning with 3,4-dihydro-2H-benzo[1,4]thiazine or 3,4-dihydro-2H-benzo[1,4]oxazine by the same techniques described for the compounds of formula (ix). The corresponding sulfoxide and sulfones may be prepared at any convenient point in the synthesis by oxidation with an appropriate reagent, such as meta-chloroperbenzoic acid.

4,5,6,7-tetrahydroazepino[3,2,1-hi]indole

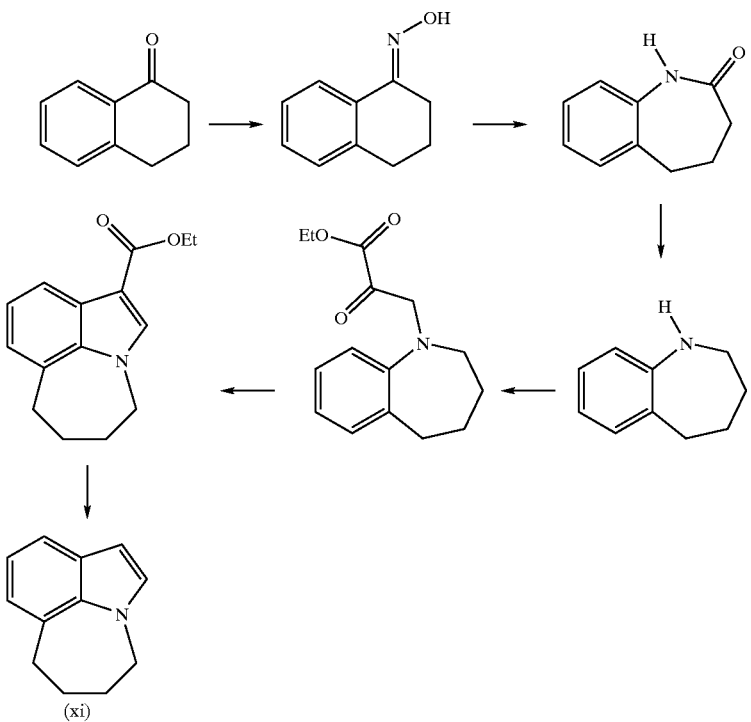

An appropriately substituted 1-tetralone is reacted with hydroxylamine hydrochloride under standard conditions to provide the corresponding oxime. This oxime is heated in a strong acid, such as polyphosphoric acid, for about 10 minutes. The reaction mixture was treated with ice and water to precipitate the corresponding 1,3,4,5-tetrahydrobenz[b]azepin-2-one. This lactam is reduced under standard conditions to provide the corresponding 2,3,4,5-tetrahydro-1H-benzo[b]azepine. Reaction of this amine with ethyl bromopyruvate, followed by treatment with magnesium chloride, ester hydrolysis, and decarboxylation as described above for compounds of formula (ix), provides the compounds of formula (xi).

5,6-dihydro-6H-[1,4]diazepino[6,7,1-hi]indoles

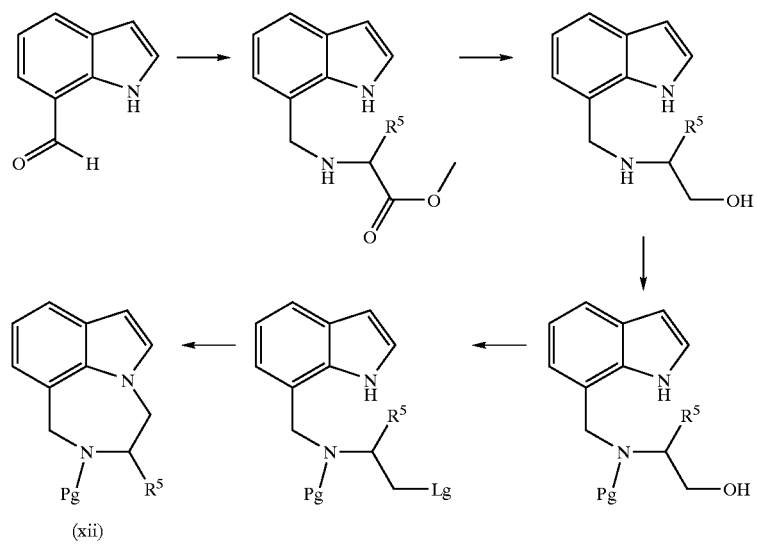

(xii)

An appropriately substituted indole-7-carboxaldehyde in an appropriate solvent, such as 1,2-dichloroethane, is reacted with an appropriately substituted amino acid methyl ester and acetic acid. This reaction is conducted under nitrogen at about ambient temperature in the presence of a mild reducing agent, such as sodium cyanoborohydride or sodium triacetoxyborohydride. The reaction mixture is stirred for about 24 hours, and the resulting amino ester is isolated by standard techniques. The ester moiety is reduced to the corresponding alcohol by treatment with a suitable reducing agent, typically lithium aluminum hydride, in an appropriate solvent, typically tetrahydrofuran or diethyl ether. The secondary amine moiety is now reacted with an appropriate reagent to introduce a suitable amino protecting group "Pg", such as a formyl group, acetyl group, or preferably a tert-butoxycarbonyl moeity. Techniques for the introduction of these groups are well known to the skilled artisan. A solution of this compound in an appropriate solvent, such as dichloromethane or diethyl ether, is reacted with an appropriate reagent to activate the hydroxy moiety, providing a leaving group ("Lg"). The skilled artisan would appreciate that appropriate leaving groups include halides, oxonium ions, alkyl perchlorates, ammonioalkanesulfonate esters, alkyl fluorosulfonates, nonaflates, tresylates, triflates, and sulfonic esters, preferably the mesylate or tosylate. Techniques for the introduction of these groups are well known to the skilled artisan. (See for example: March, "Advanced Organic Chemistry," John Wiley and Sons, New York, N.Y., 1992, pg. 352–362). The activated compound is then dissolved in an appropriate solvent, such as tetrahydrofuran, diethyl ether or N,N-dimethylformamide and is reacted with a strong base, such as potassium hydride or sodium hydride. The reaction is conducted under nitrogen at about 0° C. and stirred for 30–120 minutes. The compound of formula (xii) is isolated and purified by standard techniques. The skilled artisan will appreciate that the nitrogen-protecting groups may be removed at any convenient point in the synthesis of the compounds of the present invention. Methods of removing an amino-protecting group are well known in the art (for example, see: T. W. Greene, "Protective Groups in Organic Synthesis," John Wiley and Sons, New York, N.Y., 1991, Chapter 7).

5,6-dihydro-6H-[1,4]homodiazepino-[6,7,1-hi]indoles

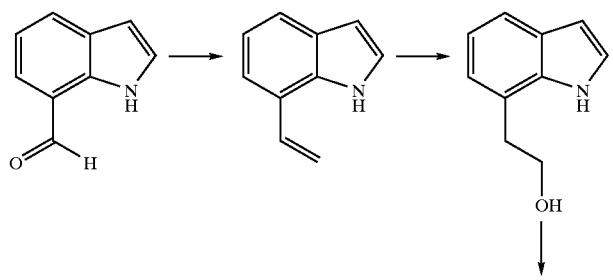

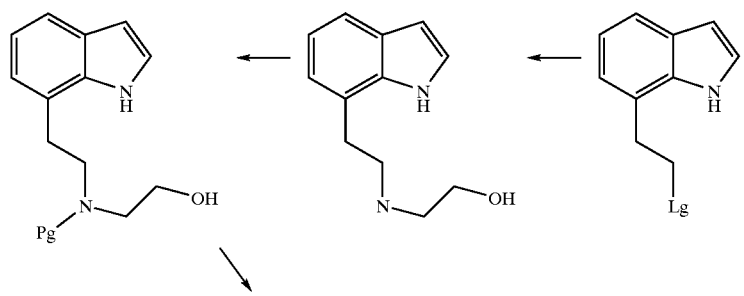

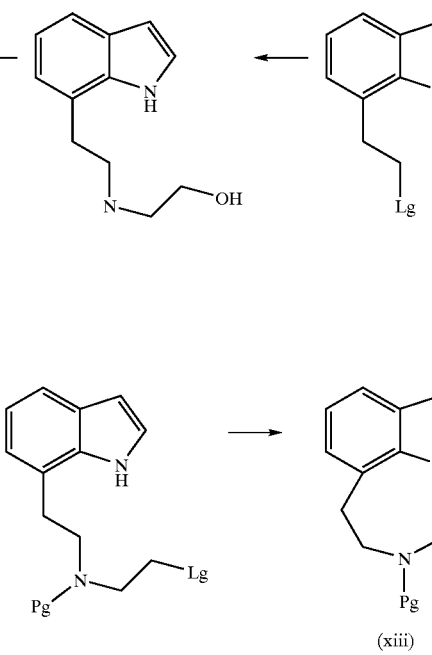

(xiii)

An appropriately substituted indole-7-carboxaldehyde in an appropriate solvent, such as tetrahydrofuran or toluene, is reacted with a suitable methylenating reagent at about ambient temperature. Suitable methylenating reagents include Tebbe reagent ($\mu$-chloro-$\mu$-methylene[bis(cyclopentadienyl)titanium]dimethylaluminum) and appropriate Wittig reagents, such as methyltriphenylphosphonium bromide, in the presence as a suitable base, such as potassium tert-butoxide. The reaction mixture is stirred for 1–6 hours, after which the resultant vinylindole is isolated under standard techniques. This compound is then hydroborated and oxidized under standard conditions to provide the corresponding hydroxyethylindole. This alcohol is then activated as previously described, and reacted with ethanolamine or an appropriate amino acid ester. When aminoethanol is employed, the resulting alcohol is activated and the compound cyclized as previously described. When an amino acid ester is employed, the resulting ester is first reduced, and then activated and the compound cyclized as previously described to provide compounds of formula (xiii). The skilled artisan will appreciate that the nitrogen-protecting groups may be removed at any convenient point in the synthesis of the compounds of the present invention.

Pyrrolo[3,2,1-kl]benzo[b]azacyclooctane

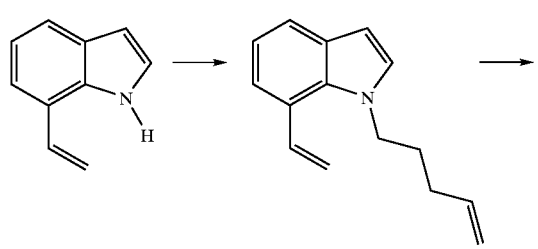

-continued

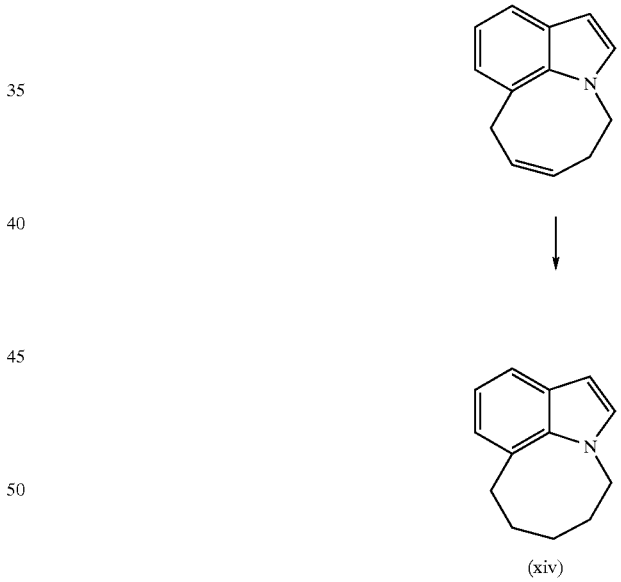

(xiv)

An appropriately substituted 7-vinylindole is alkylated with an appropriate bromoalkene under standard conditions and the resulting diene is reacted with bis(tricyclohexylphosphine)benzylidine ruthenium (IV) dichloride (Grubb's catalyst) at room temperature in a suitable solvent, such as dichloromethane. After about 24 hours the cyclized alkene is isolated by standard techniques. The double bond may then be reduced under standard hydrogenation conditions to provide the compounds of formula (xiv).

[1,5]diazaperhydroonino[8,9,1-hi]indoles

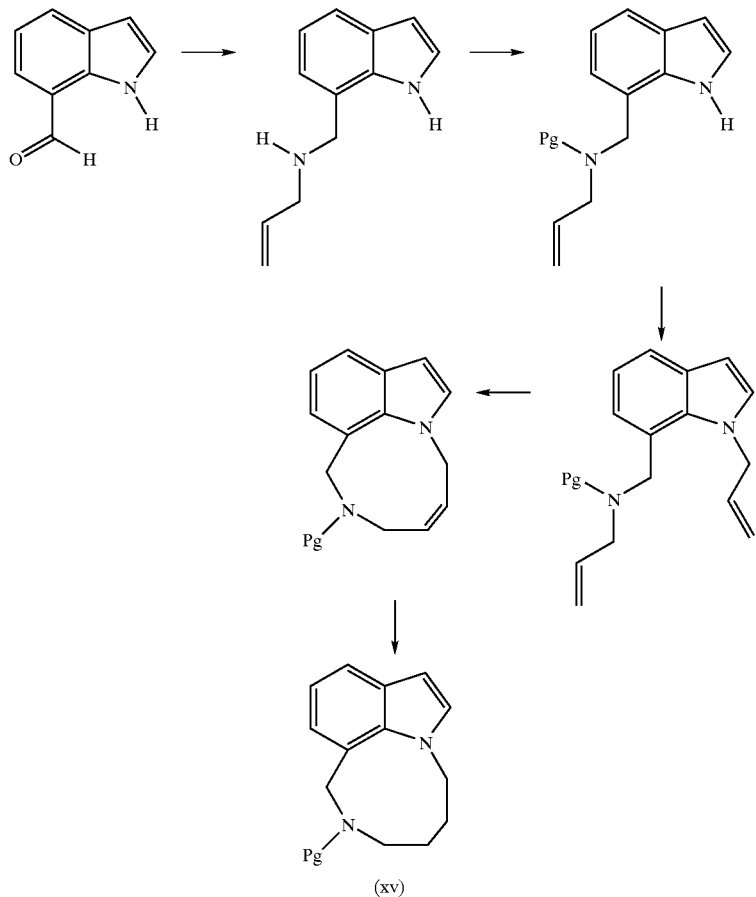

(xv)

An appropriately substituted indole-7-carboxaldehyde was reductively aminated with allylamine in the presence of a suitable acid, such as acetic acid, and an appropriate reducing agent, such as sodium cyanoborohydride or sodium triacetoxyborohydride in an appropropriate solvent, such as 1,2-dichloroethane. The mixture is stirred at room temperature for about 24 hours and the resulting amine is isolated and purified by standard techniques. The amine is then protected as previously described and the indole nitrogen alkylated with allyl bromide under standard conditions. The diene is then cyclized as previously described to provide the cyclic alkene. The double bond may then be reduced under standard hydrogenation conditions to provide the compounds of formula (xv).

The skilled artisan will appreciate that compounds of the invention where variables A and B are independently S may be prepared by treating either the final compound or an appropriate carbonyl starting material with [2,4-bis(4-methoxyphenyl)-1,3-dithia-2,4-diphosphetane-2,4-disulfide] (Lawesson's Reagent) or phosphorus pentasulfide.

Many of the compounds of the present invention are not only inhibitors of CDK4, but are also useful intermediates for the preparation of additional compounds of the present invention. For example, secondary amines may be acylated, alkylated or coupled with simple carboxylic acids or amino acids under standard conditions. Furthermore, ester moieties may be reduced to the corresponding alcohols. These alcohols may then be activated and displaced by a number of nucleophiles to provide other compounds of the invention.

The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired. Furthermore, the skilled artisan will appreciate that in many circumstances, the order in which moieties are introduced is not critical. The following preparations and examples will further illustrate the preparation of compounds of the present invention.

Preparation I 5,6-Dihydro-4H-pyrrolo[3,2,1-ij]quinoline
3-(3,4-Dihydro-2H-quinolin-1-yl)-2-oxopropionic acid ethyl ester To a solution of 1,2,3,4-tetrahydroquinoline (75.5 mL, 0.59 mol) in tetrahydrofuran (300 mL) was added bromoethyl pyruvate (40 mL, 0.29 mol) dropwise over 30 minutes. Following 24 hours of stirring, the reaction mixture was filtered, the filter cake rinsed well with tetrahydrofuran (100 mL) and the filtrate concentrated under reduced pressure to dryness to give 79.7 g of the desired compound as a red oil. 5,6-Dihydro-4H-pyrrolo[3,2,1-ij]quinoline-1-carboxylic acid ethyl ester Magnesium chloride (27.7 g, 0.29 mol) was added to 2-methoxyethanol (400 mL) and the mixture heated to reflux. A solution of 3-(3,4-Dihydro-2H-quinolin-1-yl)-2-oxopropionic acid ethyl ester (0.29 mol) in 2-methoxyethanol (100 mL) and tetrahydrofuran (40 mL) was slowly added to the MgCl$_2$ mixture over 1 hour. Upon completion of addition, the mixture was stirred for 5 hours at reflux, and then concentrated in vacuo. The concentrated crude mixture was treated with 2N hydrochloric acid (500 mL) and extracted with dichloromethane (3×400 mL). The combined organic layers were dried over Na$_2$SO$_4$, filtered and concentrated in vacuo. The residue was subjected to silica gel chromatography, eluting with 20% ethyl acetate/hexanes. Fractions containing product were combined and concentrated under reduced pressure to provide 31.6 g (48%) of the desired compound as an orange solid.

MS (IS, m/z) C$_{14}$H$_{15}$NO$_2$ (M$^+$+1)=230.

5,6-Dihydro-4H-pyrrolo[3,2,1-ij]quinoline-1-carboxylic acid

To a solution of 5,6-Dihydro-4H-pyrrolo[3,2,1-ij]quinoline-1-carboxylic acid ethyl ester (31 g, 0.14 mol) in ethanol (200 mL) and water (70 mL) was added 5 N aqueous sodium hydroxide (60 mL, 0.3 mol) and the resulting mixture stirred at reflux for 3 hours. The reaction mixture was cooled to 20–24° C., diluted with water (2 L) and washed with dichloromethane (2×200 mL) and diethyl ether (1×200 mL). The aqueous layer was filtered through Celite and the filtrate was acidified with conc. HCl (25 mL) to precipitate the product. The solid was filtered, washed with water (200 mL), and dried in vacuo to give 23.2 g (85%) of the desired compound as a light yellow solid.

MS (IS, m/z) C$_{12}$H$_{11}$NO$_2$ (M$^+$+1)=202.

Decarboxylation

To a solution of 5,6-Dihydro-4H-pyrrolo[3,2,1-ij]quinoline-1-carboxylic acid (3.7 g, 18.4 mmol) in 20 mL of quinoline was added copper chromite (1.5 g, 4.8 mmol). The resulting mixture was stirred at 185° C. for 4 hours and then cooled to 20–24° C., diluted with dichloromethane (100 mL) and filtered through Celite. The filtrate was then washed sequentially with 2 N hydrochloric acid (2×50 mL) and 2 N aqueous sodium hydroxide (25 mL). The remaining organic phase was concentrated in vacuo. The residue was subjected to silica gel chromatography, eluting with 5% EtOAc/Hexanes. Fractions containing product were combined and concentrated under reduced pressure to provide 1.67 g (58%) of the desired compound as a light tan solid.

$^1$H NMR (400 MHz, DMSO-d$_6$) δ 7.31–7.29 (d, 1H, J=7.8 Hz), 7.28–7.27 (d, 1H, J=2.93 Hz), 6.9–6.86 (t, 1H, J=7.6 Hz), 6.82–6.8 (dd, 1H, J=6.8, 1.0 Hz), 6.33–6.32 (d, 1H, J=2.93 Hz), 4.15–4.12 (t, 2H, J=5.6 Hz), 2.92–2.89 (t, 2H, J=6.1 Hz), 2.15–2.08 (m, 2H).

Preparation II (5,6-Dihydro-4H-pyrrolo[3,2,1-ij]quinolin-1-yl) oxoacetic Acid Methyl Ester To a solution of 5,6-Dihydro-4H-pyrrolo[3,2,1-ij]quinoline (1.67 g, 10.6 mmol) in 150 mL of anhydrous diethyl ether at 0° C. was added dropwise oxalyl chloride (1.05 mL, 12.08 mmol) and the resulting solution was stirred at 0° C. for 40 minutes. The mixture was then cooled to −78° C. and sodium methoxide (42 mL, 21 mmol, 0.5 M in methanol) was added slowly. Upon completion of the addition, the dry ice bath was removed and the reaction was warmed to 20–24° C. over 2 hours. The mixture was diluted with ethyl acetate (200 mL), washed with water (100 mL) and the layers were separated. The organic layer was washed with saturated aqueous sodium chloride (50 mL), dried over sodium sulfate, filtered and concentrated in vacuo. The residue was dissolved in ethyl acetate (100 mL), filtered through a 2 inch plug of coarse silica gel and concentrated in vacuo to give 2.16 g (84%) of the desired compound as a yellow solid.

MS (EI, m/z) C$_{14}$H$_{13}$NO$_3$ (M$^+$−59)=184.

Preparation III 2-(trimethylsilyloxy)methyl)-11H, 12H, 14H-pyrrolo[3,4-c]quinolino[8',8a',1':3,2,1]pyrrolo[2,3-a]carbazole-5,7-dione Beginning with 3-(5,6-dihydro-4H-pyrrolo[3,2,1-ij]quinolin-1-yl)-4-(6-(triisopropylsilyloxy)methyl)-1H-indol-3-yl)pyrrole-2,5-dione, the title compound was prepared essentially as described in Example 52.

$^1$H NMR (DMSO-d$_6$, 400 MHz): δ: 1.10 (18H, d, J=6.8 Hz), 1.14–1.21 (3H, m), 2.36–2.37 (2H, m), 3.11 (2H, t, J=6.0 Hz), 4.89 (2H, t, J=5.6 Hz), 5.03 (2H, s), 7.24 (2H, t, J=7.8 Hz), 7.30 (1H, d, J=6.0 Hz), 7.79 (1H, s), 8.71 (1H, d, J=7.8 Hz), 8.94 (1H, d, J=8.4 Hz), 10.94 (1H, 1H, s), 12.01 (1H, s)

Preparation IV

S-6-(tert-butoxycarbonyl)-5-(tert-Butoxy)methyl-5,6-dihydro-6H-[1,4]diazepino[6,7,1-hi]indole S-3-(tert-Butoxy)-2-(N-[(1H-indol-7-yl)methyl]amino)-propionic acid methyl ester To a solution of indole-7-carboxaldehyde (0.500 g, 3.44 mmol) in 1,2-dichloroethane (30 mL) under nitrogen was added S-(O-tert-butyl)serine methyl ester hydrochloride (1.09 g, 5.16 mmol), acetic acid (0.206 g, 0.197 mL, 3.44 mMol), and sodium triacetoxyborohydride (1.46 g, 6.88 mmol). The resulting mixture was stirred at 20–24° C. for 24 hours. The reaction mixture was then quenched by the addition of aqueous saturated sodium bicarbonate. The organic phase was extracted with dichloromethane and washed with saturated aqueous sodium chloride. The organic phase was dried over magnesium sulfate, filtered and the filtrate was concentrated under reduced pressure. The residue was subjected to silica gel chromatography, eluting with ethyl acetate:hexane (3:7). Fractions containing product were combined and concentrated under reduced pressure to give 0.96 g (92%) of the desired product as an oil.

MS (ES, m/z) (M+1)=305.0

S-3-(tert-Butoxy)-2-(N-[(1H-indol-7-yl)methyl]amino) propan-1-ol

To a solution of S-3-(tert-Butoxy)-2-(N-[(1H-indol-7-yl)methyl]amino)propionic acid methyl ester (0.960 g, 3.15 mmol) in tetrahydrofuran (20 ml) at −78° C. was added lithium aluminum hydride (1 M in toluene, 6.31 mL) dropwise. The resulting reaction solution was warmed to 0° C. and stirred for 1 hour then warmed to 20–24° C. and stirred for 1 hour. It was cooled to 0° C., and was then quenched by the sequential addition of methanol followed by water. The suspension was filtered, washed with methanol and the filtrate concentrated under reduced pressure. The residue was dissolved in ethyl acetate, dried over magnesium sulfate, filtered, and the filtrate concentrated under reduced pressure. The residue was subjected to silica gel chromatography, eluting with methanol:ethylacetate (1:9). Fractions containing product were combined and concentrated under reduced pressure to provide 0.51 g (59%) of the desired compound.

MS (ES, m/z) (M−1)=275.1, (M+1)=277.1.

S-3-(tert-Butoxy)-2-(N-[(1H-indol-7-yl)methyl]-N-[tert-butoxycarbonyl]amino)propan-1-ol A solution of S-3-(tert-Butoxy)-2-(N-[(1H-indol-7-yl)methyl]amino)propan-1-ol (0.510 g, 1.85 mmol) and di(tert-butyl) dicarbonate (0.480 g, 2.21 mmol) in tetrahydrofuran (20 ml) was refluxed under nitrogen for 1.5 hours. The reaction mixture was cooled to room temperature and was then concentrated under reduced pressure. The residue was subjected to silica gel chromatography, eluting with ethyl acetate:hexane (1:1). Fractions containing product were combined to provide 0.58 g (84%) of the desired product as an oil.

MS (ES, m/z) (M+1)=377.1, (M−1)=375.1.

S-3-(tert-Butoxy)-2-(N-[(1H-indol-7-yl)methyl]-N-[tert-butoxycarbonyl]amino)-1-(methanesulfonyloxy)propane To a solution S-3-(tert-Butoxy)-2-(N-[(1H-indol-7-yl) methyl]-N-[tert-butoxycarbonyl]amino)propan-1-ol (0.522 g, 1.39 mmol) in dichloromethane (15 ml) at 0° C. under nitrogen was added triethylamine (0.94 mL, 0.680 g, 6.70 mMol) followed by the dropwise addition of a solution of methanesulfonyl chloride (0.159 g, 1.39 mmol) in dichloromethane (5 ml). The resulting solution was stirred at 0° C. for 1 hour. Ice-cooled water was added and the resulting mixture was extracted with dichloromethane. The organic phase was washed with saturated aqueous sodium chloride, dried over magnesium sulfate, filtered and concentrated under reduced pressure. The crude product was used without further purification.

MS (ES, m/z) (M−1)=453.1

Ring Closure

To a solution of S-3-(tert-Butoxy)-2-(N-[(1H-indol-7-yl) methyl]-N-[tert-butoxycarbonyl]amino)-1-(methanesulfonyloxy)propane in dimethylformamide at 0° C. under nitrogen was added sodium hydride (0.083 g, 2.09 mmol, 60% suspension in oil). The mixture was stirred for 1 hour and then it was partitioned between ethyl acetate and saturated aqueous ammonium chloride. The organic phase was separated, washed with saturated aqueous sodium chloride, dried over magnesium sulfate, filtered, and the filtrate concentrated under reduced pressure. The residue was subjected to silica gel chromatography, eluting with ethyl acetate:hexane (1:1). Fractions containing product were combined and concentrated under reduced pressure to provide 0.34 g (68%) of the title compound as a white solid.

MS (ES, m/z) (M+1)=359.1

Preparation V (S-6-(tert-butoxycarbonyl)-5-(tert-Butoxy)methyl-5, 6-dihydro-6H-[1,4]diazepino[6,7,1-hi]indol-1-yl) oxoacetic Acid Methyl Ester To a solution of S-6-(tert-butoxycarbonyl)-5-(tert-butoxy) methyl-5,6-dihydro-6H-[1,4]diazepino[6,7,1-hi]indole (0.330 g, 0.920 mmol) in dichloromethane (10 ml) at 0° C. under nitrogen was added oxalyl chloride (0.46 ml, 0.920 mmol, 1M in dichloromethane) dropwise. The mixture was stirred at 0° C. for 1 hour and then cooled to −78° C. Sodium methoxide (0.40 ml, 1.84 mmol, 4.63 M in methanol) was added and the resulting reaction mixture was warmed to room temperature. The mixture was then washed with saturated aqueous sodium chloride, dried over magnesium sulfate, filtered and then concentrated under reduced pressure. The residue was subjected to silica gel chromatography, eluting with ethyl acetate:hexane (1:1). Fractions containing product were combined and concentrated under reduced pressure to provide 0.35 g (85%) of the title compound as a white solid.

MS (ES, m/z) (M+1) 445.1.

Preparation VI 6-(tert-butoxycarbonyl)-5-methyl-5,6-dihydro-6H-[1,4]diazepino[6,7,1-hi]indole Beginning with indole-7-carboxaldehyde and DL-alanine methylester hydrochloride (0.72 g, 5.16 mmol), the title compound was prepared essentially as described in Preparation IV.

MS (ES, m/z) (M+1)=287.0.

Preparation VII 6-(tert-butoxycarbonyl)-5-methyl-5,6-dihydro-6H-[1,4]diazepino[6,7,1-hi]indol-1-yl)oxoacetic acid Methyl Ester Beginning with 6-(tert-butoxycarbonyl)-5-methyl-5,6-dihydro-6H-[1,4]diazepino[6,7,1-hi]indole, the title compound was prepared essentially as described in Preparation V.

MS (ES, m/z) (M+1)=373.0

Preparation VIII

S-6-(tert-butoxycarbonyl)-5-(4-tert-butoxyphenyl) methyl-5,6-dihydro-6H-[1,4]diazepino[6,7,1-hi] indole Beginning with indole-7-carboxaldehyde and S-(O-tert-butyl)tyrosine methyl ester hydrochloride, the title compound was prepared essentially as described in Preparation IV.

MS (ES, m/z) 435.1 (M+1)

Preparation IX (6-(tert-butoxycarbonyl)-5-(4-tert-butoxyphenyl) methyl-5,6-dihydro-6H-[1,4]diazepino[6,7,1-hi] indol-1-yl)oxoacetic Acid Methyl Ester Beginning with S-6-(tert-butoxycarbonyl)-5-(4-tert-butoxyphenyl)methyl-5,6-dihydro-6H-[1,4]diazepino[6,7,1-hi]indole, the title compound was prepared essentially as described in Preparation V.

MS (ES, m/z) 521.1 (M+1).

Preparation X 4,5,6,7-Tetrahydroazepino[3,2,1-hi]indole 3,4-Dihydro-2H-naphthalen-1-one oxime To a solution of α-tetralone (100.0 g, 0.68 mol) in 300 mL of methanol was added hydroxylamine hydrochloride (71.0 g, 1.03 mol) and the resulting solution was stirred at reflux for 2 hours. The mixture was allowed to cool to 20–24° C. and was concentrated under reduced pressure. The resulting mixture was diluted with 1 L of water and extracted with dichloromethane. The organic layer was washed with saturated aqueous sodium chloride, dried over sodium sulfate, filtered and concentrated under reduced pressure. The residue was crystallized from isopropanol to provide 70.0 g (63%) of the desired compound as an off-white solid.

MS (FIA, m/z) $C_{10}H_{11}NO$ ($M^+$+1)=162.4.

1,3,4,5-Tetrahydrobenzo[b]azepin-2-one

A 1L 3-neck round bottom flask equipped with a mechanical stirrer was charged with neat polyphosphoric acid (100 g) and the acid heated to 125° C. while being stirred under nitrogen. 3,4-Dihydro-2H-naphthalen-1-one oxime (15.0 g, 93 mmol) was added carefully to control exotherm, keeping the temperature below 175° C. Following 10 minutes of heating the mixture was cooled to 20–24° C. and the reaction quenched with ice and water to generate a precipitate. The aqueous suspension was filtered and the precipitate washed with water until the filtrate became neutral. The filtered solid was dried under vacuum to provide 12.8 g (85%) of the desired compound as an off-white solid.

MS (ES, m/z) $C_{10}H_{11}NO$ ($M^+$+1)=161.9

2,3,4,5-Tetrahydro-1H-benzo[b]azepine

To a solution of 1,3,4,5-tetrahydrobenzo[b]azepin-2-one (12.9 g, 80.0 mmol) in 720 mL of tetrahydrofuran was added 80 mL of lithium aluminum hydride (1 M solution in tetrahydrofuran). The reaction mixture was stirred at reflux for 3 hours and cooled to 0° C. The reaction was quenched by the sequential addition of 3 mL of water, 3 mL of 15% sodium hydroxide, and 9 mL of water. The mixture was filtered through Celite and the filter cake rinsed with ethyl acetate. The filtrate was concentrated under reduced pressure to provide 10.0 g (85%) of the desired compound as an orange solid.

MS (FIA, m/z) $C_{10}H_{13}N$ ($M^+$+1)=148.2.

2-Oxo-3-(2,3,4,5-tetrahydro-benzo[b]azepin-1-yl)-propionic Acid Ethyl Ester

To a 0° C. suspension of 60% sodium hydride (3.0 g, 0.12 mol) in 300 mL of dimethylformamide was added 2,3,4,5-tetrahydro-1H-benzo[b]azepine in small portions. Upon complete addition of the amine, the ice bath was removed and the reaction stirred at 20–24° C. for 40 minutes. Ethyl bromopyruvate (22.6 mL, 0.16 mol) was then added and the resulting mixture stirred at 20–24° C. for 6 hours. An additional 5 mL of ethyl bromopyruvate was added and the mixture stirred for 1 hour. The reaction was quenched by the addition of 50 mL of water followed by dilution with 1.5 L of dichloromethane. The layers were separated and the organic layer was washed with water (2×500 mL) and saturated aqueous sodium chloride (500 mL). The organic phase was dried over sodium sulfate, filtered and concentrated under reduced pressure at 60° C. The residual brown oil was dissolved in ethyl acetate (500 mL) and was washed 3 times with water (100 mL) and once with saturated aqueous sodium chloride, dried over sodium sulfate, filtered and concentrated under reduced pressure. The residue was subjected to silica gel chromatography, eluting with 5–10% EtOAc/hexanes to provide 7.0 g (40%) of the desired compound as an off white solid.

MS (FID, m/z) $C_{15}H_{19}NO_3$ ($M^+$)=261.13.

4,5,6,7-Tetrahydroazepino[3,2,1-hi]indole-1-carboxylic acid ethyl ester

Magnesium chloride (2.55 g, 26.8 mmol) was added to 30 mL of 2-methoxyethanol and the mixture heated to reflux. A solution of 2-oxo-3-(2,3,4,5-tetrahydro-benzo[b]azepin-1-yl)-propionic acid ethyl ester (7.0 g, 26.8 mmol) in 2-methoxyethanol (20 mL) was slowly added to the $MgCl_2$ mixture over 1 hour. The resulting mixture was stirred for 6 hours at reflux, cooled to 20–24° C. and concentrated under reduced pressure. The residue was diluted with 400 mL of dichloromethane and washed with 2 N hydrochloric acid (100 mL), followed by saturated aqueous sodium bicarbonate (100 mL) and finally saturated aqueous sodium chloride (100 mL). The organic layer was dried over sodium sulfate, filtered and concentrated under reduced pressure. This residue was subjected to silica gel chromatography, eluting with 20% EtOAc/Hexane. Fractions containing product were combined and concentrated under reduced pressure to provide 3.1 g (48%) of the desired compound as a yellow oil.

MS (FIA, m/z) $C_{15}H_{17}NO_2$ ($M^+$+1)=244.4.

4,5,6,7-Tetrahydroazepino[3,2,1-hi]indole-1-carboxylic acid

To a solution of 4,5,6,7-tetrahydroazepino[3,2,1-hi]indole-1-carboxylic acid ethyl ester (2.0 g, 8.22 mmol) in ethanol (13 mL) and water (9 mL) was added powdered sodium hydroxide (0.71 g, 17.8 mmol) and the resulting mixture stirred at reflux for 4 hours. The reaction mixture was cooled to room temperature, diluted with water (100 mL) and washed with dichloromethane (2×50 mL). The layers were separated and the aqueous layer was filtered through Celite and the filtrate was acidified with concentrated hydrochloric acid. The suspension was filtered and the recovered solid washed with water and dried under reduced pressure to provide 1.59 g (90%) of the desired compound as a white solid.

MS (FIA, m/z) $C_{13}HL_{13}NO_2$ ($M^+$+1)=216.3

Decarboxylation

To a solution of 4,5,6,7-tetrahydroazepino[3,2,1-hi]indole-1-carboxylic acid (1.4 g, 6.5 mmol) in 7.5 mL of quinoline was added copper chromite (0.55 g, 1.77 mmol). The resulting mixture was stirred at 185° C. for 4 hours and then cooled to room temperature, diluted with dichloromethane and filtered through Celite. The filtrate was washed with 2 N hydrochloric acid (2×25 mL) followed by 2 N sodium hydroxide (25 mL). The organic layer was concentrated under reduced pressure and the residue subjected to silica gel chromatography, eluting with 5% EtOAc/Hexane to provide 0.85 g (76%) of the title compound as an orange solid.

MS (EI, m/z) $C_{12}H_{13}N$ ($M^+$)=171.4

Preparation XI (4,5,6,7-tetrahydroazepino[3,2,1-hi]indol-1-yl) oxoacetic Acid Methyl Ester Beginning with 4,5,6,7-tetrahydroazepino[3,2,1-hi] indole, the title compound was prepared essentially as described in Preparation V.

MS (FIA, m/z) $C_{15}H_{15}NO_3$ ($M^+$+1)=258.2

Preparation XII

S-6-(tert-butoxycarbonyl)-5,6-dihydro-6H-[1,4] diazepino[6,7,1-hi]indole

Beginning with indole-7-carboxaldehyde and ethanolamine, the title compound was prepared essentially as described in Preparation IV.

MS (IS, m/z) $C_{16}H_{20}N_2O_2$ ($M^+$+1)=273

Preparation XIII (6-(tert-butoxycarbonyl)-5,6-dihydro-6H-[1,4] diazepino[6,7,1-hi]indol-1-yl)oxoacetic Acid Methyl Ester Beginning with S-6-(tert-butoxycarbonyl)-5,6-dihydro-6H-[1,4]diazepino[6,7,1-hi]indole, the title compound was prepared essentially as described in Preparation V.

MS (IS, m/z) $C_{16}H_{20}N_2O_2$ ($M^+$+1)=273

Preparation XIV 8,9-Dehydropyrrolo[3,2,1-kl]benzo[b] azacyclooctane

7-Vinyl-1H-indole

To 7-bromo-1H-indole (6.0 g, 30.6 mmol) in 150 mL of dimethylformamide was added tributyl(vinyl)tin (9.8 mL, 33.7 mmol), triphenylphosphine (0.4 g, 1.53 mmol), diphenyl-palladium (II) dichloride (1.07 g, 1.53 mmol) and lithium chloride (4.0 g, 94.4 mmol), and the resulting mixture was heated at 100° C. overnight. The reaction mixture was cooled to 20–24° C. and poured into 150 mL of water and 150 mL of ethyl acetate. The aqueous layer was washed with additional ethyl acetate (3×100 mL) and the combined organic layers were washed with saturated aqueous sodium chloride, dried over magnesium sulfate, filtered and concentrated under reduced pressure. The residue was subjected to silica gel chromatography, eluting with 5–10% ethyl acetate in hexanes. Fractions containing product were combined and concentrated under reduced pressure to provide 3.5 g (80%) of the desired compound as a clear oil.

MS (FIA, m/z) $C_{10}H_9N$ ($M^+$+1)=144.2

1-(Pent-4-en-1-yl)-7-vinyl-1H-indole

To a 0° C. solution of 7-vinylindole (5.0 g, 34.9 mmol) in 140 mL of dimethylformamide was added sodium hydride (60% dispersion in mineral oil) (3.5 g, 87.3 mmol). The ice bath was removed and the solution was warmed to 20–24° C. and stirred an additional 30 minutes. 5-Bromo-1-pentene (20 mL, 175 mmol) was added dropwise and stirring continued for 3 hrs. The solution was poured into 150 mL of water and 150 mL of ethyl acetate. The aqueous layer was washed with additional ethyl acetate (3×100 mL) and the combined organic layers were washed with saturated aqueous sodium chloride, dried over sodium sulfate, filtered and concentrated under reduced pressure. The residue was subjected to silica gel chromatography, eluting with 5–10% ethyl acetate in hexanes. Fractions containing product were combined and concentrated under reduced pressure to provide 5.39 g (73%) of the desired compound as a clear oil.

MS (ES, m/z) $C_{15}H_{17}N$ ($M^+$+1)=212

Ring Closure

To a solution of 1-(Pent-4-en-1-yl)-7-vinyl-1H-indole (4.4 g, 20.8 mmol) in anhydrous dichloromethane (3.0 L) was added 1.4 g of bis(tricyclohexylphosphine)benzylidine ruthenium (IV) dichloride (Grubb's catalyst). The resulting solution was stirred at 20–24° C. for 24 hours. An additional 1.0 g of Grubb's catalyst was added to the reaction and the solution was stirred for 4 hours. The reaction was then concentrated under reduced pressure and the residue subjected to silica gel chromatography, eluting with 2–5% ethyl acetate in hexanes. Fractions containing product were combined and concentrated under reduced pressure to provide 3.0 g (79%) of the title compound as a brown oil.

$^1$H NMR (400 MHz, DMSO-$d_6$) δ 7.41–7.39 (dd, 1H, J=7.81, 0.98 Hz), 7.22–7.21 (d, 1H, J=3.42 Hz), 6.94–6.9 (d, 1H, J=7.57 Hz), 6.81–6.8 (d, 1H, J=2.93 Hz), 6.79 (s, 1H), 6.36–6.35 (d, 1H, J=2.93 Hz), 5.69–5.62 (m, 1H), 4.45–4.3 (bs, 2H), 2.19–2.14 (m, 2H), 1.75–1.55 (bs, 2H).

Preparation XV (8,9-Dehydropyrrolo[3,2,1-kl]benzo[b]azacyclooct-1-yl)oxoacetic Acid Methyl Ester Beginning with 8,9-Dehydropyrrolo[3,2,1-kl]benzo[b]azacyclooctane, the title compound was prepared essentially as described in Preparation V.

$^1$H NMR (400 MHz, DMSO-$d_6$) δ 8.44 (s, 1H), 8.13–8.11 (dd, 1H, J=7.81, 0.98 Hz), 7.26–7.22 (t, 1H, J=7.81 Hz), 7.06–7.04 (d, 1H, J=7.33 Hz), 6.86–6.84 (d, 1H, J=11.2 Hz), 5.84–5.74 (m, 1H), 4.6–4.4 (bs, 4H), 3.87 (s, 3H), 2.25–2.0 (bs, 2H)

Preparation XVI

Pyrrolo[3,2,1-kl]benzo[b]azacyclooctane

A solution of 8,9-Dehydropyrrolo[3,2,1-kl]benzo[b]azacyclooctane (0.66 g, 3.6 mmol) in ethanol (130 mL) was hydrogenated in the presence of platinum oxide (100 mg) under balloon pressure for three hours. The mixture was filtered through Celite using dichloromethane and the filtrate was concentrated under reduced pressure to provide 0.65 g (97%) of the title compound as a light yellow oil.

MS (ES, m/z) $C_{13}H_{15}N$ ($M^+$+1)=186

Preparation XVII (Pyrrolo[3,2,1-kl]benzo[b]azacyclooct-1-yl)oxoacetic Acid Methyl Ester Beginning with pyrrolo[3,2,1-kl]benzo[b]azacyclooctane, the title compound was prepared essentially as described in Preparation V.

$^1$H NMR (400 MHz, DMSO-$d_6$) δ 8.38 (s, 1H), 8.05–8.03 (d, 1H, J=7.81 Hz), 7.18–7.15 (t, 1H, J=7.57 Hz), 7.03–7.01 (d, 1H, J=6.84 Hz), 4.65–4.62 (t, 2H, J=6.1 Hz), 3.86 (s, 3H), 3.3–3.15 (bs, 2H), 1.94–1.91 (t, 2H, J=6.1 Hz), 1.82–1.79 (t, 2H, J=5.86 Hz), 1.3–1.15 (bs, 2H).

Preparation XVIII 8-(tert-butoxycarbonyl)-[1,5]diazaperhydroonino[8,9,1-hi]indole N-Allyl N-[(1H-indol-7-yl)methyl]amine To a solution of indole-7-carboxaldehyde 1 (4.00 g, 27.6 mmol) in 1,2-dichloroethane (120 mL) at 20–24° C. was added allylamine (2.50 mL, 33.1 mmol), acetic acid (3.4 mL), and sodium triacetoxyborohydride (5.85 g, 27.6 mmol). The resulting mixture was stirred at 20–24° C. for 5 hours. An additional 1.5 g (7.1 mmol) of sodium triacetoxyborohydride was added and the resulting mixture was stirred overnight. The mixture was diluted with dichloromethane (300 mL), washed carefully with aqueous sodium bicarbonate (100 mL), and the layers were separated. The organic layer was washed with water (100 mL), saturated aqueous sodium chloride (100 mL), dried over sodium sulfate, filtered and concentrated under reduced pressure. The residue was subjected to silica gel chromatography, eluting with 10–30% ethyl acetate in hexanes. Fractions containing product were combined and concentrated under reduced pressure to provide 4.21 g (82%) of the desired compound as a light yellow oil.

N-[tert-butoxycarbonyl] N-allyl N-[(1H-indol-7-yl)methyl]amine

To a 0° C. solution of N-allyl N-[(1H-indol-7-yl)methyl]amine (4.21 g, 22.6 mmol) in anhydrous tetrahydrofuran (100 mL) was added a 0° C. solution of di-tert-butyl dicarbonate (4.93 g, 22.6 mmol) in anhydrous tetrahydrofuran (20 mL). The resulting solution was stirred for two hours and allowed to warm to 20–24° C. The reaction mixture was diluted with ethyl acetate (500 mL). The phases were separated and the organic layer was washed with water (2×150 mL), saturated aqueous sodium chloride (100 mL), dried over sodium sulfate, filtered and concentrated under reduced pressure to provide 6.5 g (100%) of the desired compound as a light yellow oil.

$^1$H NMR (400 MHz, DMSO-$d_6$) δ 11.08–10.65 (m, 1H), 7.5–7.4 (m, 1H), 7.38–7.3 (bs, 1H), 6.97–6.94 (t, 1H, J=7.32 Hz), 6.92–6.8 (bs, 1H), 6.45–6.4 (m, 1H), 5.8–5.65 (m, 1H), 5.1–5.0 (m, 2H), 4.59 (s, 2H), 3.85–3.68 (m, 2H), 1.5–1.2 (m, 9H)

MS (ES, m/z) $C_{17}H_{22}N_2O_2$ ($M^+$+1)=287.2

N-[tert-butoxycarbonyl] N-allyl N-[(1-allyl-1H-indol-7-yl)methyl]amine

To a 0° C. solution of N-[tert-butoxycarbonyl] N-allyl N-[(1H-indol-7-yl)methyl]amine (6.6 g, 23 mmol) in anhydrous dimethylformamide was added slowly sodium hydride (60% dispersion in mineral oil, 1.75 g, 43.7 mmol). The mixture was warmed to 20–24° C. and stirred for 30 minutes, followed by the addition of allyl bromide (4.0 mL, 46 mmol). The reaction was then stirred at 20–24° C. overnight. The reaction mixture was diluted with ethyl acetate (450 mL), washed with water (2×100 mL), saturated aqueous sodium chloride (150 mL), and the organic layer dried over sodium sulfate, filtered and concentrated under reduced pressure. The residue was subjected to silica gel chromatography, eluting with 10% ethyl acetate in hexanes. Fractions containing product were combined and concentrated under reduced pressure to provide 6.8 g (91%) of the desired compound as a light brown oil.

MS (ES, m/z) $C_{20}H_{26}N_2O_2$ (M$^+$+Na)=349.2

Ring Closure

Beginning with N-[tert-butoxycarbonyl] N-allyl N-[(1-allyl-1H-indol-7-yl)methyl]amine, the ring closure was performed essentially as described in Preparation XIV.

MS (ES, m/z) $C_{18}H_{22}N_2O_2$ (M$^+$+Na)=321.2

Reduction

Beginning with the alkene prepared in the previous paragraph, the double bond was reduced to provide the title compound essentially as described in Preparation XVI.

MS (ES, m/z) $C_{18}H_{25}N_2O_2$ (M$^+$)=301.2

Preparation XIX (8-(tert-butoxycarbonyl)-[1,5]diazaperhydroonino[8,9,1-hi]indol-1-yl)oxoacetic Acid Methyl Ester Beginning with 8-(tert-butoxycarbonyl)-[1,5] diazaperhydroonino[8,9,1-hi]indole, the title compound was prepared essentially as described in Preparation V.

MS (IS, m/z) $C_{21}H_{26}N_2O_5$ (M$^+$+1)=387.

Preparation XX

N-[methyl] 11-(aminomethyl)indolo[2,3-a]pyrrolo[3,4-c]carbazole-5,7-dione Hydrochloride 3-(indol-3-yl)-4-(N-[tert-butoxycarbonyl] N-[methyl] 7-aminomethylindol-3-yl)pyrrole-2,5-dione Beginning with (N-[tert-butoxycarbonyl] N-[methyl] 7-(aminomethyl)indol-3-yl)oxoacetic acid methyl ester and (indol-3-yl)acetamide, the title compound was prepared essentially as described in Example 1, infra.

MS (m/z): 471.01 (M$^+$+1)

N-[tert-butoxycarbonyl] N-[methyl] 11-aminomethylindolo[2,3-a]pyrrolo[3,4-c]carbazole-5,7-dione Beginning with 3-(indol-3-yl)-4-(N-[tert-butoxycarbonyl] N-[methyl] 7-aminomethylindol-3-yl)pyrrole-2,5-dione, the desired compound was prepared essentially as described in Example 58, infra.

MS (m/z): 466.9 (M$^+$−1)

Deprotection

Beginning with N-[tert-butoxycarbonyl] N-[methyl] 11-(aminomethyl)-indolo[2,3-a]pyrrolo[3,4-c]carbazole-5,7-dione, the title compound was prepared essentially as described in Example 136, infra.

MS (m/z): 404.9 (M$^+$+1)

Preparation XXI

N-[methyl] 11-(aminomethyl)-2-fluoroindolo[2,3-a] pyrrolo[3,4-c]carbazole-5,7-dione hydrochloride Beginning with (N-[tert-butoxycarbonyl] N-[methyl] 7-aminomethylindol-3-yl)oxoacetic acid methyl ester and (6-fluoroindol-3-yl)acetamide, the title compound was prepared essentially as described in Preparation XX.

MS (m/z): 421.1 (M$^+$−1)

Preparation XXII

S-6-(tert-butoxycarbonyl)-5-(N-[tert-butoxycarbonyl] N-[methyl] 4-aminobutyl-1-yl)-5,6-dihydro-6H-[1,4]diazepino[6,7,1-hi]indole Beginning with indole-7-carboxaldehyde and lysine methyl ester, the title compound was prepared essentially as described in Preparation IV.

MS (m/z): 458.0 (M$^+$+1)

Preparation XXIII (S-6-(tert-butoxycarbonyl)-5-(N-[tert-butoxycarbonyl] N-[methyl] 4-aminobut-1-yl)-5,6-dihydro-6H-[1,4]diazepino[6,7,1-hi]indol-1-yl) oxoacetic Acid Methyl Ester Beginning with S-6-(tert-butoxycarbonyl)-5-(N-[tert-butoxycarbonyl] N-[methyl] 4-aminobut-1-yl)-5,6-dihydro-6H-[1,4]diazepino[6,7,1-hi]indole, the title compound was prepared essentially as described in Preparation V.

MS (m/z): 544.0 (M$^+$+1)

Preparation XXIV

S-4-amino-5-hydroxy-pentanoic Acid Tert-butyl Ester

S-4-benzyloxycarbonylamino-5-hydroxy-pentanoic acid tert-butyl ester

To a solution of N-[benzyloxycarbonyl]-L-glutamic acid γ-tert-butyl ester (3.37 g, 10.0 mmol) in 1,2-dimethoxy ethane (10 ml) at −15° C. under nitrogen was added N-methyl-morpholine (1.11 ml, 10 mmol) and isobutyl chloroformate (1.36 ml, 10 mmol). The resulting suspension was immediately filtered and washed with 1,2-dimethoxyethane. To the filtrate was added a solution of sodium borohydride (0.57 g, 15.0 mmol) in water (5 ml) and then water (250 ml) was added. The reaction mixture was extracted with ethyl acetate and the organic layer was washed with saturated aqueous sodium chloride, dried over magnesium sulfate, filtered and concentrated to give 3.08 g (95%) of the desired compound as an oil.

MS (ES, m/z) (M+1)=324.0, (M−1)=321.9.

N-Deprotection

A solution of S-4-(Benzyloxycarbonyl)amino-5-hydroxy-pentanoic acid tert-butyl ester (5.13 g, 15.9 mmol) in methanol (50 ml) was added to a suspension of Pd/C (1.69 g, 10%) in methanol (50 ml) and the mixture was stirred under a hydrogen atmosphere for 6 h. The catalyst was carefully filtered off and the filtrate was concentrated under reduced pressure to provide 2.95 g (98%) of the title compound as a white solid.

MS (ES, m/z) (M+1)=189.9

Preparation XXV

S-6-(tert-butoxycarbonyl)-5-(2-(tert-butoxycarbonyl) eth-1-yl)-5,6-dihydro-6H-[1,4]diazepino[6,7,1-hi] indole Beginning with indole-7-carboxaldehyde and S-4-amino-5-hydroxypentanoic acid tert-butyl ester, the title compound was prepared essentially as described in Preparation IV.

MS (ES, m/z), (M+1) 401.0

Preparation XXVI (S-6-(tert-butoxycarbonyl)-5-(2-(tert-butoxycarbonyl)eth-1-yl)-5,6-dihydro-6H-[1,4] diazepino [6, 7,1-hi]indol-1-yl)oxoacetic Acid Methyl Ester Beginning with S-6-(tert-butoxycarbonyl)-5-(2-(tert-butoxycarbonyl)eth-1-yl)-5,6-dihydro-6H-[1,4] diazepino-[6,7,1-hi]indole, the title compound was prepared essentially as described in Preparation V.

MS (ES, m/z) (M+1)=487.0

Preparation XXVII

N-[benzyloxycarbonyl] N-[(indol-7-yl)methyl]-5-hydroxypentanoic Acid Tert-butyl Ester To a solution of 5-hydroxy-4-[(1H-indol-7-ylmethyl)-amino]pentanoic acid tert-butyl ester (3.60 g, 11.3 mmol) in tetrahydrofuran (100 ml) was added triethylamine (4.72 ml, 33.9 mmol) and N-[benzyloxycarbonyl]succinimide (2.54 g, 10.2 mmol) under nitrogen. Following 2 hours of stirring at room temperature the reaction mixture was concentrated under reduced pressure. The residue was subjected to silica gel chromatography, eluting with ethyl acetate:hexanes (1:1). Fractions containing product were combined and concentrated under reduced pressure to provide 3.96 g (86%) of the title compound as an oil.

MS (ES, m/z) 451.0 (M−1)

Preparation XXVIII

S-6-(benzyloxycarbonyl)-5-(2-(tert-butoxycarbonyl)eth-1-yl)-5,6-dihydro-6H-[1,4]diazepino[6,7,1-hi]indol Beginning with N-[benzyloxycarbonyl] N-[(indol-7-yl)methyl]-5-hydroxypentanoic acid tert-butyl ester, the title compound was prepared essentially as described in Preparation IV.

$^1$H NMR (400 MHz, CDCl$_3$) δ 7.43 (m, 1H), 7.23 (m, 3H), 7.05–6.90 (m, 5H), 6.40 (m, 1H), 5.10–4.60 (m, 4H), 4.40–4.10 (m, 3H), 2.20 (m, 2H), 1.90 (m, 2H), 1.46 (s, 9H).

Preparation XXIX

(S-6-(benzyloxycarbonyl)-5-(2-(tert-butoxycarbonyl)eth-1-yl)-5,6-dihydro-6H-[1,4]diazepino[6,7,1-hi]indol-1-yl)oxoacetic Acid Methyl Ester Beginning with S-6-(benzyloxycarbonyl)-5-(0.2-(tert-butoxycarbonyl)eth-1-yl)-5,6-dihydro-6H-[1,4]diazepino-[6,7,1-hilindole, the title compound was prepared essentially as described in Preparation V.

MS (ES, m/z) 520.9 (M+1).

Preparation XXX

3,4-Dihydro-5-thia-2a-aza-acenaphthalene 3,4-Dihydro-2H-benzo[1,4]thiazine.

A solution of (2H)1,4-benzothiazin-3(4H)-one (20.0 g, 121.1 mmol) in anhydrous tetrahydrofuran (100 mL) was added to a stirred suspension of lithium aluminum hydride in anhydrous tetrahydrofuran (80 mL) under nitrogen at 0° C. The mixture was heated at reflux for 2 hrs and then poured into a mixture of ethyl acetate (300 mL) and ice (500 g). The organic layer was separated and the aqueous layer extracted with ethyl acetate. The combined organic layer was dried and concentrated under reduced pressure to provide 17.68 g (96.5%) of the desired compound which was used without further purification.

IS-MS, m/e 151.9 (m+1)

Ring Formation/Decarboxylation

Beginning with 3,4-dihydro-2H-benzo[1,4]thiazine, the title compound was prepared essentially as described in Preparation I.

IS-MS, m/e 175.9 (m+1).

Preparation XXXI

(3,4-Dihydro-5-thia-2a-aza-acenaphthylen-1-yl)oxoacetic Acid Methyl Ester

Beginning with 3,4-dihydro-5-thia-2a-aza-acenaphthylene, the title compound was prepared essentially as described in Preparation II.

IS-MS, m/e 261.9 (m+1)

Preparation XXXII

1,2,3,4-tetrahydro-2,2-dimethylquinoline

N-[3,3-dimethylpropyn-3-yl]aniline

A mixture of aniline (21.8 g, 234 mmol) and triethylamine (26.6 g, 263.3 mmol) in 100 mL ether, 25 mL water, 0.2 g copper (I) chloride and 0.2 g copper bronze was prepared under nitrogen in a three-neck flask equipped with mechanical stirrer. 3-Chloro-3-methyl-1-butyne (20 g, 195 mmol) in ether (25 mL) was slowly added with stirring while maintaining an inside temperature at 10–20° C. After stirring for an additional 2 hours at room temperature, the mixture was poured into a mixture of 200 mL ether and 100 mL water. The ethereal layer was washed with cold water, dried for 15 minutes over anhydrous potassium carbonate and filtered, redried with potassium hydroxide pellets overnight. The solution was filtered and concentrated under reduced pressure.

1,2-Dihydro-2,2-dimethylquinoline

A mixture of N-[3,3-dimethylpropyn-3-yl]aniline and cuprous chloride (3.9 g) in toluene (140 mL) was refluxed under nitrogen for 4½ hrs. The reaction mixture was filtered and the filtrate washed with saturated aqueous sodium chloride, dried over sodium sulfate, and concentrated under reduced pressure. The residue was subjected to silica gel chromatography, eluting with dichloromethane:hexane (1:1) to provide the desired compound.

Reduction 1,2-Dihydro-2,2-dimethylquinoline (13.69 g, 86.0 mmol) was hydrogenated over 5% platinum on carbon (12.5 g) in ethyl acetate (500 mL) at room temperature and 60 PSI to give 12.8 g (92.4% yield) of the title compound.

IS-MS, m/e 162.0 (m+1)

Preparation XXXIII

6-(4-fluorophenyl)indole

A degassed solution of 6-bromoindole (1.0 g, 5.1 mmol), 4-fluorobenzeneboronic acid (0.928 g, 6.63 mmol), potassium phosphate (2.7 g, 153 mmol) and palladium (0)tetrakis-(triphenylphosphine) (0.294 g, 0.255 mmol) in dimethylacetamide (50 mL) was heated at 120° C. for 14 hours. After cooling to room temperature, the mixture was diluted with water. The suspension was filtered, the solid washed with water and then dissolved in ethyl acetate (100 mL), dried over sodium sulfate, and concentrated under reduced pressure. The residue was subjected to silica gel chromatography, eluting with ethyl acetate:hexane (1:4) to give 0.411 g (38.2%) of the title compound as a white crystalline solid.

IS-MS, m/e 209.9 (m−1)

Preparation XXXIV

(6-(4-fluorophenyl)-1H-indol-3-yl]Oxoacetic Acid Methyl Ester

Beginning with 6-(4-fluorophenyl)indole, the title compound was prepared essentially as described in Preparation II.

IS-MS, m/e 295.9 (m−1).

Preparation XXXV

(6-(pyridin-3-yl)indol-3-yl)oxoacetic Acid Methyl Ester

Beginning with 6-bromoindole and pyridine-3-boronic acid, the title compound was prepared essentially as described in Preparation XXXIII and XXXIV.

IS-MS, m/e 278.9 (m−1).

Preparation XXXVI

4,5-dihydro-pyrrolo[3,2,1-hi]indole and pyrrolo[3,2,1-hi]indole

Pyrrolo[3,2,1-hi]indole-2-carboxylic acid, 4,5-dihydro-, ethyl ester

To a solution of N-amino-indoline (Wijngaarden, Ineke van, et al., *J. Med. Chem.*, 36, 3693 (1993)) (1.0 g, 7.45 mmol) in 15 mL absolute ethanol was added ethyl pyruvate (0.88 ml, 7.88 mmol) and the mixture was heated to reflux under nitrogen for one hour. After cooling, the solvents were removed under reduced pressure to give 1.61 g (93%) of the crude product as a tan solid. The crude imine (0.5 g, 2.15 mmol) was dissolved in 5 mL of glacial acetic acid and treated with boron trifluoride etherate (0.28 mL, 2.21 mmol). The reaction mixture was heated at reflux for 45 minutes, cooled and poured into 25 mL ice-water. Extraction with ethyl acetate (2×25 mL) was followed by washing of the combined organic layers with saturated aqueous sodium bicarbonate (1×20 mL), water (1×20 mL) and saturated aqueous sodium chloride (1×10 mL). After drying over sodium sulfate, the ethyl acetate extracts were filtered and concentrated under reduced pressure. The residue was dissolved in dichloromethane and filtered through a plug of flash silica gel, washing with 15 mL of 2% methanol in dichloromethane. Concentration under reduced pressure gave the product in 19% yield as a yellow solid.

MS (EI, M/z) $C_{13}H_{13}N_1O_2$ ($M^+$)=215.

4,5-dihydro-pyrrolo[3,2,1-hi]indole-2-carboxylic acid

To a solution of the ester (2.2 g, 10.2 mmol) in 50 mL of ethanol was added 50 mL of 1N aqueous sodium hydroxide and the mixture was heated at reflux for 40 minutes. After cooling in an ice-bath, the reaction was neutralized with 50 mL of 1N hydrochloric acid and extracted with dichloromethane (3×50 mL). The combined organic extracts were dried over sodium sulfate, filtered and concentrated under reduced pressure to give the product (1.78 g, 94%) as a yellow solid. MS (EI, m/z) $C_{11}H_9N_1O_2$ ($M^+$, $M^+$—$CO_2H$)= 187, 142.

Decarboxylation

A solution of the carboxylic acid (1.5 g, 8.0 mmol) and copper (II) oxide (2.5 g, 31.4 mmol) in 40 mL of quinoline was heated to 200° C. for 90 minutes. After cooling to room temperature the reaction mixture was diluted with ethyl acetate (300 mL), filtered through Celite and washed with 2.0 M hydrochloric acid (3×50 mL), water (1×50 mL) and saturated aqueous sodium chloride (1×50 mL). The organic layer was filtered through a pad of flash silica gel and evaporated to 1.5 g of a dark oil. Chromatography (1–3% ethyl acetate in hexanes) gave 4,5-dihydro-pyrrolo[3,2,1-hi] indole (0.364 g) in 33% yield as a tan solid.

MS (IS, m/z) $C_{10}H_9N_1$ ($M^+$+1)=144.

Also isolated was 0.245 g of pyrrolo[3,2,1hi]indole as a white solid.

MS (EI, m/z) $C_{10}H_7N_1$ ($M^+$, $M^+$+1)=141, 142.

Preparation XXXVII

(4,5-Dihydropyrrolo[3,2,1-hi] indol-1-yl)oxoacetic Acid Methyl Ester.

Beginning with 4,5-dihydropyrrolo[3,2,1-hi]indole, the title compound was prepared essentially as described in Preparation II.

MS (IS, M/z) $C_{13}H_{11}N_1O_3$ ($M^+$+1, $M^+$+2)=230, 231.

Preparation XXXVIII

(5,6-Dihydro-4H-pyrrolo[3,2,1-ij]quinolin-1-yl) acetamide (5,6-Dihydro-4H-pyrrolo[3,2,1-ij]quinolin-1-yl)oxoacetamide To a solution of (5,6-Dihydro-4H-pyrrolo[3,2,1-ij] quinolin-1-yl)oxoacetic acid methyl ester (0.50 g, 2.06 mmol) in 10 mL of tetrahydrofuran at 0° C. was added concentrated ammonium hydroxide (2 mL). The bath was removed and the mixture stirred 3 hours. After diluting with 20 mL of water, the suspension was filtered, washed with 10 mL of water followed by 10 mL of diethyl ether, and dried under reduced pressure to provide 0.403 g (86%) of the desired compound as a light yellow solid.

MS (IS, m/z) $C_{13}H_{12}N_2O_2$ ($M^+$+1)=229

Reduction

To a solution of (5,6-dihydro-4H-pyrrolo[3,2,1-ij] quinolin-1-yl)acetamide (0.30 g, 1.31 mmol) in dioxane (6 mL) and water (2 mL) was added 10% palladium on carbon (0.060 g), followed by the careful addition of $NaH_2PO_2H_2O$ (0.60 g, 5.67 mmol) and the reaction was brought to reflux under nitrogen. After 3 hours an additional 0.60 g of $NaH_2PO_2.H_2O$ was added and the reaction was heated at reflux for another 6 hrs. The mixture was cooled, filtered through a pad of Celite, and washed well with ethyl acetate (100 mL). The solution was concentrated under reduced pressure and the residue triturated with water (20 mL). The resulting suspension was filtered and the recovered solid dried under reduced pressure to provide 0.27 g (96%) of the title compound as a white solid.

MS (IS, M/z) $C_{13}H_{14}N_2O_3$ ($M^+$+1)=215

Preparation XXXIX

2-(6,6-Dimethyl-5,6-dihydro-4H-pyrrolo[3,2,1-ij]quinolin-1-yl)acetamide (6,6-Dimethyl-5,6-dihydro-4H-pyrrolo[3,2,1-ij]quinolin-1-yl)acetic acid To a solution of glacial acetic acid (80 mL) and concentrated hydrochloric acid (9 mL) was added 3,4-dihydro-4,4-dimethyl-1-(2H)-quinolinamine (9.5 g, 53.9 mmol) and 2-ketoglutaric acid (9.7 g, 65.1 mmol) and the suspension heated at reflux for 3 hours. After cooling the solvents were removed under reduced pressure and the residue dissolved in 500 mL of ethyl acetate. The ethyl acetate solution was washed with water (3×150 mL) and saturated aqueous sodium chloride (1×50 mL), dried over sodium sulfate, filtered and concentrated under reduced pressure. The residue was subjected to silica gel chromatography, eluting with 1–4% methanol in dichloromethane. Fractions containing product were combined and concentrated under reduced pressure to provide 4.45 g (34%) of the desired compound as a tan foam. An impure fraction was extracted with 1N sodium hydroxice (2×50 mL) and the combined aqueous layers washed with diethyl ether (20 mL) and made acidic with concentrated hydrochloric acid (8 mL). This aqueous mixture was extracted with dichloromethane (2×100 mL), followed by drying ($Na_2SO_4$) to provide an additional 2.55 g (19%) of desired product MS (IS, m/z) $C_{15}H_{17}N_1O_2$ ($M^+$+1)=244

Amide Formation

To a solution of (6,6-dimethyl-5,6-dihydro-4H-pyrrolo[3,2,1-ij]quinolin-1-yl)acetic acid (5.7 g, 23.4 mmol) in 100 mL of dry tetrahydrofuran at 0° C. was added N-methylmorpholine (2–0.9 mL, 26.1 mmol) and 2-chloro-4,6-dimethoxy-1,3,5-triazine (CDMT, 4.5 g, 24.9 mmol) and the reaction mixture allowed to come to room temperature overnight. After cooling to 0° C., another 4.5 g of CDMT was added and stirring was continued at room temperature for another 2 hours. The solution of activated ester was cooled to −30° C. and 25 mL of ammonia was condensed directly into the flask. After stirring at −30° C. for 1 hour, the reaction was allowed to come to room temperature. The resulting suspension was filtered, and the recovered solid rinsed with 250 mL of tetrahydrofuran. The filtrate was concentrated under reduced pressure and the residue was partitioned between ethyl acetate (500 mL) and water (100 mL). The organic phase was washed with 0.1 N sodium hydroxide (1×100 mL), water (1×100 mL) and saturated aqueous sodium chloride (1×50 mL), dried over sodium sulfate and filtered through a 1-inch pad of flash silica gel. The filtrate was concentrated under reduced pressure and the resulting solid was slurried with 50 mL of diethyl ether, filtered and dried under reduced pressure to provide 3.3 g (58%) of the title compound as an off-white solid.

MS (IS, m/z) $C_{15}H_{18}N_2O_1$ (M$^+$+1)=243.

Preparation XL 2-(8-Fluoro-6,6-dimethyl-5,6-dihydro-4H-pyrrolo[3,2,1-ij]quinolin-1-yl)acetamide Beginning with 2-(8-fluoro-6,6-dimethyl-5,6-dihydro-4H-pyrrolo[3,2,1-ij]quinolin-1-yl)oxoacetic acid methyl ester, the title compound was prepared essentially as described in Preparation XXXVII.

MS (IS, MI/z) $C_{15}H_{17}FN_2O$ (M$^+$+1)=261

Preparation XLI (5-phenoxy-1H-indol-3-yl)oxoacetic Acid Methyl Ester

Beginning with 5-phenoxyindole, the title compound was prepared essentially as described in Preparation II.

MS (IS, MI/z) $C_{17}H_{13}NO_4$ (M$^+$−1)=294

Preparation XLII (5,6-Difluoro-1H-indol-3-yl)acetamide

Beginning with 5,6-difluoroindole, the title compound was prepared essentially as described in Preparations II and XXXVII.

MS (IS, m/z) $C_{10}H_8F_2N_2O$ (M$^+$+1)=211

Preparation XLIII (5-Benzyloxy-1H-indol-3-yl)oxoacetic Acid Methyl Ester

Beginning with 5-benzyloxyindole, the title compound was prepared essentially as described in Preparation II.

MS (IS, m/z) $C_{18}H_{15}NO_4$ (M$^+$+1)=310.

Preparation XLIV (7-(2-(triisopropylsilyloxy)eth-1-yl)-1H-indol-3-yl) oxoacetic Acid Methyl Ester To a solution of 7-(2-hydroxyethyl)indole (2.86 g, 17.7 mmol) in 25 mL of dry dimethylformamide was added imidazole (2.54 g, 37.3 mmol) followed by triisopropylsilyl chloride (4.35 mL, 19.7 mmol) and the mixture stirred at room temperature under nitrogen for 3 hours. After diluting with hexanes (500 mL) the organic layer was washed with water (2×50 mL) and saturated aqueous sodium chloride (1×50 mL) and dried over magnesium sulfate. The mixture was filtered and concentrated under reduced pressure to provide 7-(2-(triisopropylsilyloxy)eth-1-yl)indole. This indole was reacted essentially as described in Preparation II to provide the title compound as a yellow solid.

MS (IS, m/z) $C_{22}H_{33}NO_4Si$ (M$^+$+1)=404

Preparation XLV 6-(tert-butoxycarbonyl)-5,6-dihydro-6H-[1,4] homodiazepino-[6,7,1-hi]indole 7-vinylindole To a solution of methyl triphenylphosphonium bromide (5.05 g, 14.1 mmol) in tetrahydrofuran (80 mL) was added potassium tert-butoxide (1 M in tetrahydrofuran, 14.1 mL, 14.1 mmol) and the reaction stirred for 45 minutes at room temperature. Next a prepared solution of 7-formylindole (1.00 g, 6.89 mmol) in tetrahydrofuran (10 mL) was added and the reaction stirred for 1.5 hours. The reaction mixture was diluted with ethyl acetate (250 mL) and washed with an 8:1 mixture of water and 1 N hydrochloric acid (2×100 mL), saturated aqueous sodium chloride (100 mL), and dried over sodium sulfate. The solution was filtered and the filtrate concentrated under reduced pressure. The residue was subjected to silica gel chromatography. Fractions containing product were combined and concentrated under reduced pressure to provide the desired compound as a brown oil.

MS (IS, m/z) $C_{10}H_9N$ (M$^+$+1)=144

Hydroboration/Oxidation

To a 0° C. solution of 7-vinylindole 1 (0.95 g, 6.6 mmol) in anhydrous tetrahydrofuran (60 mL) was added 1 M borane-tetrahydrofuran complex in tetrahydrofuran (9.95 mL, 9.95 mmol) and the reaction stirred overnight at room temperature. 1 N sodium hydroxide (25 mL) and 30% hydrogen peroxide (35 mL) were then added and the mixture stirred at reflux for 1 hour. The reaction mixture was cooled to room temperature, diluted with ethyl acetate (100 mL), washed with water (50 mL) and saturated aqueous sodium chloride (2×50 mL), dried over sodium sulfate and concentrated under reduced pressure. The residue was subjected to silica gel chromatography, eluting with 50% ethyl acetate in hexanes. Fractions containing product were combined and concentrated under reduced pressure to provide 0.60 g (56%) of the desired compound as a yellow oil.

MS (IS, M/z) $C_{10}H_{11}NO$ (M$^+$+1)=162.

Alcohol Activation

A solution of 7-(2-hydroxyeth-1-yl)indole (0.54 g, 3.34 mmol) and triethylamine (2.3 mL, 16.7 mmol) in dichloromethane (45 mL) was stirred at 0° C. To this was added a prepared solution of methanesulfonyl chloride (0.29 mL, 3.68 mmol) in dichloromethane (5 mL) dropwise over 30 minutes and the reaction was stirred for an additional 2 hours at room temperature. Upon completion the reaction was diluted with dichloromethane (50 mL) and washed with water (30 mL) and saturated aqueous sodium chloride (2×30 mL) and dried over sodium sulfate. The drying agent was then filtered and the filtrate was concentrated under reduced pressure.

Nucleophilic Displacement

To a solution of 7-(2-(methanesulfonyloxy)eth-1-yl) indole (0.79 g, 3.3 mmol) in ethanol (50 mL) was added ethanolamine (5 mL, 82 mmol) and the reaction stirred at reflux overnight. The reaction was diluted with ethyl acetate (150 mL) and washed with water (3×50 mL), saturated aqueous sodium chloride (2×50 mL) and dried over sodium sulfate, filtered and concentrated under reduced pressure to provide 0.57 g (85%) 7-(2-(N-[2-hydroxyeth-1-yl]amino) eth-1-yl)indole as a light-brown solid.

MS (IS, MI/z) $C_{12}H_{16}N_2O$ (M$^+$+1)=205

Ring Formation

Beginning with 7-(2-(N-[2-hydroxyeth-1-yl]amino)eth-1-yl)indole, the title compound was prepared essentially as described in Preparation IV.

MS (IS, m/z) $C_{17}H_{22}N_2O_2$ (M$^+$+1)=287

Preparation XLVI (6-(tert-butoxycarbonyl)-5,6-dihydro-6H-[1,4] homodiazepino-[6,7,1-hi]indol-1-yl)oxoacetic Acid Methyl Ester Beginning with 6-(tert-butoxycarbonyl)-5,6-dihydro-6H-[1,4]homodiazepino[6,7,1-hi]indole, the title compound was prepared essentially as described in Preparation II.

MS (IS, m/z) $C_{20}H_{24}N_2O_5$ $(M^++1)=373$

Preparation XLVII 6-((triisopropylsilyloxy)methyl)indole
indole-6-carboxylic acid methyl ester To a solution of indole-6-carboxylic acid (39.5 g, 245 mmol) in methanol (200 mL) and dichloromethane (750 mL) was added 2 M (trimethylsilyl)diazomethane in hexanes (160 mL, 320 mmol) dropwise over 1 hour. The reaction was stirred at room temperature overnight. The following day the reaction was concentrated to a thick brown crude oil that was diluted with ethyl acetate (500 mL) and washed with saturated aqueous sodium bicarbonate (2×200 mL), saturated aqueous sodium chloride (2×200 mL) and dried over sodium sulfate. The mixture was then filtered and the filtrate concentrated under reduced pressure to form a suspension. The suspension was filtered to provide 43 g of the desired compound as an off-white solid.

6-(hydroxymethyl)indole

To a solution of indole-6-carboxylic acid methyl ester (20.0 g, 114 mmol) in anhydrous tetrahydrofuran (1.6 L) stirring under nitrogen at room temperature was added carefully lithium aluminum hydride (8.7 g, 230 mmol) while purging with nitrogen. Following this addition, the reaction mixture was stirred at room temperature for 3 hours and was then cooled to 0° C. This mixture was treated sequentially with water (9 mL), 15% sodium hydroxide (9 mL), and additional water (25 mL). The resulting suspension was filtered and the filtrate concentrated under reduced pressure. The residue was subjected to silica gel chromatography, eluting with 30%–60% ethyl acetate in hexanes. Fractions containing product were combined and concentrated under reduced pressure to provide 16.0 g (95%) of the desired compound as an off-white solid.

IS-MS, m/e 146.0 (m−1).

Silylation

To a solution of 6-(hydroxymethyl)indole (16.0 g, 110 mmol) in dichloromethane (800 mL) stirring at 0° C. under nitrogen was added triethylamine (22.5 mL, 160 mmol). Next a prepared solution of triisopropylsilyl trifluoromethanesulfonate (30.5 mL, 115 mmol) in dichloromethane (200 mL) was added slowly using an addition funnel. The reaction was stirred at 0° C. for 3 hours. The reaction was then diluted with dichlormethane (200 mL) and washed with water (2×200 mL), saturated aqueous sodium chloride (2×200 mL) and dried over sodium sulfate. The solution was filtered and the filtrate concentrated under reduced pressure. The residue was sujected to silica gel chromatography. Fractions containing product were combined and concentrated under reduced pressure to provide the title compound.

IS-MS, m/e 302 (m−1).

Preparation XLVIII (6-((triisopropylsilyloxy)methyl)indol-3-yl)oxoacetic Acid Methyl Ester Beginning with 6-((triisopropylsilyloxy)methyl)indole, the title compound was prepared as described in Preparation II.

IS-MS, m/e 388 (m−1)

Preparation XLIX

9-Chloro-5,6-dihydro-4H-pyrrolo-[3,2,1-ij]quinoline
5-Chloro-1,2,3,4-tetrahydroquinoline A mixture of 5-chloroquinoline (10.0 g) and platinum oxide (50 mg) in acetic acid was shaken under a hydrogen atmosphere at room temperature for 4 hours. The mixture was diluted with diethyl ether and filtered through Celite. The volatiles were removed under reduced pressure and the residue was partitioned between saturated aqueous sodium bicarbonate and ethyl acetate (3×300 mL). The organic extracts were dried over sodium sulfate, filtered and concentrated under reduced pressure. The residue was purified over silica gel and the fractions containing product were combined and concentrated under reduced pressure to provide 7.0 g (69%) of the desired compound.

MS (EI m/z) $C_9H_{10}ClN$ (M+1)

Ring Formation/Decarboxylation

Beginning with 5-chloro-1,2,3,4-tetrahydroquinoline, the title compound was prepared essentially as described in Preparation I.

MS (EI m/z) $C_{11}H_{10}ClN$ (M+) 192.1

Analysis for $C_{11}H_{10}ClN$:

| | | | |
|---|---|---|---|
| Calcd: | C, 68.93; | H 5.25; | N, 7.30; |
| Found: | C, 69.18; | H, 5.25; | N, 6.97. |

Preparation L (9-chloro-5,6-dihydro-4H-pyrrolo[3,2,1-ij]quinolin-1-yl)oxoacetic Acid Methyl Ester Beginning with 9-chloro-5,6-dihydro-4H-pyrrolo-[3,2,1-ij]quinoline, the title compound was prepared essentially as described in Preparation II.

MS (IS m/z) $C_{14}H_{12}ClNO_3$ (M+1) 278

Analysis for $C_{14}H_{12}ClNO_3$:

| | | | |
|---|---|---|---|
| Calcd: | C, 60.55; | H, 4.36; | N, 5.04; |
| Found: | C, 60.62; | H, 4.46; | N, 5.00. |

Preparation LI 8-chloro-5,6-dihydro-4H-pyrrolo[3,2,1-ij]quinoline

Beginning with 6-chloroquinoline, the title compound was prepared essentially as described in Preparation XLVIII.

MS (IS, m/z) $C_{11}H_{10}ClN$ (M+) 191.9

Preparation LII (8-chloro-5,6-dihydro-4H-pyrrolo-[3,2,1-ij]quinolin-1-yl)oxoacetic Acid Methyl Ester Beginning with 8-chloro-5,6-dihydro-4H-pyrrolo-[3,2,1-ij]quinoline, the title compound was prepared essentially as described in Preparation II.

MS (IS, m/z) $C_{14}H_{12}ClNO_3$ (M+1) 277.8

Analysis for $C_{14}H_{12}ClNO_3$:

| | | | |
|---|---|---|---|
| Calcd: | C, 60.55; | H, 4.36; | N, 5.04; |
| Found: | C, 60.70; | H, 4.35; | N, 4.83. |

Preparation LIII 5-fluoro-1,2,3,4-tetrahydroquinoline
5-fluoroquinoline

To a suspension of 5-aminoquinoline (50 g, 347 mmol) in 48% $HBF_4$ (200 mL) at 0° C. was added portionwise sodium nitrite. This was stirred for 1 hour and then poured into 1:1 ethyl acetate/diethyl ether (500 mL). The resulting suspension was filtered and the solid dried. This solid (82.5 g, 338 mmol) was added portionwise to refluxing xylene (1 L) and stirred for 2 hours then allowed to cool. The xylene was decanted off and the residue dissolved in 1N hydrochloric acid (600 mL). After neutralization with sodium carbonate, the mixture was extracted with ethyl acetate (10×500 mL). The extracts were dried over sodium sulfate, filtered and the volatiles removed under reduced pressure. The residue was subjected to silica gel chromatography, eluting with 10–20% diethyl ether in hexanes. Fractions containing product were combined and concentrated under reduced pressure to provide 28.1 g (55%) of the desired compound.

MS (EI, m/z) $C_9H_6FN$ (M+1) 148.0

Reduction

A mixture of 5-fluoroquinoline (28.1 g), 5% palladium on carbon (5.6 g) in methanol was shaken over night at 40° C. under 60 psi hydrogen. The mixture was filtered through celite and concentrated under reduced pressure. The residue was subjected to silica gel chromatography, eluting with 5–10% ethyl acetate in hexanes. Fractions containing product were combined and concentrated under reduced pressure to provide 22.5 g (78%) of the title compound.

MS (EI, m/z) $C_9H_{10}FN$ (M+1) 152.0

Preparation LIV

7-Fluoro-5,6-dihydro-4H-pyrrolo[3,2,1-ij]quinoline

Beginning with 5-fluoro-1,2,3,4-tetrahydroquinoline, the title compound was prepared essentially as described in Preparation I.

MS (EI, m/z) $C_{11}H_{10}FN$ (M+1) 176.1

Analysis for $C_{11}H_{10}FN$:

| Calcd: | C, 75.40; | H, 5.75; | N, 7.99; |
|---|---|---|---|
| Found: | C, 75.04; | H, 5.64; | N, 7.95. |

Preparation LV (7-Fluoro-5,6-dihydro-4H-pyrrolo[3,2,1-ij]quinolin-1-yl)-oxoacetic Acid Methyl Ester Beginning with 7-fluoro-5,6-dihydro-4H-pyrrolo-[3,2,1-ij]quinoline, the title compound was prepared essentially as described in Preparation II.

MS (EI, m/z) $C_{14}H_{12}FNO_3$ (M+1) 262.1

Analysis for $C_{14}H_{12}FNO_3$:

| Calcd: | C, 64.36; | H, 4.63; | N, 5.36; |
|---|---|---|---|
| Found: | C, 64.07; | H, 4.56; | N, 5.06. |

Preparation LVI

6-Fluoro-1,2,3,4-tetrahydroquinoline

Beginning with 6-aminoquinoline, the title compound was prepared essentially as described in Preparation LIII.

MS (EI, m/z) $C_9H_{10}FN$ (M+1) 152.0.

Preparation LVII

8-Fluoro-5,6-dihydro-4H-pyrrolo[3,2,1-ij]quinoline

Beginning with 6-fluoro-1,2,3,4-tetrahydroquinoline, the title compound was prepared essentially as described in Preparation I.

MS (EI, m/z) $C_{11}H_{10}FN$ (M+) 175.1

Analysis for $C_{11}H_{10}FN$:

| Calcd: | C, 75.40; | H, 5.75; | N, 7.99; |
|---|---|---|---|
| Found: | C, 75.95; | H, 5.84; | N, 8.20. |

Preparation LVIII (8-Fluoro-5,6-dihydro-4H-pyrrolo[3,2,1-ij]quinolin-1-yl)-oxoacetic Acid Methyl Ester Beginning with 8-fluoro-5,6-dihydro-4H-pyrrolo[3,2,1-ij]quinoline, the title compound was prepared essentially as described in Preparation II.

MS (EI, m/z) $C_{14}H_{12}FNO_3$ (M+1) 262.1

Analysis for $C_{14}H_{12}FNO_3$:

| Calcd: | C, 64.36; | H, 4.63; | N, 5.36; |
|---|---|---|---|
| Found: | C, 64.01; | H, 4.60; | N, 5.05. |

Preparation LIX

N-[tert-butoxycarbonyl] 2-(1H-Indol-6-yl)ethylamine

Indole-6-carboxaldehyde

To a solution of 6-cyanoindole (15.0 g) and sodium hypophosphite (90 g) in water (326 mL), acetic acid (326 mL), and pyridine (652 mL) was added Raney Nickel catalyst and the mixture stirred at 45° C. for 45 minutes. The mixture was filtered through Celite and the filtrate extracted with ethyl acetate (3×500 mL). The extracts were dried over sodium sulfate, filtered, and the filtrate concentrated under reduced pressure. The residue was crystallized from a mixture of dichloromethane and hexanes to provide 13.6 g (89%) of the title compound.

MS (EI, m/z) $C_9H_7NO$ (M+1) 145.9

6-(2-Nitrovinyl)-1H-indole

A mixture of indole-6-carboxaldehyde (2.8 g), nitromethane (30 mL) and ammonium acetate (0.560 g) was stirred at 100° C. for 30 minutes. The excess nitromethane was removed under reduced pressure and the residue washed with water, dissolved in ethyl acetate (500 mL), dried over sodium sulfate, filtered, and the filtrate concentrated under reduced pressure to a volume of about 50 mL. This solution was then diluted with petroleum ether and the resulting suspension filtered and dried to provide 3.3 g (91%) of the desired compound.

MS (EI, m/z) $C_{10}H_8N_2O_2$ (M−1) 186.9

2-(1H-Indol-6-yl)ethylamine

To a solution of 6-(2-Nitrovinyl)-1H-indole (1.0 g) in tetrahydrofuran (100 mL) was added portionwise lithium aluminum hydride (0.95 g) and the resulting mixture stirred at reflux for 1 hour. The reaction mixture was treated sequentially with water (0.95 mL), 15% sodium hydroxide (0.95 mL), and water (2.85 mL). The resulting suspension was filtered and the filtrate diluted with ethyl acetate (200 mL), washed with saturated aqueous sodium bicarbonate (100 mL), saturated aqueous sodium chloride, dried over sodium sulfate, filtered and the filtrate concentrated under reduced pressure. The residue was subjected to silica gel chromatography. Fractions containing product were combined and concentrated under reduced pressure to provide 0.525 g (62%) of the desired compound.

MS (EI, m/z) $C_{10}H_{12}N_2$ (M+1) 160.9

Nitrogen Protection

To a solution of 2-(1H-Indol-6-yl)ethylamine (0.50 g) in acetonitrile (25 mL) was added dimethylaminopyridine followed by di-tert-butyl dicarbonate (45 mg). After stirring at room temperature for 24 hours, the mixture was diluted with ethyl acetate (500 mL), washed with saturated aqueous sodium bicarbonate (200 mL), water (2×200 mL), saturated aqueous sodium chloride, dried over sodium sulfate, filtered and the filtrate concentrated under reduced pressure. The residue was subjected to silica gel chromatography, eluting with 20–40% ethyl acetate in hexanes. Fractions containing product were combined and concentrated under reduced pressure to provide 0.42 g (52%) of the title compound.

MS (EI, m/z) $C_{15}H_{20}N_2O_2$ (M−1) 258.9

Preparation LX (6-(N-[tert-Butoxycarbonyl] 2-aminoethyl)-1H-indol-3-yl)-oxoacetic Acid Methyl Ester Beginning with N-[tert-butoxycarbonyl] 2-(1H-indol-6-yl)ethylamine, the title compound was prepared essentially as described in Preparation II.

MS (EI, m/z) $C_{18}H_{22}N_2O_5$ (M−1) 345.1

Preparation LXI 5-(hydroxymethyl)-5,6-dihydro-4H-pyrrolo[3,2,1-ij]quinoline

4H-Pyrrolo[3,2,1-ij]quinoline-5-carboxylic acid methyl ester and 6H-Pyrrolo[3,2,1-ij]quinoline-5-carboxylic acid methyl ester To a solution of 7-formylindole (30 g, 0.206 mol) in dimethylformamide (930 mL) was added cesium carbonate (148.2 g, 0.454 mol) and the mixture was stirred vigorously at room temperature for 30 min. Methyl 3-bromopropionate (51.6 g, 0.308 mol) was added and the reaction mixture was heated to 80° C. for 24 hours. The mixture was cooled to room temperature, diluted with ethyl acetate and filtered through a pad of Celite. The filtrate was washed with water and saturated aqueous sodium chloride, and the aqueous layers were back extracted with ethyl acetate. The combined organic layers were dried over sodium sulfate and concentrated under reduced pressure. The crude product was passed through a short silica plug and concentrated under reduced pressure. Recrystallization of the crude product from chloroform and hexanes gave 4H-pyrrolo[3,2,1-ij]quinoline-5-carboxylic acid methyl ester (17 g, 38.7% yield). Chromatography of the mother liquor gave additional 4H-pyrrolo[3,2,1-ij]quinoline-5-carboxylic acid methyl ester (1.27 g, 2.9% yield) and 6H-Pyrrolo[3,2,1-ij]quinoline-5-carboxylic acid methyl ester (0.51 g, 1.2% yield).

4H-Pyrrolo[3,2,1-ij] quinoline-5-carboxylic acid methyl ester $^1$H NMR (CDCl$_3$, 400 MHz) δ 3.82 (s, 3H), 5.27 (d, J=1.47 Hz, 2H), 6.45 (d, J=2.93 Hz, 1H), 6.89~6.93 (m, 2H), 7.05 (d, J=2.93 Hz, 1H), 7.45 (dd, J$_1$=2.45 Hz, J$_2$=6.36 Hz, 1H), 7.64 (t, J=1.95 Hz, 1H); MS (ES, m/z) $C_{13}H_{10}NO_2$ 212.2 (M$^+$+1).

6H-Pyrrolo[3,2,1-ij]quinoline-5-carboxylic acid methyl ester $^1$H NMR (CDCl$_3$, 400 MHz)δ 3.73 (s, 3H), 3.94 (d, J=1.0 Hz, 2H), 6.38 (d, J=3.4 Hz, 1H), 6.88 (d, J=7.33 Hz, 1H), 6.92 (d, J=2.94 Hz, 1H), 7.02 (t, J=7.58 Hz, 1H), 7.21 (d, J=7.82 Hz, 1H), 7.73 (t, J=1.46 Hz, 1H).

5,6-dihydro-4H-Pyrrolo[3,2,1-ij]quinoline-5-carboxylic acid methyl ester

4H-Pyrrolo[3,2,1-ij]quinoline-5-carboxylic acid methyl ester (10.9 g, 51.1 mmol) and palladium on carbon (5%, 1.1 g) were taken into tetrahydrofuran (300 mL), and the mixture was stirred under 60 psi of hydrogen at room temperature for 8 hours. Additional palladium on carbon (5%, 0.6 g) was added, and the mixture stirred under 60 psi of hydrogen for another 15 hours. Filtration and concentration of filtrate gave the desired compound.

Reduction

To a solution of 5,6-dihydro-4H-pyrrolo[3,2,1-ij]quinoline-5-carboxylic acid methyl ester (8.78 g, 40.8 mmol) in tetrahydrofuran (420 mL) at 0° C. was added a solution of lithium aluminum hydride in tetrahydrofuran (1.0 M, 100 mL, 100 mmol) dropwise, and the mixture was allowed to warm to room temperature slowly. After stirring at room temperature for 2 hours, the reaction was quenched by water carefully. The mixture was passed through a short pad of Celite, and concentration of the filtrate gave the title compound.

MS (electrospray, m/z) $C_{12}H_{13}NO$: 188.1 (M$^+$+1), 186.1 (M$^+$−1)

Preparation LXII (5-(tert-butyldimethylsilyloxymethyl)-5,6-dihydro-4H-pyrrolo[3,2,1-ij]quinolin-1-yl)oxoacetic Acid Methyl Ester and (5-hydroxymethyl-5,6-dihydro-4H-pyrrolo[3,2,1-ij]quinolin-1-yl)oxoacetic Acid Methyl Ester To a solution of 5-(hydroxymethyl)-5,6-dihydro-4H-pyrrolo[3,2,1-ij]quinoline (47 mmol) in dichloromethane (143 mL) at 0° C. was added tert-butyldimethylsilyl chloride (7.63 g, 49.4 mmol), followed by triethylamine (7.92 mL, 56.4 mmol) and dimethylaminopyridine (0.58 g, 4.7 mmol). The reaction was allowed to warm to room temperature and stirred 2 hours. The reaction was quenched with water, extracted with dichloromethane and the combined organics dried over sodium sulfate. The organic phase was concentrated under reduced pressure to provide 5-(tert-butyldimethylsilyloxymethyl)-5,6-dihydro-4H-pyrrolo[3,2,1-ij]quinoline. This material was treated essentially as described in Preparation II to provide the title compounds.

(5-(tert-butyldimethylsilyloxymethyl)-5,6-dihydro-4H-pyrrolo[3,2,1-ij]quinolin-1-yl)oxoacetic acid methyl ester: $^1$H NMR (400 MHz, CDCl$_3$) δ 0.00 (s, 6H), 0.85 (s, 9H), 2.45~2.40 (m, 1H), 2.83~2.76 (m, 1H), 3.00~2.90 (m, 1H), 3.58~3.53 (m, 1H), 3.74 (dd, J$_1$=4.9 Hz, J$_2$=10.27 Hz, 1H), 3.89 (s, 3H), 4.01~3.95 (m, 1H), 4.30~4.27 (m, 1H), 7.01 (dd, J$_1$=1.0 Hz, J$_2$=7.33 Hz, 1H), 7.22~7.18 (m, 1H), 8.09 (d, J=8.31 Hz, 1H), 8.29 (s, 1H).

(5-Hydroxymethyl-5,6-dihydro-4H-pyrrolo[3,2,1-ij]quinolin-1-yl)oxoacetic acid methyl ester: MS (ES, m/z) $C_{15}H_{15}NO_4$: 274.1 (M$^+$+1)

Preparation LXIII

4-Hydroxymethyl-5,6-dihydro-4H-pyrrolo[3,2,1-ij]quinoline 2-hydroxymethyl-1,2,3,4-tetrahydroquinoline Sodium borohydride (21.7 g, 0.57 mol) was added in portions to a solution of quinoline-2-carboxaldehyde (30 g, 0.191 mol) in ethanol (300 mL) at 0° C. The reaction mixture was warmed to room temperature, stirred at room temperature for 2 hrs, and quenched by water. Volatiles were removed under reduced pressure and the residue dissolved in ethyl acetate, washed with water and saturated aqueous sodium chloride, dried over sodium sulfate, and concentrated under reduced pressure. The residue was subjected to silica gel chromatography. Fractions containing product were combined and concentrated under reduced pressure to provide the desired compound and 2-(hydroxymethyl) quinoline. A solution of the recovered 2-(hydroxymethyl) quinoline in ethanol (250 mL) and tetrahydrofuran (250 mL) was hydrogenated at 60 psi in the presence of 5% platinum on carbon at 40° C. for 48 hours. The reaction mixture was filtered and the filtrate concentrated under reduced pressure to provide the title compound.

$^1$H NMR (400 MHz, CDCl$_3$) δ 1.64~1.74 (m, 1H), 1.85~1.91 (m, 1H), 1.4~2.3 (br, 2H), 2.68~2.75 (m, 1H), 2.78~2.85 (m, 1H), 3.40~3.46 (m, 1H), 3.51~3.56 (m, 1H), 3.73 (dd, J$_1$=3.91 Hz, J$_2$=10.26 Hz, 1H), 6.51 (dd, J$_1$=1.0 Hz, J$_2$=7.83 Hz, 1H), 6.61 (dt, J$_1$=1.0 Hz, J$_2$=7.33 Hz, 1H), 6.93~6.98 (m, 2H).

Ring Formation/Decarboxylation

Beginning with 2-hydroxymethyl-1,2,3,4-tetrahydroquinoline, the title compound was prepared essentially as described in Preparation I.

MS (ES, m/z)188.1 (M$^+$+1), 186.1 (M$^+$−1)

Preparation LXIV (4-hydroxymethyl-5,6-dihydro-4H-pyrrolo[3,2,1-ij]quinolin-1-yl)oxoacetic Acid Methyl Ester and (4-(tert-butyldimethylsilyloxymethyl)-5,6-dihydro-4H-pyrrolo[3,2,1-ij]quinolin-1-yl]oxoacetic Acid Methyl Ester Beginning with 4-hydroxymethyl-5,6-dihydro-4H-pyrrolo[3,2,1-ij]quinoline, the title compounds were prepared essentially as described in Preparation LXI. (4-Hydroxymethyl-5,6-dihydro-4H-pyrrolo[3,2,1-ij]quinolin-1-yl)oxoacetic acid methyl ester: $^1$H NMR (400 MHz, CDCl$_3$) δ 8.47 (s, 1H), 8.03 (d, J=7.81 Hz, 1H), 7.18 (t, J=7.33 Hz, 1H), 7.01 (d, J=6.84 Hz, 1H), 4.43~4.40 (m, 1H), 3.98~3.88 (m, 2H), 3.77 (s, 3H), 3.00~2.93 (m, 2H), 2.38 (br, 1H), 2.24~2.18 (m, 2H).

(4-(tert-butyldimethylsilyloxymethyl)-5,6-dihydro-4H-pyrrolo[3,2,1-ij]quinolin-1-yl]oxoacetic acid methyl ester $^1$H NMR (400 MHz, CDCl$_3$) δ 8.49 (s, 1H), 8.18 (d, J=7.33 Hz, 1H), 7.27 (t, J=7.58 Hz, 1H), 7.07 (dd, J$_1$=1.0 Hz, J$_2$=7.33 Hz, 1H), 4.44~4.41(m, 1H), 3.94 (s, 3H), 3.92~3.82 (m, 2H), 3.01~2.98 (m, 2H), 2.26~2.23(m, 2H), 0.89 (s, 9H), 0.00 (s, 6H).

Preparation LXV 6-(tert-butyldiphenylsilyloxymethyl)-5,6-dihydro-4H-pyrrolo[3,2,1-I,j]quinoline 4-(hydroxymethyl)-1,2,3,4-tetrahydroquinoline Beginning with quinoline-4-carboxaldehyde, the desired compound was prepared essentially as described in Preparation LXII.

$^1$H NMR (400 MHz, CDCl$_3$) δ 1.85~2.00 (m, 2H), 2.82~2.90 (m, 1H), 3.15~3.26 (m, 2H), 3.66~3.75 (m, 2H), 6.43 (d, J=7.33 Hz, 1H), 6.55 (dt, J$_1$=1.50 Hz, J$_2$=7.33 Hz, 1H), 6.92 (dt, J$_1$=1.50 Hz, J$_2$=7.82 Hz, 1H), 6.98 (d, J=7.33 Hz, 1H).

4-(tert-Butyldiphenylsilyloxymethyl)-1,2,3,4-tetrahydroquinoline

To a solution of 4-(hydroxymethyl)-1,2,3,4-tetrahydroquinoline (16.07 g, 0.098 mol) in dichloromethane (100 mL) at 0° C. were added sequentially triethylamine (16.3 mL, 0.12 mol), tert-butyldiphenylsilylchloride (28.4 g, 0.103 mol) and 4-(dimethylamino)pyridine (0.6 g, 4.9 mmol). After 30 minutes, the solution was warmed to room temperature and stirred for another 2 hours. The reaction mixture was diluted with dichlormethane (200 mL), washed with water (50 mL) and saturated aqueous sodium chloride solution (50 mL). The organic layers were collected, dried over sodium sulfate, filtered and concentrated under reduced pressure. The residue was subjected to silica gel chromatography to provide 22.1 g (56%) of the desired compound.

Ring Formation/Decarboxylation

Beginning with 4-(tert-butyldiphenylsilyloxy)-1,2,3,4-tetrahydroquinoline, the title compound was prepared essentially as described in Preparation I.

MS (ES, m/z) 426.1 (M$^+$+1)

Preparation LXVI 6-(tert-butyldiphenylsilyloxymethyl)-5,6-dihydro-4H-pyrrolo[3,2,1-I,j]quinolin-1-yl)oxoactic acid methyl ester Beginning with 6-(tert-butyldiphenylsilyloxymethyl)-5,6-dihydro-4H-pyrrolo[3,2,1-I,j]quinoline, the title compound was prepared essentially as described in Preparation II.

MS (ES, m/z) 512.2 (M$^+$+1)

Preparation LXVII 6-(hydroxymethyl)-4,5,6,7-tetrahydroazepino[3,2,1-hi]indole

Beginning with indole-7-carboxaldehyde and methyl 4-bromobutyrate, the title compound was prepared essentially as described in Preparation LXI.

$^1$H NMR (400 MHz, CDCl$_3$) δ 1.78~1.82 (m, 1H), 2.10~2.30 (m, 2H), 2.90~3.00 (m, 1H), 3.10~3.20 (m, 1H), 3.57~3.60 (m, 2H), 3.94~4.05 (m, 1H), 4.30~4.40 (m, 1H), 6.36 (d, J=3.43 Hz, 1H), 6.87~6.93 (m, 3H), 7.38~7.40 (m, 1H)

Preparation LXVIII (6-(hydroxymethyl)-4,5,6,7-tetrahydroazepino[3,2,1-hi] indol-1-yl)oxoacetic Acid Methyl Ester Beginning with 6-(hydroxymethyl)-4,5,6,7-tetrahydroazepino[3,2,1-hi]indole, the title compound was prepared essentially as described in Preparation II.

MS (ES, m/z) C$_{16}$H$_{17}$NO$_4$ 288.1 (M$^+$+1), 286.2 (M$^+$−1)

Preparation LXIX 5,5-dimethyl-4,6-dihydro-4H-pyrrolo[3,2,1-ij]quinoline

Beginning with 3,3-dimethyl-1,2,3,4-tetrahydroquinoline (J. Chem. Soc. (Perkin I) 1635–1640 (1987)), the title compound was prepared as described in Preparation I.

Preparation LXX (5,5-dimethyl-4,6-dihydro-4H-pyrrolo[3,2,1-ij]quinolin-1-yl)oxoacetic Acid Methyl Ester Beginning with 5,5-dimethyl-4,6-dihydro-4H-pyrrolo[3,2,1-ij]quinoline, the title compound was prepared essentially as described in Preparation II.

MS (IS): m/e=272 (M+1)

Preparation LXXI

8-fluoro-6,6-dimethyl-4,6-dihydro-4H-pyrrolo[3,2,1-ij]quinoline

Beginning with 6-fluoro-4,4-dimethyl-1,2,3,4-tetrahydroquinoline (*Bioorg. Med. Chem. Lett.* 1335–1340 (1999)), the title compound was prepared as described in Preparation I.

MS (ES): m/e=204.2 (M+1)

Preparation LXXII

(8-fluoro-6,6-dimethyl-4,6-dihydro-4H-pyrrolo[3,2,1-ij]quinolin-1-yl)oxoacetic Acid Methyl Ester Beginning with 8-fluoro-6,6-dimethyl-4,6-dihydro-4H-pyrrolo[3,2,1-ij]quinoline, the title compound was prepared essentially as described in Preparation II.

MS (ES): m/e=290 (M+1)

EA: Calculated for: $C_{16}H_{16}FNO_3$: Theory: C, 66.43; H, 5.58; N, 4.84. Found: C, 66.29; H, 5.50; N, 4.90.

EXAMPLE 1

3-(5,6-dihydro-4H-pyrrolo[3,2,1-ij]quinolin-1-yl)-4-(1H-indol-3-yl)pyrrole-2,5-dione To a 0° C. solution of 5,6-dihydro-4H-pyrrolo[3,2,1-ij]quinolin-1-yl)oxoacetic acid methyl ester (0.5 g, 2.06 mmol) and indole-3-acetamide (0.394 g, 2.26 mmol) in 10 mL of tetrahydrofuran was added dropwise potassium tert-butoxide (16.4 mL, 16.4 mmol, 1 M in tetrahydrofuran). Following 2 hours at 0° C., 5.0 mL of concentrated hydrochloric acid was added and the reaction mixture stirred at room temperature for 1 more hour. The mixture was diluted with 100 mL of ethyl acetate, and the organic layer washed with water (2×25 mL), saturated aqueous sodium chloride (25 ml), dried over sodium sulfate, filtered and concentrated in vacuo. The residue was subjected to silica gel chromatography, eluting with a gradient of dichloromethane containing from 1–5% methanol. Fractions containing product were combined and concentrated under reduced pressure to provide 0.598 g (79%) of the title compound as a red solid.

MS (IS, m/z) $C_{23}H_{17}N_3O_2$ (M$^+$+1)=368.

EXAMPLE 2

1-methyl-3-(5,6-dihydro-4H-pyrrolo[3,2,1-ij]quinolin-1-yl)-4-(1H-indol-3-yl)pyrrole-2,5-dione A mixture of 3-(5,6-dihydro-4H-pyrrolo[3,2,1-ij]quinolin-1-yl)-4-(1H-indol-3-yl)pyrrole-2,5-dione (0.1 g, 0.27 mmol) in 4.5 ml of dimethylformamide was treated with potassium carbonate (0.038 g, 0.27 mmol) and stirred for 1 h at rt. Methyl iodide was added (0.034 ml, 0.55 mmol) and the solution was stirred overnight at room temperature. The mixture was treated with cold water and stirred. Crystals were collected by filtration, washed with water and dried under vacuum to give 0.098 g (95%) of the title compound.

$^1$H NMR (500 MHz, CDCl$_3$) δ 8.5 (s, 1H), 7.7 (s, 1H), 7.6 (s, 1H), 7.3 (m, 1H), 7.2 (m, 1H), 7.1 (m, 1H), 6.8 (m, 2H), 6.6 (m, 2H), 4.2 (m, 2H), 3.2 (m, 3H), 2.9 (m, 2H), 2.2 (m, 2H).

EXAMPLE 3

3-(5,6-dihydro-4H-pyrrolo[3,2,1-ij]quinolin-1-yl)-4-(4-fluoro-1H-indol-3-yl)pyrrole-2,5-dione Beginning with 4-fluoroindole-3-acetamide and 5,6-dihydro-4H-pyrrolo[3,2,1-ij]quinolin-1-yl)oxoacetic acid methyl ester, the title compound was prepared as a red foam essentially as described in Example 1.

MS (IS, m/z) $C_{23}H_{16}FN_3O_2$ (M$^+$+1)=386

EXAMPLE 4

3-(8-fluoro-5,6-dihydro-4H-pyrrolo[3,2,1-ij]quinolin-1-yl)-4-(1H-indol-3-yl)pyrrole-2,5-dione Beginning with indole-3-acetamide and 8-fluoro-5,6-dihydro-4H-pyrrolo[3,2,1-ij]quinolin-1-yl)oxoacetic acid methyl ester, the title compound was prepared essentially as described in Example 1.

MS (EI, m/z) $C_{23}H_{16}FN_3O_2$ (M+1)=386

EXAMPLE 5

3-(7-fluoro-5,6-dihydro-4H-pyrrolo[3,2,1-ij]quinolin-1-yl)-4-(1H-indol-3-yl)pyrrole-2,5-dione Beginning with indole-3-acetamide and 7-fluoro-5,6-dihydro-4H-pyrrolo[3,2,1-ij]quinolin-1-yl)oxoacetic acid methyl ester, the title compound was prepared essentially as described in Example 1.

MS (EI, m/z) $C_{23}H_{16}FN_3O_2$ (M+1)=386

EXAMPLE 6

3-(5,6-dihydro-4H-pyrrolo[3,2,1-ij]quinolin-1-yl)-4-(6-chloro-1H-indol-3-yl)pyrrole-2,5-dione Beginning with 6-chloroindole-3-glyoxylic acid methyl ester and 2-(5,6-Dihydro-4H-pyrrolo[3,2,1-ij]quinolin-1-yl)-acetamide, the title compound was prepared as a dark red foam essentially as described in Example 1.

MS (IS, m/z) $C_{23}H_{16}ClN_3O_2$ (M$^+$+1)=402

EXAMPLE 7

3-(8-chloro-5,6-dihydro-4H-pyrrolo[3,2,1-ij]quinolin-1-yl)-4-(1H-indol-3-yl)pyrrole-2,5-dione Beginning with indole-3-acetamide and (8-chloro-5,6-dihydro-4H-pyrrolo[3,2,1-ij]quinolin-1-yl)oxoacetic acid methyl ester, the title compound was prepared essentially as described in Example 1.

MS (EI, m/z) $C_{23}H_{16}ClN_3O_2$ (M+1)=402

EXAMPLE 8

3-(7-chloro-5,6-dihydro-4H-pyrrolo[3,2,1-ij]quinolin-1-yl)-4-(1H-indol-3-yl)pyrrole-2,5-dione Beginning with indole-3-acetamide and (7-chloro-5,6-dihydro-4H-pyrrolo[3,2,1-ij]quinolin-1-yl)oxoacetic acid methyl ester, the title compound was prepared essentially as described in Example 1.

MS (EI, m/z) $C_{23}H_{16}ClN_3O_2$ (M+1)=402

EXAMPLE 9

3-(5,6-dihydro-4H-pyrrolo[3,2,1-ij]quinolin-1-yl)-4-(7-cyano-1H-indol-3-yl)pyrrole-2,5-dione Beginning with 7-cyanoindole-3-glyoxylic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{24}H_{16}N_4O_2$ (M$^+$−1)=391

EXAMPLE 10

3-(5,6-dihydro-4H-pyrrolo[3,2,1-ij]quinolin-1-yl)-4-(6-cyano-1H-indol-3-yl)pyrrole-2,5-dione Beginning with 6-cyanoindole-3-glyoxylic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{24}H_{16}N_4O_2$ (M−1)=391

EXAMPLE 11

3-(5-methyl-5,6-dihydro-4H-pyrrolo[3,2,1-ij]quinolin-1-yl)-4-(1H-indol-3-yl)pyrrole-2,5-dione Beginning with indole-3-acetamide and (5-methyl-5,6-dihydro-4H-pyrrolo[3,2,1-ij]quinolin-1-yl)oxoacetic acid methyl ester, the title compound was prepared essentially as described in Example 1.

MS (EI, m/z) $C_{24}H_{19}N_3O_2$ (M+1)=382

EXAMPLE 12

3-(1H-Indol-3-yl)-4-(8-methoxy-5,6-dihydro-4H-pyrrolo[3,2,1-ij]quinolin-1-yl)-pyrrole-2,5-dione Beginning with indole-3-acetamide and (8-methoxy-5,6-dihydro-4H-pyrrolo[3,2,1-ij]quinolin-1-yl)oxoacetic acid methyl ester, the title compound was prepared essentially as described in Example 1.

MS (IS, m/z) $C_{24}H_{19}N_3O_3$ (M+1)=398

EXAMPLE 13

3-(7-Benzyloxy-1H-indol-3-yl)-4-(5,6-dihydro-4H-pyrrolo [3,2,1-ij]quinolin-1-yl)-pyrrole-2,5-dione Beginning with 7-(benzyloxy)indole-3-glyoxylic acid methyl ester and 2-(5,6-dihydro-4H-pyrrolo[3,2,1-ij]quinolin-1-yl)-acetamide, the title compound was prepared essentially as described in Example 1.

MS (IS, m/z) $C_{30}H_{23}N_3O_3$ (M⁺−1)=472

EXAMPLE 14

3-(7-(Triisopropylsilyloxy)methyl-1H-indol-3-yl)-4-(5,6-dihydro-4H-pyrrolo [3,2,1-ij]quinolin-1-yl)-pyrrole-2,5-dione Beginning with 7-((triisopropylsilyloxy)methyl)indole-3-glyoxylic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{33}H_{38}N_3O_3Si$ (M⁺−1)=552

EXAMPLE 15

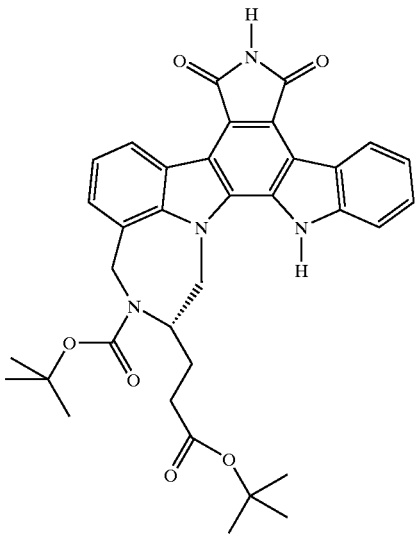

S-12-(tert-butoxycarbonyl)-13-(2-(tert-butoxycarbonyl)eth-1-yl)-11,12,13,14-tetrahydro-12H,15H-pyrrolo[3,4-c]benzo[1,4]diazepino[9',9a',1':3,2,1]-pyrrolo[2,3-a]carbazole-5,7-dione Beginning with 3-(S-6-(tert-butoxycarbonyl)-5-(2-(tert-butoxycarbonyl)eth-1-yl)-5,6-dihydro-6H-[1,4]diazepino-[6,7,1-hi]indol-1-yl)-4-(indol-3-yl)pyrrole-2,5-dione, the title compound was prepared essentially as described in Example 58, infra.

MS (IS, m/z) (M⁺−1)=607

EXAMPLE 16

3-(7-(Triisopropylsilyloxy)propyl-1H-indol-3-yl)-4-(6,6-dimethyl-5,6-dihydro-4H-pyrrolo [3,2,1-ij]quinolin-1-yl)-pyrrole-2,5-dione Beginning with 7-((triisopropylsilyloxy)propyl)indole-3-glyoxylic acid methyl ester and 2-(6,6-dimethyl-5,6-dihydro-4H-pyrrolo[3,2,1-ij]quinolin-1-yl)acetamide, the title compound was prepared essentially as described in Example 1.

IS-MS, m/e 608.4 (m⁻¹)

EXAMPLE 17

3-(5,6-Dihydro-4H-pyrrolo[3,2,1-ij]quinolin-1-yl)-4-[6-(3-(triisopropylsilyloxy)prop-1-yl)-1H-indol-3-yl]-pyrrole-2,5-dione Beginning with 6-((triisopropylsilyloxy)propyl)indole-3-glyoxylic acid methyl ester and 2-(5,6-dihydro-4H-pyrrolo [3,2,1-ij]quinolin-1-yl)-acetamide, the title compound was prepared essentially as described in Example 1.

MS (IS, m/z) $C_{35}H_{43}N_3O_3Si$ (M⁺−1)=580

EXAMPLE 18

3-(5,6-Dihydro-4H-pyrrolo[3,2,1-ij]quinolin-1-yl)-4-[7-(3-(triisopropylsilyloxy)prop-1-yl)-1H-indol-3-yl] pyrrole-2,5-dione Beginning with 7-((triisopropylsilyloxy)propyl)indole-3-glyoxylic acid methyl ester and 2-(5,6-dihydro-4H-pyrrolo

[3,2,1-ij]quinolin-1-yl)acetamide, the title compound was prepared essentially as described in Example 1.

MS (IS, m/z) $C_{35}H_{43}N_3O_3Si$ (M$^+$+1)=582

EXAMPLE 19

3-(5,6-Dihydro-4H-pyrrolo[3,2,1-ij]quinolin-1-yl)-4-[6-([N-tert-butoxycarbonyl]aminomethyl)-1H-indol-3-yl]pyrrole-2,5-dione Beginning with (6-([N-tert-butoxycarbonyl]aminomethyl)indol-3-yl)oxoacetic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{29}H_{28}N_4O_4$ (M$^+$−1)=495

EXAMPLE 20

3-(5,6-Dihydro-4H-pyrrolo[3,2,1-ij]quinolin-1-yl)-4-[7-([N-methyl N-tert-butoxycarbonyl]aminomethyl)-1H-indol-3-yl]pyrrole-2,5-dione Beginning with (7-([N-methyl N-tert-butoxycarbonyl]-aminomethyl)indol-3-yl)oxoacetic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{30}H_{30}N_4O_4$ (M$^+$+1)=511

EXAMPLE 21

3-(5,6-Dihydro-4H-pyrrolo[3,2,1-ij]quinolin-1-yl)-4-(5,6-difluoro-1H-indol-3-yl)pyrrole-2,5-dione Beginning with (5,6-difluoroindol-3-yl)oxoacetic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{23}H_{15}N_3O_2F_2$ (M$^+$+1)=404

EXAMPLE 22

3-(5,6-Dihydro-4H-pyrrolo[3,2,1-ij]quinolin-1-yl)-4-(5-fluoro-6-chloro-1H-indol-3-yl)pyrrole-2,5-dione Beginning with (5-fluoro-6-chloroindol-3-yl)oxoacetic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{23}H_{15}N_3O_2ClF$ (M$^+$+1)=420

EXAMPLE 23

3-(4-Methyl-5,6-dihydro-4H-pyrrolo[3,2,1-ij]quinolin-1-yl)-4-(4-fluoro-1H-indol-3-yl)pyrrole-2,5-dione Beginning with (4-fluoroindol-3-yl)acetamide and (4-methyl-5,6-dihydro-4H-pyrrolo[3,2,1-ij]quinolin-1-yl)oxo-acetic acid methyl ester, the title compound was prepared essentially as described in Example 1.

MS (IS, m/z) $C_{24}H_{18}N_3O_2F$ (M$^+$+1)=400

EXAMPLE 24

3-(6,6-dimethyl-5,6-dihydro-4H-pyrrolo[3,2,1-ij]quinolin-1-yl)-4-(1H-indol-3-yl)pyrrole-2,5-dione Beginning with (indol-3-yl)acetamide and (6,6-dimethyl-5,6-dihydro-4H-pyrrolo[3,2,1-ij]quinolin-1-yl)oxo-acetic acid methyl ester, the title compound was prepared essentially as described in Example 1.

MS (IS, m/z) $C_{25}H_{21}N_3O_2$ (M$^+$+1)=396

EXAMPLE 25

3-(5,5-dimethyl-5,6-dihydro-4H-pyrrolo[3,2,1-ij]quinolin-1-yl)-4-(1H-indol-3-yl)pyrrole-2,5-dione Beginning with (indol-3-yl)acetamide and (5,5-dimethyl-5,6-dihydro-4H-pyrrolo[3,2,1-ij]quinolin-1-yl)oxo-acetic acid methyl ester, the title compound was prepared essentially as described in Example 1.

MS (IS, m/z) $C_{25}H_{21}N_3O_2$ (M$^+$−1)=394

EXAMPLE 26

3-(4,4-dimethyl-5,6-dihydro-4H-pyrrolo[3,2,1-ij]quinolin-1-yl)-4-(1H-indol-3-yl)pyrrole-2,5-dione Beginning with (indol-3-yl)acetamide and (4,4-dimethyl-5,6-dihydro-4H-pyrrolo[3,2,1-ij]quinolin-1-yl)oxo-acetic acid methyl ester, the title compound was prepared essentially as described in Example 1.

MS (IS, m/z) $C_{25}H_{21}N_3O_2$ (M$^+$+1)=396

EXAMPLE 27

3-(4-methyl-8-fluoro-5,6-dihydro-4H-pyrrolo[3,2,1-ij]quinolin-1-yl)-4-(4-fluoro-1H-indol-3-yl)pyrrole-2,5-dione Beginning with (4-fluoroindol-3-yl)acetamide and (4-methyl-8-fluoro-5,6-dihydro-4H-pyrrolo[3,2,1-ij]quinolin-1-yl)oxoacetic acid methyl ester, the title compound was prepared essentially as described in Example 1.

MS (EI, m/z) $C_{24}H_{17}N_3O_2F_2$ (M$^+$+1)=418

EXAMPLE 28

3-(6,6-dimethyl-8-fluoro-5,6-dihydro-4H-pyrrolo[3,2,1-ij]quinolin-1-yl)-4-(1H-indol-3-yl)pyrrole-2,5-dione Beginning with (indol-3-yl)acetamide and (6,6-dimethyl-8-fluoro-5,6-dihydro-4H-pyrrolo[3,2,1-ij]quinolin-1-yl)oxoacetic acid methyl ester, the title compound was prepared essentially as described in Example 1.

MS (IS, m/z) $C_{25}H_{20}N_3O_2F$ (M$^+$+1)=414

EXAMPLE 29

3-(6,6-dimethyl-5,6-dihydro-4H-pyrrolo[3,2,1-ij]quinolin-1-yl)-4-(6-fluoro-1H-indol-3-yl)pyrrole-2,5-dione Beginning with (6-fluoroindol-3-yl)acetamide and (6,6-dimethyl-5,6-dihydro-4H-pyrrolo[3,2,1-ij]quinolin-1-yl)oxoacetic acid methyl ester, the title compound was prepared essentially as described in Example 1.

MS (IS, m/z) $C_{25}H_{20}N_3O_2F$ (M$^+$+1)=414

EXAMPLE 30

3-(6,6-dimethyl-5,6-dihydro-4H-pyrrolo[3,2,1-ij]quinolin-1-yl)-4-(6-trifluoromethyl-1H-indol-3-yl)pyrrole-2,5-dione Beginning with (6-(trifluoromethyl)indol-3-yl)acetamide and (6,6-dimethyl-5,6-dihydro-4H-pyrrolo[3,2,1-ij]

quinolin-1-yl)oxoacetic acid methyl ester, the title compound was prepared essentially as described in Example 1.

MS (IS, m/z) $C_{26}H_{20}N_3O_2F_3$ (M$^+$+1)=464

EXAMPLE 31

3-(5,5-dimethyl-5,6-dihydro-4H-pyrrolo[3,2,1-ij]quinolin-1-yl)-4-(6-fluoro-1H-indol-3-yl)pyrrole-2,5-dione Beginning with (6-fluoroindol-3-yl)acetamide and (5,5-dimethyl-5,6-dihydro-4H-pyrrolo[3,2,1-ij]quinolin-1-yl)oxoacetic acid methyl ester, the title compound was prepared essentially as described in Example 1.

MS (IS, m/z) $C_{25}H_{20}N_3O_2F$ (M$^+$−1)=412

EXAMPLE 32

3-(4,4-dimethyl-5,6-dihydro-4H-pyrrolo[3,2,1-ij]quinolin-1-yl)-4-(6-fluoro-1H-indol-3-yl)pyrrole-2,5-dione Beginning with (6-fluoroindol-3-yl)acetamide and (4,4-dimethyl-5,6-dihydro-4H-pyrrolo[3,2,1-ij]quinolin-1-yl)oxoacetic acid methyl ester, the title compound was prepared essentially as described in Example 1.

MS (IS, m/z) $C_{25}H_{20}N_3O_2F$ (M$^+$−1)=412

EXAMPLE 33

3-(4,4,6,9-tetramethyl-5,6-dihydro-4H-pyrrolo[3,2,1-ij]quinolin-1-yl)-4-(1H-indol-3-yl)pyrrole-2,5-dione Beginning with (indol-3-yl)acetamide and (4,4,6,9-tetramethyl-5,6-dihydro-4H-pyrrolo[3,2,1-ij]quinolin-1-yl)oxoacetic acid methyl ester, the title compound was prepared essentially as described in Example 1.

MS (IS, m/z) $C_{27}H_{25}N_3O_2$ (M$^+$+1)=424

EXAMPLE 34

3-(6,6-dimethyl-8-fluoro-5,6-dihydro-4H-pyrrolo[3,2,1-ij]quinolin-1-yl)-4-(4-fluoro-1H-indol-3-yl)pyrrole-2,5-dione Beginning with (4-fluoroindol-3-yl)acetamide and (6,6-dimethyl-8-fluoro-5,6-dihydro-4H-pyrrolo[3,2,1-ij]quinolin-1-yl)oxoacetic acid methyl ester, the title compound was prepared essentially as described in Example 1.

MS (IS, m/z) $C_{25}H_{19}N_3O_2F_2$ (M$^+$+1)=432

EXAMPLE 35

3-(6,6-dimethyl-8-fluoro-5,6-dihydro-4H-pyrrolo[3,2,1-ij]quinolin-1-yl)-4-(6-fluoro-1H-indol-3-yl)pyrrole-2,5-dione Beginning with (6-fluoroindol-3-yl)acetamide and (6,6-dimethyl-8-fluoro-5,6-dihydro-4H-pyrrolo[3,2,1-ij]quinolin-1-yl)oxoacetic acid methyl ester, the title compound was prepared essentially as described in Example 1.

MS (IS, m/z) $C_{25}H_{19}N_3O_2F_2$ (M$^+$−1)=430

EXAMPLE 36

3-(6,6-dimethyl-8-fluoro-5,6-dihydro-4H-pyrrolo[3,2,1-ij]quinolin-1-yl)-4-(6-bromo-1H-indol-3-yl)pyrrole-2,5-dione Beginning with (6-bromoindole)-3-glyoxylic acid methyl esterand 2-(6,6-dimethyl-8-fluoro-5,6-dihydro-4H-pyrrolo[3,2,1-ij]quinolin-1-yl)-acetamide, the title compound was prepared essentially as described in Example 1.

MS (IS, m/z) $C_{25}H_{19}N_3O_2BrF$ (M$^+$+1)=492

EXAMPLE 37

3-(6,6-dimethyl-8-fluoro-5,6-dihydro-4H-pyrrolo[3,2,1-ij]quinolin-1-yl)-4-(6-methoxy-1H-indol-3-yl)pyrrole-2,5-dione Beginning with (6-methoxyindol-3-yl)acetamide and (6,6-dimethyl-8-fluoro-5,6-dihydro-4H-pyrrolo[3,2,1-ij]quinolin-1-yl)oxoacetic acid methyl ester, the title compound was prepared essentially as described in Example 1.

EXAMPLE 38

3-(5,6-dihydro-4H-pyrrolo[3,2,1-ij]quinolin-1-yl)-4-(6-(pyridin-3-yl)-1H-indol-3-yl)pyrrole-2,5-dione Beginning with (6-(pyridin-3-yl)indol-3-yl)oxoacetic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{28}H_{20}N_4O_2$ (M$^+$−1)=443

EXAMPLE 39

3-(5,6-dihydro-4H-pyrrolo[3,2,1-ij]quinolin-1-yl)-4-(6-(pyridin-4-yl)-1H-indol-3-yl)pyrrole-2,5-dione Beginning with (6-(pyridin-4-yl)indol-3-yl)oxoacetic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{28}H_{20}N_4O_2$ (M$^+$−1)=443

EXAMPLE 40

3-(5,6-dihydro-4H-pyrrolo[3,2,1-ij]quinolin-1-yl)-4-(6-(4-fluorophenyl)-1H-indol-3-yl)pyrrole-2,5-dione Beginning with (6-(4-fluorophenyl)indole)-3-glyoxylic acid methyl ester and 2-(5,6-dihydro-4H-pyrrolo[3,2,1-ij]quinolin-1-yl)acetamide, the title compound was prepared essentially as described in Example 1.

MS (IS, M/z) $C_{29}H_{20}N_3O_2F$ (M$^+$−1)=460

EXAMPLE 41

3-(8-fluoro-6,6-dimethyl-5,6-dihydro-4H-pyrrolo[3,2,1-ij]quinolin-1-yl)-4-(6-(pyridin-3-yl)-1H-indol-3-yl)pyrrole-2,5-dione Beginning with (6-(pyridin-3-yl)indole)-3-glyoxylic acid methyl ester and 2-(8-fluoro-6,6-dimethyl-5,6-dihydro-4H-pyrrolo[3,2,1-ij]quinolin-1-yl)acetamide, the title compound was prepared essentially as described in Example 1.

MS (IS, M/z) $C_{30}H_{23}N_4O_2F$ (M$^+$−1)=489

EXAMPLE 42

3-(5,6-dihydro-4H-pyrrolo[3,2,1-ij]quinolin-1-yl)-4-(7-(1-carboxyeth-2-yl)-1H-indol-3-yl)pyrrole-2,5-dione Beginning with (7-(1-carboxyeth-2-yl)indol-3-yl)-3-glyoxylic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{26}H_{21}N_3O_4$ (M$^+$+1)=440

EXAMPLE 43

3-(5,6-dihydro-4H-pyrrolo[3,2,1-ij]quinolin-1-yl)-4-(7-(1-(triisopropylsilyloxy)prop-3-yl)-1H-indol-3-yl)pyrrole-2,5-dione Beginning with (7-(1-triisopropylsilyloxy)prop-3-yl)indole)-3-glyoxylic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{35}H_{43}N_3O_3Si$ (M$^+$+1)=582

EXAMPLE 44

3-(8-fluoro-6,6-dimethyl-5,6-dihydro-4H-pyrrolo[3,2,1-ij]quinolin-1-yl)-4-(7-(1-(triisopropylsilyloxy)prop-3-yl)-1H-indol-3-yl)pyrrole-2,5-dione Beginning with (7-(1-triisopropylsilyloxy)prop-3-yl)indole)-3-glyoxylic acid methyl ester and 2-(8-fluoro-6,6-dimethyl-5,6-dihydro-4H-pyrrolo[3,2,1-ij]quinolin-1-yl)acetamide, the title compound was prepared essentially as described in Example 1.

MS (IS, m/z) $C_{37}H_{46}N_3O_3SiF$ (M$^+$−1)=626

EXAMPLE 45

3-(5,6-dihydro-4H-pyrrolo[3,2,1-ij]quinolin-1-yl)-4-(6-(1-(ethoxycarbonyl)eth-2-yl)-1H-indol-3-yl)pyrrole-2,5-dione Beginning with (6-(1-(ethoxycarbonyl)eth-2-yl)indole)-3-glyoxylic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{28}H_{25}N_3O_4$ (M$^+$−1)=466

EXAMPLE 46

3-(5,6-dihydro-4H-pyrrolo[3,2,1-ij]quinolin-1-yl)-4-(7-(2-carboxyeth-2-yl)-1H-indol-3-yl)pyrrole-2,5-dione Beginning with (7-(2-carboxyeth-2-yl)indole)-3-glyoxylic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{26}H_{21}N_3O_4$ (M$^+$−1)=438

EXAMPLE 47

3-(5,6-dihydro-4H-pyrrolo[3,2,1-ij]quinolin-1-yl)-4-(6-(1-(triisopropylsilyloxy)prop-3-yl)-1H-indol-3-yl)pyrrole-2,5-dione Beginning with (6-(1-triisopropylsilyloxy)prop-3-yl)indole)-3-glyoxylic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{35}H_{43}N_3O_3Si$ (M$^+$−1)=580

EXAMPLE 48

3-(5,5-dimethyl-5,6-dihydro-4H-pyrrolo[3,2,1-ij]quinolin-1-yl)-4-(6-[N-tert-butoxycarbonyl]aminomethyl)-1H-indol-3-yl)pyrrole-2,5-dione Beginning with (6-[N-tert-butoxycarbonyl]aminomethyl)-indol-3-yl)acetamide and (5,5-dimethyl-5,6-dihydro-4H-pyrrolo[3,2,1-ij]quinolin-1-yl)oxoacetic acid methyl ester, the title compound was prepared essentially as described in Example 1.

MS (IS, m/z) $C_{31}H_{30}N_4O_4$ (M$^+$+1)=523

EXAMPLE 49

3-(5,6-dihydro-4H-pyrrolo[3,2,1-ij]quinolin-1-yl)-4-(6-(triisopropylsilyloxy)methyl)-1H-indol-3-yl)pyrrole-2,5-dione Beginning with (6-(triisopropylsilyloxymethyl)indole)-3-glyoxylic acid methyl ester and 2-(5,6-dihydro-4H-pyrrolo[3,2,1-ij]quinolin-1-yl)acetamide, the title compound was prepared essentially as described in Example 1.

MS (IS, m/z) $C_{33}H_{36}N_3O_3Si$ (M$^+$+1)=554

EXAMPLE 50

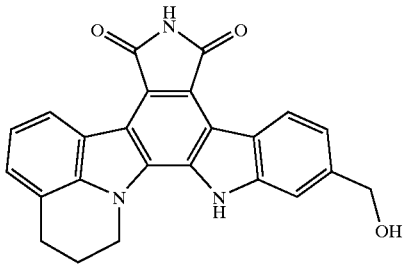

2-(hydroxymethyl)-11H, 12H, 14H-pyrrolo[3,4-c]quinolino[8',8a',1':3,2,1]pyrrolo[2,3-a]carbazole-5,7-dione Beginning with 2-(triisopropylsilyloxymethyl)-11H, 12H, 14H-pyrrolo[3,4-c]quinolino[8',8a',1':3,2,1]pyrrolo-[2,3-a]carbazole-5,7-dione, the title compound was prepared essentially as described in Example 70.

MS (IS, m/z) $C_{24}H_{17}N_3O_3$ (M$^+$−1)=394

EXAMPLE 51

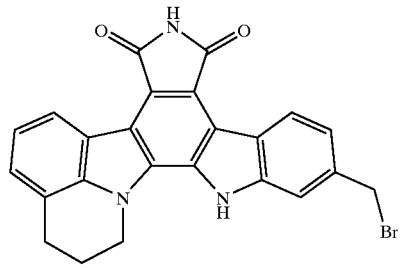

2-(bromomethyl)-11H, 12H, 14H-pyrrolo[3,4-c]quinolino[8',8a',1':3,2,1]pyrrolo[2,3-a]carbazole-5,7-dione Triphenylphosphite (2.54 g, 8.19 mmol) was added dropwise to a solution of bromine (1.30 g, 8.19 mmol) in dimethylformamide (40.0 mL) and pyridine (4 drops) at −15° C. with stirring under N$_2$. After the mixture was stirred for 15 minutes at −15° C., a solution of 2-(hydroxymethyl)-11H, 12H, 14H-pyrrolo[3,4-c]quinolino[8',8a',1':3,2,1]pyrrolo-[2,3-a]carbazole-5,7-dione (1.08 g, 2.73 mmol) in dimethylformamide (20 mL) was added dropwise at the same temperature, and the solution was stirred for 3 hours at room temperature. The mixture was concentrated in high vacuum and diluted with toluene and hexane. The crude material (1.2 g) was used directly for further reaction without additional purification.

EXAMPLE 52

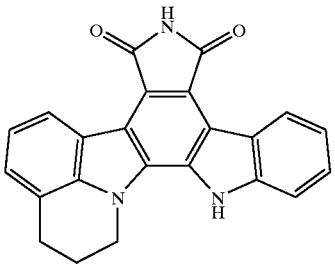

11H, 12H, 14H-pyrrolo[3,4-c]quinolino[8',8a',1':3,2,1]-pyrrolo[2,3-a]carbazole-5,7-dione A mixture of 3-(5,6-Dihydro-4H-pyrrolo[3,2,1-ij]quinolin-1-yl)-4-(1H-indol-3-yl)pyrrole-2,5-dione (1.0 g, 2.72 mmol) and Pd(OAc)$_2$ (0.611 g, 2.72 mmol) in 60 mL of AcOH was stirred at reflux for 3.5 hours. The reaction mixture was cooled to room temperature and filtered through Celite and a silica gel pad with EtOAc (200 mL) followed by DMF (200 mL). After concentration, the residue was stirred in 200 mL of EtOH for 20 minutes and the solid was filtered, rinsing with water (100 mL) and hexanes (50 mL). The product was vacuum-dried to give 725 mg (73%) of the title compound as a yellow solid.

MS (IS, m/z): $C_{23}H_{15}N_3O_2$ (M$^+$+1)=366.

EXAMPLE 53

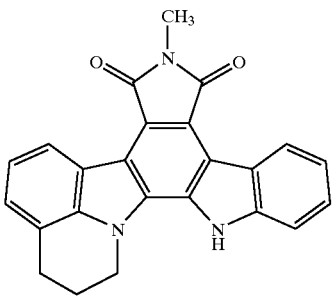

6-Methyl-11H, 12H, 14H-pyrrolo[3,4-c]-quinolino[8',8a',1':3,2,1]pyrrolo[2,3-a]carbazole-5,7-dione Beginning with 1-methyl-3-(5,6-dihydro-4H-pyrrolo[3,2,1-ij]quinolin-1-yl)-4-(1H-indol-3-yl)pyrrole-2,5-dione (1.0 g, 2.6 mmol) and Pd(OAc)$_2$ (0.58 g, 2.6 mmol), 0.72 g (73%) of the title compound were prepared essentially as described in Example 52.

$^1$H NMR (500 MHz, DMSO) δ 11.8 (bs, 1H), 9.0 (d, 1H, J=7.8 Hz), 8.6 (d, 1H, J=7.6 Hz), 7.7 (d, 1H, J=8.0 Hz), 7.5 (m, 1H), 7.3 (m, 1H), 7.2 (m, 2H), 4.6 (bs, 2H), 3.5 (s, 3H), 2.7 (s, 2H), 2.25 (s, 2H).

EXAMPLE 54

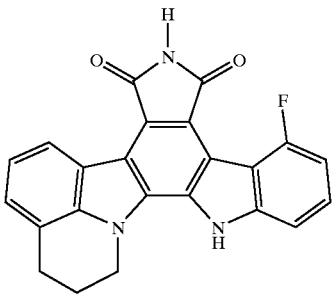

4-Fluoro-1H, 12H, 14H-pyrrolo[3,4-c]-quinolino[8',8a',1':3,2,1]pyrrolo[2,3-a]carbazole-5,7-dione Beginning with 3-(5,6-dihydro-4H-pyrrolo[3,2,1-ij]quinolin-1-yl)-4-(4-fluoro-1H-indol-3-yl)pyrrole-2,5-dione, the title compound was prepared as a yellow-green solid essentially as described in Example 52.

MS (IS, m/z) $C_{23}H_{14}FN_3O_2$ (M$^+$+1)=386

EXAMPLE 55

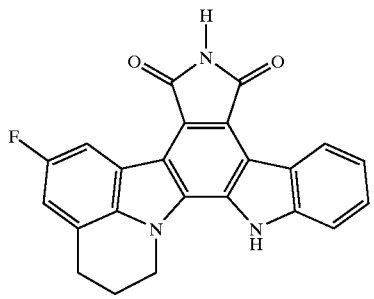

9-Fluoro-11H, 12H, 14H-pyrrolo[3,4-c]-quinolino[8',8a',1':3,2,1]pyrrolo[2,3-a]carbazole-5,7-dione A solution of 3-(8-fluoro-5,6-dihydro-4H-pyrrolo[3,2,1-ij]quinolin-1-yl)-4-(1H-indol-3-yl)pyrrole-2,5-dione (1.5 mmol) and iodine (0.020 g, 0.079 mmol) in 400 mL of dioxane was irradiated in a photochemical reactor using a medium-pressure mercury lamp. The internal temperature rose to 42° C. After 3 hours the reaction mixture was concentrated under reduced pressure to a volume of about 50 mL. The remaining material was diluted with 400 mL ethyl acetate and was washed sequentially with 50 mL of saturated aqueous sodium bisulfite, 50 mL of water, and 50 mL of saturated aqueous sodium chloride. The remaining organics were dried over sodium sulfate, filtered, and concentrated under reduced pressure. The residue was subjected to silica gel chromatography, eluting with a gradient of toluene containing 10–80% tetrahydrofuran. Fractions containing product were combined and concentrated under reduced pressure to provide the title compound.

MS (EI, m/z) $C_{23}H_{14}FN_3O_2$ (M−1)=382

EA Calculated for $C_{23}H_{14}FN_3O_{2-0.75}H_2O$: C, 69.60; H, 3.94; N, 10.59. Found: C, 69.78; H, 3.78; N, 10.13.

EXAMPLE 56

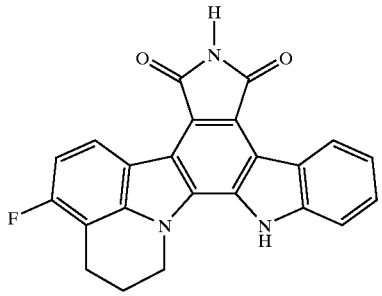

10-Fluoro-11H, 12H, 14H-pyrrolo[3,4-c]-quinolino[8',8a',1':3,2,1]pyrrolo[2,3-a]carbazole-5,7-dione Beginning with 3-(7-fluoro-5,6-dihydro-4H-pyrrolo[3,2,1-ij]quinolin-1-yl)-4-(1H-indol-3-yl)pyrrole-2,5-dione, the title compound was prepared essentially as described in Example 55.

MS (EI, m/z) $C_{23}H_{14}FN_3O_2$ (M−1)=382

EA Calculated for $C_{23}H_{14}FN_3O_2$—$H_2O$: C, 68.82; H, 4.02; N, 10.47. Found: C, 69.05; H, 3.77; N, 10.30.

EXAMPLE 57

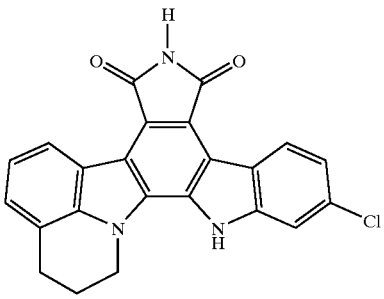

2-Chloro-11H, 12H, 14H-pyrrolo[3,4-c]-quinolino[8',8a',1':3,2,1]pyrrolo[2,3-a]carbazole-5,7-dione Beginning with 3-(5,6-dihydro-4H-pyrrolo[3,2,1-ij]quinolin-1-yl)-4-(6-chloro-1H-indol-3-yl)pyrrole-2,5-dione, the title compound was prepared essentially as described in Example 52.

MS (IS, m/z) $C_{23}H_{14}ClN_3O_2$ (M$^+$−1)=398

EXAMPLE 58

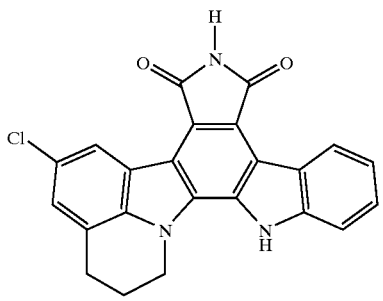

9-Chloro-11H, 12H, 14H-pyrrolo[3,4-c]-quinolino[8',8a',1':3,2,1]pyrrolo[2,3-a]carbazole-5,7-dione A mixture of 3-(8-chloro-5,6-dihydro-4H-pyrrolo[3,2,1-ij]quinolin-1-yl)-4-(1H-indol-3-yl)pyrrole-2,5-dione (1.53 mmol) and palladium acetate (0.38 g, 1.69 mmol) in 70 mL of acetic acid was stirred at 65° C. for 6.5 hours. The reaction mixture was filtered through a pad of silica gel with tetrahydrofuran. The product was concentrated under reduced pressure and the residue subjected to silica gel chromatography, eluting with a gradient of toluene containing from 5–30% tetrahydrofuran. Fractions containing product were combined and concentrated under reduced pressure to provide the title compound.

MS (EI, m/z) $C_{23}H_{14}ClN_3O_2$ (M−1)=398

EXAMPLE 59

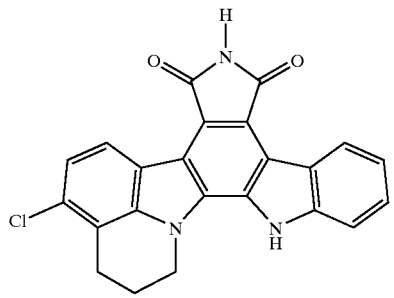

10-Chloro-11H, 12H, 14H-pyrrolo[3,4-c]-quinolino[8',8a',1':3,2,1]pyrrolo[2,3-a]carbazole-5,7-dione Beginning with 3-(7-chloro-5,6-dihydro-4H-pyrrolo[3,2,1-ij]quinolin-1-yl)-4-(1H-indol-3-yl)pyrrole-2,5-dione, the title compound was prepared essentially as described in Example 58.

MS (EI, m/z) $C_{23}H_{14}ClN_3O_2$ (M−1)=398

EXAMPLE 60

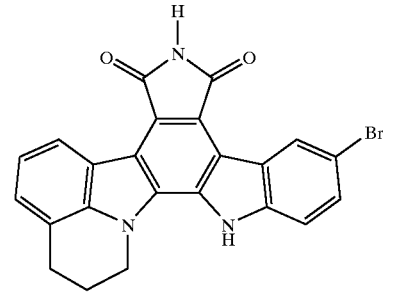

3-Bromo-11H, 12H, 14H-pyrrolo[3,4-c]-quinolino[8',8a',1':3,2,1]pyrrolo[2,3-a]carbazole-5,7-dione A solution of 3-(5,6-dihydro-4H-pyrrolo[3,2,1-ij]quinolin-1-yl)-4-(5-bromo-1H-indol-3-yl)pyrrole-2,5-dione (0.050 g, 0.11 mmol), 2,3-dichloro-5,6-dicyano-1,4-benzoquinone (DDQ, 0.028 g, 0.12 mmol) and p-toluenesulfonic acid monohydrate (1 mg) in 2 mL benzene was stirred for 4 hours at reflux and then at room temperature overnight. The reaction mixture was diluted with 20 mL of ethyl acetate and 5 mL of tetrahydrofuran. The resulting solution was then washed sequentially with 2×10 mL 2N sodium hydroxide, 2×10 mL of water, and 2×10 mL of saturated aqueous sodium chloride. The remaining organic phase was concentrated under reduced pressure and the residue treated with methanol. The resulting suspension was filtered to provide 0.025 g (50%) of the title compound as a yellow solid.

MS (IS, m/z) $C_{23}H_{14}BrN_3O_2$ (M$^+$−1)=442

EXAMPLE 61

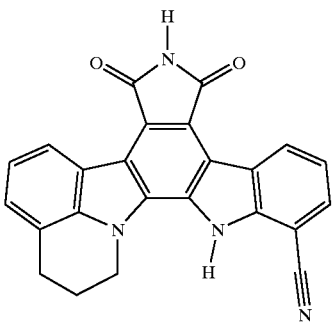

1-Cyano-11H, 12H, 14H-pyrrolo[3,4-c]-quinolino[8',8a',1':3,2,1]pyrrolo[2,3-a]carbazole-5,7-dione Beginning with 3-(5,6-dihydro-4H-pyrrolo[3,2,1-ij]quinolin-1-yl)-4-(7-cyano-1H-indol-3-yl)pyrrole-2,5-dione, the title compound was prepared essentially as described in Example 58.

$^1$H NMR (DMSO-$d_6$, 400 MHz) δ: 2.18 (2H, br), 2.93 (2H, br), 4.25–4.26 (2H, m), 7.30 (1H, d, J=6.8 Hz), 7.36 (1H, t, J=8.0 Hz), 7.72 (1H, d, J=8.0 Hz), 8.14 (1H, d, J=7.2 Hz), 8.73 (1H, t, J=8.2 Hz), 9.13 (1H, d, J=8.0 Hz), 11.13 (1H, s), 12.51 (1H, s)

MS (EI, m/z) $C_{24}H_{14}N_4O_2$ (M$^+$+1)=391

EXAMPLE 62

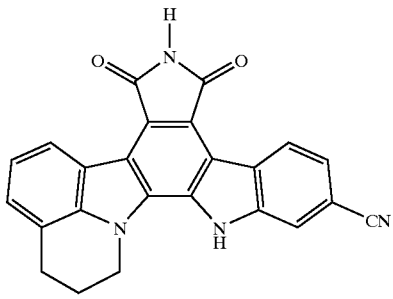

2-Cyano-11H, 12H, 14H-pyrrolo[3,4-c]-quinolino[8',8a',1':3,2,1]pyrrolo[2,3-a]carbazole-5,7-dione Beginning with 3-(5,6-dihydro-4H-pyrrolo[3,2,1-ij]quinolin-1-yl)-4-(6-cyano-1H-indol-3-yl)pyrrole-2,5-dione, the title compound was prepared essentially as described in Example 58.

MS (EI, m/z) $C_{24}H_{14}N_4O_2$ (M$^+$−1)=389

EXAMPLE 63

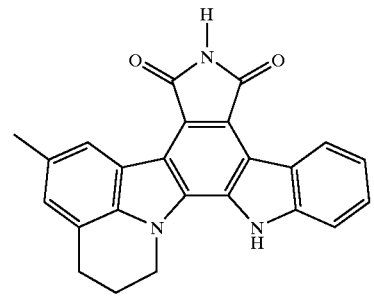

9-Methyl-11H, 12H, 14H-pyrrolo[3,4-c]-quinolino[8',8a',1':3,2,1]pyrrolo[2,3-a]carbazole-5,7-dione Beginning with 3-(8-methyl-5,6-dihydro-4H-pyrrolo[3,2,1-ij]quinolin-1-yl)-4-(1H-indol-3-yl)pyrrole-2,5-dione, the title compound was prepared essentially as described in Example 58.

MS (EI, m/z) $C_{24}H_{17}N_3O_2$ (M$^+$+1)=380

EXAMPLE 64

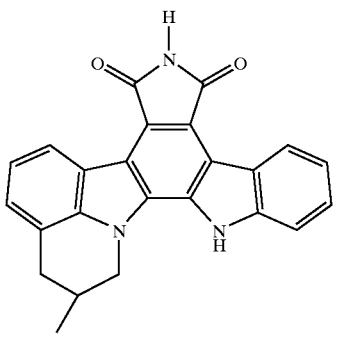

12-Methyl-11H, 12H, 14H-pyrrolo[3,4-c]-quinolino[8',8a',1':3,2,1]pyrrolo[2,3-a]carbazole-5,7-dione Beginning with 3-(5-methyl-5,6-dihydro-4H-pyrrolo[3,2,1-ij]quinolin-1-yl)-4-(1H-indol-3-yl)pyrrole-2,5-dione, the title compound was prepared essentially as described in Example 58.

MS (EI, M/z) $C_{24}H_{17}N_3O_2$ (M$^+$+1)=380

EXAMPLE 65

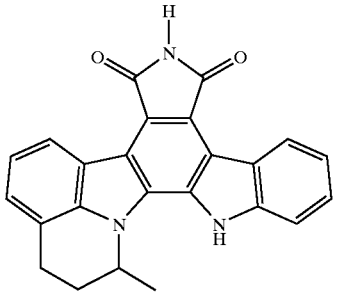

13-Methyl-11H, 12H, 14H-pyrrolo[3,4-c]-quinolino[8',8a',1':3,2,1]pyrrolo[2,3-a]carbazole-5,7-dione Beginning with 3-(4-methyl-5,6-dihydro-4H-pyrrolo[3,2,1-ij]quinolin-1-yl)-4-(1H-indol-3-yl)pyrrole-2,5-dione, the title compound was prepared essentially as described in Example 58.

MS (EI, m/z) $C_{24}H_{17}N_3O_2$ $(M^+-1)=378$

EXAMPLE 66

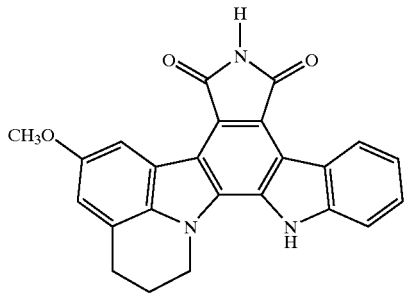

9-Methoxy-11H, 12H, 14H-pyrrolo[3,4-c]-quinolino[8',8a',1':3,2,1]pyrrolo[2,3-a]carbazole-5,7-dione Beginning with 3-(8-methoxy-5,6-dihydro-4H-pyrrolo[3,2,1-ij]quinolin-1-yl)-4-(1H-indol-3-yl)pyrrole-2,5-dione, the title compound was prepared essentially as described in Example 58.

MS (IS, m/z) $C_{24}H_{17}N_3O_3$ $(M^++1)=396$

EXAMPLE 67

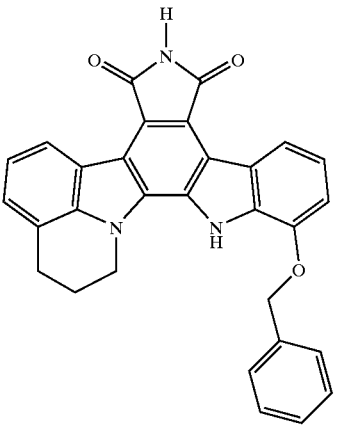

1-Benzyloxy-11H, 12H, 14H-pyrrolo[3,4-c]-quinolino[8',8a',1':3,2,1]pyrrolo[2,3-a]carbazole-5,7-dione A solution of 3-(5,6-dihydro-4H-pyrrolo[3,2,1-ij]quinolin-1-yl)-4-(7-benzyloxy-1H-indol-3-yl)pyrrole-2,5-dione (49.0 mg, 0.084 mmol) in 20 mL of tetrahydrofuran and 4 mL of acetone was irradiated (wavelength 280–380 nm) at room temperature for three weeks essentially as described in Example 150 to provide 31.0 mg (77.9%) of the title compound.

MS (IS, m/z) $C_{30}H_{21}N_3O_3$ $(M^+-1)=470$

EXAMPLE 68

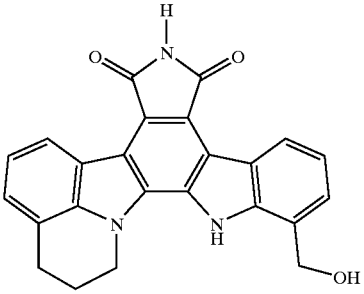

1-(Hydroxymethyl)-11H, 12H, 14H-pyrrolo[3,4-c]-quinolino[8',8a',1':3,2,1]pyrrolo[2,3-a]carbazole-5,7-dione Beginning with 3-(7-(Triisopropylsilyloxy)methyl-1H-indol-3-yl)-4-(5,6-dihydro-4H-pyrrolo [3,2,1-ij]quinolin-1-yl)-pyrrole-2,5-dione, the title compound was prepared essentially as described in Example 58 and 70.

MS (IS, m/z) $C_{33}H_{38}N_3O_3Si$ $(M^+-1)=552$

EXAMPLE 69

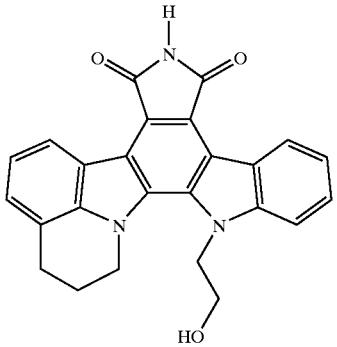

14-(2-Hydroxyeth-1-yl)-11H, 12H, 14H-pyrrolo[3,4-c]-quinolino[8',8a',1':3,2,1]pyrrolo[2,3-a]carbazole-5,7-dione.

A solution of 3-(5,6-dihydro-4H-pyrrolo[3,2,1-ij]quinolin-1-yl)-4-(1H-indol-3-yl)-1-methyl-pyrrole-2,5-dione (3.8 g, 9.96 mmol) and potassium tert-butoxide (1.2 g, 10.96 mmol) in 100 mL dimethylformamide was stirred for 45 minutes at room temperature. To this solution were then added 2-bromoethyl acetate (1.2 mL, 10.96 mmol) and the resulting mixture was stirred for 10 hours at 50° C. The mixture was then poured into 500 mL of cold water and stirred. The resulting suspension was filtered and the filter cake was rinsed with water and dried. This solid was then dissolved in 146 mL methanol and the resulting solution was treated with 7.2 mL of 1.5 N sodium hydroxide in methanol. After stirring for 6 hours at room temperature the resulting suspension was filtered and the recovered solid dissolved in dichloromethane. The resulting solution was washed sequentially with dilute hydrochloric acid, water, and saturated aqueous sodium chloride. The remaining organic phase was dried over sodium sulfate, filtered, and concentrated under reduced pressure. The residue was subjected to silica gel chromatography, eluting with dichloromethane containing ethanol. Fractions containing product were combined and concentrated under reduced pressure to provide the title compound.

$^1$H NMR (500 MHz, DMSO) δ 11.0 (bs, 1H), 9.25 (d, 1H, J=7.9 Hz), 8.9 (d, 1H, J=8.0 Hz), 7.9 (d, 1H, J=8.3 Hz), 7.6 (m, 1H), 7.4 (m, 3H), 4.9 (bs, 1H), 3.8 (bs, 2H), 3.1 (bs, 2H), 2.05 (bs, 2H).

EXAMPLE 70

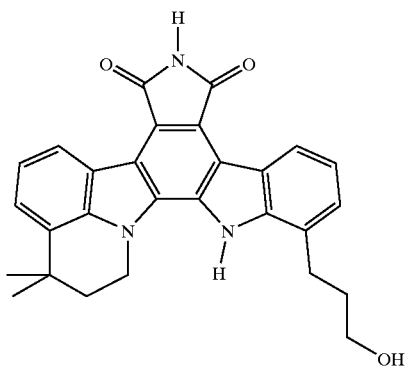

10,10-Dimethyl-1-(3-hydroxy)prop-1-yl)-11H, 12H, 14H-pyrrolo[3,4-c]-quinolino[8',8a',1':3,2,1]pyrrolo-[2,3-a]carbazole-5,7-dione Beginning with 3-(7-(3-(triisopropyl)silyloxyprop-1-yl)-1H-indol-3-yl)-4-(6,6-dimethyl-5,6-dihydro-4H-pyrrolo[3,2,1-ij]quinolin-1-yl)pyrrole-2,5-dione, 10,10-dimethyl-1-(3-(triisopropylsilyloxy)prop-1-yl)-11H, 12H, 14H-pyrrolo[3,4-c]-quinolino[8',8a',1':3,2,1]pyrrolo-[2,3-a]carbazole-5,7-dione was prepared essentially as described in Example 58.

MS (IS, m/z) $C_{37}H_{44}N_3O_3Si$ (M$^+$−1)=607

A solution of 10,10-Dimethyl-1-(3-(triisopropylsilyloxy)prop-1-yl)-11H, 12H, 14H-pyrrolo[3,4-c]quinolino-[8',8a',1':3,2,1]pyrrolo-[2,3-a]carbazole-5,7-dione (3.80 mMol) in 200 mL of anhydrous tetrahydrofuran was treated with tetrabutylammonium fluoride (3.8 mL, 3.8 mmol, 1M in tetrahydrofuran). The reaction mixture was stirred at room temperature for 8 hours and the resulting solid was filtered and recrystallized from tetrahydrofuran to provide the title compound.

MS (IS, m/z) $C_{28}H_{24}N_3O_3$ (M$^+$−1)=450

EXAMPLE 71

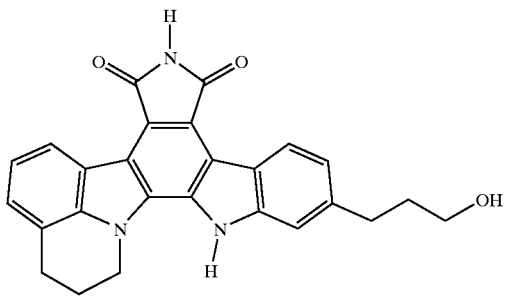

2-(3-hydroxyprop-1-yl)-11H, 12H, 14H-pyrrolo[3,4-c]-quinolino[8',8a',1':3,2,1]pyrrolo[2,3-a]carbazole-5,7-dione Beginning with 3-(6-(3-(triisopropylsilyloxy)prop-1-yl)-1H-indol-3-yl)-4-(5,6-dihydro-4H-pyrrolo[3,2,1-ij]quinolin-1-yl)pyrrole-2,5-dione, the title compound was prepared essentially as described in Example 70.

MS (IS, m/z) $C_{26}H_{22}N_3O_3$ (M$^+$−1)=422

EXAMPLE 72

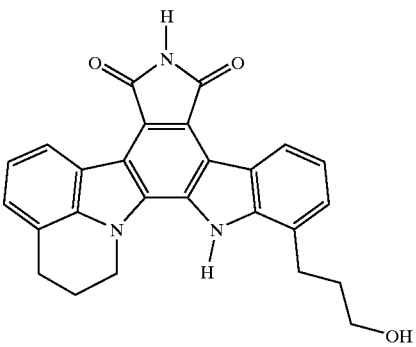

1-(3-hydroxyprop-1-yl)-11H, 12H, 14H-pyrrolo[3,4-c]-quinolino[8',8a',1':3,2,1]pyrrolo[2,3-a]carbazole-5,7-dione Beginning with 3-(7-(3-(triisopropylsilyloxy)prop-1-yl)-1H-indol-3-yl)-4-(5,6-dihydro-4H-pyrrolo[3,2,1-ij]quinolin-1-yl)pyrrole-2,5-dione, the title compound was prepared essentially as described in Example 70.

MS (IS, m/z) $C_{26}H_{22}N_3O_3$ (M$^+$−1)=422

EXAMPLE 73

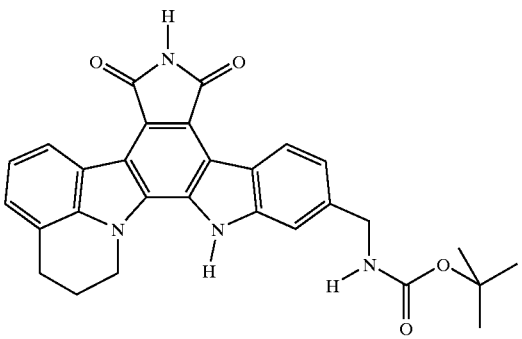

2-([N-tert-butoxycarbonyl]aminomethyl)-11H, 12H, 14H-pyrrolo[3,4-c]-quinolino[8',8a',1':3,2,1]pyrrolo[2,3-a]carbazole-5,7-dione Beginning with 3-(5,6-Dihydro-4H-pyrrolo[3,2,1-ij]quinolin-1-yl)-4-[6-([N-tert-butoxycarbonyl]aminomethyl)-1H-indol-3-yl]pyrrole-2,5-dione, the title compound was prepared essentially as described in Example 55.

MS (IS, m/z) $C_{29}H_{26}N_4O_4$ (M$^+$−1)=493

EXAMPLE 74

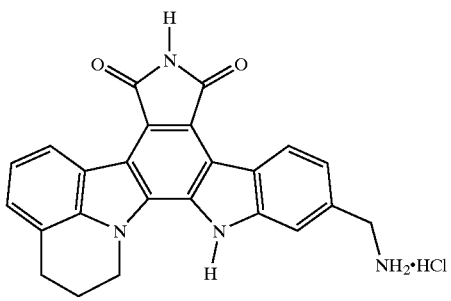

2-(aminomethyl)-11H, 12H, 14H-pyrrolo[3,4-c]-quinolino[8',8a',1':3,2,1]pyrrolo[2,3-a]carbazole-5,7-dione Hydrochloride A mixture of 2-([N-tert-butoxycarbonyl]aminomethyl)-11H, 12H, 14H-pyrrolo[3,4-c]-quinolino[8',8a',1':3,2,1]pyrrolo[2,3-a]carbazole-5,7-dione in dichloromethane and 4M hydrogen chloride in dioxane was stirred at room temperature for 18 hours. The mixture was concentrated under reduced pressure and the residue suspended in diethyl ether. The resulting suspension was filtered and dried under reduced pressure to provide the title compound.

$^1$H NMR (DMSO-$d_6$, 400 MHz) δ: 2.45–2.49 (2H, m), 3.18 (2H, t, J=6.4 Hz), 4.33 (2H, d, J=6.4 Hz), 4.97 (2H, t, J=6.0 Hz), 7.33 (1H, t, J=8.0 Hz), 7.39 (1H, d, J=7.6 Hz), 7.49 (1H, d, J=8.0 Hz), 7.88 (1H, s), 8.37 (3H, br), 8.79 (1H, d, J=8.0 Hz), 9.10 (1H, d, J=8.0 Hz), 11.08 (1H, s), 12.34 (1H, s)

EXAMPLE 75

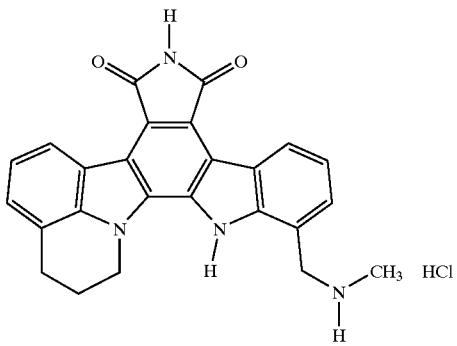

1-(aminomethyl)-11H, 12H, 14H-pyrrolo[3,4-c]-quinolino[8',8a',1':3,2,1]pyrrolo[2,3-a]carbazole-5,7-dione Hydrochloride Beginning with 3-(5,6-Dihydro-4H-pyrrolo[3,2,1-ij]quinolin-1-yl)-4-[7-([N-methyl N-tert-butoxycarbonyl]-aminomethyl)-1H-indol-3-yl]pyrrole-2,5-dione, the title compound was prepared essentially as described in Examples 73 and 74.

MS (IS, m/z) $C_{25}H_{20}N_4O_2$ (M$^+$−1)=407

EXAMPLE 76

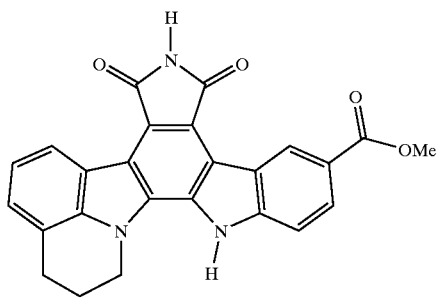

3-(methoxycarbonyl)-11H, 12H, 14H-pyrrolo[3,4-c]-quinolino[8',8a',1':3,2,1]pyrrolo[2,3-a]carbazole-5,7-dione Beginning with 3-(5,6-Dihydro-4H-pyrrolo[3,2,1-ij]quinolin-1-yl)-4-[5-(methoxycarbonyl)-1H-indol-3-yl]pyrrole-2,5-dione, the title compound was prepared essentially as described in Example 52.

MS (IS, m/z) $C_{25}H_{17}N_3O_2$ (M$^+$−1)=422

EXAMPLE 77

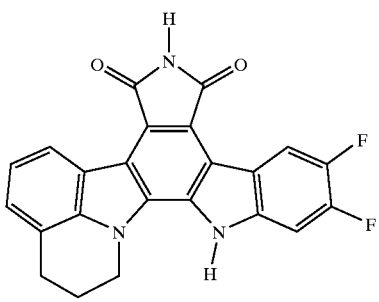

2,3-difluoro-11H, 12H, 14H-pyrrolo[3,4-c]-quinolino[8',8a',1':3,2,1]pyrrolo[2,3-a]carbazole-5,7-dione Beginning with 3-(5,6-Dihydro-4H-pyrrolo[3,2,1-ij]quinolin-1-yl)-4-[5,6-difluoro-1H-indol-3-yl]pyrrole-2,5-dione, the title compound was prepared essentially as described in Example 52.

MS (IS, m/z) $C_{23}H_{13}N_3O_2F_2$ (M$^+$+1)=402

EXAMPLE 78

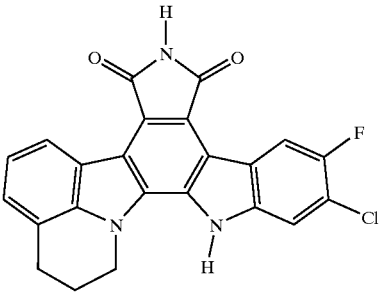

2-chloro-3-fluoro-11H, 12H, 14H-pyrrolo[3,4-c]-quinolino[8',8a',1':3,2,1]pyrrolo[2,3-a]carbazole-5,7-dione Beginning with 3-(5,6-Dihydro-4H-pyrrolo[3,2,1-ij]quinolin-1-yl)-4-[5-fluoro-6-chloro-1H-indol-3-yl]pyrrole- 2,5-dione, the title compound was prepared essentially as described in Example 58.

MS (IS, m/z) $C_{23}H_{13}N_3O_2ClF$ (M$^+$−1)=416

EXAMPLE 79

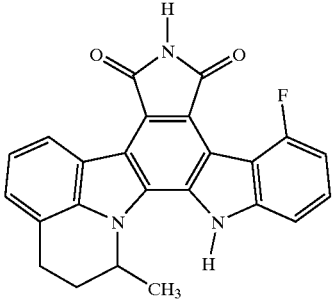

4-fluoro-13-methyl-11H, 12H, 14H-pyrrolo[3,4-c]-quinolino[8',8a',1':3,2,1]pyrrolo[2,3-a]carbazole-5,7-dione Beginning with 3-(4-methyl-5,6-dihydro-4H-pyrrolo[3,2,1-ij]quinolin-1-yl)-4-(4-fluoro-1H-indol-3-yl)pyrrole-2,5-dione, the title compound was prepared essentially as described in Example 58.

MS (EI, m/z) $C_{24}H_{16}N_3O_2F$ (M$^+$+1)=398

EXAMPLE 80

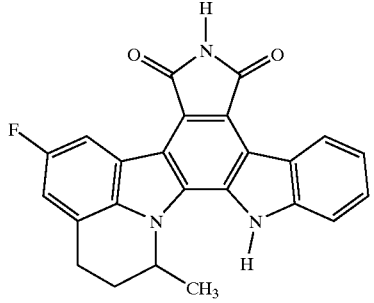

9-fluoro-13-methyl-1H, 12H, 14H-pyrrolo[3,4-c]-quinolino[8',8a',1':3,2,1]pyrrolo[2,3-a]carbazole-5,7-dione Beginning with 3-(4-methyl-8-fluoro-5,6-dihydro-4H-pyrrolo[3,2,1-ij]quinolin-1-yl)-4-[1H-indol-3-yl]pyrrole-2,5-dione, the title compound was prepared essentially as described in Example 58.

MS (EI, m/z) $C_{24}H_{16}N_3O_2F$ (M$^+$+1)=398

EXAMPLE 81

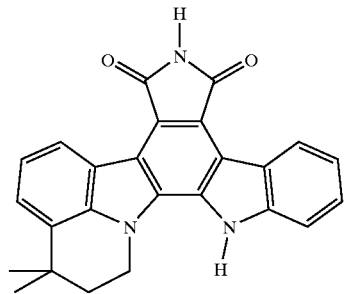

11,11-dimethyl-11H, 12H, 14H-pyrrolo[3,4-c]-quinolino[8',8a',1':3,2,1]pyrrolo[2,3-a]carbazole-5,7-dione Beginning with 3-(6,6-dimethyl-5,6-dihydro-4H-pyrrolo[3,2,1-ij]quinolin-1-yl)-4-(1H-indol-3-yl)pyrrole-2,5-dione, the title compound was prepared essentially as described in Example 52.

MS (IS, m/z) $C_{25}H_{19}N_3O_2$ (M$^+$+1)=394

EXAMPLE 82

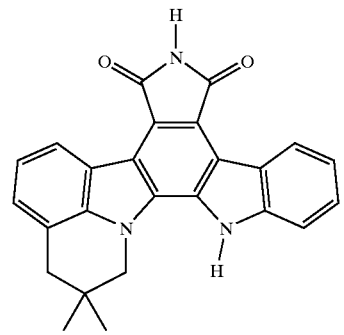

12,12-dimethyl-11H, 12H, 14H-pyrrolo[3,4-c]-quinolino[8',8a',1':3,2,1]pyrrolo[2,3-a]carbazole-5,7-dione Beginning with 3-(5,5-dimethyl-5,6-dihydro-4H-pyrrolo[3,2,1-ij]quinolin-1-yl)-4-(1H-indol-3-yl)pyrrole-2,5-dione, the title compound was prepared essentially as described in Example 55.

MS (IS, m/z) $C_{25}H_{19}N_3O_2$ (M$^+$−1)=392

EXAMPLE 83

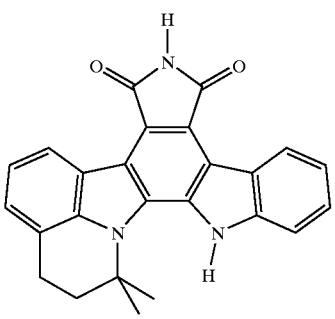

13,13-dimethyl-11H, 12H, 14H-pyrrolo[3,4-c]-quinolino[8',8a',1':3,2,1]pyrrolo[2,3-a]carbazole-5,7-dione Beginning with 3-(4,4-dimethyl-5,6-dihydro-4H-pyrrolo[3,2,1-ij]quinolin-1-yl)-4-(1H-indol-3-yl)pyrrole-2,5-dione, the title compound was prepared essentially as described in Example 55.

MS (IS, m/z) $C_{25}H_{19}N_3O_2$ (M$^+$+1)=394

EXAMPLE 84

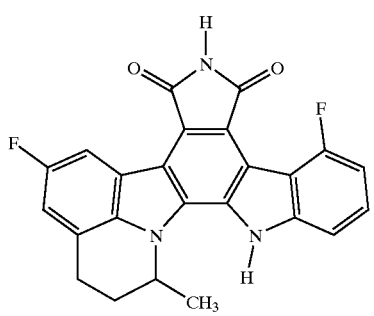

4,9-difluoro-13-methyl-11H, 12H, 14H-pyrrolo[3,4-c]-quinolino[8',8a',1':3,2,1]pyrrolo[2,3-a]carbazole-5,7-dione Beginning with 3-(4-methyl-8-fluoro-5,6-dihydro-4H-pyrrolo[3,2,1-ij]quinolin-1-yl)-4-(4-fluoro-1H-indol-3-yl)pyrrole-2,5-dione, the title compound was prepared essentially as described in Example 58.

MS (EI, m/z) $C_{24}H_{15}N_3O_2F_2$ (M$^+$+1)=416

EXAMPLE 85

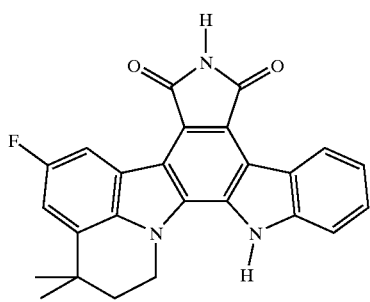

9-fluoro-11,11-dimethyl-11H, 12H, 14H-pyrrolo[3,4-c]-quinolino[8',8a',1':3,2,1]pyrrolo[2,3-a]carbazole-5,7-dione Beginning with 3-(6,6-dimethyl-8-fluoro-5,6-dihydro-4H-pyrrolo[3,2,1-ij]quinolin-1-yl)-4-(1H-indol-3-yl)pyrrole-2,5-dione, the title compound was prepared essentially as described in Example 55.

MS (IS, m/z) $C_{25}H_{18}N_3O_2F$ (M$^+$-1)=410

EXAMPLE 86

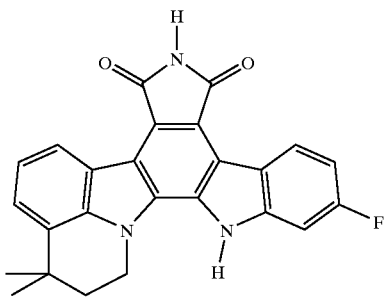

2-fluoro-11,11-dimethyl-11H, 12H, 14H-pyrrolo[3,4-c]-quinolino[8',8a',1':3,2,1]pyrrolo[2,3-a]carbazole-5,7-dione Beginning with 3-(6,6-dimethyl-5,6-dihydro-4H-pyrrolo[3,2,1-ij]quinolin-1-yl)-4-(6-fluoro-1H-indol-3-yl)pyrrole-2,5-dione, the title compound was prepared essentially as described in Example 52.

MS (IS, m/z) $C_{25}H_{18}N_3O_2F$ (M$^+$-1)=410

EXAMPLE 87

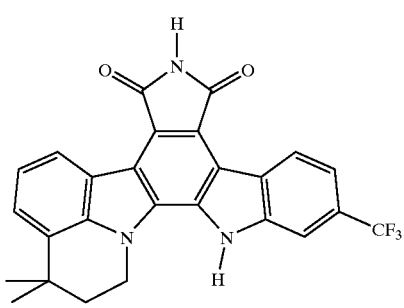

2-trifluoromethyl-11,11-dimethyl-11H, 12H, 14H-pyrrolo[3,4-c]quinolino[8',8a',1':3,2,1]pyrrolo[2,3-a]carbazole-5,7-dione Beginning with 3-(6,6-dimethyl-5,6-dihydro-4H-pyrrolo[3,2,1-ij]quinolin-1-yl)-4-(6-trifluoromethyl-1H-indol-3-yl)pyrrole-2,5-dione, the title compound was prepared essentially as described in Example 52.

MS (IS, m/z) $C_{26}H_{18}N_3O_2F_3$ (M$^+$-1)=460

EXAMPLE 88

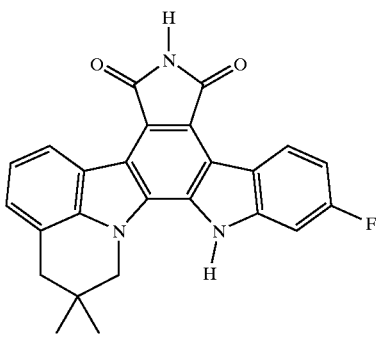

2-fluoro-12,12-dimethyl-11H, 12H, 14H-pyrrolo[3,4-c]-quinolino[8',8a',1':3,2,1]pyrrolo[2,3-a]carbazole-5,7-dione Beginning with 3-(5,5-dimethyl-5,6-dihydro-4H-pyrrolo[3,2,1-ij]quinolin-1-yl)-4-(6-fluoro-1H-indol-3-yl)pyrrole-2,5-dione, the title compound was prepared essentially as described in Example 58.

MS (IS, m/z) $C_{25}H_{18}N_3O_2F$ (M$^+$−1)=410

EXAMPLE 89

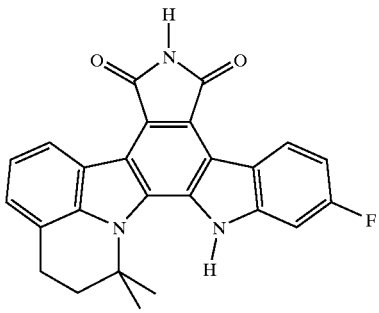

2-fluoro-13,13-dimethyl-11H, 12H, 14H-pyrrolo[3,4-c]-quinolino[8',8a',1':3,2,1]pyrrolo[2,3-a]carbazole-5,7-dione Beginning with 3-(4,4-dimethyl-5,6-dihydro-4H-pyrrolo[3,2,1-ij]quinolin-1-yl)-4-(6-fluoro-1H-indol-3-yl)pyrrole-2,5-dione, the title compound was prepared essentially as described in Example 55.

MS (IS, m/z) $C_{25}H_{18}N_3O_2F$ (M$^+$−1)=410

EXAMPLE 90

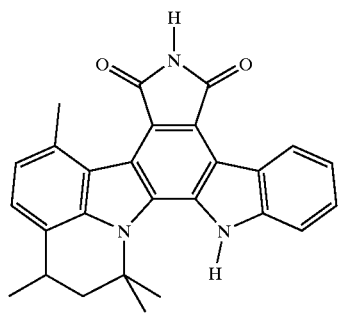

8,11,13,13-tetramethyl-11H, 12H, 14H-pyrrolo[3,4-c]-quinolino[8',8a',1':3,2,1]pyrrolo[2,3-a]carbazole-5,7-dione Beginning with 3-(4,4,6,9-tetramethyl-5,6-dihydro-4H-pyrrolo[3,2,1-ij]quinolin-1-yl)-4-(1H-indol-3-yl)pyrrole-2,5-dione, the title compound was prepared essentially as described in Example 55.

MS (IS, m/z) $C_{27}H_{23}N_3O_2$ (M$^+$+1)=422

EXAMPLE 91

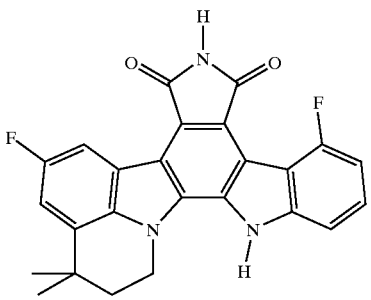

4,9-difluoro-11,11-dimethyl-11H, 12H, 14H-pyrrolo[3,4-c]-quinolino[8',8a',1':3,2,1]pyrrolo[2,3-a]carbazole-5,7-dione Beginning with 3-(6,6-dimethyl-8-fluoro-5,6-dihydro-4H-pyrrolo[3,2,1-ij]quinolin-1-yl)-4-(4-fluoro-1H-indol-3-yl)pyrrole-2,5-dione, the title compound was prepared essentially as described in Example 58.

MS (IS, m/z) $C_{25}H_{17}N_3O_2F_2$ (M$^+$+1)=430

EXAMPLE 92

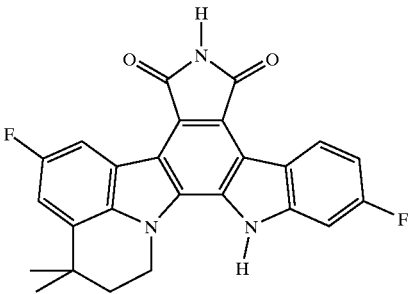

2,9-difluoro-11,11-dimethyl-11H, 12H, 14H-pyrrolo[3,4-c]-quinolino[8',8a',1':3,2,1]pyrrolo[2,3-a]carbazole-5,7-dione Beginning with 3-(6,6-dimethyl-8-fluoro-5,6-dihydro-4H-pyrrolo[3,2,1-ij]quinolin-1-yl)-4-(6-fluoro-1H-indol-3- yl)pyrrole-2,5-dione, the title compound was prepared essentially as described in Example 58.

MS (IS, m/z) $C_{25}H_{17}N_3O_2F_2$ (M$^+$−1)=428

EXAMPLE 93

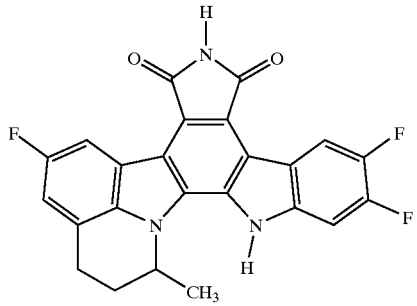

2,3,9-trifluoro-13-methyl-11H, 12H, 14H-pyrrolo[3,4-c]-quinolino[8',8a',1':3,2,1]pyrrolo[2,3-a]carbazole-5,7-dione Beginning with 3-(4-methyl-8-fluoro-5,6-dihydro-4H-pyrrolo[3,2,1-ij]quinolin-1-yl)-4-(5,6-difluoro-1H-indol-3-yl)pyrrole-2,5-dione, the title compound was prepared essentially as described in Example 55.

MS (EI, m/z) $C_{24}H_{14}N_3O_2F_3$ (M$^+$+1)=434

EXAMPLE 94

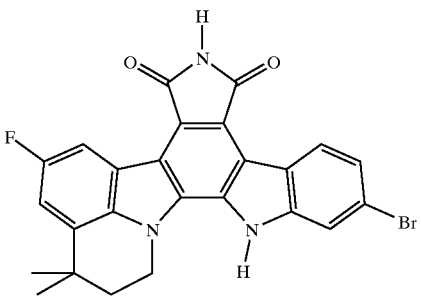

2-bromo-9-fluoro-11,11-dimethyl-11H, 12H, 14H-pyrrolo[3,4-c]-quinolino[8',8a',1':3,2,1]pyrrolo[2,3-a]carbazole-5,7-dione Beginning with 3-(6,6-dimethyl-8-fluoro-5,6-dihydro-4H-pyrrolo[3,2,1-ij]quinolin-1-yl)-4-(6-bromo-1H-indol-3-yl)pyrrole-2,5-dione, the title compound was prepared essentially as described in Example 60.

MS (IS, m/z) $C_{25}H_{17}N_3O_2BrF$ (M$^+$+1)=491

EXAMPLE 95

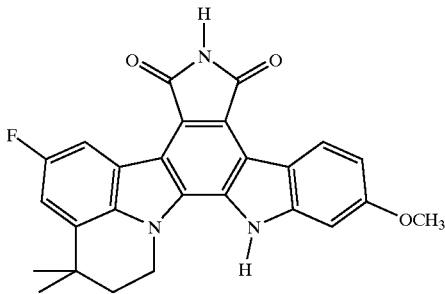

2-methoxy-9-fluoro-11,11-dimethyl-11H, 12H, 14H-pyrrolo[3,4-c]quinolino[8',8a',1':3,2,1]pyrrolo[2,3-a]carbazole-5,7-dione Beginning with 3-(6,6-dimethyl-8-fluoro-5,6-dihydro-4H-pyrrolo[3,2,1-ij]quinolin-1-yl)-4-(6-methoxy-1H-indol-3-yl)pyrrole-2,5-dione, the title compound was prepared essentially as described in Example 58.

MS (IS, m/z) $C_{26}H_{20}N_3O_3F$ (M$^+$+1)=442

EXAMPLE 96

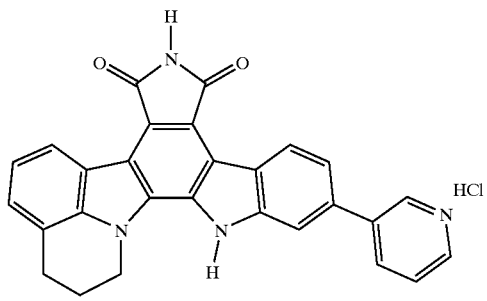

2-(pyridin-3-yl)-11H, 12H, 14H-pyrrolo[3,4-c]quinolino[8',8a',1':3,2,1]pyrrolo[2,3-a]carbazole-5,7-dione Hydrochloride Beginning with 3-(5,6-dihydro-4H-pyrrolo[3,2,1-ij]quinolin-1-yl)-4-(6-(pyridin-3-yl)-1H-indol-3-yl)pyrrole-2,5-dione, the title compound was prepared essentially as described in Example 55 and 136.

MS (IS, m/z) $C_{28}H_{18}N_4O_2$ (M$^+$−1)=441

EXAMPLE 97

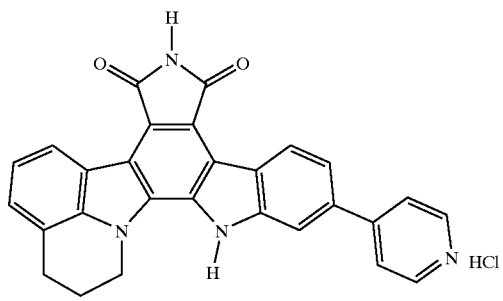

2-(pyridin-4-yl)-11H, 12H, 14H-pyrrolo[3,4-c]quinolino[8',8a',1':3,2,1]pyrrolo[2,3-a]carbazole-5,7-dione Hydrochloride Beginning with 3-(5,6-dihydro-4H-pyrrolo[3,2,1-ij]quinolin-1-yl)-4-(6-(pyridin-4-yl)-1H-indol-3-yl)pyrrole-2, 5-dione, the title compound was prepared essentially as described in Example 55 and 136.

MS (IS, m/z) $C_{28}H_{18}N_4O_2$ (M$^+$−1)=441

EXAMPLE 98

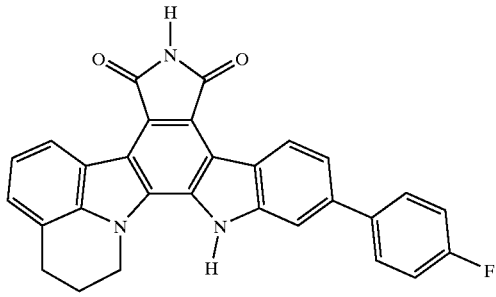

2-(4-fluorophenyl)-11H, 12H, 14H-pyrrolo[3,4-c] quinolino[8',8a',1':3,2,1]pyrrolo[2,3-a]carbazole-5,7-dione Beginning with 3-(5,6-dihydro-4H-pyrrolo[3,2,1-ij] quinolin-1-yl)-4-(6-(4-fluorophenyl)-1H-indol-3-yl) pyrrole-2,5-dione, the title compound was prepared essentially as described in Example 55.

MS (IS, m/z) $C_{29}H_{18}FN_3O_2$ (M$^+$−1)=458

EXAMPLE 99

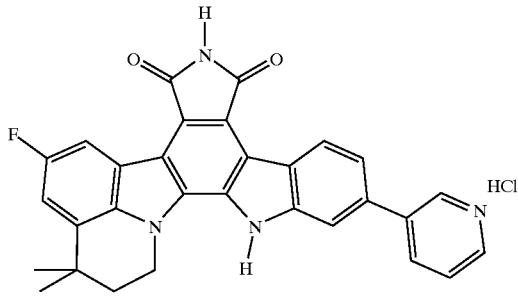

2-(pyridin-3-yl)-9-fluoro-11,11-dimethyl-11H, 12H, 14H-pyrrolo[3,4-c]quinolino[8',8a',1':3,2,1]pyrrolo [2,3-a]carbazole-5,7-dione Hydrochloride Beginning with 3-(8-fluoro-6,6-dimethyl-5,6-dihydro-4H-pyrrolo[3,2,1-ij]quinolin-1-yl)-4-(6-(pyridin-3-yl)-1H-indol-3-yl)pyrrole-2,5-dione, the title compound was prepared essentially as described in Example 55 and 136.

MS (IS, m/z) $C_{30}H_{21}N_4O_2F$ (M$^+$−1)=487

EXAMPLE 100

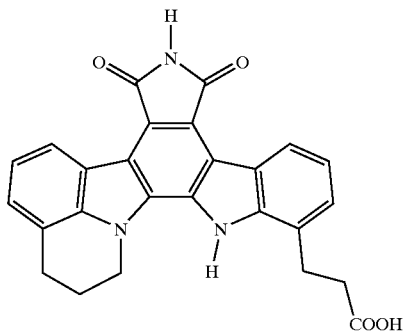

1-(1-carboxyeth-2-yl)-11H, 12H, 14H-pyrrolo[3,4-c] quinolino[8',8a',1':3,2,1]pyrrolo[2,3-a]carbazole-5,7-dione Beginning with 3-(5,6-dihydro-4H-pyrrolo[3,2,1-ij] quinolin-1-yl)-4-(7-(1-carboxyeth-2-yl)-1H-indol-3-yl) pyrrole-2,5-dione, the title compound was prepared essentially as described in Example 55.

MS (IS, m/z) $C_{26}H_{19}N_3O_4$ (M$^+$−1)=436

EXAMPLE 101

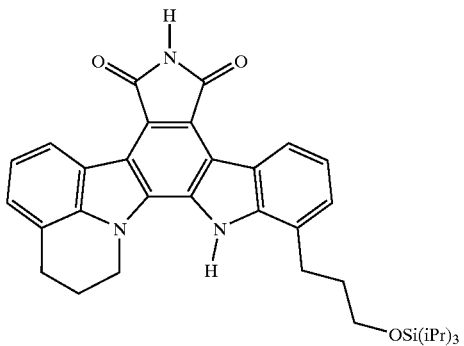

1-(1-(trimethylsilyloxy)prop-3-yl)-11H, 12H, 14H-pyrrolo[3,4-c]quinolino[8',8a',1':3,2,1]pyrrolo[2,3-a] carbazole-5,7-dione Beginning with 3-(5,6-dihydro-4H-pyrrolo[3,2,1-ij] quinolin-1-yl)-4-(7-(1-(triisopropylsilyloxy)prop-3-yl)-1H-indol-3-yl)pyrrole-2,5-dione, the title compound was prepared essentially as described in Example 58.

MS (IS, m/z) $C_{35}H_{41}N_3O_3Si$(M$^+$+1)=580

EXAMPLE 102

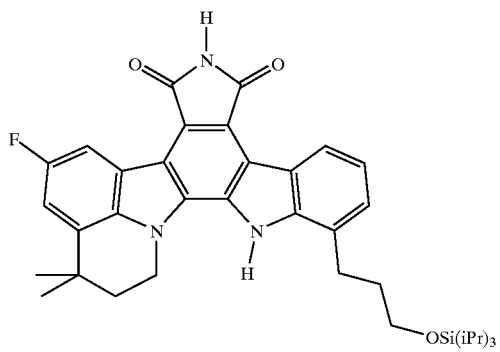

1-(1-(trimethylsilyloxy)prop-3-yl)-9-fluoro-11,11-dimethyl-11H, 12H, 14H-pyrrolo[3,4-c]quinolino[8', 8a',1':3,2,1]-pyrrolo[2,3-a]carbazole-5,7-dione Beginning with 3-(8-fluoro-6,6-dimethyl-5,6-dihydro-4H-pyrrolo[3,2,1-ij]quinolin-1-yl)-4-(7-(1-(triisopropylsilyloxy)prop-3-yl)-1H-indol-3-yl)pyrrole-2,5-dione, the title compound was prepared essentially as described in Example 58.

MS (IS, m/z) $C_{37}H_{44}N_3O_3SiF$ (M$^+$−1)=624

EXAMPLE 103

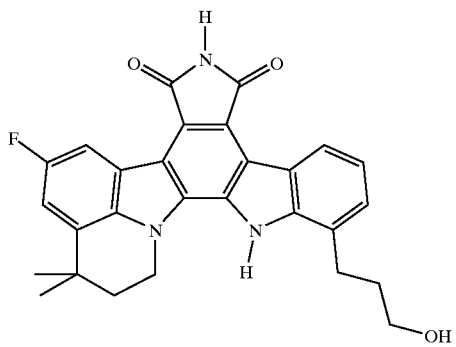

1-(1-hydroxyprop-3-yl)-9-fluoro-11,11-dimethyl-11H, 12H, 14H-pyrrolo[3,4-c]quinolino[8',8a',1':3,2,1]-pyrrolo[2,3-a]carbazole-5,7-dione Beginning with 1-(1-hydroxyprop-3-yl)-9-fluoro-11,11-dimethyl-11H, 12H, 14H-pyrrolo[3,4-c]quinolino-[8',8a',1':3,2,1]pyrrolo[2,3-a]carbazole-5,7-dione, the title compound was prepared essentially as described in Example 70.

MS (IS, m/z) $C_{28}H_{24}N_3O_3F$ (M$^+$−1)=468

EXAMPLE 104

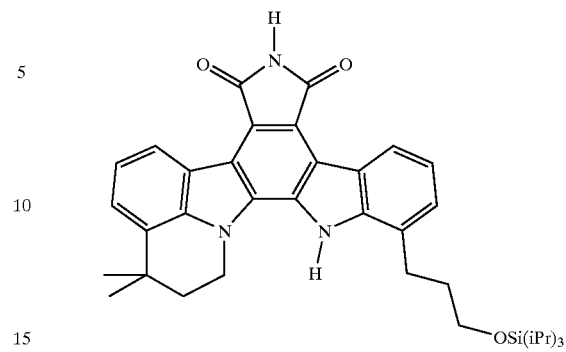

1-(1-(trimethylsilyloxy)prop-3-yl)-11,11-dimethyl-11H, 12H, 14H-pyrrolo[3,4-c]quinolino[8',8a',1':3,2,1]-pyrrolo[2,3-a]carbazole-5,7-dione Beginning with 3-(6,6-dimethyl-5,6-dihydro-4H-pyrrolo[3,2,1-ij]quinolin-1-yl)-4-(7-(1-(triisopropylsilyloxy)prop-3-yl)-1H-indol-3-yl)pyrrole-2,5-dione, the title compound was prepared essentially as described in Example 58.

MS (IS, m/z) $C_{37}H_{45}N_3O_3Si$ (M$^+$−1)=606

EXAMPLE 105

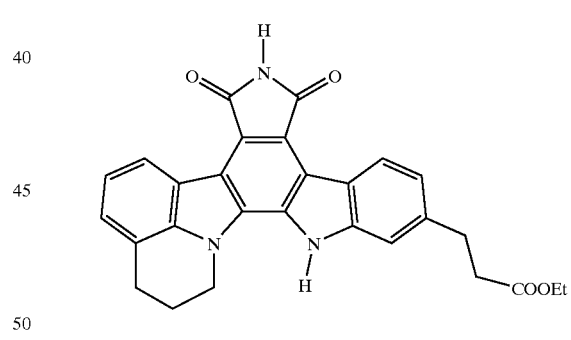

2-(1-(ethoxycarbonyl)eth-2-yl)-11H, 12H, 14H-pyrrolo[3,4-c]quinolino[8',8a',1':3,2,1]pyrrolo[2,3-a]carbazole-5,7-dione Beginning with 3-(5,6-dihydro-4H-pyrrolo[3,2,1-ij]quinolin-1-yl)-4-(6-(1-(ethoxycarbonyl)eth-2-yl)-1H-indol-3-yl)pyrrole-2,5-dione, the title compound was prepared essentially as described in Example 58.

MS (IS, m/z) $C_{28}H_{23}N_3O_4$ (M$^+$−1)=464

EXAMPLE 106

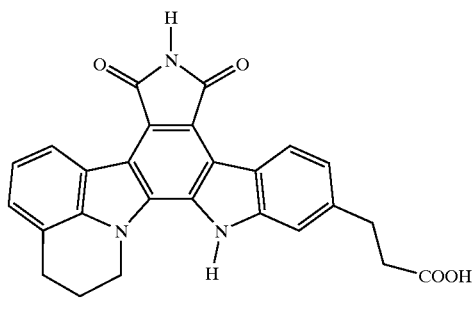

2-(1-carboxyeth-2-yl)-11H, 12H, 14H-pyrrolo[3,4-c]quinolino[8',8a',1':3,2,1]pyrrolo[2,3-a]carbazole-5,7-dione Beginning with 3-(5,6-dihydro-4H-pyrrolo[3,2,1-ij]quinolin-1-yl)-4-(6-(1-carboxyeth-2-yl)-1H-indol-3-yl)pyrrole-2,5-dione, the title compound was prepared essentially as described in Example 58.

MS (IS, m/z) $C_{26}H_{19}N_3O_4$ (M$^+$−1)=436

EXAMPLE 107

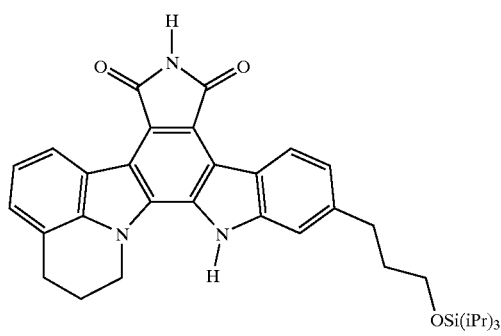

2-(1-(trimethylsilyloxy)prop-3-yl)-11H, 12H, 14H-pyrro[3,4-c]quinolino[8',8a',1':3,2,1]pyrrolo[2,3-a]carbazole-5,7-dione Beginning with 3-(5,6-dihydro-4H-pyrrolo[3,2,1-ij]quinolin-1-yl)-4-(7-(1-(triisopropylsilyloxy)prop-3-yl)-1H-indol-3-yl)pyrrole-2,5-dione, the title compound was prepared essentially as described in Example 58.

MS (IS, m/z) $C_{35}H_{41}N_3O_3Si$ (M$^+$−1)=578

EXAMPLE 108

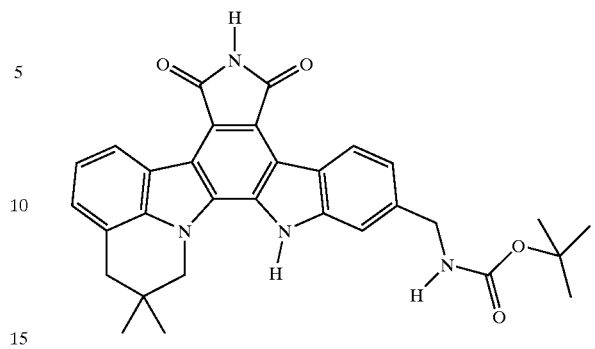

2-([N-tert-butoxycarbonyl]aminomethyl)-12,12-dimethyl-11H, 12H, 14H-pyrrolo[3,4-c]quinolino[8',8a',1':3,2,1]-pyrrolo[2,3-a]carbazole-5,7-dione Beginning with 3-(5,5-dimethyl-5,6-dihydro-4H-pyrrolo[3,2,1-ij]quinolin-1-yl)-4-(6-[N-tert-butoxycarbonyl]aminomethyl)-1H-indol-3-yl)pyrrole-2,5-dione, the title compound was prepared essentially as described in Example 55.

MS (IS, m/z) $C_{31}H_{30}N_4O_4$ (M$^+$−1)=521

EXAMPLE 109

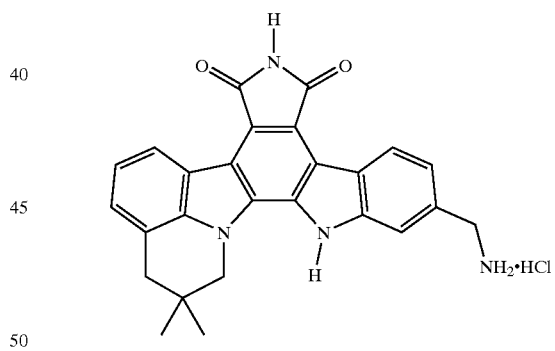

2-(aminomethyl)-12,12-dimethyl-11H, 12H, 14H-pyrrolo[3,4-c]quinolino[8',8a',1':3,2,1]-pyrrolo[2,3-a]carbazole-5,7-dione Hydrochloride Beginning with 2-([N-tert-butoxycarbonyl]aminomethyl)-12,12-dimethyl-11H, 12H, 14H-pyrrolo[3,4-c]quinolino-[8',8a',1':3,2,1]pyrrolo[2,3-a]carbazole-5,7-dione, the title compound was prepared essentially as described in Example 74.

MS (IS, m/z) $C_{26}H_{22}N_4O_2$ (M$^+$−1)=421

EXAMPLE 110

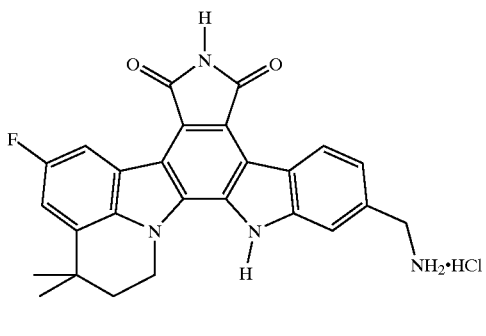

2-(aminomethyl)-9-fluoro-11,11-dimethyl-11H, 12H, 14H-pyrrolo[3,4-c]quinolino[8',8a',1':3,2,1]-pyrrolo[2,3-a]carbazole-5,7-dione Hydrochloride Beginning with 2-([N-tert-butoxycarbonyl]aminomethyl)-11,11-dimethyl-11H, 12H, 14H-pyrrolo[3,4-c]quinolino-[8',8a',1':3,2,1]pyrrolo[2,3-a]carbazole-5,7-dione, the title compound was prepared essentially as described in Example 74.

MS (IS, m/z) $C_{26}H_{21}FN_4O_2$ (M$^+$−1)=439

EXAMPLE 111

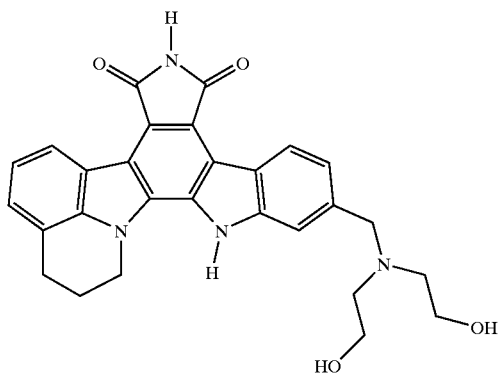

2-([N,N-di(1-hydroxyeth-2-yl)]aminomethyl)-11H, 12H, 14H-pyrrolo[3,4-c]quinolino[8',8a',1':3,2,1]-pyrrolo[2,3-a]carbazole-5,7-dione 2-Amino-1,3-propanediol (88.2 mg, 1.0 mmol) was added dropwise to a solution of 2-(bromomethyl)-11H, 12H, 14H-pyrrolo[3,4-c]quinolino[8',8a',1':3,2,1]pyrrolo-[2,3-a]carbazole-5,7-dione (100 mg, 0.2 mmol) in N-methylpyrrolidinone (5.0 mL) at room temperature. The reaction mixture was stirred under $N_2$ overnight. Water was added to dilute the solution, and the solid was filtered, washed with water, and dried over high vacuum to provide 51 mg (55%) of the title compound as a light yellow solid.

$^1$H NMR (DMSO-$d_6$, 400 MHz): δ 2.38–2.39 (2H, m), 2.67 (1H, br), 3.10 (2H, t, J=4.8 Hz), 3.45 (4H, d, J=11.4 Hz), 4.04 (2H, s), 4.88 (2H, t, J=4.8 Hz), 7.29 (2H, t, J=7.6 Hz), 7.30 (1H, d, J=8.0 Hz), 7.76 (1H, s), 8.72 (1H, d, J=8.0 Hz), 8.92 (1H, d, J=8.0 Hz), 10.95 (1H, 1H, s), 12.03 (1H, s)

EXAMPLE 112

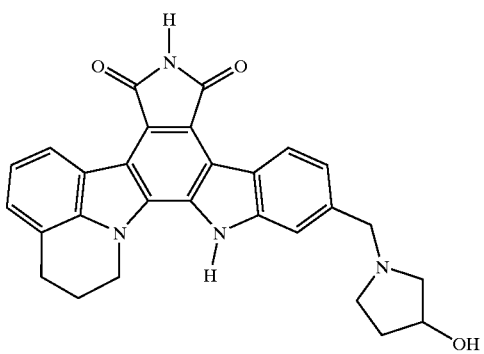

2-((3-hydroxypyrrolidin-1-yl)methyl)-11H, 12H, 14H-pyrrolo[3,4-c]quinolino[8',8a',1':3,2,1]-pyrrolo[2,3-a]carbazole-5,7-dione Beginning with 3-hydroxypyrrolidine and 2-(bromomethyl)-11H, 12H, 14H-pyrrolo[3,4-c]quinolino-[8',8a',1':3,2,1]pyrrolo[2,3-a]carbazole-5,7-dione, the title compound was prepared essentially as described in Example 111.

MS (IS, m/z) $C_{28}H_{24}N_4O_3$ (M$^+$+1)=465

EXAMPLE 113

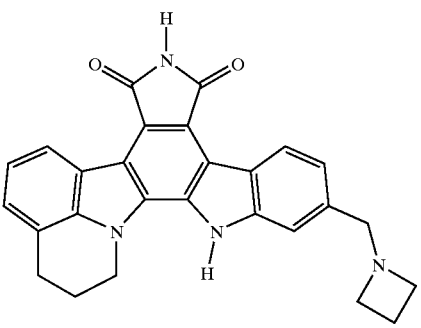

2-((azetidin-1-yl)methyl)-11H, 12H, 14H-pyrrolo[3, 4-c]quinolino[8',8a',1':3,2,1]-pyrrolo[2,3-a]carbazole-5,7-dione Beginning with azetidine and 2-(bromomethyl)-11H, 12H, 14H-pyrrolo[3,4-c]quinolino[8',8a',1':3,2,1]pyrrolo[2,3-a]carbazole-5,7-dione, the title compound was prepared essentially as described in Example 111.

MS (IS, m/z) $C_{27}H_{22}N_4O_2$ (M$^+$−1)=433

EXAMPLE 114

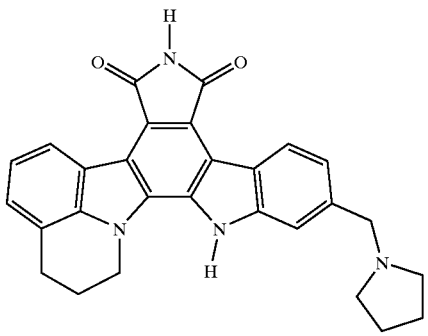

2-((azetidin-1-yl)methyl)-11H, 12H, 14H-pyrrolo[3,4-c]quinolino[8',8a',1':3,2,1]-pyrrolo[2,3-a]carbazole-5,7-dione Beginning with pyrrolidine and 2-(bromomethyl)-11H, 12H, 14H-pyrrolo[3,4-c]quinolino[8',8a',1':3,2,1]pyrrolo-[2,3-a]carbazole-5,7-dione, the title compound was prepared essentially as described in Example 111.

MS (IS, m/z) $C_{28}H_{24}N_4O_2$ (M$^+$+1)=449

EXAMPLE 115

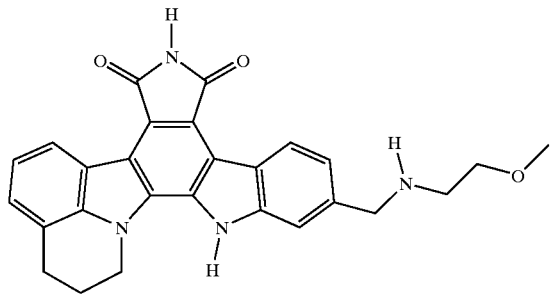

2-([N-(2-methoxyeth-1-yl)]aminomethyl)-11H, 12H, 14H-pyrrolo[3,4-c]quinolino[8',8a',1':3,2,1]-pyrrolo[2,3-a]carbazole-5,7-dione Trifluoroacetate A solution of (2-methoxyeth-1-yl)amine (0.4 mmol) in 1 mL N-methylpyrrolidinone was treated with a solution of 2-(bromomethyl)-11H, 12H, 14H-pyrrolo[3,4-c]quinolino-[8',8a',1':3,2,1]pyrrolo[2,3-a]carbazole-5,7-dione (1.0 mmol) in 3 mL of N-methylpyrrolidinone and was stirred for 18 hours at 60° C. The mixture was diluted with 7 mL of water and the resulting suspension filtered. The recovered solid was washed with water and dried then purified by HPLC with CH$_3$CN/H$_2$O and 1% trifluoroacetic acid.

$^1$H NMR (400 MHz, CD$_3$OD) δ 8.1 (s, 1H), 7.5 (s, 1H), 7.0 (m, 2H), 6.65 (m, 1H), 6.45 (m, 1H), 4.15 (s, 2H), 4.0 (m, 2H), 3.55 (m, 2H), 3.35 (s, 3H), 3.1 (m, 2H), 2.95 (m, 2H), 2.25 (m, 2H).

EXAMPLE 116

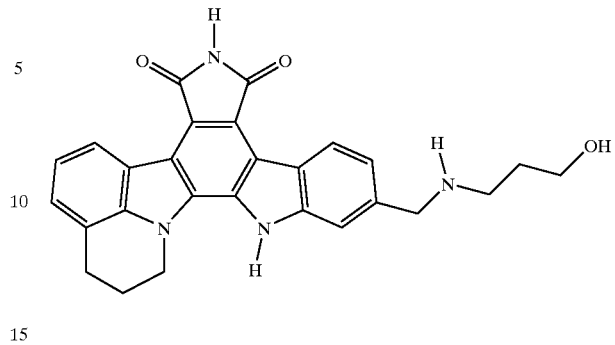

2-([N-(3-hydroxyprop-1-yl)]aminomethyl)-11H, 12H, 14H-pyrrolo[3,4-c]quinolino[8',8a',1':3,2,1]-pyrrolo[2,3-a]carbazole-5,7-dione Trifluoroacetate Beginning with propanolamine and 2-(bromomethyl)-11H, 12H, 14H-pyrrolo[3,4-c]quinolino[8',8a',1':3,2,1]-pyrrolo[2,3-a]carbazole-5,7-dione, the title compound was prepared essentially as described in Example 115.

$^1$H NMR (400 MHz, CD$_3$OD) δ 8.1 (s, 1H), 7.5 (s, 1H), 7.0 (m, 2H), 6.7 (m, 1H), 6.45 (m, 1H), 4.15 (s, 2H), 4.0 (m, 2H), 3.65 (m, 2H), 3.05 (m, 2H), 2.95 (m, 2H), 2.3 (m, 2H), 1.85 (m, 2H).

EXAMPLE 117

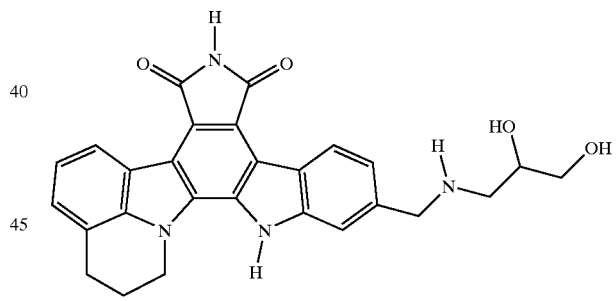

2-([N-(2,3-dihydroxyprop-1-yl)]aminomethyl)-11H, 12H, 14H-pyrrolo[3,4-c]quinolino[8',8a',1':3,2,1]-pyrrolo[2,3-a]carbazole-5,7-dione Trifluoroacetate Beginning with (2,3-dihydroxy)propylamine and 2-(bromomethyl)-11H, 12H, 14H-pyrrolo[3,4-c]quinolino-[8',8a',1':3,2,1]pyrrolo[2,3-a]carbazole-5,7-dione, the title compound was prepared essentially as described in Example 115.

$^1$H NMR (400 MHz, CD$_3$OD) δ 8.1 (s, 1H), 7.5 (s, 1H), 7.05 (m, 2H), 6.6 (m, 1H), 6.45 (m, 1H), 4.2 (s, 2H), 4.0 (m, 2H), 3.85 (m, 1H), 3.5 (m, 2H), 3.05 (m, 1H), 2.9 (m, 3H), 2.3 (m, 2H).

EXAMPLE 118

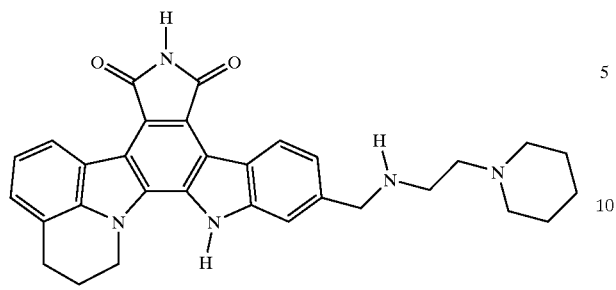

2-([N-(2,3-dihydroxyprop-1-yl)]aminomethyl)-11H, 12H, 14H-pyrrolo[3,4-c]quinolino[8',8a',1':3,2,1]-pyrrolo[2,3-a]carbazole-5,7-dione di-trifluoroacetate Beginning with 1-(2-aminoeth-1-yl)piperidine and 2-(bromomethyl)-11H, 12H, 14H-pyrrolo[3,4-c]quinolino-[8',8a',1':3,2,1]pyrrolo[2,3-a]carbazole-5,7-dione, the title compound was prepared essentially as described in Example 115.

$^1$H NMR (400 MHz, CD$_3$OD) δ 8.1 (s, 1H), 7.5 (s, 1H), 7.0 (m, 2H), 6.7 (m, 1H), 6.5 (m, 1H), 4.2 (s, 2H), 4.0 (m, 2H), 3.4 (m, 2H), 3.3 (m, 2H), 3.25 (m, 4H), 2.9 (m, 2H), 2.25 (m, 2H), 1.8 (bs, 4H), 1.65 (bs, 2H).

EXAMPLE 119

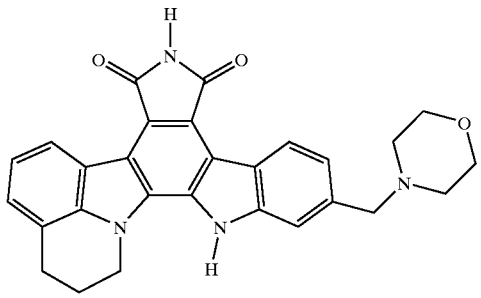

2-(morpholin-1-yl)methyl-11H, 12H, 14H-pyrrolo[3,4-c]quinolino[8',8a',1':3,2,1]-pyrrolo[2,3-a]carbazole-5,7-dione Beginning with morpholine and 2-(bromomethyl)-11H, 12H, 14H-pyrrolo[3,4-c]quinolino[8',8a',1':3,2,1]pyrrolo-[2,3-a]carbazole-5,7-dione, the title compound was prepared essentially as described in Example 111.

MS (IS, m/z) C$_{28}$H$_{24}$N$_4$O$_3$ (M$^+$+1)=465

EXAMPLE 120

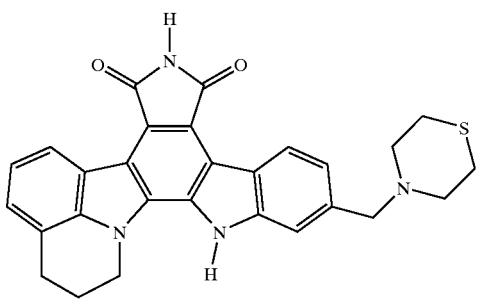

2-(thiomorpholin-1-yl)methyl-11H, 12H, 14H-pyrrolo[3,4-c]quinolino[8',8a',1':3,2,1]-pyrrolo[2,3-a]carbazole-5,7-dione Beginning with thiomorpholine and 2-(bromomethyl)-11H, 12H, 14H-pyrrolo[3,4-c]quinolino[8',8a',1':3,2,1]-pyrrolo[2,3-a]carbazole-5,7-dione, the title compound was prepared essentially as described in Example 111.

MS (IS, m/z) C$_{28}$H$_{24}$N$_3$O$_2$S (M$^+$+1)=481

EXAMPLE 121

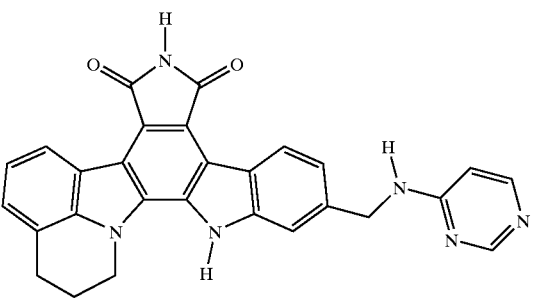

2-([N-(pyrimidin-4-yl)]aminomethyl)-11H, 12H, 14H-pyrrolo[3,4-c]quinolino[8',8a',1':3,2,1]-pyrrolo[2,3-a]carbazole-5,7-dione Trifluoroacetate Beginning with 4-aminopyrimidine and 2-(bromomethyl)-11H, 12H, 14H-pyrrolo[3,4-c]quinolino[8',8a',1':3,2,1]-pyrrolo[2,3-a]carbazole-5,7-dione, the title compound was prepared essentially as described in Example 115.

$^1$H NMR (400 MHz, CD$_3$OD) δ 11.55 (s, 1H), 8.85 (s, 1H), 8.7 (s, 1H), 8.05 (s, 1H), 8.0 (m, 1H), 7.45 (s, 1H), 7.0 (m, 2H), 6.7 (m, 1H), 6.6 (m, 1H), 6.4 (m, 1H), 5.25 (m, 2H), 4.0 (m, 2H), 2.95 (m, 2H), 2.2 (m, 2H).

EXAMPLE 122

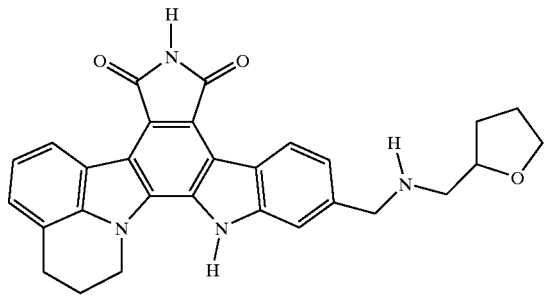

2-([N-((tetrahydrofur-2-yl)methyl)]aminomethyl)-
11H, 12H, 14H-pyrrolo[3,4-c]quinolino[8',8a',1':3,2,
1]-pyrrolo[2,3-a]carbazole-5,7-dione
Trifluoroacetate Beginning with 2-(aminomethyl)tetrahydrofuran and 2-(bromomethyl)-11H, 12H, 14H-pyrrolo[3,4-c]quinolino-[8',8a',1':3,2,1]pyrrolo[2,3-a]carbazole-5,7-dione, the title compound was prepared essentially as described in Example 115.

$^1$H NMR (400 MHz, CD$_3$OD) δ 8.1 (s, 1H), 7.5 (s, 1H), 7.0 (m, 2H), 6.7 (m, 1H), 6.45 (m, 1H), 4.2 (s, 2H), 4.0 (m, 2H), 3.85 (m, 1H), 3.8 (m, 1H), 3.0 (m, 2H), 2.9 (m, 2H), 2.85 (m, 1H), 2.3 (m, 2H), 2.05 (m, 1H), 1.95 (m, 2H), 1.5 (m, 1H).

EXAMPLE 123

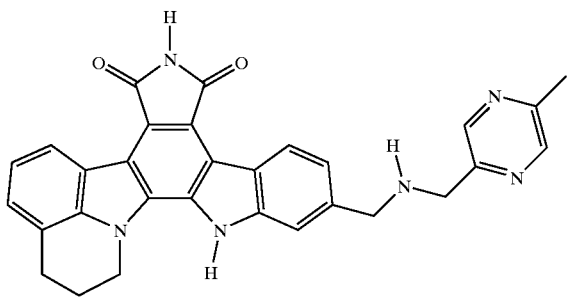

2-([N-(2-methylpyrazin-5-yl)]aminomethyl)-11H,
12H, 14H-pyrrolo[3,4-c]quinolino[8',8a',1':3,2,1]
pyrrolo[2,3-a]carbazole-5,7-dione Trifluoroacetate Beginning with 2-(aminomethyl)-5-methylpyrazine and 2-(bromomethyl)-11H, 12H, 14H-pyrrolo[3,4-c]quinolino-[8',8a',1':3,2,1]pyrrolo[2,3-a]carbazole-5,7-dione, the title compound was prepared essentially as described in Example 115.

$^1$H NMR (400 MHz, CD$_3$OD) δ 8.55 (s, 1H), 8.45 (s, 1H), 8.1 (s, 1H), 7.5 (s, 1H), 7.0 (m, 2H), 6.7 (m, 1H), 6.5 (m, 1H), 4.3 (m, 4H), 4.0 (m, 2H), 2.95 (m, 2H), 2.55 (s, 3H), 2.25 (m, 2H).

EXAMPLE 124

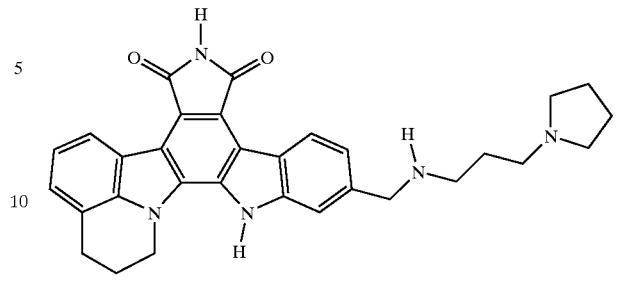

2-([N-(3-(pyrrolidin-1-yl)prop-1-yl)]aminomethyl)-
11H, 12H, 14H-pyrrolo[3,4-c]quinolino[8',8a',1':3,2,
1]pyrrolo[2,3-a]carbazole-5,7-dione di-
trifluoroacetate Beginning with 1-(3-aminoprop-1-yl)pyrrolidine and 2-(bromomethyl)-11H, 12H, 14H-pyrrolo[3,4-c]quinolino-[8',8a',1':3,2,1]pyrrolo[2,3-a]carbazole-5,7-dione, the title compound was prepared essentially as described in Example 115.

$^1$H NMR (400 MHz, CD$_3$OD) δ 8.1 (s, 1H), 7.5 (s, 1H), 7.0 (m, 2H), 6.7 (m, 1H), 6.5 (m, 1H), 4.2 (s, 2H), 4.0 (m, 2H), 3.65 (m, 2H), 3.25 (m, 2H), 3.05 (m, 2H), 3.0 (m, 2H), 2.0–2.3 (m, 10H).

EXAMPLE 125

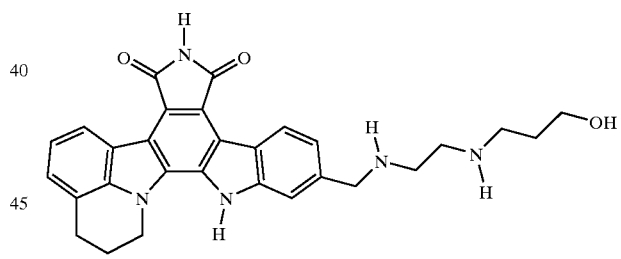

2-([N-(2-[N'-(3-hydroxyprop-1-yl]aminoeth-1-yl)]
aminomethyl)-11H, 12H, 14H-pyrrolo[3,4-c]
quinolino[8',8a',1':3,2,1]pyrrolo[2,3-a]carbazole-5,7-
dione di-trifluoroacetate Beginning with N-[(3-hydroxyprop-1-yl)] N-[(2-aminoeth-1-yl]amine and 2-(bromomethyl)-11H, 12H, 14H-pyrrolo[3,4-c]quinolino[8',8a',1':3,2,1]pyrrolo[2,3-a]carbazole-5,7-dione, the title compound was prepared essentially as described in Example 115.

$^1$H NMR (400 MHz, CD$_3$OD) δ 8.15 (2, 1H), 7.55 (s, 1H), 7.05 (m, 2H), 6.75 (m, 1H), 6.5 (m, 1H), 4.0 (m, 2H), 3.6 (m, 2H), 3.4 (m, 3H), 3.3 (m, 4H), 3.25 (m, 3H), 2.95 (m, 2H), 2.3 (m, 2H), 1.85 (m, 2H).

EXAMPLE 126

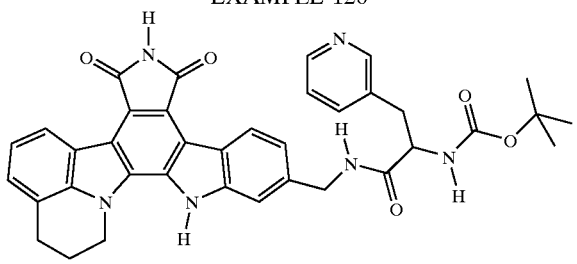

2-([N-([N'-(tert-butoxycarbonyl)] 3-(pyridin-3-yl)alanyl]-aminomethyl)-11H, 12H, 14H-pyrrolo[3,4-c]quinolino-[8',8a',1':3,2,1]pyrrolo[2,3-a]carbazole-5,7-dione A solution of 1-(3-dimethylaminopropyl)-3-ethylcarbodiimide hydrochloride (0.126 g, 0.66 mmol), 1-hydroxybenzotriazole hydrate (0.090 g, 0.67 mmol) and N-(tert-butoxycarbonyl)-3-(pyridin-3-yl)alanine (0.66 mmol) in 2 mL of dimethylformamide was stirred at room temperature for 1 hour and then 2-aminomethyl-11H, 12H, 14H-pyrrolo[3,4-c]quinolino-[8',8a',1':3,2,1]pyrrolo[2,3-a]carbazole-5,7-dione (0.131 mmol) was added. The reaction mixture was stirred for three hours and was then poured into 100 mL of ethyl acetate. The organic phase was washed sequentially with 50 mL portions of 0.1 N hydrochloric acid, water, saturated aqueous sodium bicarbonate, water and saturated aqueous sodium chloride. The organic phase was then dried over sodium sulfate, filtered, and concentrated under reduced pressure. The residue was subjected to silica gel chromatography, eluting with ethyl acetate. Fractions containing product were combined and concentrated under reduced pressure to provide the title compound.

MS (IS, m/z) $C_{37}H_{34}N_6O_5$ (M$^+$+1)=643

EXAMPLE 127

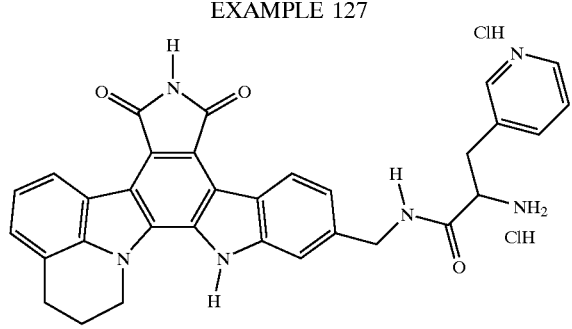

2-([N-(3-(pyridin-3-yl)alanyl]aminomethyl)-11H, 12H, 14H-pyrrolo[3,4-c]quinolino-[8',8a',1':3,2,1]pyrrolo[2,3-a]carbazole-5,7-dione Dihydrochloride Beginning with 2-([N-([N'-(tert-butoxycarbonyl)] 3-(pyridin-3-yl)alanyl]aminomethyl)-11H, 12H, 14H-pyrrolo-[3,4-c]quinolino-[8',8a',1':3,2,1]pyrrolo[2,3-a]carbazole-5,7-dione, the title compound was prepared essentially as described in Example 74.

MS (IS, m/z) $C_{32}H_{26}N_6O_3$ (M$^+$+1)=543

EXAMPLE 128

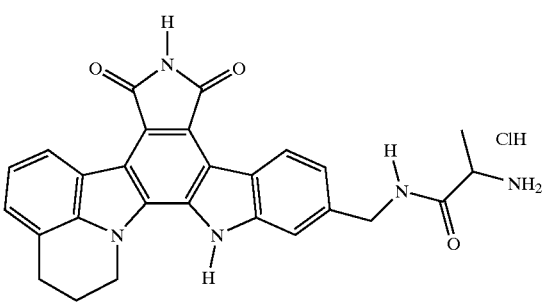

2-([N-alanyl]aminomethyl)-11H, 12H, 14H-pyrrolo[3,4-c]quinolino-[8',8a',1':3,2,1]pyrrolo[2,3-a]carbazole-5,7-dione Hydrochloride Beginning with 2-([N-([N'-(tert-butoxycarbonyl)]-alanyl]aminomethyl)-11H, 12H, 14H-pyrrolo-[3,4-c]quinolino-[8',8a',1':3,2,1]pyrrolo[2,3-a]carbazole-5,7-dione, the title compound was prepared essentially as described in Example 74.

MS (IS, m/z) $C_{27}H_{23}N_5O_3$ (M$^+$+1)=466

EXAMPLE 129

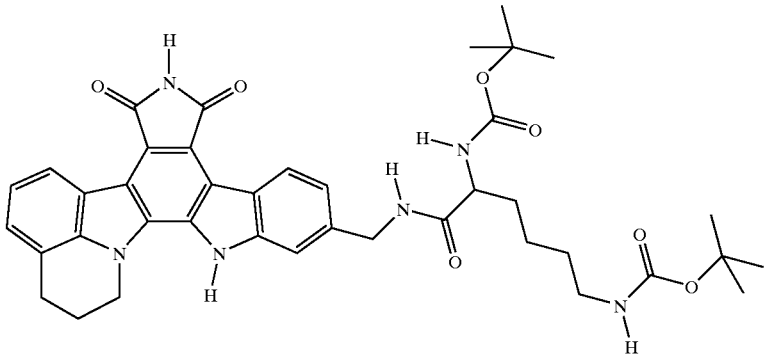

2-([N-[N$_\alpha$, N$_\epsilon$-di(tert-butoxycarbonyl)]lysinyl]
aminomethyl)-11H, 12H, 14H-pyrrolo[3,4-c]
quinolino[8',8a',1':3,2,1]-pyrrolo[2,3-a]carbazole-5,
7-dione Beginning with 2-aminomethyl-11H, 12H, 14H-pyrrolo [3,4-c]quinolino[8',8a',1':3,2,1]pyrrolo[2,3-a]carbazole-5,7-dione and N$_\alpha$, N$_\epsilon$-[di(tert-butoxycarbonyl)]lysine, the title compound was prepared essentially as described in Example 126.

$^1$H NMR (DMSO-d$_6$, 400 MHz): δ: 1.25 (2H, br), 1.27 (18H, s), 2.68 (2H, br), 2.56–2.58 (2H, m), 2.18–2.21 (4H, m), 4.08–4.10 (1H, m), 4.51–4.53 (2H, m), 4.85–4.87 (2H, m), 7.23–7.30 (4H, m), 7.54–7.58 (1H, m), 7.88–8.04 (1H, m), 8.65–8.68 (2H, m), 8.71 (1H, d, J=7.2 Hz), 10.96 (1H, s), 12.08 (1H, s)

EXAMPLE 130

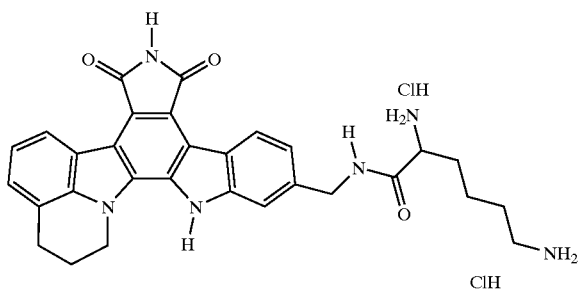

2-(N-[lysinyl]aminomethyl)-11H, 12H, 14H-pyrrolo
[3,4-c]quinolino[8',8a',1':3,2,1]pyrrolo[2,3-a]
carbazole-5,7-dione di-hydrochloride Beginning with 2-([N-[N$_\alpha$, N$_\epsilon$-di (tert-butoxycarbonyl)]-lysinyl]aminomethyl)-11H, 12H, 14H-pyrrolo[3,4-c] quinolino-[8',8a',1':3,2,1]pyrrolo[2,3-a]carbazole-5,7-dione, the title compound was prepared essentially as described in Example 74.

$^1$H NMR (DMSO-d$_6$, 400 MHz): δ: 1.68–1.842 (4H, m), 2.37–2.38 (2H, m), 2.88–2.89 (4H, m), 3.08–3.16 (2H, m), 4.67–4.74 (1H, m), 4.98 (2H, br), 7.25–7.35 (3H, m), 7.81 (1H, s), 8.20 (3H, br), 8.46 (3H, br), 8.72 (1H, d, J=7.7 Hz), 8.98 (2H, d, J=8.0 Hz), 9.42 (1H, t, J=4.8 Hz), 10.96 (1H, s), 12.46 (1H, s)

EXAMPLE 131

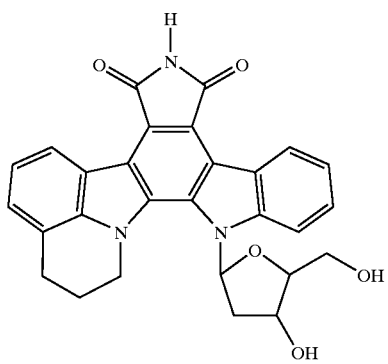

14-(2-deoxy-α-D-ribofuranos-1-yl)-11H, 12H, 14H-
pyrrolo[3,4-c]quinolino[8',8a',1':3,2,1]pyrrolo[2,3-a]
carbazole-5,7-dione A solution of 1H, 12H, 14H-pyrrolo[3,4-c]quinolino-[8', 8a',1':3,2,1]pyrrolo[2,3-a]carbazole-5,7-dione (0.090 g, 0.24 mmol) in 4.8 ml of tetrahydrofuran was treated under argon at −20° C. with potassium tert-butoxide (0.059 g, 0.52 mmol). After 30 minutes a solution of 3,5-Di-O-(p-toluyl)-2-deoxy-α-D-ribofuranosylchloride (0.188 g, 0.48 mmol) in 2.4 ml of tetrahydrofuran was added dropwise at −20° C. After stirring overnight at room temperature the mixture was diluted with water and extracted with ethyl acetate. The combined organic extracts were washed with water and saturated aqueous sodium chloride, dried over sodium sulfate and concentrated under reduced pressure. The residue was subjected to silica gel chromatography, eluting with toluene and acetone. Fractions containing product were combined and concentrated under reduced pressure to provide 14-(3,5-Di-O-(p-toluyl)-2-deoxy-α-D-ribofuranos-1-yl)-11H, 12H, 14H-pyrrolo[3,4-c]quinolino[8',8a',1':3,2,1]-pyrrolo[2,3-a]carbazole-5,7-dione.

A mixture of this product in 5.4 mL of 1,4-dioxane and 2.2 ml of 5% KOH in water was stirred overnight at room temperature. The mixture was treated with cold water and extracted with dichloromethane. The organic layer was washed with water and saturated aqueous sodium chloride, dried over sodium sulfate and concentrated under reduced pressure. The crude product was subjected to silica gel chromatography, eluting with toluene and acetone. Fractions containing the desired product were combined and concentrated under reduced pressure. The residue was diluted with dichloromethane, washed with saturated aqueous sodium bicarbonate and then with water acidified with acetic acid. The organic layer was dried over sodium sulfate and filtered. The filtrate was concentrated under reduced pressure and the residue dissolved in 1.6 mL of dimethylformamide and 2.1 mL of concentrated ammonium hydroxide were added. The mixture was heated in an autoclave at 110° C. for 80 minutes. The mixture was cooled, diluted with water, extracted with ethyl acetate, washed with water and saturated aqueous sodium chloride and dried over sodium sulfate. The organic phase was concentrated under reduced pressure and the residue subjected to silica gel chromatography, eluting with toluene and acetone. Fractions containing product were combined and concentrated under reduced pressure to provide the title compound (0.009 g, 30%).

$^1$H NMR (300 MHz, acetone) δ 10.0 (bs, 1H), 9.4 (d, 1H, J=7.9 Hz), 9.0 (d, 1H, J=7.8 Hz), 8.4 (d, 1H, J=8.2 Hz), 7.5 (m, 1H), 7.4 (m, 1H), 7.0 (m, 2H), 5.0 (bs, 1H), 4.6 (m, 1H), 4.0 (m, 2H), 3.8 (m, 2H), 3.2 (m, 2H), 2.5 (m, 2H), 1.0 (bs, 2H).

EXAMPLE 132

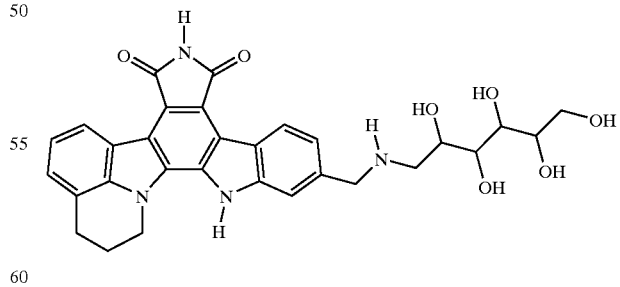

2-(N-[2,3,4,5,6-pentahydroxyhex-1-yl]
aminomethyl)-11H, 12H, 14H-pyrrolo[3,4-c]
quinolino[8',8a',1':3,2,1]-pyrrolo[2,3-a]carbazole-5,
7-dione Beginning with 1-amino-2,3,4,5,6-pentahydroxyhexane and 2-(bromomethyl)-11H, 12H, 14H-pyrrolo[3,4-c]

quinolino-[8',8a',1':3,2,1]pyrrolo[2,3-a]carbazole-5,7-dione, the title compound was prepared essentially as described in Example 60.

$^1$H NMR (DMSO-d$_6$, 400 MHz): δ 2.21 (3H, s), 2.38 (2H, br), 3.10 (2H, br), 3.47 (1H, br), 3.49 (1H, br), 3.60 (2H, br), 3.71 (1H, br), 3.77 (2H, br), 3.83 (1H, br), 4.33 (1H, br), 4.49 (1H, br), 4.89 (2H, br), 7.26 (2H, t, J=8.0 Hz), 7.30 (1H, d, J=7.2 Hz), 7.69 (1H, s), 8.71 (1H, d, J=7.6 Hz), 8.93 (1H, d, J=8.0 Hz), 11.69 (1H, s), 12.03 (1H, s)

EXAMPLE 133

3-(S-6-(tert-butoxycarbonyl)-5-(tert-butoxy)methyl-4,5-dihydro-6H-[1,4]diazepino[6,7,1-hi]indol-1-yl)-4-(1H-indol-3-yl)pyrrole-2,5-dione Beginning with (S-6-(tert-butoxycarbonyl)-5-(tert-Butoxy)methyl-4,5-dihydro-6H-[1,4]diazepino[6,7,1-hi] indol-1-yl)oxoacetic acid methyl ester and indole-3-acetamide, 3-3-(S-5-(tert-butoxy)methyl-4,5-dihydro-6H-[1,4]diazepino-[6,7,1-hi]indol-1-yl)-4-(1H-indol-3-yl) pyrrole-2,5-dione was prepared essentially as described in Example 1. The title compound was prepared by further treating a tetrahydrofuran solution of this material with di(tert-butoxy) dicarbonate and refluxing for 1 hour. The reaction mixture was cooled to 20–24° C. and then concentrated under reduced pressure. The residue was subjected to silica gel chromatography, eluting with ethyl acetate:hexane (1:1) to provide the title compound as a red solid.

MS (ES, m/z) (M−1)=567.1

EXAMPLE 134

S-3-(5-hydroxymethyl-4,5-dihydro-6H-[1,4] diazepino[6,7,1-hi]indol-1-yl)-4-(1H-indol-3-yl) pyrrole-2,5-dione To a suspension of indole-3-acetamide (0.501 g, 2.34 mmol) and (S-6-(tert-butoxycarbonyl)-5-(tert-Butoxy) methyl-4,5-dihydro-6H-[1,4]diazepino[6,7,1-hi]indol-1-yl) oxo-acetic acid methyl ester (1.00 g, 2.34 mmol) in tetrahydrofuran (10 ml) at 0° C. was added potassium tert-butoxide (9.36 mmol, 9.36 ml, 1M in THF). The reaction was allowed to warm to 20–24° C. and stirred for 15 hours. The reaction was quenched with concentrated hydrochloric acid (5 ml) and stirred for 30 minutes. The reaction was then basified with 5N sodium hydroxide and extracted with ethyl acetate. The organic phase was washed with saturated aqueous sodium chloride, dried over magnesium sulfate, filtered and concentrated under reduced pressure. The residue was dissolved in ethanol (10 ml) and 5N hydrochloric acid (10 ml) was added. The reaction mixture was then stirred for 30 minutes, cooled to room temperature and concentrated under reduced pressure. The residue was made basic with 5N sodium hydroxide and extracted with ethyl acetate. The organic phase was washed with saturated aqueous sodium chloride, dried over magnesiun sulfate, filtered and concentrated under reduced pressure. The residue was then subjected to silica gel chromatography, eluting with ethyl acetate:methanol (9:1). Fractions containing the desired compound were combined and concentrated under reduced pressure to provide 0.60 g (65%) of the title compound as a red solid.

MS (ES, m/z) (M+1)=413.0.

EXAMPLE 135

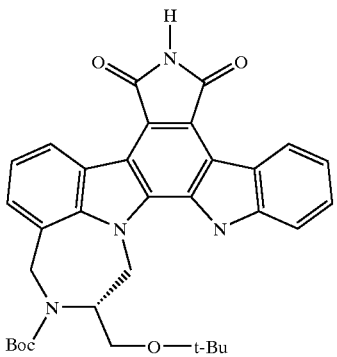

12-(tert-butoxycarbonyl)-13-(tert-butoxy)methyl-11,12,13,14-tetrahydro-12H,15H-pyrrolo[3,4-c]benzo [1,4]diazepino-[9',9a',1':3,2,1]pyrrolo[2,3-a] carbazole-5,7-dione Beginning with 3-(5-hydroxymethyl-4,5-dihydro-6H-[1, 4]diazepino[6,7,1-hi]indol-1-yl)-4-(1H-indol-3-yl)pyrrole-2,5-dione, the title compound was prepared as a red solid essentially as described in Example 58.

MS (ES, m/z) (M−1)=565.1.

EXAMPLE 136

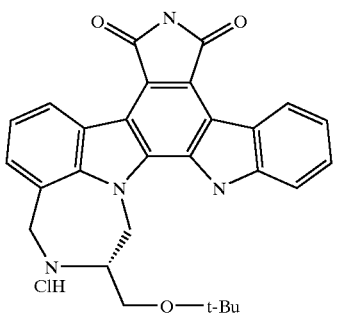

13-(tert-butoxy)methyl-11,12,13,14-tetrahydro-12H, 15H-pyrrolo[3,4-c]benzo[1,4]diazepino[9',9a',1':3,2, 1]pyrrolo-[2,3-a]carbazole-5,7-dione Hydrochloride To a solution of 12-(tert-butoxycarbonyl)-13-(tert-butoxy)methyl-11,12,13,14-tetrahydro-12H,15H-pyrrolo[3, 4-c]benzo[1,4]diazepino-[9',9a',1':3,2,1]pyrrolo[2,3-a] carbazole-5,7-dione (0.045 g, 0.079 mmol) in methanol (3 ml) was added hydrogen chloride (6 ml, 4 N in dioxane) at 20–24° C. The reaction mixture was stirred for 30 minutes and was then concentrated under reduced pressure. The residue was suspended in ethyl acetate, filtered, and the solid dried under reduced pressure to provide 0.36 g (90%) of the title compound.

MS (ES, m/z) (M−1)=465.1

EXAMPLE 137

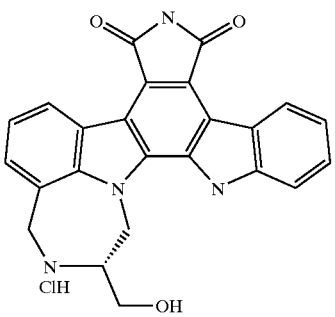

13-hydroxymethyl-11,12,13,14-tetrahydro-12H,15H-pyrrolo[3,4-c]benzo[1,4]diazepino-[9',9a',1':3,2,1]pyrrolo[2,3-a]carbazole-5,7-dione Hydrochloride To a solution of 13-(tert-butoxy)methyl-11,12,13,14-tetrahydro-12H,15H-pyrrolo[3,4-c]benzo[1,4]diazepino-[9',9a',1':3,2,1]pyrrolo[2,3-a]carbazole-5,7-dione hydrochloride (0.0180 g, 0.0360 mmol) in methanol (3 ml) was added hydrogen chloride (6 ml, 4N in dioxane) at 20–24° C. The reaction mixture was stirred at 90° C. for 30 minutes and then cooled to 20–24° C. The resulting suspension was filtered, the solid washed with methanol and dried under reduced pressure to provide 0.015 g (95%) of the title compound.

$^1$H NMR (400 MHz, DMSO) δ 12.37 (s, 1H), 11.13 (s, 1H), 10.05 (s, br, 1H), 9.54 (s, br, 1H), 9.08 (d, J=6.8 Hz, 1H), 9.07 (d, J=8.5 Hz, 1H), 7.80 (d, J=8.3 Hz, 1H), 7.58 (m, 2H), 7.42 (m, 2H), 5.82 (s, br, 1H), 5.22 (d, J=15.1 Hz, 1H), 5.04 (m, 2H), 4.75 (d, J=15.1 Hz, 1H), 4.15 (m, 1H), 4.04 (m, 1H), 3.90 (m, 1H).

EXAMPLE 138

3-(6-(tert-butoxycarbonyl)-5-methyl-5,6-dihydro-6H-[1,4]diazepino[6,7,1-hi]indol-1-yl)-4-(1H-indol-3-yl)pyrrole-2,5-dione and 3-(5-methyl-5,6-dihydro-6H-[1,4]diazepino[6,7,1-hi]indol-1-yl)-4-(1H-indol-3-yl)pyrrole-2,5-dione Beginning with 6-(tert-butoxycarbonyl)-5-methyl-5,6-dihydro-6H-[1,4]diazepino[6,7,1-hi]indol-1-yl)oxoacetic acid methyl ester and indole-3-acetamide, a mixture of the title compounds was prepared essentially as described in Example 1. The compounds were separated by subjecting the residue to silica gel chromatography, eluting with ethylacetate:hexane (1:1) to provide 3-(6-(tert-butoxycarbonyl)-5-methyl-5,6-dihydro-6H-[1,4]diazepino[6,7,1-hi]indol-1-yl)-4-(1H-indol-3-yl)pyrrole-2,5-dione as a red solid.

$^1$H NMR (400 MHz, DMSO-d$_6$) δ 11.64 (s, 1H), 10.88 (s, 1H), 7.73 (s, 1H), 7.62 (d, J=7.3 Hz, 1H), 7.34 (d, J=8.3 Hz, 1H), 6.94 (m, 1H), 6.77–6.52 (m, 5H), 4.91 (m, 1H), 4.68–4.40 (m, 4H), 1.35, 1.15 (2s, 9H)

MS (ES, m/z) (M−1)=495.0.

Eluting with methanol:ethylacetate (1:9) provided 3-(5-methyl-5,6-dihydro-6H-[1,4]diazepino[6,7,1-hi]indol-1-yl)-4-(1H-indol-3-yl)pyrrole-2,5-dione as a red solid.

$^1$H NMR (400 MHz, DMSO-d$_6$) δ 11.63 (s, 1H), 10.89 (s, 1H), 7.68 (s, 1H), 7.63 (s, 1H), 7.74 (d, J=8.3 Hz), 6.98 (m, 1H), 6.84 (d, J=7.8 Hz, 1H), 6.80–6.63 (m, 3H), 6.53 (m, 1H), 4.46 (m, 1H), 4.20–4.00 (m, 2H), 3.86 (m, 1H), 3.31 (m, 1H), 1.15 (d, J=6.3 Hz, 3H)

EXAMPLE 139

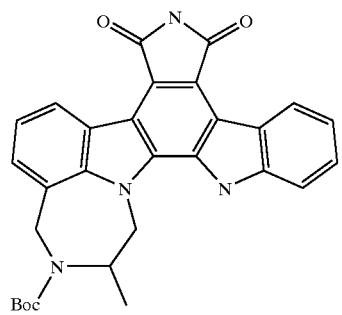

12-(tert-butoxycarbonyl)-13-methyl-11,12,13,14-tetrahydro-12H,15H-pyrrolo[3,4-c]benzo[1,4]diazepino-[9',9a',1':3,2,1]pyrrolo[2,3-a]carbazole-5,7-dione Beginning with 3-(6-(tert-butoxycarbonyl)-5-methyl-5,6-dihydro-6H-[1,4]diazepino[6,7,1-hi]indol-1-yl)-4-(1H-indol-3-yl)pyrrole-2,5-dione, the title compound was prepared essentially as described in Example 58.

MS (ES, m/z) (M−1)=493.0.

EXAMPLE 140

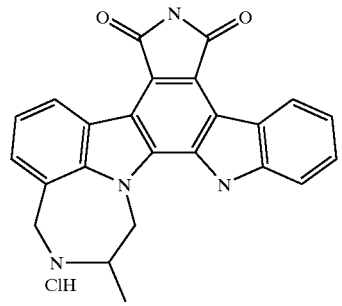

13-methyl-11,12,13,14-tetrahydro-12H,15H-pyrrolo[3,4-c]benzo[1,4]diazepino-[9',9a',1':3,2,1]pyrrolo[2,3-a]carbazole-5,7-dione Hydrochloride Beginning with 12-(tert-butoxycarbonyl)-13-methyl-11,12,13,14-tetrahydro-12H,15H-pyrrolo[3,4-c]benzo[1,4]diazepino[9',9a',1':3,2,1]pyrrolo[2,3-a]carbazole-5,7-dione, the title compound was prepared essentially as described in Example 136.

MS (ES, m/z) (M+1)=395.1, (M−1) 393.1

EXAMPLE 141

3-((6-(tert-butoxycarbonyl)-5-(4-hydroxyphenyl)methyl-5,6-dihydro-6H-[1,4]diazepino[6,7,1-hi]indol-1-yl)-4-(1H-indol-3-yl)pyrrole-2,5-dione Beginning with 6-(tert-butoxycarbonyl)-5-(4-tert-butoxyphenyl)methyl-5,6-dihydro-6H-[1,4]diazepino[6,7,1-hi]indol-1-yl)oxoacetic acid methyl ester and indole-3-acetamide, the title compound was prepared essentially as described in Example 138.

MS (ES, m/z) 587.1 (M−1)

EXAMPLE 142

3-(5-(4-hydroxyphenyl)methyl-5,6-dihydro-6H-[1,4]diazepino[6,7,1-hi]indol-1-yl)-4-(1H-indol-3-yl)pyrrole-2,5-dione A solution of 3-((6-(tert-butoxycarbonyl)-5-(4-hydroxyphenyl)methyl-5,6-dihydro-6H-[1,4]diazepino[6,7, 1-hi]indol-1-yl)-4-(1H-indol-3-yl)pyrrole-2,5-dione (0.110 g, 0.187 mmol) in ethanol was treated with 5 mL 5N hydrochloric acid. The mixture was stirred for 30 minutes and was then treated with 6 mL of 5N sodium hydroxide. The mixture was then extracted with ethyl acetate, dried over magnesium sulfate, filtered and concentrated under reduced pressure. The residue was suspended in hexane and then filtered. The solid was dried under reduced pressure to provide the title compound as a red solid (0.075 g, 82%).

MS (ES, m/z) (M+1)=489.0

EXAMPLE 143

12-(tert-butoxycarbonyl)-13-(4-hydroxyphenyl) methyl-11,12,13,14-tetrahydro-12H,15H-pyrrolo[3, 4-c]benzo[1,4]diazepino-[9',9a',1':3,2,1]pyrrolo[2,3-a]carbazole-5,7-dione Beginning with 3-((6-(tert-butoxycarbonyl)-5-(4-hydroxyphenyl)methyl-5,6-dihydro-6H-[1,4]diazepino[6,7, 1-hi]indol-1-yl)-4-(1H-indol-3-yl)pyrrole-2,5-dione, the title compound was prepared essentially as described in Example 58.

MS (ES, m/z) 585.0 (M−1)

EXAMPLE 144

13-(4-hydroxyphenyl)methyl-11,12,13,14-tetrahydro-12H,15H-pyrrolo[3,4-c]benzo[1,4]diazepino[9',9a',1':3,2,1]-pyrrolo[2,3-a]carbazole-5,7-dione Hydrochloride Beginning with 12-(tert-butoxycarbonyl)-13-(4-hydroxyphenyl)methyl-11,12,13,14-tetrahydro-12H, 15H-pyrrolo[3,4-c]benzo[1,4]diazepino[9',9a',1':3,2,1]pyrrolo-[2,3-a]carbazole-5,7-dione, the title compound was prepared essentially as described in Example 136.

MS (ES, m/z) 486.9 (M+1), 485.0 (M−1).

EXAMPLE 145

3-(4,5,6,7-tetrahydroazepino[3,2,1-hi]indol-1-yl)-4-(1H-indol-3-yl)pyrrole-2,5-dione Beginning with (4,5,6,7-tetrahydroazepino[3,2,1-hi] indol-1-yl)oxoacetic acid methyl ester and indole-3-acetamide, the title compound was prepared essentially as described in Example 1.

MS (FIA, m/z) $C_{24}H_{19}N_3O_2$ ($M^+$−1)=380.4

EXAMPLE 146

11,12,13,14-tetrahydro-15H-pyrrolo[3,4-c]benz[b] azepino[9',9a'1':3,2,1]pyrrolo[2,3-a]carbazole-5,7-dione Beginning with 3-(4,5,6,7-tetrahydroazepino[3,2,1-hi] indol-1-yl)-4-(1H-indol-3-yl)pyrrole-2,5-dione, the title compound was prepared essentially as described in Example 52.

$^1$H NMR (400 MHz, DMSO-$d_6$) δ 12.2–12.0 (bs, 1H), 11.2–10.8 (bs, 1H), 9.07–9.05 (d, 1H, J=8.3 Hz), 8.95–8.93 (d, 1H, J=7.8 Hz), 7.75–7.73 (d, 1H, J=7.8 Hz), 7.56–7.52 (t, 1H, J=7.6 Hz), 7.34–7.29 (m, 2H), 7.24–7.2 (t, 1H, J=7.6 Hz), 4.82–4.7 (m, 2H), 3.3–3.2 (m, 2H), 2.35–2.25 (m, 2H), 2.15–2.05 (m, 2H)

MS (FIA, m/z) $C_{24}H_{17}N_3O_2$ ($M^+$+1)=380.3

EXAMPLE 147

3-(6-methoxy-1H-indol-3-yl)-4-(4,5,6,7-tetrahydroazepino[3,2,1-hi]indol-1-yl)pyrrole-2,5-dione Beginning with 6-methoxyindole-3-acetamide and (4,5,6, 7-tetrahydroazepino[3,2,1-hi]indol-1-yl)oxo-acetic acid methyl ester, the title compound was prepared essentially as described in Example 1.

MS (FD, m/z) $C_{25}H_{21}N_3O_3$ ($M^+$)=411.

EXAMPLE 148

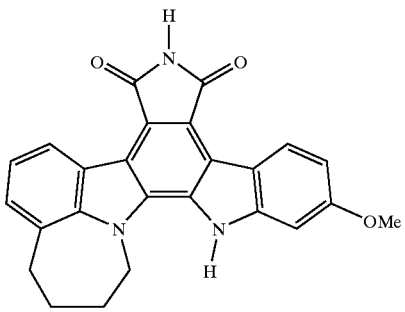

2-methoxy-11,12,13,14-tetrahydro-15H-pyrrolo[3,4-c]benz[b]azepino[9',9a'1':3,2,1]pyrrolo[2,3-a]carbazole-5,7-dione Beginning with 3-(4,5,6,7-tetrahydroazepino[3,2,1-hi]indol-1-yl)-4-(6-methoxy-1H-indol-3-yl)pyrrole-2,5-dione, the title compound was prepared essentially as described in Example 52.

MS (FIA, m/z) $C_{25}H_{19}N_3O_3$ (M$^+$-1)=408.3.

EXAMPLE 149

3-(4,5,6,7-tetrahydroazepino[3,2,1-hi]indol-1-yl)-4-(6-bromo-1H-indol-3-yl)pyrrole-2,5-dione Beginning with (6-bromoindole)-3-glyoxylic acid methyl ester and 2-(4,5,6,7-tetrahydroazepino[3,2,1-hi]indol-1-yl)acetamide, the title compound was prepared essentially as described in Example 1.

MS (IS, m/z) $C_{23}H_{16}BrN_3O_2$ (M$^+$-1)=444, (M$^+$-1+2)=446.

EXAMPLE 150

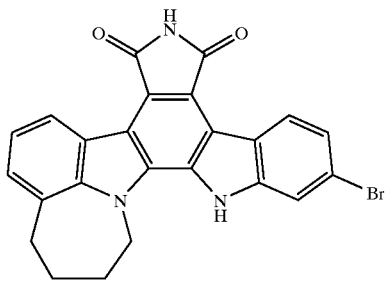

2-bromo-11,12,13,14-tetrahydro-15H-pyrrolo[3,4-c]benz[b]azepino[9',9a'1':3,2,1]pyrrolo[2,3-a]carbazole-5,7-dione A solution of 3-(4,5,6,7-tetrahydroazepino[3,2,1-hi]indol-1-yl)-4-(6-bromo-1H-indol-3-yl)pyrrole-2,5-dione (0.69 g, 1.5 mmol) in 400 mL of dioxane containing iodine (0.020 g, 0.079 mmol) was irradiated in an Ace photochemical reactor using a medium-pressure mercury lamp. The internal temperature rose to 42° C. and the starting material was consumed after 3 hours. After concentration in vacuo to 50 mL, the reaction mixture was diluted with EtOAc (400 mL) and washed with saturated NaHSO$_3$ (1×50 mL), water (1×50 mL), brine (1×50 mL), dried over Na$_2$SO$_4$, filtered and concentrated. The residue was chromatographed on silica gel (10–80% THF/toluene) to give the desired product in 47% yield as a yellow solid.

MS (IS, m/z) $C_{23}H_{14}BrN_3O_2$ (M$^+$-1)=443, (M$^+$-1+2)=445

EXAMPLE 151

3-(4,5,6,7-tetrahydroazepino[3,2,1-hi]indol-1-yl)-4-(6-fluoro-1H-indol-3-yl)pyrrole-2,5-dione Beginning with (4,5,6,7-tetrahydroazepino[3,2,1-hi]indol-1-yl)oxoacetic acid methyl ester and 6-fluoroindole-3-acetamide, the title compound was prepared essentially as described in Example 1.

MS (IS, m/z) $C_{23}H_{16}FN_3O_2$ (M$^+$-1)=384

EXAMPLE 152

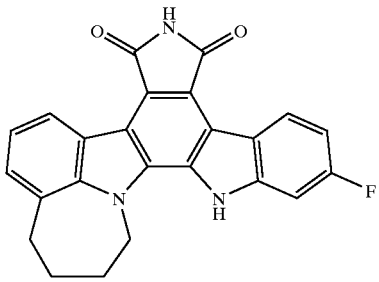

2-fluoro-11,12,13,14-tetrahydro-15H-pyrrolo[3,4-c]benz[b]azepino[9',9a'1':3,2,1]pyrrolo[2,3-a]carbazole-5,7-dione Beginning with 3-(4,5,6,7-tetrahydroazepino[3,2,1-hi]indol-1-yl)-4-(6-fluoro-1H-indol-3-yl)-pyrrole-2,5-dione, the title compound was prepared essentially as described in Example 52.

MS (FD, m/z) $C_{23}H_{14}FN_3O_2$ (M$^+$)=383

EXAMPLE 153

3-(5,6-dihydro-4H-pyrrolo[3,2,1-ij]quinolin-1-yl)-4-(6-trifluoromethyl-1H-indol-3-yl)pyrrole-2,5-dione Beginning with (5,6-dihydro-4H-pyrrolo[3,2,1-ij]quinolin-1-yl)oxoacetic acid methyl ester and 6-(trifluoromethyl)indole-3-acetamide, the title compound was prepared essentially as described in Example 1.

$^1$H NMR (400 MHz, DMSO-d$_6$) δ 11.96 (s, 1H), 10.94 (s, 1H), 7.93 (S, 1H), 7.8–7.79 (d, 1H, J=2.44 Hz), 7.73 (s, 1H), 7.21–7.19 (d, 1H, J=8.3 Hz), 7.03–7.01 (d, 1H, J=7.32 Hz), 6.73–6.72 (d, 1H, J=6.84 Hz), 6.52–6.48 (t, 1H, J=7.57 Hz), 6.26–6.24 (d, 1H, J=8.3 Hz), 4.24–4.22 (t, 2H, J=5.62 Hz), 2.89–2.87 (t, 2H, J=5.62 Hz), 2.05–2.15 (m, 2H)

EXAMPLE 154

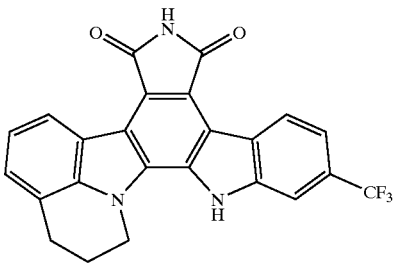

2-trifluoromethyl-11H, 12H, 14H-pyrrolo[3,4-c]
quinolino[8',8a',1':3,2,1]-pyrrolo[2,3-a]carbazole-5,
7-dione Beginning with 3-(5,6-dihydro-4H-pyrrolo[3,2,1-ij]
quinolin-1-yl)-4-(6-trifluoromethyl-1H-indol-3-yl)pyrrole-
2,5-dione, the title compound was prepared essentially as
described in Example 52.

MS (IS, m/z) $C_{24}H_{14}F_3N_3O_2$ (M$^+$−1)=432

EXAMPLE 155

3-(5,6-dihydro-4H-pyrrolo[3,2,1-ij]quinolin-1-yl)-4-
[1-(3-hydroxy-propyl)-1H-indol-3-yl]-pyrrole-2,5-
dione Beginning with 2-(5,6-dihydro-4H-pyrrolo[3,2,1-ij]
quinolin-1-yl)acetamide and 1-(3-hydroxypropyl)indole-3-
glyoxylic acid methyl ester, the title compound was prepared
essentially as described in Example 1.

MS (IS, m/z) $C_{26}H_{23}N_3O_3$ (M$^+$+1)=426

EXAMPLE 156

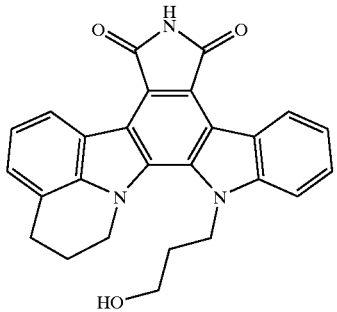

15-(3-hydroxyprop-1-yl)-11H, 12H, 14H-pyrrolo[3,
4-c]quinolino[8',8a',1':3,2,1]-pyrrolo[2,3-a]
carbazole-5,7-dione Beginning with 3-(5,6-dihydro-4H-pyrrolo[3,2,1-ij]
quinolin-1-yl)-4-[1-(3-hydroxypropyl)-1H-indol-3-yl]-
pyrrole-2,5-dione, the title compound was prepared essentially as described in Example 52.

MS (IS, m/z) $C_{26}H_{21}N_3O_3$ (M$^+$+1)=424

EXAMPLE 157

3-(5,6-dihydro-4H-pyrrolo[3,2,1-ij]quinolin-1-yl)-4-
[1-(4-hydroxybutyl)-1H-indol-3-yl]pyrrole-2,5-dione Beginning with 2-(5,6-dihydro-4H-pyrrolo[3,2,1-ij]
quinolin-1-yl)acetamide and 1-(4-hydroxybutyl)indole-3-
glyoxylic acid methyl ester, the title compound was prepared
essentially as described in Example 1.

MS (IS, m/z) $C_{27}H_{25}N_3O_3$ (M$^+$+1)=440

EXAMPLE 158

3-[1-(4-Bromobutyl)-1H-indol-3-yl]-4-[5,6-dihydro-
4H-pyrrolo[3,2,1-ij]quinolin-1-yl]pyrrole-2,5-dione A solution of 3-(5,6-dihydro-4H-pyrrolo[3,2,1-ij]
quinolin-1-yl)-4-[1-(4-hydroxybutyl)-1H-indol-3-yl]
pyrrole-2,5-dione (0.11 g, 0.25 mmol) and triphenylphosphine (0.08 g, 0.31 mmol) in dichloromethane (3 mL) was
treated with carbon tetrabromide (0.095 g, 0.286 mmol) and
stirred for 3 hours. The reaction mixture was then concentrated under reduced pressure and the residue subjected to
silica gel chromatography, eluting with 2% methanol in
dichloromethane. Fractions containing product were combined and concentrated under reduced pressure to provide
0.101 g (80%) of the title compound as a dark red foam.

$^1$H NMR (400 MHz, DMSO-d$_6$) δ 10.87 (s, 1H), 7.88 (s,
1H), 7.65 (s, 1H), 7.5–7.48 (d, 1H, J=7.81 Hz), 7.06–7.03
(dt, 1H, J=7.08 1.0 Hz), 7.0–6.98 (d, 1H, J=8.3 Hz),
6.75–6.7 (m, 2H), 6.5–6.47 (t, 1H, J=7.57 Hz), 6.3–6.28 (d,
1H, J=7.81 Hz), 4.25–4.2 (m, 4H), 3.52–3.48 (t, 1H, J=6.59
Hz), 2.9–2.82 (m, 2H), 2.15–2.05 (m, 2H), 1.85–1.76 (m,
2H), 1.75–1.65 (m, 2H)

EXAMPLE 159

3-[1-(4-Aminobutyl)-1H-indol-3-yl]-4-(5,6-dihydro-
4H-pyrrolo[3,2,1-ij]quinolin-1-yl)pyrrole-2,5-dione A solution of 3-[1-(4-bromobutyl)-1H-indol-3-yl]-4-[(5,
6-dihydro-4H-pyrrolo[3,2,1-ij]quinolin-1-yl]pyrrole-2,5-
dione (0.1 g, 0.2 mmol) in tetrahydrofuran (2 mL) was
treated with ammonium hydroxide (1 mL) and heated at 80°
C. in a sealed tube for 4 hours. After cooling, the mixture
was extracted with dichloromethane (3×25 mL) and the
combined extracts concentrated under reduced pressure. The
residue was subjected to silica gel chromatography, eluting
with 80/16/1/3% dichloromethane/methanol/acetic acid/
water. Fractions containing product were combined and
concentrated under reduced pressure to provide 0.075 g
(86%) of the title compound as a dark red foam.

MS (IS, m/z) $C_{27}H_{26}N_4O_2$ (M$^+$+1)=439

EXAMPLE 160

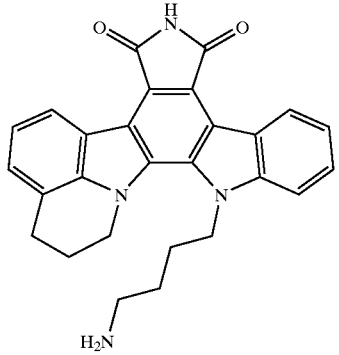

15-(4-aminobut-1-yl)-11H, 12H, 14H-pyrrolo[3,4-c]
quinolino[8',8a',1':3,2,1]-pyrrolo[2,3-a]carbazole-5,
7-dione Beginning with 3-[1-(4-Aminobutyl)-1H-indol-3-yl]-4-
(5,6-dihydro-4H-pyrrolo[3,2,1-ij]quinolin-1-yl)pyrrole-2,5- dione, the title compound was prepared essentially as described in Example 52.

$^1$H NMR (400 MHz, DMSO-d$_6$) δ 11.07 (s, 1H), 9.21–9.18 (d, 1H, J=8.3 Hz), 8.91–8.89 (d, 1H, J=7.33 Hz), 7.89–7.87 (d, 1H, J=8.3 Hz), 7.65–7.6 (m, 3H), 7.4–7.25 (m, 3H), 4.9–4.87 (t, 1H, J=5.37 Hz), 4.84–4.8 (t, 1H, J=7.57 Hz), 3.15–3.08 (m, 2H), 2.9–2.8 (m, 2H), 2.2–2.1 (m, 2H), 1.74–1.65 (m, 2H), 1.15–1.05 (m, 2H)

EXAMPLE 161

3-(6-(tert-butoxycarbonyl)-4,5-dihydro-6H-[1,4] diazepino[6,7,1-hi]indol-1-yl)-4-(1H-indol-3-yl) pyrrole-2,5-dione and 3-(4,5-dihydro-6H-[1,4] diazepino[6,7,1-hi]indol-1-yl)-4-(1H-indol-3-yl) pyrrole-2,5-dione Beginning with (6-(tert-butoxycarbonyl)-4,5-dihydro-6H-[1,4]diazepino[6,7,1-hi]indol-1-yl)oxoacetic acid methyl ester and indole-3-acetamide, both title compounds were prepared essentially as described in EXAMPLE 1.

$^1$H NMR (400 MHz, DMSO-d$_6$) δ 11.65–11.64 (d, 1H, J=1.95 Hz), 10.91 (s, 1H), 7.72 (s, 1H), 7.67 (s, 1H), 7.36–7.34 (d, 1H, J=7.81 Hz), 7.0–6.9 (m, 1H), 6.85–6.5 (m, 5H), 4.79–4.75 (d, 2H, J=15.6 Hz), 4.5–4.0 (m, 2H), 3.85–3.8 (m, 2H), 1.37 and 1.25 (2 singlets, 9H) and 3-(4,5-dihydro-6H-[1,4]diazepino[6,7,1-hi]indol-1-yl)-4-(1H-indol-3-yl)pyrrole-2,5-dione.

MS (IS, m/z) C$_{23}$H$_{18}$N$_4$O$_2$ (M$^+$+1)=383

EXAMPLE 162

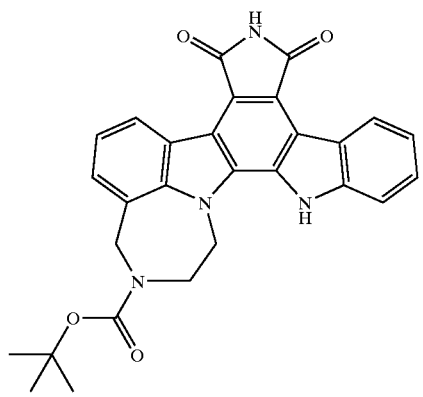

12-(tert-butoxycarbonyl)-11,12,13,14-tetrahydro-12H,15H-pyrrolo[3,4-c]benzo[1,4]diazepino[9',9a', 1':3,2,1]pyrrolo-[2,3-a]carbazole-5,7-dione Beginning with 3-(6-(tert-butoxycarbonyl)-4,5-dihydro-6H-[1,4]diazepino[6,7,1-hi]indol-1-yl)-4-(1H-indol-3-yl) pyrrole-2,5-dione, the title compound was prepared essentially as described in Example 58.

MS (IS, m/z) C$_{28}$H$_{24}$N$_4$O$_4$ (M$^+$−1)=479

EXAMPLE 163

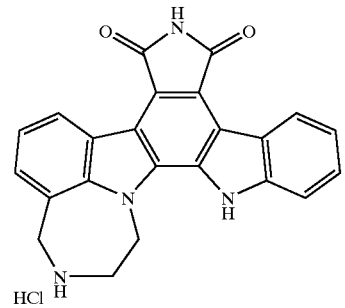

11,12,13,14-tetrahydro-12H,15H-pyrrolo[3,4-c] benzo[1,4]diazepino[9',9a',1':3,2,1]pyrrolo-[2,3-a] carbazole-5,7-dione Hydrochloride Beginning with 12-(tert-butoxycarbonyl)-11,12,13,14-tetrahydro-12H,15H-pyrrolo[3,4-c]benzo[1,4]diazepino-[9', 9a',1':3,2,1]pyrrolo-[2,3-a]carbazole-5,7-dione, the title compound was prepared essentially as described in Example 136.

MS (IS, m/z) C$_{23}$H$_{16}$N$_4$O$_2$ (M$^+$+1)=381

EXAMPLE 164

3-(6-(tert-butoxycarbonyl)-4,5-dihydro-6H-[1,4] diazepino[6,7,1-hi]indol-1-yl)-4-(6-fluoro-1H-indol-3-yl)pyrrole-2,5-dione Beginning with (6-(tert-butoxycarbonyl)-4,5-dihydro-6H-[1,4]diazepino[6,7,1-hi]indol-1-yl)oxoacetic acid methyl ester and 6-fluoroindole-3-acetamide, the title compound was prepared essentially as described in EXAMPLE 133.

$^1$H NMR (400 MHz, DMSO-d$_6$) δ 11.68 (s, 1H), 10.94 (s, 1H), 7.71–7.7 (d, 2H), 7.14–7.12 (d, 1H, J=9.28 Hz), 6.85–6.4 (m, 5H), 4.87 and 4.75 (2 singlets, 2H), 4.49 and 4.44 (2 singlets, 2H), 3.86 (bs, 2H), 1.37 and 1.25 (2 singlets, 9H).

EXAMPLE 165

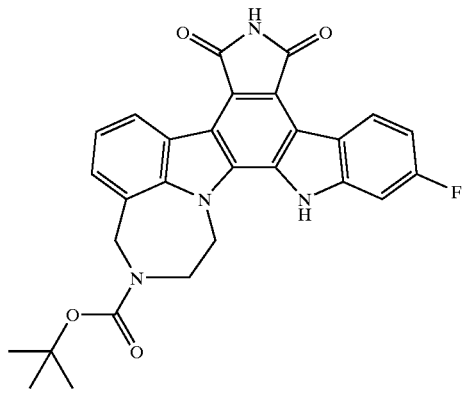

2-fluoro-12-(tert-butoxycarbonyl)-11,12,13,14-tetrahydro-12H,15H-pyrrolo[3,4-c]benzo[1,4] diazepino[9',9a',1':3,2,1]-pyrrolo[2,3-a]carbazole-5, 7-dione Beginning with 3-(6-(tert-butoxycarbonyl)-4,5-dihydro-6H-[1,4]diazepino[6,7,1-hi]indol-1-yl)-4-(1H-indol-3-yl)

pyrrole-2,5-dione, the title compound was prepared essentially as described in Example 58.

¹H NMR (400 MHz, DMSO-d₆) δ 12.23 (s, 1H), 11.68 (s, 1H), 9.1–8.95 (m, 2H), 7.5–7.1 (m, 4H), 5.0–4.8 (m, 4H), 4.2–4.1 (m, 2H).

EXAMPLE 166

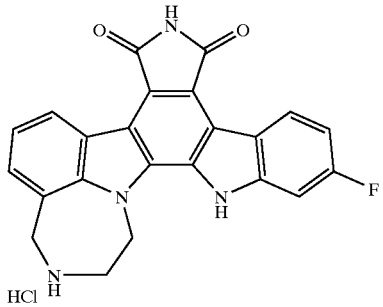

2-fluoro-11,12,13,14-tetrahydro-12H,15H-pyrrolo[3,4-c]benzo[1,4]diazepino[9',9a',1':3,2,1]-pyrrolo[2,3-a]carbazole-5,7-dione Hydrochloride Beginning with 2-fluoro-12-(tert-butoxycarbonyl)-11,12,13,14-tetrahydro-12H,15H-pyrrolo[3,4-c]benzo[1,4]-diazepino[9',9a',1':3,2,1]pyrrolo[2,3-a]carbazole-5,7-dione, the title compound was prepared essentially as described in Example 136.

MS (IS, m/z) $C_{23}H_{15}FN_4O_2$ (M⁺+1)=399

EXAMPLE 167

3-(7,8-Dehydropyrrolo[3,2,1-kl]benzo[b]azacyclooct-1-yl)-4-(1H-indol-3-yl)-pyrrole-2,5-dione Beginning with (7,8-Dehydropyrrolo[3,2,1-kl]benzo[b]azacyclooct-1-yl)oxoacetic acid methyl ester and indole-3-acetamide, the title compound was prepared essentially as described in Example 1.

MS (ES, m/z) $C_{25}H_{19}N_3O_2$ (M⁺-1)=392.

EXAMPLE 168

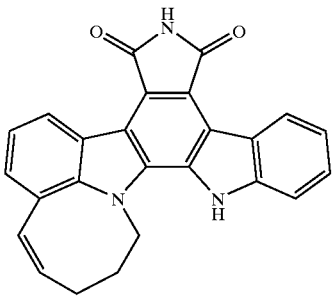

11,12-dehydro-16H-pyrrolo[3,4-c]benz[b]azacyclooctano[10',10a',1':3,2,1]pyrrolo[2,3-a]carbazole-5,7-dione Beginning with 3-(7,8-Dehydropyrrolo[3,2,1-kl]benzo[b]azacyclooct-1-yl)-4-(1H-indol-3-yl)pyrrole-2,5-dione, the title compound was prepared essentially as described in Example 52.

MS (ES, m/z) $C_{25}H_{17}N_3O_2$ (M⁺-1)=390

EXAMPLE 169

3-(pyrrolo[3,2,1-kl]benzo[b]azacyclooct-1-yl)-4-(1H-indol-3-yl)pyrrole-2,5-dione Beginning with (pyrrolo[3,2,1-kl]benzo[b]azacyclooct-1-yl)oxoacetic acid methyl ester and indole-3-acetamide, the title compound was prepared essentially as described in Example 1.

MS (ES, m/z) $C_{25}H_{21}N_3O_2$ (M⁺-1)=394

EXAMPLE 170

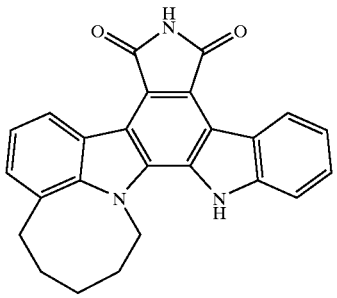

16H-pyrrolo[3,4-c]benz[b]azacyclooctano-[10',10a',1':3,2,1]pyrrolo[2,3-a]carbazole-5,7-dione Beginning with 3-(pyrrolo[3,2,1-kl]benzo[b]azacyclooct-1-yl)-4-(1H-indol-3-yl)-pyrrole-2,5-dione, the title compound was prepared essentially as described in Example 52.

MS (ES, m/z) $C_{25}H_{19}N_3O_2$ (M⁺-1)=392

EXAMPLE 171

3-(indol-3-yl)-4-(8-(tert-butoxycarbonyl)-[1,5]diazaperhydroonino[8,9,1-hi]indol-1-yl)pyrrole-2,5-dione Beginning with (8-(tert-butoxycarbonyl)-[1,5]diazaperhydroonino[8,9,1-hi]indol-1-yl)oxoacetic acid methyl ester and indole-3-acetamide, the title compound was prepared essentially as described in Example 1.

¹H NMR (400 MHz, DMSO-d₆) δ 11.68 (s, 1H), 10.9 (s, 1H), 7.86–7.85 and 7.83–7.82 (2 doublets, 1H, J=2.93 Hz), 7.54 (s, 1H), 7.33–7.3 (m, 1H), 7.07–7.05 and 7.02–7.0 (2 doublets, 1H, J=7.32 Hz), 6.94–6.86 (m, 2H), 6.64–6.44 (m, 3H), 4.77 and 4.74 (2 singlets, 2H), 4.5 (bs, 2H), 3.45 (bs, 2H), 1.68–1.67 (bd, 2H, J=4.88 Hz), 1.5–1.4 (m, 2H), 1.34 and 1.29 (2 singlets, 9H)

EXAMPLE 172

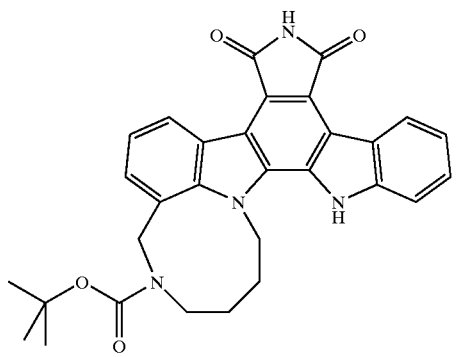

12-(tert-butoxycarbonyl)-pyrrolo[3,4-c]benzo[1,5]
diazaperhydroonino[12',12a',1':3,2,1]pyrrolo[2,3-a]
carbazole-5,7-dione Beginning with 3-(indol-3-yl)-4-(8-(tert-butoxycarbonyl)-[1,5]diazaperhydroonino[8,9,1-hi]indol-1-yl)pyrrole-2,5-dione, the title compound was prepared essentially as described in Example 58.

MS (IS, m/z) $C_{30}H_{28}N_4O_4$ ($M^+-1$)=507.1

EXAMPLE 173

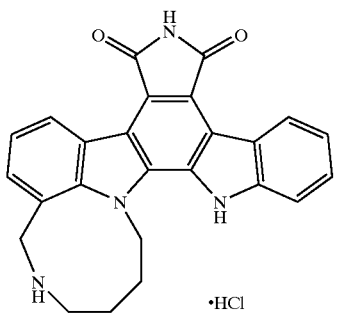

pyrrolo[3,4-c]benzo[1,5]diazaperhydroonino-[12',
12a',1':3,2,1]pyrrolo[2,3-a]carbazole-5,7-dione
Hydrochloride Beginning with 12-(tert-butoxycarbonyl)-pyrrolo[3,4-c]benzo[1,5]diazaperhydroonino[12',12a',1':3,2,1]pyrrolo[2,3-a]carbazole-5,7-dione, the title compound was prepared essentially as described in Example 136.

MS (IS, m/z) $C_{25}H_{20}N_4O_2$ ($M^+-1$)=407.1

EXAMPLE 174

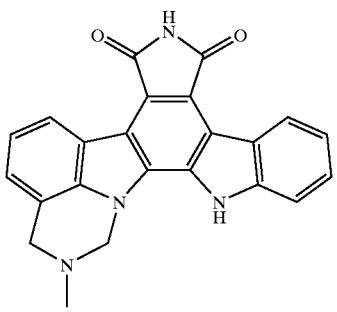

12-methyl-12-aza-11H, 12H, 14H-pyrrolo[3,4-c]-
quinolino[8',8a',1':3,2,1]pyrrolo[2,3-a]carbazole-5,7-
dione To a solution of formallin (37% solution in water, 0.5 ml) in 2 ml glacial acetic acid was added 20 mg of N-[methyl] 11-(aminomethyl)indolo[2,3-a]pyrrolo[3,4-c]carbazole-5,7-dione hydrochloride in 1.0 ml dimethylformamide at room temperature. The solution was stirred at 65° C. for 2 hour and poured into ice water. The resulting precipitate was filtered and the filter cake was washed with water and dried to provide 10 mg (48%) of the title compound as a yellowish solid.

MS (m/z): 380.9 ($M^++1$), 378.9 ($M^+-1$)

EXAMPLE 175

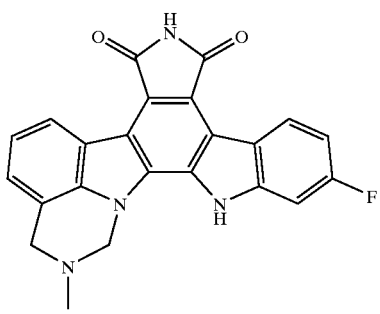

2-fluoro-12-methyl-12-aza-11H, 12H, 14H-pyrrolo
[3,4-c]-quinolino[8',8a',1':3,2,1]pyrrolo[2,3-a]
carbazole-5,7-dione Beginning with N-[methyl] 11-(aminomethyl)-2-fluoroindolo[2,3-a]pyrrolo[3,4-c]carbazole-5,7-dione hydrochloride, the title compound was prepared essentially as described in Example 174.

MS (m/z): 397.1 ($M^+-1$)

EXAMPLE 176

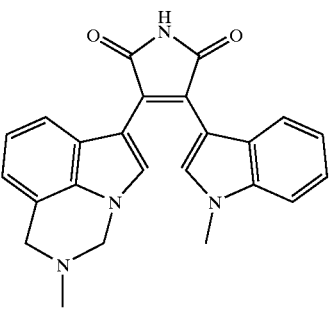

3-(5-methyl-5-aza-5,6-dihydro-4H-pyrrolo[3,2,1-ij]
quinolin-1-yl)-4-[1-methyl-1H-indol-3-yl]pyrrole-2,
5-dione Beginning with (N-[tert-butoxycarbonyl] N-[methyl]
7-aminomethylindol-3-yl)oxoacetic acid methyl ester and
1-methylindole-3-acetamide, the title compound was prepared essentially as described in Preparation XX and Example 174.

MS (m/z): 397.1 (M$^+$+1), 395.3 (M$^+$−1)

EXAMPLE 177

3-(S-6-(tert-butoxycarbonyl)-5-(N-[tert-
butoxycarbonyl] N-[methyl] 5-aminopent-1-yl)-5,6-
dihydro-6H-[1,4]diazepino[6,7,1-hi]indol-1-yl)-4-
(indol-3-yl)pyrrole-2,5-dione Beginning with (S-6-(tert-butoxycarbonyl)-5-(N-[tert-butoxycarbonyl] N-[methyl] 5-aminopent-1-yl)-5,6-dihydro-6H-[1,4]diazepino[6,7,1-hi]indol-1-yl)oxoacetic acid methyl ester and (indol-3-yl)acetamide, the title compound was prepared essentially as described in Example 1.

MS (m/z): 668.0 (M$^+$+1), 666.0 (M$^+$−1)

EXAMPLE 178

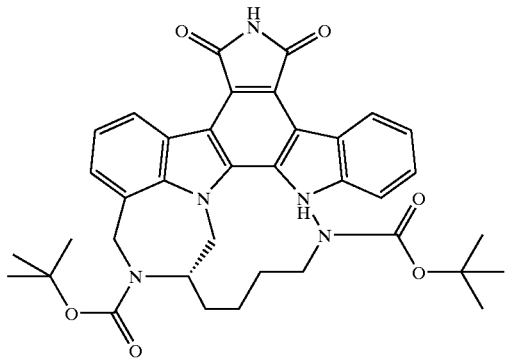

12-(tert-butoxycarbonyl)-13-(N-[tert-
butoxycarbonyl] N-[methyl]-4-aminobut-1-yl)-11,
12,13,14-tetrahydro-12H,15H-pyrrolo[3,4-c]benzo
[1,4]diazepino[9',9a',1':3,2,1]-pyrrolo[2,3-a]
carbazole-5,7-dione Beginning with 3-(S-6-(tert-butoxycarbonyl)-5-(N-[tert-butoxycarbonyl] N-[methyl] 5-aminopent-1-yl)-5,6-dihydro-6H-[1,4]diazepino[6,7,1-hi]indol-1-yl)-4-(indol-3-yl)pyrrole-2,5-dione, the title compound was prepared essentially as described in Example 58.

MS (m/z): 666.0 (M$^+$+1), 664.0 (M$^+$−1)

EXAMPLE 179

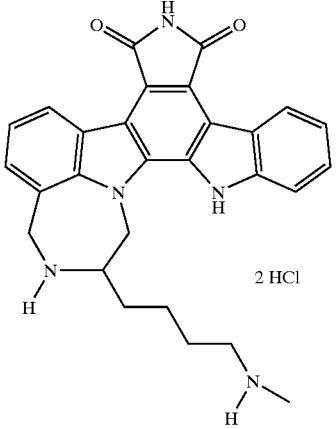

13-(N-[methyl]-4-aminobut-1-yl)-11,12,13,14-
tetrahydro-12H,15H-pyrrolo[3,4-c]benzo[1,4]
diazepino[9',9a',1':3,2,1]-pyrrolo[2,3-a]carbazole-5,
7-dione Dihydrochloride Beginning with 12-(tert-butoxycarbonyl)-13-(N-[tert-butoxycarbonyl]N-[methyl)-4-aminobut-1-yl)-11,12,13,14-tetrahydro-12H,15H-pyrrolo[3,4-c]benzo[1,4]diazepino-[9',9a',1':3,2,1]pyrrolo[2,3-a]carbazole-5,7-dione, the title compound was prepared essentially as described in Example 136.

MS (m/z): 466.9 (M$^+$+2)

EXAMPLE 180

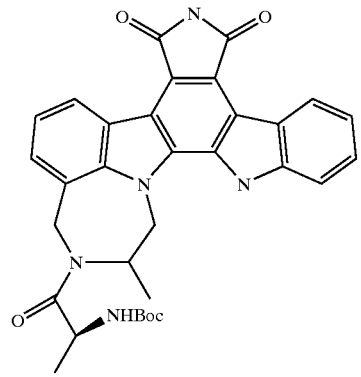

12-(N-(tert-butoxycarbonyl)-L-alaninyl)-13-methyl-
11,12,13,14-tetrahydro-12H,15H-pyrrolo[3,4-c]
benzo[1,4]diazepino-[9',9a',1':3,2,1]pyrrolo[2,3-a]
carbazole-5,7-dione Beginning with 13-methyl-11,12,13,14-tetrahydro-12H, 15H-pyrrolo[3,4-c]benzo[1,4]diazepino[9',9a',1':3,2,1]-pyrrolo[2,3-a]carbazole-5,7-dione and N-[tert-butoxycarbonyl]-L-alanine, the title compound was prepared essentially as described in Example 126.

MS (ES, m/z) (M−1)=564.0.

EXAMPLE 181

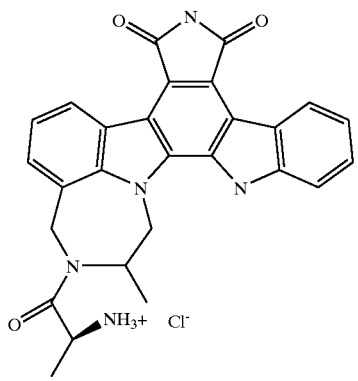

12-(N-(L-alaninyl)-13-methyl-11,12,13,14-tetrahydro-12H,15H-pyrrolo[3,4-c]benzo[1,4]diazepino[9',9a',1':3,2,1]-pyrrolo[2,3-a]carbazole-5,7-dione Hydrochloride Beginning with 12-(N-(tert-butoxycarbonyl)-L-alaninyl)-13-methyl-11,12,13,14-tetrahydro-12H,15H-pyrrolo[3,4-c]benzo[1,4]diazepino[9',9a',1':3,2,1]pyrrolo[2,3-a]carbazole-5,7-dione, the title compound was prepared essentially as described in Example 136.

MS (ES, m/z) (M−1)=463.9

EXAMPLE 182

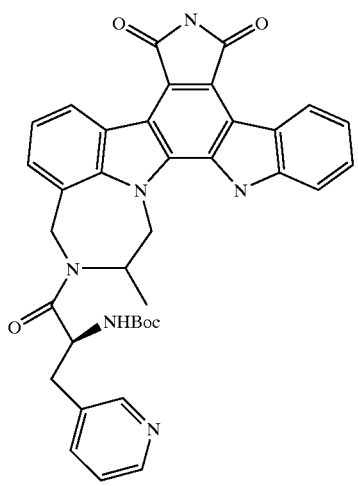

12-(N-(tert-butoxycarbonyl)-L-(β-(pyridin-3-yl)alaninyl)-13-methyl-11,12,13,14-tetrahydro-12H,15H-pyrrolo[3,4-c]benzo[1,4]diazepino-[9',9a',1':3,2,1]pyrrolo[2,3-a]carbazole-5,7-dione Beginning with 13-methyl-11,12,13,14-tetrahydro-12H,15H-pyrrolo(3,4-c]benzo[1,4]diazepino[9',9a',1':3,2,1]-pyrrolo[2,3-a]carbazole-5,7-dione and N-[tert-butoxycarbonyl]-L-(β-(pyridin-3-yl))alanine, the title compound was prepared essentially as described in Example 126.

MS (ES, m/z) (M−1)=640.9.

EXAMPLE 183

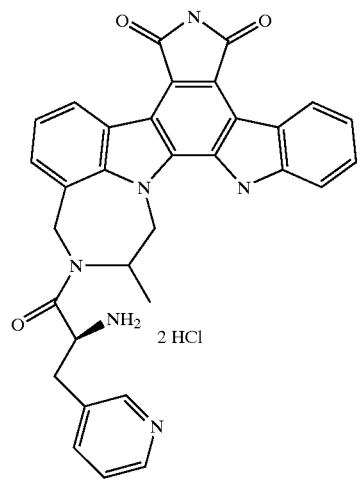

12-(L-(β-(pyridin-3-yl)alaninyl)-13-methyl-11,12,13,14-tetrahydro-12H,15H-pyrrolo[3,4-c]benzo[1,4]diazepino-[9',9a',1':3,2,1]pyrrolo[2,3-a]carbazole-5,7-dione Dihydrochloride Beginning with 12-(N-(tert-butoxycarbonyl)-L-(β-(pyridin-3-yl)alaninyl)-13-methyl-11,12,13,14-tetrahydro-12H,15H-pyrrolo[3,4-c]benzo[1,4]diazepino[9',9a',1':3,2,1]-pyrrolo[2,3-a]carbazole-5,7-dione, the title compound was prepared essentially as described in Example 136.

MS (ES, m/z) (M−1)=540.91, (M+1)=542.9.

EXAMPLE 184

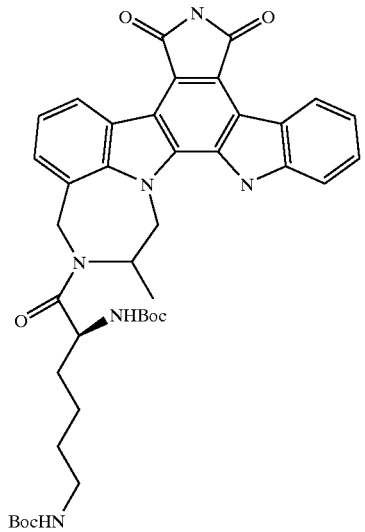

12-(N-(tert-butoxycarbonyl)-N'-(tert-butoxycarbonyl)-L-(histidinyl))-13-methyl-11,12,13,14-tetrahydro-12H,15H-pyrrolo[3,4-c]benzo[1,4]diazepino-[9',9a'1':3,2,1]pyrrolo[2,3-a]carbazole-5,7-dione Beginning with 13-methyl-11,12,13,14-tetrahydro-12H,15H-pyrrolo[3,4-c]benzo[1,4]diazepino[9',9a',1':3,2,1]-pyrrolo[2,3-a]carbazole-5,7-dione and N-[tert-butoxycarbonyl]-N'-[tert-butoxy-carbonyl]-L-histidine, the title compound was prepared essentially as described in Example 126.

EXAMPLE 185

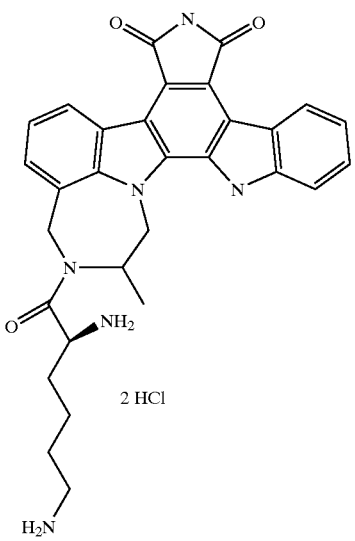

2 HCl 12-(L-(histidinyl))-13-methyl-11,12,13,14-tetrahydro-12H,15H-pyrrolo[3,4-c]benzo[1,4]diazepino[9',9a',1':3,2,1]-pyrrolo[2,3-a]carbazole-5,7-dione Dihydrochloride Beginning with 12-(N-(tert-butoxycarbonyl)-N'-(tert-butoxycarbonyl)-L-(histidinyl))-13-methyl-11,12,13,14-tetrahydro-12H,15H-pyrrolo[3,4-c]benzo[1,4]diazepino-[9',9a',1':3,2,1]pyrrolo[2,3-a]carbazole-5,7-dione, the title compound was prepared essentially as described in Example 136.

MS (ES, m/z), (M−1)=521.0.

EXAMPLE 186

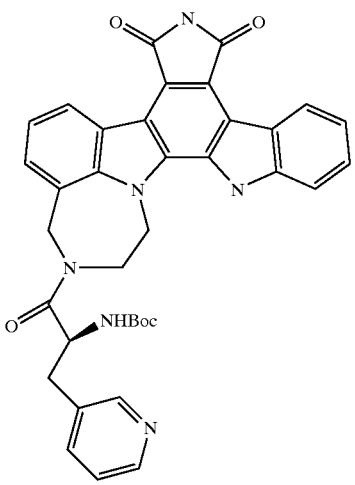

12-(N-(tert-butoxycarbonyl)-L-(β-(pyridin-3-yl)alaninyl))-11,12,13,14-tetrahydro-12H,15H-pyrrolo[3,4-c]benzo[1,4]diazepino-[9',9a',1':3,2,1]pyrrolo[2,3-a]carbazole-5,7-dione Beginning with 11,12,13,14-tetrahydro-12H,15H-pyrrolo[3,4-c]benzo[1,4]diazepino[9',9a',1':3,2,1]-pyrrolo[2,3-a]carbazole-5,7-dione and N-[tert-butoxycarbonyl]-L-(β-(pyridin-3-yl))alanine, the title compound was prepared essentially as described in Example 126.

MS (ES, m/z), (M−1)=627.0.

EXAMPLE 187

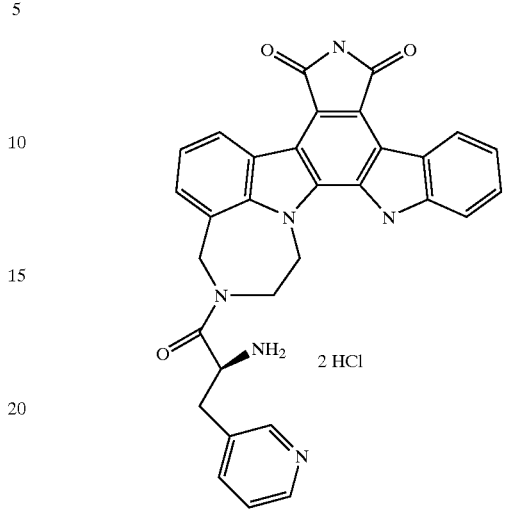

2 HCl 12-(L-(β-(pyridin-3-yl)alaninyl)-11, 12,13, 14-tetrahydro-12H,15H-pyrrolo[3,4-c]benzo[1,4]diazepino-[9',9a',1':3,2,1]pyrrolo[2,3-a]carbazole-5,7-dione Dihydrochloride Beginning with 12-(N-(tert-butoxycarbonyl)-L-(β-(pyridin-3-yl)alaninyl)-11,12,13,14-tetrahydro-12H, 15H-pyrrolo[3,4-c]benzo[1,4]diazepino[9',9a',1':3,2,1]-pyrrolo[2,3-a]carbazole-5,7-dione, the title compound was prepared essentially as described in Example 136.

MS (ES, m/z), (M−1)=527.0.

EXAMPLE 188

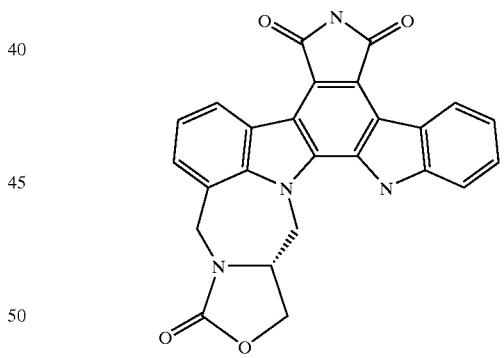

To a suspension of 12-(tert-butoxycarbonyl)-13-(hydroxymethyl)-11,12,13,14-tetrahydro-12H,15H-pyrrolo[3,4-c]benzo[1,4]diazepino[9',9a',1':3,2,1]pyrrolo[2,3-a]carbazole-5,7-dione (0.034 g, 0.0666 mmol) in dichloromethane (15 ml) was added triethylamine (0.046 ml, 0.333 mmol) and triphenylphosphine dibromide (0.197 g, 0.466 mmol) at 0° C. under nitrogen. The mixture was warmed to room temperature and stirred overnight. The reaction mixture was concentrated under reduced pressure and the residue subjected to silica gel chromatography, eluting with ethyl acetate:methanol (9:1). Fractions containing product were combined and concentrated under reduced pressure to provide the desired compound.

MS (ES, m/z) (M−1)=434.9

EXAMPLE 189

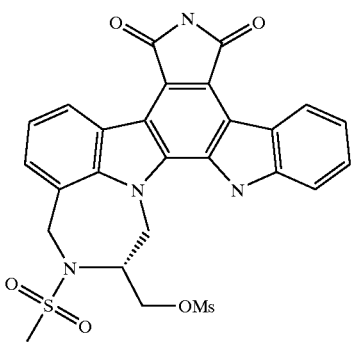

12-(methanesulfonyl)-13-((methanesulfonyloxy)methyl)-11,12,13,14-tetrahydro-12H,15H-pyrrolo[3,4-c]benzo[1,4]-diazepino[9',9a',1':3,2,1]pyrrolo[2,3-a]carbazole-5,7-dione To a suspension of 13-(hydroxymethyl)-11,12,13,14-tetrahydro-12H,15H-pyrrolo[3,4-c]benzo[1,4]diazepino-[9',9a',1':3,2,1]pyrrolo[2,3-a]carbazole-5,7-dione (0.046 g, 0.103 mmol) in tetrahydrofuran (10 ml) at room temperature under nitrogen were added diisopropylethylamine (0.09 ml, 0.515 mmol) and methanesulfonyl chloride (0.02 ml, 0.26 mmol). The solution was allowed to warm to room temperature and was stirred overnight. The reaction mixture was quenched with water and extracted with ethyl acetate. The combined organic layer was dried over magnesium sulfate, filtered and the filtrate concentrated under reduced pressure. The residue was subjected to silica gel chromatgraphy, eluting with ethyl acetate. Fractions containing product were combined and concentrated under reduced pressure to provide 0.03 g (52%) of the title compound as a yellow solid.

MS (ES, m/z) (M−1)=564.8

EXAMPLE 190

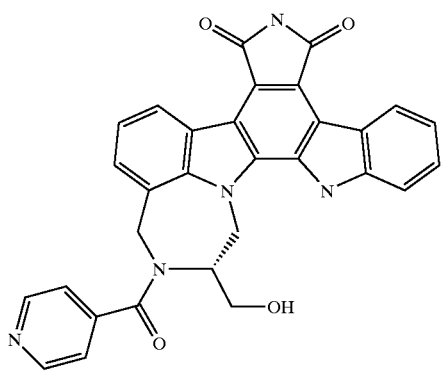

12-(pyridine-4-carbonyl)-13-(hydroxyymethyl)-11,12,13,14-tetrahydro-12H,15H-pyrrolo[3,4-c]benzo[1,4]diazepino-[9',9a',1':3,2,1]pyrrolo[2,3-a]carbazole-5,7-dione A suspension of 13-(hydroxymethyl)-11,12,13,14-tetrahydro-12H,15H-pyrrolo [3,4-c]benzo[1,4]diazepino-[9',9a',1':3,2,1]pyrrolo[2,3-a]carbazole-5,7-dione (0.03 g, 0.067 mmol), triethylamine (0.028 ml, 0.201 mmol) and isonicotinyl chloride hydrochloride (0.012 g, 0.067 mmol) in tetrahydrofuran (10 ml) under nitrogen was refluxed for 1 hour. The solution was cooled to room temperature and partitioned between ethyl acetate and saturated aqueous sodium bicarbonate. The organic phase was washed with saturated aqueous sodium chloride, dried over magnesium sulfate, filtered and the filtrate concentrated under reduced pressure. The residue was subjected to silica gel chromatography, eluting with ethyl acetate:methanol (9:1). Fractions containing product were combined and concentrated under reduced pressure to provide 0.02 g (54%) of the title compound as a yellow solid.

MS (IS, m/z) (M−1)=514.5

EXAMPLE 191

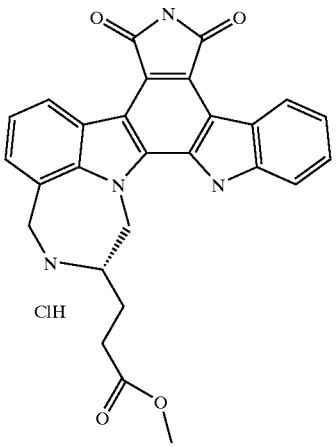

13-(2-(methoxycarbonyl)eth-1-yl)-11,12,13,14-tetrahydro-12H,15H-pyrrolo[3,4-c]benzo[1,4]diazepino[9',9a',1':3,2,1]-pyrrolo[2,3-a]carbazole-5,7-dione Hydrochloride To a suspension of 12-(tert-butoxycarbonyl)-13-(2-(tert-butoxycarbonyl)eth-1-yl)-11,12,13,14-tetrahydro-12H,15H-pyrrolo[3,4-c]benzo[1,4]diazepino[9',9a',1':3,2,1]-pyrrolo[2,3-a]carbazole-5,7-dione (0.015 g) in methanol (1 ml) was added hydrogen chloride (1 ml, 4N in dioxane). The reaction mixture was stirred at 60° C. for 10 min and then cooled to room temperature. The precipitate was isolated by filtration while washing with methanol to provide after vacuum drying the title compound as a yellow solid.

MS (ES, m/z), (M+1)=466.9, (M−1)=464.9

EXAMPLE 192

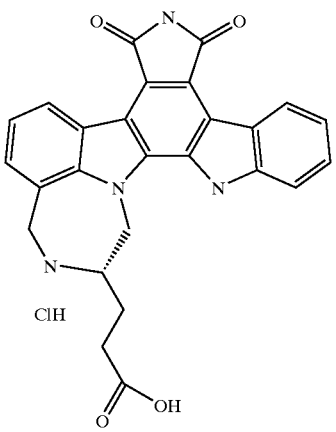

13-(2-(carboxy)eth-1-yl)-11,12,13,14-tetrahydro-12H,15H-pyrrolo[3,4-c]benzo[1,4]diazepino[9',9a',1':3,2,1]-pyrrolo[2,3-a]carbazole-5,7-dione Hydrochloride A suspension of 12-(tert-butoxycarbonyl)-13-(2-(tert-butoxycarbonyl)eth-1-yl)-11,12,13,14-tetrahydro-12H,15H- pyrrolo[3,4-c]benzo[1,4]diazepino[9',9a',1':3,2,1]-pyrrolo[2,3-a]carbazole-5,7-dione (0.010 g) in hydrogen chloride (1 ml, 4N in dioxane) was stirred at 60° C. for 10 minutes and then cooled to room temperature. The precipitate was isolated by filtration while washing with methanol to yield after vacuum drying the desired product as a yellow solid.

MS (Es, m/z), (M+1)=452.9, (M−1)=450.9

EXAMPLE 193

3-(S-6-(benzyloxycarbonyl)-5-(2-(tert-butoxycarbonyl)eth-1-yl)-5,6-dihydro-6H-[1,4] diazepino-[6,7,1-hi] indol-1-yl)-4-(indol-3-yl) pyrrole-2,5-dione Beginning with (S-6-(benzyloxycarbonyl)-5-(2-(tert-butoxycarbonyl)eth-1-yl)-5,6-dihydro-6H-[1,4]diazepino-[6,7,1-hi]indol-1-yl)oxoacetic acid methyl ester and indole-3-acetamide, the title compound was prepared essentially as described in Example 1.

EXAMPLE 194

3-(S-6-(tert-butoxycarbonyl)-5-(2-(tert-butoxycarbonyl)eth-1-yl)-5,6-dihydro-6H-[1,4] diazepino-[6,7,1-hi]indol-1-yl)-4-(indol-3-yl) pyrrole-2,5-dione Beginning with (S-6-(tert-butoxycarbonyl)-5-(2-(tert-butoxycarbonyl)eth-1-yl)-5,6-dihydro-6H-[1,4]diazepino-[6,7,1-hi]indol-1-yl)oxoacetic acid methyl ester and indole-3-acetamide, the title compound was prepared essentially as described in Example 1.

EXAMPLE 195

3-(S-6-(benzyloxycarbonyl)-5-(2-(carboxy)eth-1-yl)-5,6-dihydro-6H-[1,4]diazepino-[6,7,1-hi]indol-1-yl)-4-(indol-3-yl)pyrrole-2,5-dione Beginning with 3-(S-6-(benzyloxycarbonyl)-5-(2-(tert-butoxycarbonyl)eth-1-yl)-5,6-dihydro-6H-[1,4]diazepino-[6,7,1-hi]indol-1-yl)-4-(indol-3-yl)pyrrole-2,5-dione, the title compound was prepared essentially as described in Example 136.

MS (ES, m/z) 585.8 (M−1)

EXAMPLE 196

3-(3,4-Dihydro-5-thia-2a-aza-acenaphthylen-1-yl)-4-(1H-indol-3-yl)-pyrrole-2,5-dione Beginning with (3,4-dihydro-5-thia-2a-aza-acenaphthylen-1-yl)oxoacetic acid methyl ester and (indol-3-yl)acetamide, the title compound was prepared essentially as described in Example 1.

IS-MS, m/e 386.0 (m+1)

EXAMPLE 197

3-(1H-Indol-3-yl)-4-(5-oxo-4,5-dihydro-3H-5-thia-2a-aza-acenaphthylen-1-yl)pyrrole-2,5-dione To a solution of 3-(3,4-Dihydro-5-thia-2a-aza-acenaphthylen-1-yl)-4-(1H-indol-3-yl)-pyrrole-2,5-dione (0.50 g, 1.3 mmol) in dichloromethane was added meta-chloroperbenzoic acid (0.224 g, 1.3 mmol) at 0° C. The reaction mixture was stirred for 24 hours at room temperature and a saturated solution of sodium bisulfite and sodium bicarbonate (20 mL) was added. The mixture was extracted with ethyl acetate (2×20 mL). The organic layer was subjected to silica gel chromatography, eluting with ethyl acetate/hexanes (1:1). Fractions containing product were combined and concentrated under reduced pressure to provide 0.168 g (32.3%) of the title compound.

IS-MS, m/e 402.0 (m+1)

EXAMPLE 198

3-(1H-Indol-3-yl)-4-(5,5-dioxo-4,5-dihydro-3H-5-thia-2a-aza-acenaphthylen-1-yl)pyrrole-2,5-dione To a solution of 3-(1H-indol-3-yl)-4-(4,5-dihydro-3H-5-thia-2a-aza-acenaphthylen-1-yl)pyrrole-2,5-dione (0.50 g, 1.3 mmol) in dichloromethane was added meta-chloroperbenzoic acid (0.671 g, 3.89 mmol) at 0° C. After 24 hrs at room temperature, a saturated solution of sodium bisulfite and sodium bicarbonate was added, and the mixture was extracted with ethyl acetate. The organic layer was subjected to silica gel chromatography, eluting with ethyl acetate/hexane (4:1) to give 0.120 g (23.8%) of the title compound.

IS-MS, m/e 418.0 (m+1)

EXAMPLE 199

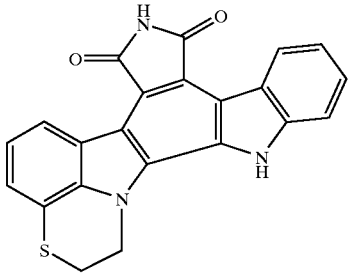

12H, 13H, 14H-pyrrolo[3,4-c]benzo[1,4]thiazino-[8',8a',1':3,2,1]pyrrolo[2,3-a]carbazole-5,7-dione Beginning with 3-(1H-Indol-3-yl)-4-(5,5-dioxo-4,5-dihydro-3H-5-thia-2a-aza-acenaphthylen-1-yl)pyrrole-2,5-dione, the title compound was prepared essentially as described in Example 58.

IS-MS, m/e 382.0 (m−1)

EXAMPLE 200

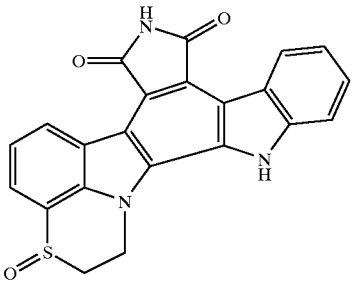

11-oxo-12H, 13H, 14H-pyrrolo[3,4-c]benzo[1,4] thiazino-[8',8a',1':3,2,1pyrrolo[2,3-a]carbazole-5,7-dione Beginning with 12H, 13H, 14H-pyrrolo[3,4-c]benzo[1,4]-thiazino[8',8a',1':3,2,1]pyrrolo[2,3-a]carbazole-5,7- dione, the title compound was prepared essentially as described in Example 197.

IS-MS, m/e 398.0 (m−1)

EXAMPLE 201

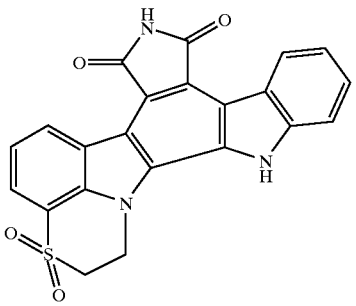

11,11-dioxo-12H, 13H, 14H-pyrrolo[3,4-c]benzo[1,4]thiazino-[8',8a',1':3,2,1]pyrrolo[2,3-a]carbazole-5,7-dione Beginning with 12H, 13H, 14H-pyrrolo[3,4-c]benzo[1,4]-thiazino[8',8a',1':3,2,1]pyrrolo[2,3-a]carbazole-5,7-dione, the title compound was prepared essentially as described in Example 198.

IS-MS, m/e 414.0 (m−1)

EXAMPLE 202

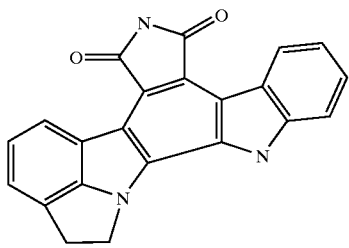

11H, 12H, 13H-pyrrolo[3,4-c]indolo[7',7a',1':3,2,1]-pyrrolo[2,3-a]carbazole-5,7-dione and

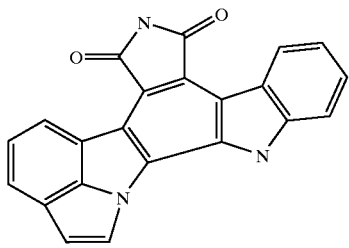

14H-pyrrolo[3,4-c]indolo[7',7a'1':3,2,1]pyrrolo[2,3-a]carbazole-5,7-dione

Beginning with 3-(5,4-dihydro-4H-pyrrolo[3,2,1-ij]indol-1-yl)-4-(1H-indol-3-yl)pyrrole-2,5-dione, the title compounds were prepared essentially as described in Example 52.

(Saturated) MS (IS, m/z) $C_{22}H_{13}N_3O_2$ (M$^+$−1)=350
(Unsaturated) MS (IS, m/z) $C_{22}H_{11}N_3O_2$ (M$^+$−1)=348

EXAMPLE 203

3-((6-(tert-butoxycarbonyl)-5,6-dihydro-6H-[1,4]diazepino[6,7,1-hi]indol-1-yl)-4-(1-methyl-1H-indol-3-yl)pyrrole-2,5-dione Beginning with 6-(tert-butoxycarbonyl)-5,6-dihydro-6H-[1,4]diazepino[6,7,1-hi]indol-1-yl)oxoacetic acid methyl ester and 1-methyl-indole-3-acetamide, the title compound was prepared essentially as described in Example 1.

MS (IS, m/z) $C_{29}H_{28}N_4O_4$ (M$^+$−1)=495

EXAMPLE 204

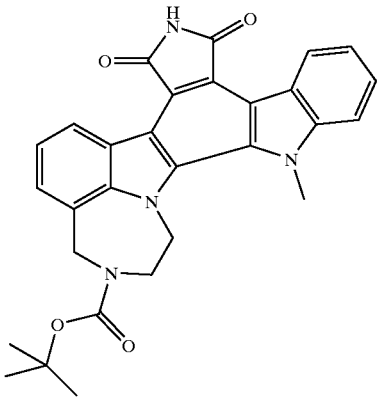

12-(tert-butoxycarbonyl)-15-methyl-11, 12,13,14-tetrahydro-12H,15H-pyrrolo[3,4-c]benzo[1,4]diazepino[9',9a',1':3,2,1]-pyrrolo[2,3-a]carbazole-5,7-dione Beginning with 3-((6-(tert-butoxycarbonyl)-5,6-dihydro-6H-1,4]diazepino[6,7,1-hi]indol-1-yl)-4-(1-methyl-1H-indol-3-yl)pyrrole-2,5-dione, the title compound was prepared essentially as described in Example 58.

MS (IS, m/z) $C_{29}H_{26}N_4O_4$ (M$^+$−1)=493

EXAMPLE 205

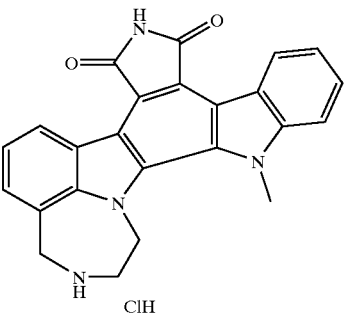

15-methyl-11,12,13,14-tetrahydro-12H,15H-pyrrolo[3,4-c]benzo[1,4]diazepino[9',9a',1':3,2,1]-pyrrolo[2,3-a]carbazole-5,7-dione Hydrochloride Beginning with 12-(tert-butoxycarbonyl)-15-methyl-11,12,13,14-tetrahydro-12H,15H-pyrrolo[3,4-c]benzo[1,4]-diazepino[9',9a',1':3,2,1]pyrrolo[2,3-a]carbazole-5,7-dione, the title compound was prepared essentially as described in Example 136.

MS (IS, m/z) $C_{24}H_{18}N_4O_2$ (M$^+$+1)=395

EXAMPLE 206

3-((6-(tert-butoxycarbonyl)-5,6-dihydro-6H-[1,4]diazepino[6,7,1-hi]indol-1-yl)-4-(5-phenoxy-1H-indol-3-yl)pyrrole-2,5-dione Beginning with 7-Carbamoylmethyl-3,4-dihydro-1H-[1,4]diazepino[6,7,1-hi]indole-2-carboxylic acid tert-butyl esterand (5-phenoxyindole)-3-glyoxylic acid methyl ester, the title compound was prepared essentially as described in Example 1.

MS (IS, m/z) $C_{34}H_{30}N_4O_5$ (M$^+$+1-Boc)=475

EXAMPLE 207

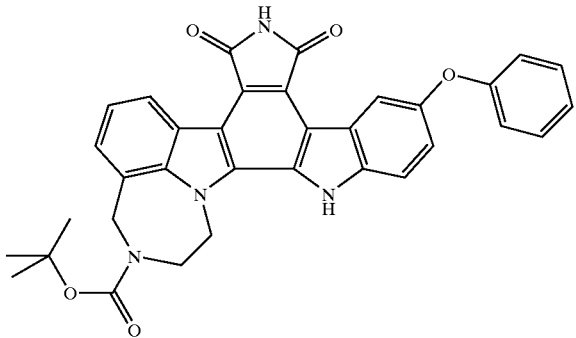

3-phenoxy-12-(tert-butoxycarbonyl)-11,12,13,14-tetrahydro-12H,15H-pyrrolo[3,4-c]benzo[1,4]diazepino[9',9a',1':3,2,1]-pyrrolo [2,3-a]carbazole-5,7-dione Beginning with 3-((6-(tert-butoxycarbonyl)-5,6-dihydro-6H-[1,4]diazepino[6,7,1-hi]indol-1-yl)-4-(5-phenoxy-1H-indol-3-yl)pyrrole-2,5-dione, the title compound was prepared essentially as described in Example 58.

MS (IS, m/z) $C_{34}H_{28}N_4O_5$ (M$^+$-1)=571

EXAMPLE 208

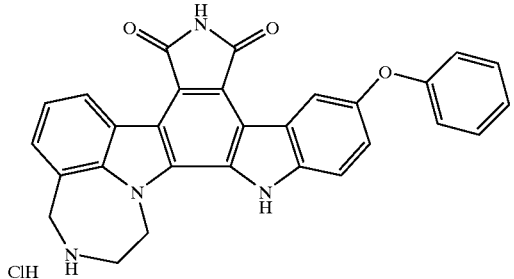

3-phenoxy-11,12,13,14-tetrahydro-12H, 15H-pyrrolo[3,4-c]benzo[1,4]diazepino[9',9a',11:3,2,1]-pyrrolo[2,3-a]carbazole-5,7-dione Hydrochloride Beginning with 5-phenoxy-12-(tert-butoxycarbonyl)-11,12,13,14-tetrahydro-12H,15H-pyrrolo[3,4-c]benzo[1,4]-diazepino[9',9a',1':3,2,1]pyrrolo[2,3-a]carbazole-5,7-dione, the title compound was prepared essentially as described in Example 136.

MS (IS, m/z) $C_{29}H_{20}N_4O_3$ (M$^+$+1)=473

EXAMPLE 209

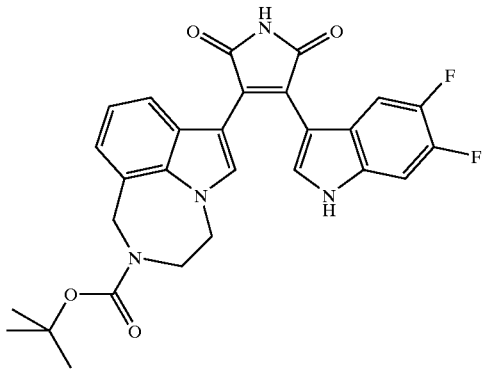

3-((6-(tert-butoxycarbonyl)-5,6-dihydro-6H-[1,4]diazepino[6,7,1-hi]indol-1-yl)-4-(5,6-difluoro-1H-indol-3-yl)pyrrole-2,5-dione Beginning with 7-Carbamoylmethyl-3,4-dihydro-1H-[1,4]diazepino[6,7,1-hi]indole-2-carboxylic acid tert-butyl esterand (5,6-difluoroindole)-3-glyoxylic acid methyl ester, the title compound was prepared essentially as described in Example 1.

MS (IS, m/z) $C_{28}H_{24}F_2N_4O_4$ (M$^+$-1)=517

EXAMPLE 210

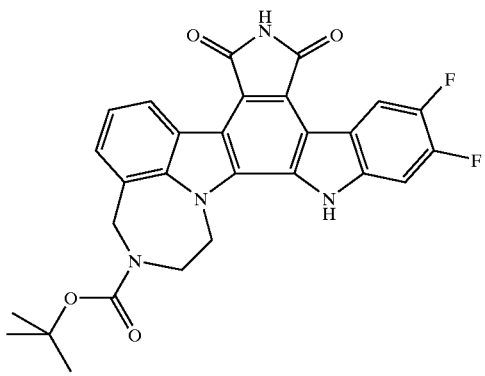

2,3-difluoro-12-(tert-butoxycarbonyl)-11,12,13,14-tetrahydro-12H,15H-pyrrolo [3,4-c]benzo [1,4]diazepino[9',9a',1':3,2,1]-pyrrolo[2,3-a]carbazole-5,7-dione Beginning with 3-((6-(tert-butoxycarbonyl)-5,6-dihydro-6H-[1,4]diazepino[6,7,1-hi]indol-1-yl)-4-(5,6-difluoro-1H-indol-3-yl)pyrrole-2,5-dione, the title compound was prepared essentially as described in Example 58.

MS (IS, m/z) $C_{28}H_{22}F_2N_4O_4$ (M$^+$-1)=515

EXAMPLE 211

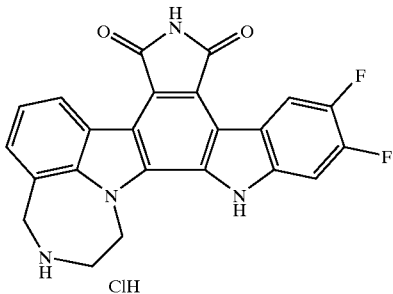

2,3-difluoro-11,12,13,14-tetrahydro-12H,15H-pyrrolo[3,4-c]benzo[1,4]diazepino[9',9a',1':3,2,1]-pyrrolo[2,3-a]carbazole-5,7-dione Hydrochloride Beginning with 2,3-difluoro-12-(tert-butoxycarbonyl)-15-methyl-11,12,13,14-tetrahydro-12H,15H-pyrrolo[3,4-c]benzo[1,4'-diazepino[9',9a',1':3,2,1]pyrrolo[2,3-a]carbazole-5,7-dione, the title compound was prepared essentially as described in Example 136.

MS (IS, m/z) $C_{23}H_{14}F_2N_4O_2$ (M$^+$−1)=415.

EXAMPLE 212

3-((6-(tert-butoxycarbonyl)-5,6-dihydro-6H-[1,4]diazepino[6,7,1-hi]indol-1-yl)-4-(5-benzyloxy-1H-indol-3-yl)pyrrole-2,5-dione Beginning with 7-Carbamoylmethyl-3,4-dihydro-1H-[1,4]diazepino[6,7,1-hi]indole-2-carboxylic acid tert-butyl esterand (5-benzyloxyindole)-3-glyoxylic acid methyl ester, the title compound was prepared essentially as described in Example 1.

MS (IS, m/z) $C_{35}H_{32}N_4O_5$ (M$^+$−1)=587.

EXAMPLE 213

3-((6-(tert-butoxycarbonyl)-5,6-dihydro-6H-[1,4]diazepino[6,7,1-hi]indol-1-yl)-4-(6-trifluoromethyl-1H-indol-3-yl)pyrrole-2,5-dione Beginning with 6-(tert-butoxycarbonyl)-5,6-dihydro-6H-[1,4]diazepino[6,7,1-hi]indol-1-yl)oxoacetic acid methyl ester and (6-trifluoromethylindole)-3-acetamide, the title compound was prepared essentially as described in Example 1.

MS (IS, m/z) $C_{29}H_{25}F_3N_4O_4$ (M$^+$−1)=549

EXAMPLE 214

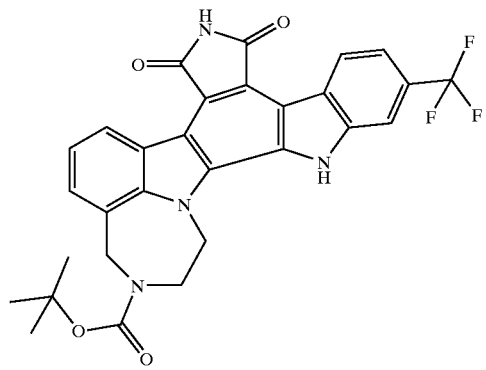

2-trifluoromethyl-12-(tert-butoxycarbonyl)-11,12,13,14-tetrahydro-12H,15H-pyrrolo[3,4-c]benzo[1,4]diazepino-[9',9a',1':3,2,1]pyrrolo[2,3-a]carbazole-5,7-dione Beginning with 3-((6-(tert-butoxycarbonyl)-5,6-dihydro-6H-[1,4]diazepino[6,7,1-hi]indol-1-yl)-4-(6-trifluoromethyl-1H-indol-3-yl)pyrrole-2,5-dione, the title compound was prepared essentially as described in Example 58.

MS (IS, m/z) $C_{29}H_{23}F_3N_4O_4$ (M$^+$−1)=547

EXAMPLE 215

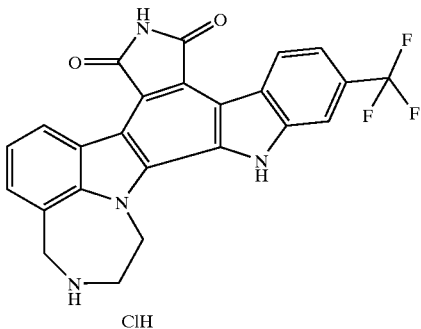

2-trifluoromethyl-11,12,13,14-tetrahydro-12H,15H-pyrrolo[3,4-c]benzo[1,4]diazepino[9',9a',1':3,2,1]-pyrrolo[2,3-a]carbazole-5,7-dione Hydrochloride Beginning with 2-trifluoromethyl-12-(tert-butoxycarbonyl)-11,12,13,14-tetrahydro-12H,15H-pyrrolo[3,4-c]benzo1,4]-diazepino[9',9a',1':3,2,1lpyrrolo[2,3-a]carbazole-5,7-dione, the title compound was prepared essentially as described in Example 136.

MS (IS, m/z) $C_{24}H_{15}F_3N_4O_2$ (M$^+$−1)=447

EXAMPLE 216

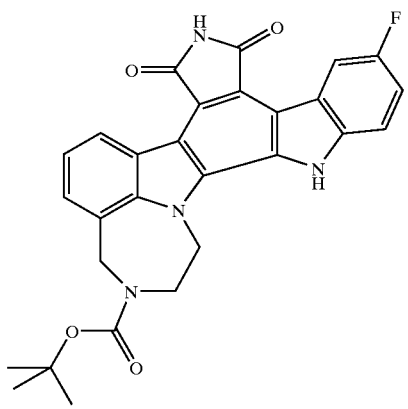

3-fluoro-12-(tert-butoxycarbonyl)-11,12,13,14-tetrahydro-12H,15H-pyrrolo[3,4-c]benzo[1,4]diazepino[9',9a',1':3,2,1]-pyrrolo[2,3-a]carbazole-5,7-dione Beginning with 3-((6-(tert-butoxycarbonyl)-5,6-dihydro-6H-[1, 4]diazepino[6,7,1-hi]indol-1-yl)-4-(5-fluoro-1H-indol-3-yl)pyrrole-2,5-dione, the title compound was prepared essentially as described in Example 58.

MS (IS, m/z) $C_{28}H_{23}F_1N_4O_4$ (M$^+$−1)=497

EXAMPLE 217

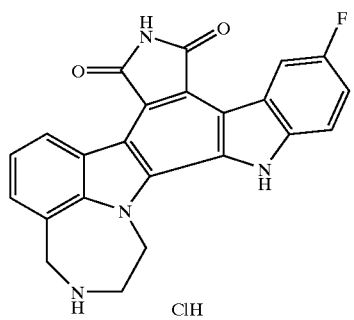

3-fluoro-11,12,13,14-tetrahydro-12H,15H-pyrrolo[3,4-c]benzo[1,4]diazepino[9',9a',1':3,2,1]-pyrrolo[2,3-a]carbazole-5,7-dione Hydrochloride Beginning with 3-fluoro-12-(tert-butoxycarbonyl)-11,12,13,14-tetrahydro-12H,15H-pyrrolo(3,4-c]benzo[1,4]-diazepino[9',9a',1':3,2,1]pyrrolo[2,3-a]carbazole-5,7-dione, the title compound was prepared essentially as described in Example 136.

MS (IS, m/z) $C_{23}H_{15}F_1N_4O_2$ (M$^+$−1)=397

EXAMPLE 218

3-((6-(tert-butoxycarbonyl)-5,6-dihydro-6H-[1,4]diazepino-[6,7,1-hi]indol-1-yl)-4-(7-(2-(triisopropylsilyloxy)eth-1-yl)-1H-indol-3-yl)pyrrole-2,5-dione Beginning with 7-Carbamoylmethyl-3,4-dihydro-1H-[1,4]diazepino[6,7,1-hi]indole-2-carboxylic acid tert-butyl ester and (7-(2-(triisopropylsilyloxy)eth-1-yl)indole-3-glyoxylic acid methyl ester, the title compound was prepared essentially as described in Example 1.

NMR. MS (IS, m/z) $C_{39}H_{50}N_4O_5Si_1$ (M$^+$+1)=683

EXAMPLE 219

3-(5,6-dihydro-6H-[1,4]diazepino-[6,7,1-hi]indol-1-yl)-4-(7-(2-(hydroxy)eth-1-yl)-1H-indol-3-yl)pyrrole-2,5-dione Hydrochloride Beginning with 3-((6-(tert-butoxycarbonyl)-5,6-dihydro-6H-[1,4]diazepino-[6,7,1-hi]indol-1-yl)-4-(7-(2-(triisopropylsilyloxy)eth-1-yl)-1H-indol-3-yl)pyrrole-2,5-dione, the title compound was prepared essentially as described in Example 136.

MS (IS, m/z) $C_{25}H_{22}N_4O_3$ (M$^+$+1)=427

EXAMPLE 220

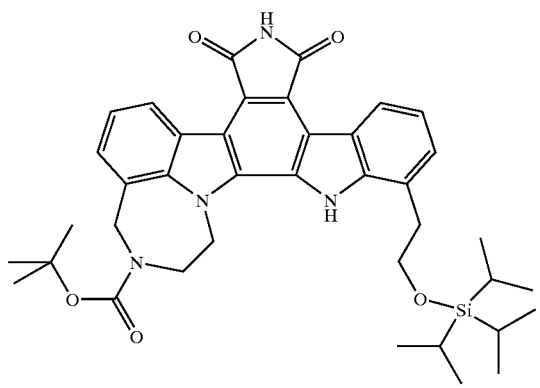

1-(2-(triisopropylsilyloxy)eth-1-yl)-12-(tert-butoxycarbonyl)-11,12,13,14-tetrahydro-12H,15H-pyrrolo[3,4-c]benzo[1,4]diazepino[9',9a',1':3,2,1]-pyrrolo[2,3-a]carbazole-5,7-dione Beginning with 3-((6-(tert-butoxycarbonyl)-5,6-dihydro-6H-[1,4]diazepino-[6,7,1-hi]indol-1-yl)-4-(7-(2-(triisopropylsilyloxy)eth-1-yl)-1H-indol-3-yl)pyrrole-2,5-dione, the title compound was prepared essentially as described in Example 58.

MS (IS, m/z) $C_{39}H_{48}N_4O_5Si_1$ (M$^+$+1)=681

EXAMPLE 221

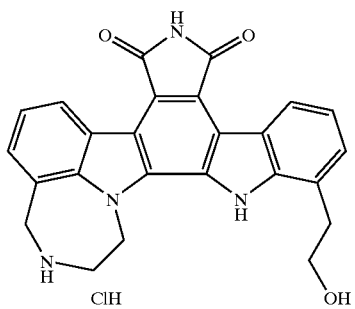

1-(2-hydroxyeth-1-yl)-11,12,13,14-tetrahydro-12H,15H-pyrrolo[3,4-c]benzo[1,4]diazepino[9',9a',1':3,2,1]-pyrrolo[2,3-a]carbazole-5,7-dione Hydrochloride Beginning with 1-(2-(triisopropylsilyloxy)eth-1-yl)-12-(tert-butoxycarbonyl)-11,12,13,14-tetrahydro-12H,15H-pyrrolo[3,4-c]benzo[1,4]diazepino[9',9a',1':3,2,1]-pyrrolo

[2,3-a]carbazole-5,7-dione, the title compound was prepared essentially as described in Example 136.

MS (IS, m/z) $C_{25}H_{20}N_4O_3$ (M$^+$+1)=425

EXAMPLE 222

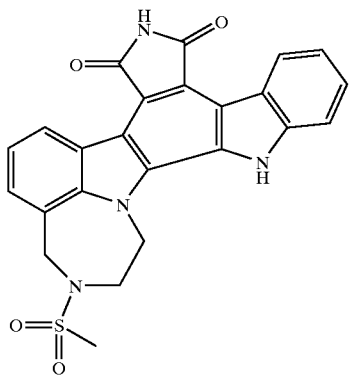

12-methanesulfonyl-11,12,13,14-tetrahydro-12H, 15H-pyrrolo[3,4-c]benzo[1,4]diazepino[9',9a',1':3,2,1]-pyrrolo[2,3-a]carbazole-5,7-dione To a solution of 11,12,13,14-tetrahydro-12H,15H-pyrrolo[3,4-c]benzo[1,4]diazepino[9',9a',1':3,2,1]-pyrrolo[2,3-a]carbazole-5,7-dione (0.025 g, 0.066 mmol) in 1 mL of tetrahydrofuran was added triethylamine (0.03 mL, 0.215 mmol) followed by the dropwise addition of methanesulfonyl chloride (0.010 mL, 0.127 mmol). After stirring at room temperature for 3 hours the solution was concentrated under reduced pressure and the residue subjected to silica gel chromatography, eluting with 50% tetrahydrofuran in toluene containing 2% triethylamine. Fractions containing product were combined and concentrated under reduced pressure to provide the title compound as a yellow solid.

NMR. MS (IS, m/z) $C_{24}H_{18}N_4O_4S_1$ (M$^+$−1)=457

EXAMPLE 223

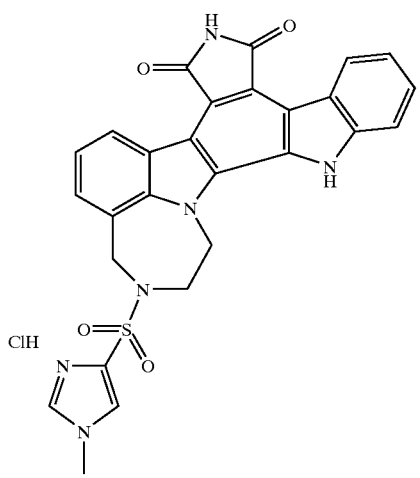

12-(1-methylimidazole-4-sulfonyl)-11,12,13,14-tetrahydro-12H, 15H-pyrrolo[3,4-c]benzo[1,4]diazepino-[9',9a',1:3,2,1]pyrrolo[2,3-a]carbazole-5,7-dione Hydrochloride To a solution of 11,12,13,14-tetrahydro-12H,15H-pyrrolo[3,4-c]benzo[1,4]diazepino[9',9a',1':3,2,1]-pyrrolo[2,3-a]carbazole-5,7-dione (0.050 g, 0.131 mmol) in 2 mL of pyridine was added N-methylimidazole sulfonyl chloride (0.034 g, 0.188 mmol) and the yellow suspension was stirred at room temperature under nitrogen. After stirring overnight an additional (0.02 g, 0.11 mmol) of the sulfonyl chloride was added and the reaction heated to 75° C. for 40 minutes. The reaction mixture was cooled and poured into 50 mL of ice-water and filtered, rinsing with 20 mL of water followed by 10 mL of ether. After drying, the solid was suspended in 5 mL of dichloromethane and treated with 1 mL of 4 M hydrogen chloride in dioxane and stirred for 2 hours. The solvents were removed under reduced pressure and the residue dissolved in 5 mL of methanol and concentrated again. The solid was suspended in 5 mL of dichloromethane and filtered, rinsing with 2 mL dichloromethane. The yellow solid was dried under reduced pressure to provide the title compound.

MS (IS, m/z) $C_{27}H_{20}N_6O_4S_1$ (M$^+$−1)=523

EXAMPLE 224

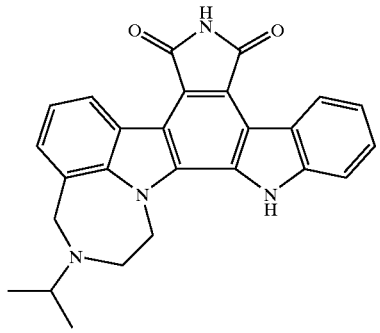

12-isopropyl-11,12,13,14-tetra-hydro-12H,15H-pyrrolo-[3,4-c]benzo[1,4]diazepino-[9',9a',1':3,2,1]pyrrolo[2,3-a]carbazole-5,7-dione Methanesulfonate To a solution of 11,12,13,14-tetrahydro-12H,15H-pyrrolo[3,4-c]benzo[1,4]diazepino[9',9a',1':3,2,1-pyrrolo[2,3-a]carbazole-5,7-dione (0.052 g, 0.137 mmol) in 5 mL of acetone was added sodium cyanoborohydride (0.025 g, 0.378 mmol) and 2 drops of glacial acetic acid and the mixture was heated to reflux under nitrogen. Three hours later an additional 0.020 g of borohydride and two more drops of acetic acid were added and after 5 hours total the reaction mixture was concentrated under reduced pressure. The residue was treated with 20 mL of water and 5 mL of 10% sodium bicarbonate. After stirring 15 minutes the suspension was filtered and the recovered solid rinsed with 5 mL of water. Vacuum-drying at 60° C. gave 0.052 g (90%) of 12-isopropyl-11,12,13,14-tetra-hydro-12H,15H-pyrrolo-[3,4-c]benzo[1,4]diazepino-[9',1,9a',1':3,2,1]pyrrolo[2,3-a]carbazole-5,7-dione as an orange solid. A solution of this compound (0.042 g, 0.1 mmol) in 2 mL of acetone containing 0.1 mL of water under nitrogen was prepared and stirred 2 hours, after which time methanesulfonic acid (0.010 mL, 0.15 mmol) was added and the mixture stirred overnight. The suspension was filtered and the recovered solid rinsed with 2 mL of acetone. Vacuum-drying at 60° C. gave the title compound as a light yellow solid.

MS (IS, m/z) $C_{26}H_{22}N_4O_2$(M$^+$−1)=421

EXAMPLE 225

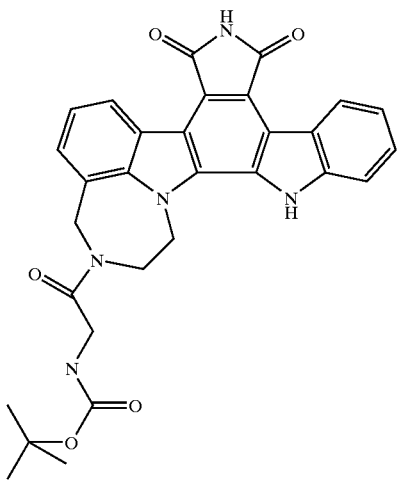

12-(N-[tert-butoxycarbonyl]alanyl)-11,12,13,14-tetrahydro-12H,15H-pyrrolo[3,4-c]benzo[1,4]diazepino[9',9a',1':3,2,1]-pyrrolo[2,3-a]carbazole-5,7-dione Beginning with 11,12,13,14-tetrahydro-12H,15H-pyrrolo[3,4-c]benzo[1,4]diazepino[9',9a',1':3,2,1]-pyrrolo[2,3-a]carbazole-5,7-dione, the title compound was prepared essentially as described in Example 126.

MS (IS, m/z) $C_{30}H_{27}N_5O_5$ (M$^+$−1)=536

EXAMPLE 226

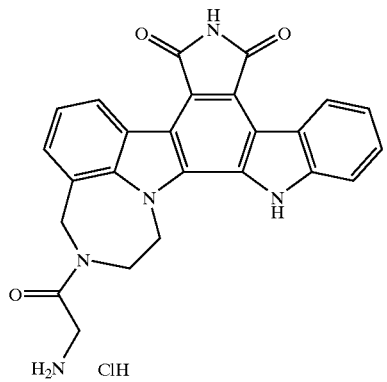

12-(alanyl)-11,12,13,14-tetrahydro-12H,15H-pyrrolo[3,4-c]benzo[1,4]diazepino[9',9a',1':3,2,1]-pyrrolo[2,3-a]carbazole-5,7-dione Hydrochloride Beginning with 12-(N-[tert-butoxycarbonyl]alanyl)-11,12,13,14-tetrahydro-12H,15H-pyrrolo[3,4-c]benzo[1,4]-diazepino[9',9a',1':3,2,1]-pyrrolo[2,3-a]carbazole-5,7-dione, the title compound was prepared essentially as described in Example 136.

MS (IS, m/z) $C_{25}H_{19}N_5O_3$ (M$^+$+1)=438

EXAMPLE 227

3-(6-(tert-butoxycarbonyl)-4,5-dihydro-6H-[1,4]homodiazepino[6,7,1-hi]indol-1-yl)-4-(1H-indol-3-yl)pyrrole-2,5-dione Beginning with 6-(tert-butoxycarbonyl)-4,5-dihydro-6H-[1,4]homodiazepino[6,7,1-hi]indol-1-yl)oxoacetic acid methyl ester and indole-3-acetamide, the title compound was prepared essentially as described in Example 1.

MS (IS, m/z) $C_{29}H_{28}N_4O_4$ (M$^+$+1)=497

EXAMPLE 228

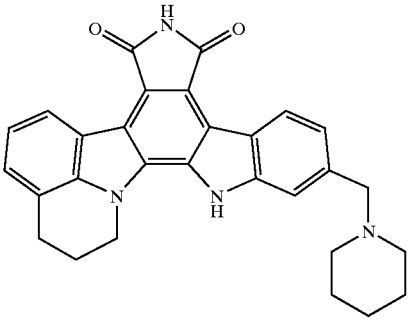

2-((piperidin-1-yl)methyl)-11H, 12H, 14H-pyrrolo[3,4-c]quinolino[8',8a',1':3,2,1]-pyrrolo[2,3-a]carbazole-5,7-dione Beginning with piperidine and 2-(bromomethyl)-11H, 12H, 14H-pyrrolo[3,4-c]quinolino[8',8a',1':3,2,1]pyrrolo[2,3-a]carbazole-5,7-dione, the title compound was prepared essentially as described in Example 111.

MS (IS, m/z) $C_{29}H_{26}N_4O_2$ (M$^+$+1)=463

EXAMPLE 229

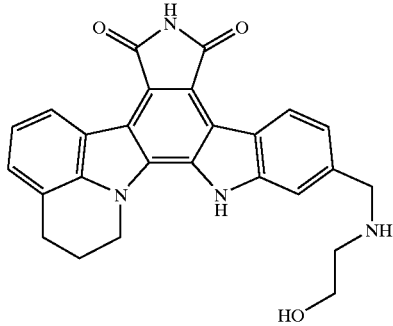

2-(N-[2-hydroxyeth-1-yl]aminomethyl)-11H, 12H, 14H-pyrrolo[3,4-c]quinolino[8',8a',1':3,2,1]-pyrrolo[2,3-a]carbazole-5,7-dione Beginning with ethanolamine and 2-(bromomethyl)-11H, 12H, 14H-pyrrolo[3,4-c]quinolino[8',8a',1':3,2,1]pyrrolo-[2,3-a]carbazole-5,7-dione, the title compound was prepared essentially as described in Example 111.

MS (IS, m/z) $C_{26}H_{22}N_4O_3$ (M$^+$+1)=439

EXAMPLE 230

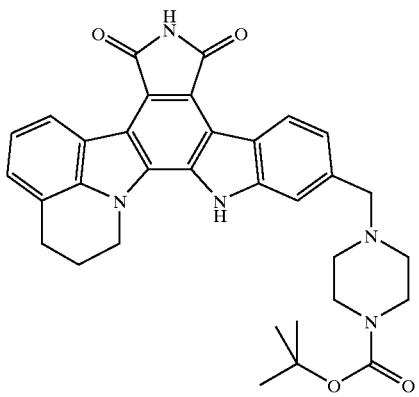

2-((4-(tert-butoxycarbonyl)piperazin-1-yl)methyl)-
11H, 12H, 14H-pyrrolo[3,4-c]quinolino[8',8a',1':3,2,
1]-pyrrolo[2,3-a]carbazole-5,7-dione Beginning with 1-(tert-butoxycarbonyl)piperazine and 2-(bromomethyl)-11H, 12H, 14H-pyrrolo[3,4-c]quinolino-[8',8a',1':3,2,1]pyrrolo[2,3-a]carbazole-5,7-dione, the title compound was prepared essentially as described in Example 111.

EXAMPLE 231

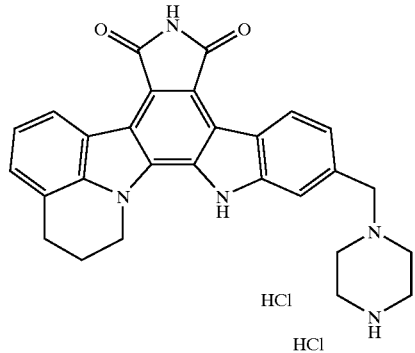

2-((piperazin-1-yl)methyl)-11H, 12H, 14H-pyrrolo
[3,4-c]quinolino[8',8a',1':3,2,1]-pyrrolo[2,3-a]
carbazole-5,7-dione Dihydrochloride Beginning with 2-((4-(tert-butoxycarbonyl)piperazin-1-yl)methyl)-11H, 12H, 14H-pyrrolo[3,4-c]quinolino-[8',8a', 1':3,2,1]pyrrolo[2,3-a]carbazole-5,7-dione, the title compound was prepared essentially as described in Example 136.

MS (IS, m/z) $C_{28}H_{25}N_5O_2$ (M$^+$+1)=464

EXAMPLE 232

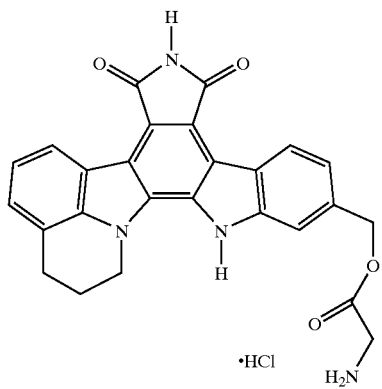

A solution of 2-(hydroxymethyl)-11H, 12H, 14H-pyrrolo[3,4-c]quinolino[8,8a',1':3,2,1]pyrrolo[2,3-a]carbazole-5,7-dione (0.050 g, 0.13 mmol), N-[tert-butoxycarbonyl]glycine (0.090 g, 0.51 mmol), dicyclohexylcarbodiimide (0.050 g, 0.25 mmol), and dimethylaminopyridine (0.030 g, 0.25 mmol) in dimethylformamide (2.5 mL) was stirred for 24 hours. The reaction mixture was diluted with ethyl acetate (20 mL), washed with water and saturated aqueous sodium chloride, dried over sodium sulfate, filtered and the filtrate concentrated under reduced pressure. The residue was subjected to silica gel chromatography, eluting with 50% ethyl acetate in hexanes. Fractions containing product were combined and concentrated under reduced pressure to provide 0.025 g (35%) of 2-(([N-tert-butoxycarbonyl]alaninyloxy) methyl)-11H, 12H, 14H-pyrrolo[3,4-c]quinolino[8',8a',1':3, 2,1]pyrrolo[2,3-a]carbazole-5,7-dione as a yellow solid. 0.018 g of this solid was then reacted essentially as described in Example 136 to provide 0.010 g (63%) of the title compound as a yellow solid.

MS (IS, m/z) $C_{26}H_{20}N_4O_4$ (M$^+$-1)=451

EXAMPLE 233

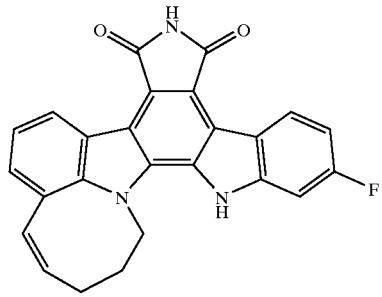

2-fluoro-13,14-dihydro-16H-pyrrolo[3,4-c]benz[b]
homoazepino[10',10a',1':3,2,1]pyrrolo[2,3-a]
carbazole-5,7-dione Beginning with 3-(9,10-Dihydro-8H-10a-aza-cycloocta-[cd]inden-2-yl)-4-(1H-indol-3-yl)pyrrole-2,5-dione, the title compound was prepared essentially as described in Example 52.

MS (IS, m/z) $C_{25}H_{16}FN_3O_2$ (M$^+$-1)=408.

EXAMPLE 234

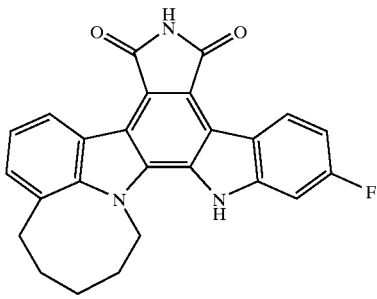

2-fluoro-11,12,13,14-tetrahydro-16H-pyrrolo[3,4-c]
benz[b]homoazepino[10',10a',1':3,2,1]pyrrolo[2,3-a]
carbazole-5,7-dione Beginning with 3-(6-fluoro-1H-indol-3-yl)-4-(7,8,9,10-tetrahydro-6H-10a-aza-cycloocta[cd]inden-2-yl)pyrrole-2,5-dione, the title compound was prepared essentially as described in Example 52.

MS (IS, m/z) $C_{25}H_{18}FN_3O_2$ $(M^+-1)=410$.

EXAMPLE 235

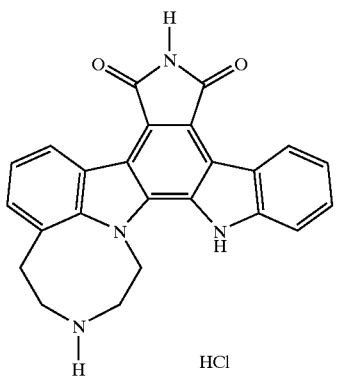

2-fluoro-11,12,13,14-tetrahydro-16H-pyrrolo[3,4-c]
benz[b]homo[1,4]diazepino[10',10a',1':3,2,1]pyrrolo
[2,3-a]carbazole-5,7-dione Hydrochloride Beginning with (6-(tert-butoxycarbonyl)-5,6-dihydro-6H-[1,4]homodiazepino[6,7,1-hi]indol-1-yl)oxoacetic acid methyl ester and indole-3-acetamide, the title compound was prepared essentially as described in Examples 1, 55, and 136.

MS (IS, m/z) $C_{24}H_{18}N_4O_2$ $(M^+-1)=393$

EXAMPLE 236

3-(5-hydroxymethyl-5,6-dihydro-4H-pyrrolo[3,2,1-ij]quinolin-1-yl)-4-(1H-indol-3-yl)-pyrrole-2,5-dione Beginning with (5-(tert-butyldimethylsilyloxymethyl)-5,6-dihydro-4H-pyrrolo[3,2,1-ij]quinolin-1-yl)oxoacetic acid methyl ester 2-(1H-indol-3-yl)acetamide, the title compound was prepared essentially as described in Example 1.

MS (ES, m/z) $C_{24}H_{19}N_3O_3$: 398.1 $(M^++1)$, 396.2 $(M^+-1)$.

EXAMPLE 237

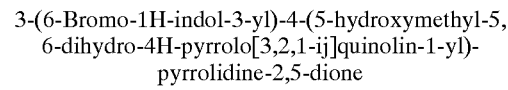

12-(hydroxymethyl)-11H, 12H, 14H-pyrrolo[3,4-c]
quinolino[8',8a',1':3,2,1]pyrrolo[2,3-a]carbazole-5,7-
dione Beginning with 3-(5-(hydroxymethyl)-5,6-dihydro-4H-pyrrolo[3,2,1-ij]quinolin-1-yl)-4-(1H-indol-3-yl)pyrrole-2,5-dione, the title compound was prepared essentially as described in Example 52.

MS (ES, m/z) $C_{24}H_{17}N_3O_3$: 396.1 $(M^++1)$, 394.2 $(M^+-1)$

EXAMPLE 238

3-(6-Bromo-1H-indol-3-yl)-4-(5-hydroxymethyl-5,
6-dihydro-4H-pyrrolo[3,2,1-ij]quinolin-1-yl)-
pyrrolidine-2,5-dione Beginning with (5-(hydroxymethyl)-5,6-dihydro-4H-pyrrolo[3,2,1-ij]quinolin-1-yl]oxoacetic acid methyl ester and (6-bromo-1H-indol-3-yl)acetamide, the title compound was prepared essentially as described in Example 1.

MS (ES, m/z): 476.1 ($^{79}$Br, $M^++1$), 478.1 ($^{81}$Br, $M^+30$ 1), 474.1 ($^{79}$Br, $M^+-1$), 476.2 ($^{81}$Br, $M^{30}$ −1).

HR MS Calcd for $C_{24}H_{19}BrN_3O_3$ 476.0610 ($M^++1$, $^{79}$Br) found: 476.0599.

EXAMPLE 239

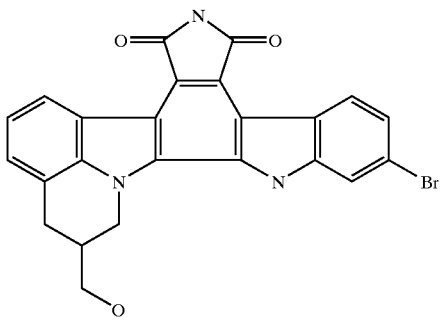

2-bromo-12-(hydroxymethyl)-11H, 12H, 14H-
pyrrolo[3,4-c]quinolino[8',8a',1':3,2,1]pyrrolo[2,3-a]
carbazole-5,7-dione Beginning with 3-(5-(hydroxymethyl)-5,6-dihydro-4H-pyrrolo[3,2,1-ij]quinolin-1-yl)-4-(6-bromo-1H-indol-3-yl)pyrrole-2,5-dione, the title compound was prepared essentially as described in Example 60.

$C_{24}H_{16}BrN_3O_3$, MS (ES, m/z): 472.1 ($^{79}$Br, $M^+-1$), 474.2 ($^{81}$Br, $M^+-1$).

EXAMPLE 240

3-(6-Fluoro-1H-indol-3-yl)-4-(5-hydroxymethyl-5,6-dihydro-4H-pyrrolo[3,2,1-ij]quinolin-1-yl)-pyrrolidine-2,5-dione Beginning with (5-(tert-butyldimethylsilyloxymethyl)-5,6-dihydro-4H-pyrrolo[3,2,1-ij]quinolin-1-yl)oxoacetic acid methyl ester and (6-fluoro-1H-indol-3-yl)acetamide, the title compound was prepared essentially as described in Example 1.

MS (ES, m/z): 416.1 ($M^++1$), 414.2 ($M^+-1$).

HRMS calcd for $C_{24}H_{19}FN_3O_3$ 416.1410($M^++1$), found 416.1410.

EXAMPLE 241

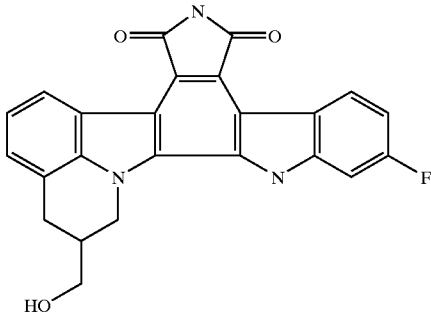

2-fluoro-12-(hydroxymethyl)-11H, 12H, 14H-pyrrolo[3,4-c]quinolino[8',8a',1':3,2,1]pyrrolo[2,3-a]carbazole-5,7-dione A mixture of 3-(5-(hydroxymethyl)-5,6-dihydro-4H-pyrrolo[3,2,1-ij]quinolin-1-yl)-4-(6-fluoro-1H-indol-3-yl)pyrrole-2,5-dione (100 mg, 2.40 mmol) and iodine (61 mg, 2.40 mmol) in 150 mL benzene and 5 mL methanol was irradiated with a Hanovia (UV 450W) lamp for 5 hours with stirring. After the reaction was cooled to room temperature, solvent was evaporated under reduced pressure. The residue was dissolved in dimethylsulfoxide (5 mL), diluted with ethyl acetate (100 mL), washed with saturated sodium bisulfide solution (50 mL) and water (50 mL), dried over sodium sulfate, filtered and concentrated under reduced pressure. The residue was slurried with chloroform-ethanol. The slurry was filtered to provide 42 mg (45%) of the title compound.

MS (ES, m/z): 414.1 ($M^++1$), 412.2 ($M^+-1$).

HRMS calcd for $C_{24}H_{17}FN_3O_3$ ($M^++1$) 414.1254, found 414.1262.

EXAMPLE 242

3-(5-Hydroxymethyl-5,6-dihydro-4H-pyrrolo[3,2,1-ij]quinolin-1-yl)-4-(6-trifluoromethyl-1H-indol-3-yl)-pyrrolidine-2,5-dione Beginning with (5-(hydroxymethyl)-5,6-dihydro-4H-pyrrolo[3,2,1-ij]quinolin-1-yl]oxo-acetic acid methyl ester and (6-(trifluoromethyl)-1H-indol-3-yl)acetamide, the title compound was prepared essentially as described in Example 1.

$C_{25}H_{18}F_3N_3O_3$, MS (ES, m/z): 466.2 ($M^++1$), 464.2 ($M^+-1$)

EXAMPLE 243

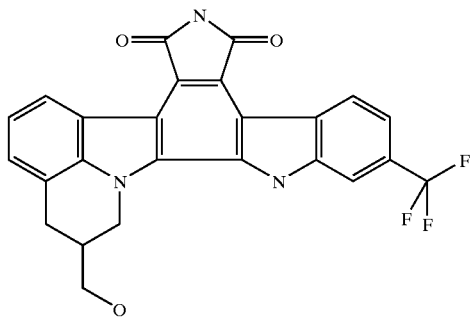

2-(trifluoromethyl)-12-(hydroxymethyl)-11H, 12H, 14H-pyrrolo[3,4-c]quinolino[8',8a',1':3,2,1]pyrrolo[2,3-a]carbazole-5,7-dione Beginning with 3-(5-Hydroxymethyl-5,6-dihydro-4H-pyrrolo[3,2,1-ij]quinolin-1-yl)-4-(6-trifluoromethyl-1H-indol-3-yl)-pyrrolidine-2,5-dione, the title compound was prepared essentially as described in Example 240.

$C_{25}H_{16}F_3N_3O_3$, MS (ES, m/z): 464.2 ($M^++1$), 462.2 ($M^+-1$)

EXAMPLE 244

3-(5-Hydroxymethyl-5,6-dihydro-4H-pyrrolo[3,2,1-ij]quinolin-1-yl)-4-(6-methoxy-1H-indol-3-yl)-pyrrolidine-2,5-dione Beginning with (5-(tert-butyldimethylsilyloxymethyl)-5,6-dihydro-4H-pyrrolo[3,2,1-ij]quinolin-1-yl)oxoacetic acid methyl ester and (6-methoxy-1H-indol-3-yl)acetamide, the title compound was prepared essentially as described in Example 1.

MS (ES, m/z): 428.2 ($M^++1$), 426.2 ($M^+-1$).

Exact Mass calcd for $C_{25}H_{22}N_3O_4$: 428.1610($M^++1$), Found 428.1615.

EXAMPLE 245

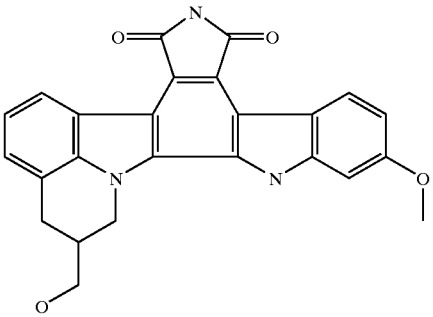

2-(methoxy)-12-(hydroxymethyl)-11H, 12H, 14H-pyrrolo[3,4-c]quinolino[8',8a',1':3,2,1]pyrrolo[2,3-a]carbazole-5,7-dione Beginning with 3-(5-Hydroxymethyl-5,6-dihydro-4H-pyrrolo[3,2,1-ij]quinolin-1-yl)-4-(6-methoxy-1H-indol-3-yl)-pyrrolidine-2,5-dione, the title compound was prepared essentially as described in Example 240.

MS (ES, m/z): $C_{25}H_{19}N_3O_4$, 426.2 ($M^++1$), 424.3 ($M^+-1$).

EXAMPLE 246

3-(5-Bromomethyl-5,6-dihydro-4H-pyrrolo[3,2,1-ij]quinolin-1-yl)-4-(6-fluoro-1H-indol-3-yl)pyrrole-2,5-dione A mixture of 3-(6-fluoro-1H-indol-3-yl)-4-(5-hydroxymethyl-5,6-dihydro-4H-pyrrolo[3,2,1-ij]quinolin-1-yl)pyrrole-2,5-dione (500 mg, 1.2 mmol), carbon tetrabromide (796 mg, 2.4 mmol), and triphenylphosphine (314 mg, 1.2 mmol) in 15 mL of dimethylformamide was stirred at room temperature for 6 hours. The reaction mixture was diluted with water and extracted with ethyl acetate (40 mL). The organic layer was washed with saturated aqueous sodium chloride (20 mL), dried over sodium sulfate, filtered and concentrated under reduced pressure. The residue was subjected to reverse phase HPLC to provide 350 mg (61%) of the title compound.

$C_{24}H_{17}BrFN_3O_2$, MS (ES, m/z): 478, 480 ($M^+$+1), 476, 478 ($M^+$−1).

EXAMPLE 247

N-[1-(3-(6-Fluoro-1H-indol-3-yl)-2,5-dioxoindol-4-yl)-5,6-dihydro-4H-pyrrolo[3,2,1-ij]quinolin-5-ylmethyl]dimethyl Aspartate Beginning with DL aspartic acid dimethyl ester and 3-(5-bromomethyl-5,6-dihydro-4H-pyrrolo[3,2,1-ij]quinolin-1-yl)-4-(6-fluoro-1H-indol-3-yl)pyrrole-2,5-dione, the title compound was prepared essentially as described in Example 111.

$C_{30}H_{27}FN_4O_6$, MS (ES, m/z): 559 ($M^+$+1), 557 ($M^+$−1)

EXAMPLE 248

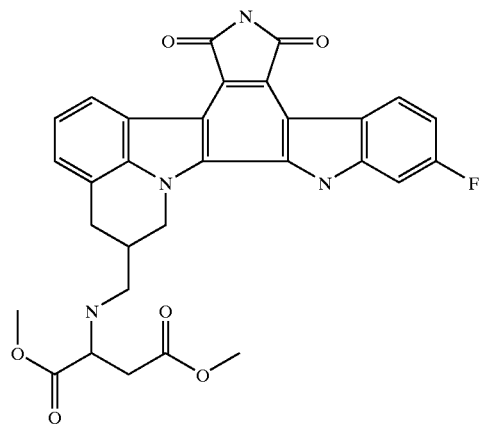

2-fluoro-12-(N-[dimethyl aspartyl]methyl)-11H, 12H, 14H-pyrrolo[3,4-c]quinolino[8',8a',1':3,2,1]pyrrolo[2,3-a]carbazole-5,7-dione Beginning with N-[1-(3-(6-Fluoro-1H-indol-3-yl)-2,5-dioxoindol-4-yl)-5,6-dihydro-4H-pyrrolo[3,2,1-ij]quinolin-5-ylmethyl]dimethyl aspartate, the title compound was prepared essentially as described in Example 240.

$C_{30}H_{25}FN_4O_6$, MS (ES, m/z): 555.2 ($M^+$−1).

EXAMPLE 249

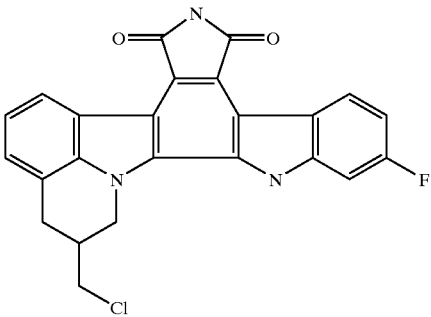

2-fluoro-12-(chloromethyl)-11H, 12H, 14H-pyrrolo[3,4-c]quinolino[8',8a',1':3,2,1]pyrrolo[2,3-a]carbazole-5,7-dione Beginning with 3-(5-chloromethyl-5,6-dihydro-4H-pyrrolo[3,2,1-ij]quinolin-1-yl)-4-(6-fluoro-1H-indol-3-yl)-pyrrolidine-2,5-dione, the title compound was prepared essentially as described in Example 241.

$C_{24}H_{15}ClFN_3O_2$, MS (ES, m/z): 430.1, 432.1 ($M^+$−1)

EXAMPLE 250

3-(1H-indol-3-yl)-4-(4-hydroxymethyl-5,6-dihydro-4H-pyrrolo[3,2,1-ij]quinolin-1-yl)pyrrole-2,5-dione Beginning with (4-hydroxymethyl-5,6-dihydro-4H-pyrrolo[3,2,1-ij]quinolin-1-yl)oxoacetic acid methyl ester and (1H-indol-3-yl)acetamide, the title compound was prepared essentially as described in Example 1.

$C_{24}H_{19}N_3O_3$: 398.0 ($M^+$+1), 396.1 ($M^+$−1).

EXAMPLE 251

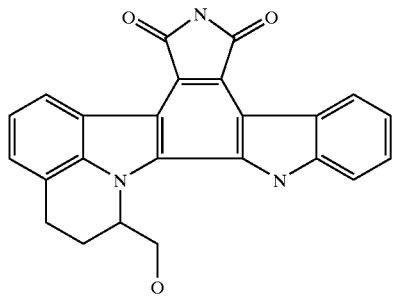

13-(hydroxymethyl)-11H, 12H, 14H-pyrrolo[3,4-c]quinolino[8',8a', 1':3,2,1]pyrrolo[2,3-a]carbazole-5,7-dione Beginning with 3-(1H-indol-3-yl)-4-(4-hydroxylmethyl-5,6-dihydro-4H-pyrrolo[3,2,1-ij]quinolin-1-yl)pyrrole-2,5-dione, the title compound was prepared essentially as described in Example 241.

MS (ES, m/z) $C_{24}H_{17}N_3O_3$: 396.2 ($M^+$+1), 394.3 ($M^+$−1).

EXAMPLE 252

3-(6-Fluoro-1H-indol-3-yl)-4-(4-hydroxylmethyl-5,6-dihydro-4H-pyrrolo[3,2,1-ij]quinolin-1-yl)pyrrole-2,5-dione Beginning with 2-(6-fluoro-1H-indol-3-yl)acetamide and (4-hydroxymethyl-5,6-dihydro-4H-pyrrolo[3,2,1-ij]

quinolin-1-yl)oxoacetic acid methyl ester, the title compound was prepared essentially as described in Example 1.

MS (ES, m/z): $C_{24}H_{18}FN_3O_3$ 416.2 (M$^+$+1).

EXAMPLE 253

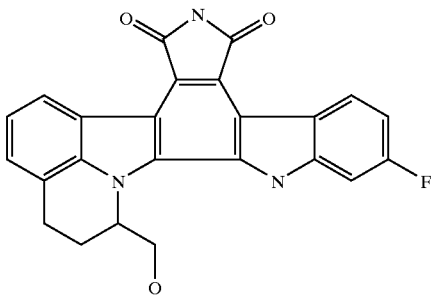

2-fluoro-13-(hydroxymethyl)-11H, 12H, 14H-pyrrolo[3,4-c]quinolino[8',8a',1':3,2,1]pyrrolo[2,3-a]carbazole-5,7-dione Beginning with 3-(6-fluoro-1H-indol-3-yl)-4-(4-hydroxylmethyl-5,6-dihydro-4H-pyrrolo [3,2,1-ij]quinolin-1-yl)pyrrole-2,5-dione, the title compound was prepared essentially as described in Example 241.

MS (ES, m/z): $C_{24}H_{16}FN_3O_3$ 414.2 (M$^+$+1)

EXAMPLE 254

3-(6-((tert-Butyldiphenylsilyloxy)methyl)-5,6-dihydro-4-H-pyrrolo[3,2,1-ij]quinolin-1-yl)-4-(1H-indol-3-yl)pyrrole-2,5-dione and 3-(6-Hydroxymethyl-5,6-dihydro-4H-pyrrolo [3,2,1-ij]quinolin-1-yl)-4-(1H-indol-3-yl)pyrrole-2,5-dione Beginning with 2-(1H-indol-3-yl)acetamide and (6-((tert-butyldiphenylsilyloxy)methyl)-5,6-dihydro-4H-pyrrolo[3,2,1-ij]quinolin-1-yl)oxoacetic acid methyl ester, the title compounds were prepared essentially as described in Example 1.

3-(6-Hydroxymethyl-5,6-dihydro-4H-pyrrolo[3,2,1-ij]quinolin-1-yl)-4-(1H-indol-3-yl)pyrrole-2,5-dione:

MS (ES, m/z): 398.1 (M$^+$+1), 396.2 (M$^+$−1).

HRMS Calcd for $C_{24}H_{20}N_3O_3$ 398.1505(M$^+$+1), found 398.1439.

3-[6-((tert-Butyldiphenylsilyloxy)methyl)-5,6-dihydro-4-H-pyrrolo[3,2,1-ij]quinolin-1-yl-4-(1H-indol-3-yl)-pyrrole-2,5-dione:

MS (ES, m/z): $C_{40}H_{37}N_3O_3Si$, 636.2 (M$^+$+1), 634.3(M$^+$−1).

EXAMPLE 255

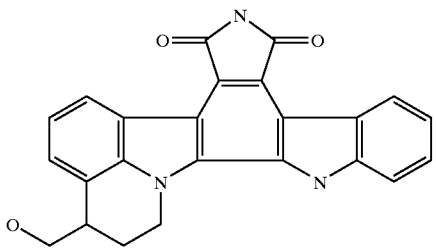

11-(hydroxymethyl)-11H, 12H, 14H-pyrrolo[3,4-c]quinolino[8',8a',1':3,2,1]pyrrolo[2,3-a]carbazole-5,7-dione Beginning with 3-(6-hydroxymethyl-5,6-dihydro-4H-pyrrolo[3,2,1-ij]quinolin-1-yl)-4-(1H-indol-3-yl)-pyrrolidine-2,5-dione, the title compound was prepared essentially as described in Example 241.

MS (ES, m/z): 396.1 (M$^+$+1), 394.2 (M$^+$−1).

Exact Mass Calcd for $C_{24}H_{18}N_3O_3$ 396.1348 (M$^+$+1), found: 396.1373.

EXAMPLE 256

3-(6-Hydroxymethyl-4,5,6,7-tetrahydroazepino[3,2,1-hi]indol-1-yl)-4-(1H-indol-3-yl)pyrrole-2,5-dione Beginning with (6-hydroxymethyl-4,5,6,7-tetrahydroazepino[3,2,1-hi]indol-1-yl)oxoacetic acid methyl ester and (1H-indol-3-yl)acetamide, the title compound was prepared essentially as described in Example 1.

MS (ES, m/z) $C_{25}H_{21}N_3O_3$: 410.2 (M$^+$−1).

EXAMPLE 257

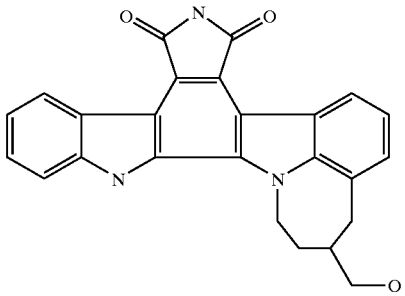

12-(hydroxymethyl)-11,12,13,14-tetrahydro-15H-pyrrolo[3,4-c]benz[b]azepino[9',9a'1':3,2,1]pyrrolo[2,3-a]carbazole-5,7-dione Beginning with 3-(6-hydroxymethyl-4,5,6,7-tetrahydroazepino[3,2,1-hi]indol-1-yl)-4-(1H-indol-3-yl)pyrrole-2,5-dione, the title compound was prepared essentially as described in Example 241.

MS (ES, m/z) $C_{25}H_{19}N_3O_3$: 408.27(M$^+$−1)

EXAMPLE 258

3-(5-(dimethylamino)methyl-5,6-dihydro-4H-pyrrolo[3,2,1-ij]quinolin-1-yl)-4-(1H-indol-3-yl)pyrrole-2,5-dione To a mixture of 3-(5-hydroxymethyl-5,6-dihydro-4H-pyrrolo[3,2,1-ij]quinolin-1-yl)-4-(1H-indol-3-yl)pyrrole-2,5-dione (0.335 g, 0.84 mmol) and methylsulfonic acid anhydride (0.3 g, 1.7 mmol) in tetrahydrofuran was added pyridine (0.245 mL, 3.4 mmol). The mixture was heated to reflux for 4.5 h, cooled to room temperature, diluted with ethyl acetate, washed with water and saturated aqueous sodium chloride. The organic layer was dried over sodium sulfate, filtered and concentrated to give an oil, which was used in the next step without further purification. The crude mesylate was dissolved in tetrahydrofuran (9 mL), then dimethylamine aqueous solution (40%, 4.22 ml, 33.6 mmol) was added. After stirring for 24 hours at room temperature, additional dimethylamine aqueous solution (40%, 4.22 mL, 33.6 mmol) was added, and the mixture stirred for an additional 48 hours. The mixture was diluted with ethyl acetate, washed with water, dried over sodium sulfate and concentrated under reduced pressure. The residue was subjected to silica gel chromatography to provide 0.38 g of the title compound.

MS (ES, m/z) $C_{26}H_{24}N_4O_2$: 425.1 (M$^+$+1), 423.2(M$^+$−1).

EXAMPLE 259

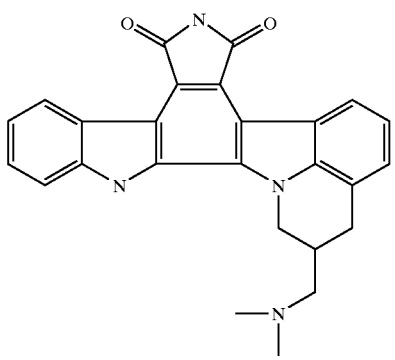

12-((dimethylamino)methyl)-11H, 12H, 14H-pyrrolo[3,4-c]quinolino[8',8a',1':3,2,1]pyrrolo[2,3-a]carbazole-5,7-dione Beginning with 3-(5-((dimethylamino)methyl)-5,6-dihydro-4H-pyrrolo [3,2,1-ij]quinolin-1-yl)-4-(1H-indol-3-yl)pyrrole-2,5-dione, the title compound was prepared essentially as described in Example 241.

MS (ES, m/z) $C_{26}H_{22}N_4O_2$: 423.1(M$^+$+1)

EXAMPLE 260

3-(5-(methylamino)methyl-5,6-dihydro-4H-pyrrolo[3,2,1-ij]quinolin-1-yl)-4-(6-fluoro-1H-indol-3-yl)pyrrole-2,5-dione 3-(5-bromomethyl-5,6-dihydro-4H-pyrrolo[3,2,1-ij]quinolin-1-yl)-4-(6-fluoro-1H-indol-3-yl)pyrrole-2,5-dione (330 mg, 0.69 mmol) was added to a solution of ammonia in tetrahydrofuran (2.0 M, 7 mL) in a pressure flask. The solution was heated at 50° C. for 26 hours. An additional 2.0 mL of ammonia in tetrahydrofuran (2.0 M) were added and the reaction mixture heated for another 18 hours. The reaction mixture was concentrated under reduced pressure and the residue subjected to silica gel chromatography to provide 210 mg of the title compound.

MS (ES, m/z) $C_{25}H_{21}FN_4O_2$: 429.19(M$^+$+1), 427.24 (M$^+$-1)

EXAMPLE 261

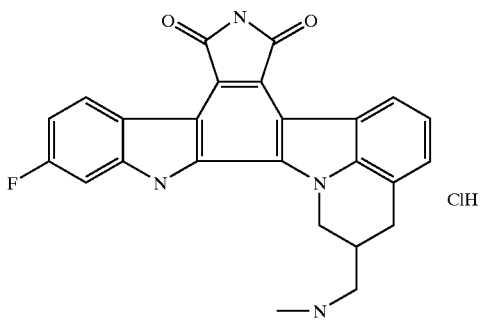

2-fluoro-12-((methylamino)methyl)-11H, 12H, 14H-pyrrolo[3,4-c]quinolino(8',8a',1':3,2,1]pyrrolo[2,3-a]carbazole-5,7-dione 3-(5-(N-[tert-butoxycarbonyl]N-[methyl]aminomethyl)-5,6-dihydro-4H-pyrrolo[3,2,1-ij]quinolin-1-yl)-4-(6-fluoro-1H-indol-3-yl)pyrrole-2,5-dione Di-(tert-butoxy) dicarbonate (0.16 g, 0.73 mmol) was added to a solution of 3-(5-N-methylaminomethyl-5,6-dihydro-4H-pyrrolo[3,2,1-ij]quinolin-1-yl)-4-(6-fluoro-1H-indol-3-yl)pyrrole-2,5-dione (300 mg, 0.7 mmol) and 4-dimethylamino-pyridine (8.6 mg, 0.07 mmol) in tetrahydrofuran (5 mL) at 0~5° C., warmed to room temperature slowly and stirred at room temperature overnight. The reaction mixture was then diluted with ethyl acetate, washed with aqueous sodium bicarbonate and saturated aqueous sodium chloride, dried over sodium sulfate, and concentrated under reduced pressure. The residue was subjected to silica gel chromatography to provide 0.24 g (65%) of the title compound.

Ring Closure

Beginning with 3-(5-(N-[tert-butoxycarbonyl]N-[methyl]aminomethyl)-5,6-dihydro-4H-pyrrolo[3,2,1-ij]quinolin-1-yl)-4-(6-fluoro-1H-indol-3-yl)pyrrole-2,5-dione, 2-fluoro-12-((N-[tert-butoxycarbonyl]N-[methyl]amino)methyl)-11H, 12H, 14H-pyrrolo[3,4-c]quinolino[8',8a',1':3,2,1]pyrrolo[2,3-a]carbazole-5,7-dione was prepared essentially as described in Example 58.

Deprotection

Beginning with 2-fluoro-12-((N-[tert-butoxycarbonyl]N-[methyl]amino)methyl)-11H, 12H, 14H-pyrrolo[3,4-c]quinolino[8',8a',1':3,2,1]pyrrolo[2,3-a]carbazole-5,7-dione, the title compound was prepared essentially as described in Example 136.

MS (ES, m/z) $C_{25}H_{19}FN_4O_2$: 427.2 (M$^+$+1-HCl), 425.3 (M$^+$-1-HCl)

EXAMPLE 262

3-(5-(methoxy)methyl-5,6-dihydro-4H-pyrrolo[3,2,1-ij]quinolin-1-yl)-4-(6-fluoro-1H-indol-3-yl)pyrrole-2,5-dione Beginning with (5-methoxymethyl-5,6-dihydro-4H-pyrrolo[3,2,1-ij]quinolin-1-yl)oxoacetic acid methyl ester and (6-fluoro-1H-indol-3-yl)acetamide, the title compound was prepared essentially as described in Example 1.

MS (ES, m/z) $C_{25}H_{20}N_3O_3$: 430.19 (M$^+$+1), 428.23 (M$^+$-1)

EXAMPLE 263

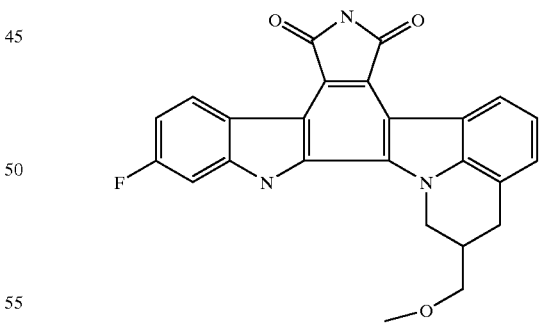

2-fluoro-12-((methoxy)methyl)-11H, 12H, 14H-pyrrolo[3,4-c]quinolino[8',8a',1':3,2,1]pyrrolo[2,3-a]carbazole-5,7-dione Beginning with 3-(5-(methoxy)methyl-5,6-dihydro-4H-pyrrolo[3,2,1-ij]quinolin-1-yl)-4-(6-fluoro-1H-indol-3-yl)pyrrole-2,5-dione, the title compound was prepared essentially as described in Example 58.

MS (ES, m/z) $C_{25}H_{18}N_3O_3$: 426.2 (M$^+$-1).

EXAMPLE 264

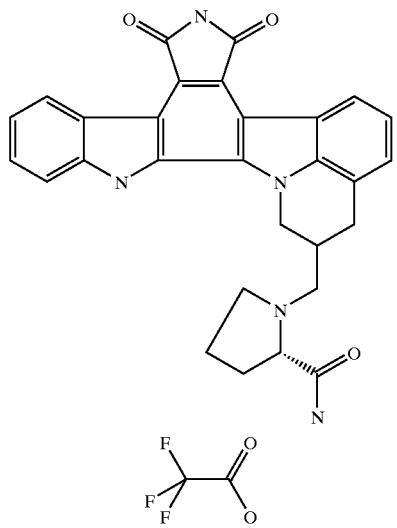

12-((prolin-1-yl)methyl)-11H, 12H, 14H-pyrrolo[3,4-c]quinolino[8',8a',1':3,2,1]pyrrolo[2,3-a]carbazole-5,7-dione Trifluoroacetate 3-(5-Bromomethyl-5,6-dihydro-4H-pyrrolo [3,2,1-ij] quinolin-1-yl)-4-(1H-indol-3-yl)pyrrole-2,5-dione Beginning with 3-(1H-indol-3-yl)-4-(5-hydroxymethyl-5,6-dihydro-4H-pyrrolo[3,2,1-ij]quinolin-1-yl)pyrrole-2,5-dione, the desired compound was prepared essentially as described in Example 51.

12-(bromomethyl)-11H, 12H, 14H-pyrrolo[3,4-c]quinolino-[8',8a',1':3,2,1]pyrrolo[2,3-a]carbazole-5,7-dione Beginning with 3-(5-Bromomethyl-5,6-dihydro-4H-pyrrolo [3,2,1-ij]quinolin-1-yl)-4-(1H-indol-3-yl)pyrrole-2,5-dione, the desired compound was prepared essentially as described in Example 241.

Alkylation

A mixture of 12-(bromomethyl)-11H, 12H, 14H-pyrrolo-[3,4-c]quinolino[8',8a',1':3,2,1]pyrrolo[2,3-a]carbazole-5,7-dione (0.164 mmol) and L-prolinamide (187 mg, 1.64 mmol) in N-methylpyrrolidinone (3 mL) was heated at 60° C. for 20 hours. The reaction mixture was subjected to reversed phase HPLC, eluting with Acetonitrile-water-trifluoroacetic acid. Fractions containing product were combined and concentrated under reduced pressure provide 50 mg (50%) of the title compound.

MS (ES, m/z) $C_{29}H_{25}N_5O_3$: 490.17 (M$^+$−1).

EXAMPLE 265

3-(5,6-dihydro-4H-pyrrolo[3,2,1-ij]quinolin-1-yl)-4-(6-bromo-1H-indol-3-yl)pyrrole-2,5-dione Beginning with 2-(5,6-Dihydro-4H-pyrrolo[3,2,1-ij] quinolin-1-yl)acetamide and (6-Bromo-1H-indol-3-yl) oxoacetic acid methyl ester, the title compound was prepared essentially as described in Example 1.

MS (FIA, m/z) $C_{23}H_{16}BrN_3O_2$ (M−1)=444

EXAMPLE 266

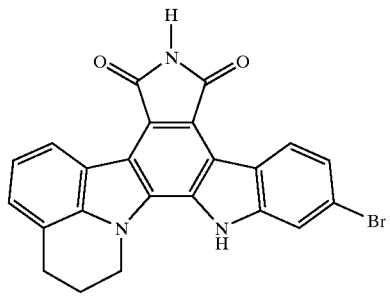

2-Bromo-11H, 12H, 14H-pyrrolo[3,4-c]quinolino-[8',8a',1':3,2,1]pyrrolo[2,3-a]carbazole-5,7-dione Beginning with 3-(5,6-dihydro-4H-pyrrolo[3,2,1-ij] quinolin-1-yl)-4-(6-bromo-1H-indol-3-yl)pyrrole-2,5-dione, the title compound was prepared essentially as described in Example 60.

MS (IS, m/z) $C_{23}H_{14}BrN_3O_2$ (M$^+$−1)=456

EXAMPLE 267

3-(5,6-dihydro-4H-pyrrolo[3,2,1-ij]quinolin-1-yl)-4-(6-fluoro-1H-indol-3-yl)pyrrole-2,5-dione Beginning with 2-(5,6-Dihydro-4H-pyrrolo[3,2,1-ij] quinolin-1-yl)-acetamide and (6-Fluoro-1H-indol-3-yl)-oxo-acetic acid methyl ester, the title compound was prepared essentially as described in Example 1.

MS (IS, m/z) $C_{23}H_{16}FN_3O_2$ (M$^+$−1)=384

EXAMPLE 268

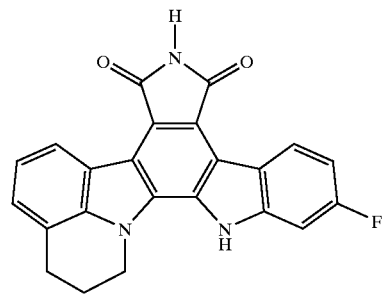

2-Fluoro-11H, 12H, 14H-pyrrolo[3,4-c]quinolino-[8',8a',1':3,2,1]pyrrolo[2,3-a]carbazole-5,7-dione Beginning with 3-(5,6-dihydro-4H-pyrrolo[3,2,1-ij] quinolin-1-yl)-4-(6-fluoro-1H-indol-3-yl)pyrrole-2,5-dione, the title compound was prepared essentially as described in Example 52.

MS (FD, m/z) $C_{23}H_{14}FN_3O_2$ (M$^+$)=383

EXAMPLE 269

3-[4-(5,6-Dihydro-4H-pyrrolo[3,2,1-ij]quinolin-1-yl)-2,5-dioxo-2,5-dihydro-1H-pyrrol-3-yl]-1H-indole-6-carboxylic Acid Methyl Ester Beginning with 2-(5,6-Dihydro-4H-pyrrolo[3,2,1-ij] quinolin-1-yl)acetamide and 3-Methoxyoxalyl-1H-indole-6-carboxylic acid methyl ester, the title compound was prepared essentially as described in Example 1.

MS (IS, m/z) $C_{25}H_{19}N_3O_4$ (M−1)=426

EXAMPLE 270

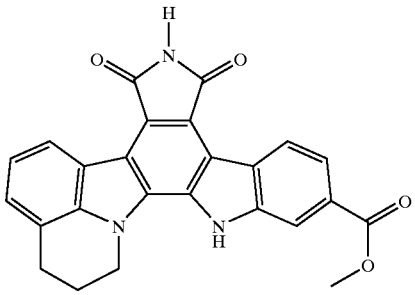

2-Carboxy-11H, 12H, 14H-pyrrolo[3,4-c]quinolino-[8',8a',1':3,2,1]pyrrolo[2,3-a]carbazole-5,7-dione Methyl Ester Beginning with 3-[4-(5,6-Dihydro-4H-pyrrolo[3,2,1-ij]quinolin-1-yl)-2,5-dioxo-2,5-dihydro-1H-pyrrol-3-yl]-1H-indole-6-carboxylic acid methyl ester, the title compound was prepared essentially as described in Example 52.

EXAMPLE 271

7-{2,5-Dioxo-4-[7-(3-triisopropylsilanyloxy-propyl)-1H-indol-3-yl]-2,5-dihydro-1H-pyrrol-3-yl}-3,4-dihydro-1H-[1,4]diazepino[6,7,1-hi]indole-2-carboxylic acid tert-butyl Ester Beginning with 7-Carbamoylmethyl-3,4-dihydro-1H-[1,4]diazepino[6,7,1-hi]indole-2-carboxylic acid tert-butyl ester and Oxo-[7-(4-triisopropylsilanyloxy-propyl)-1H-indol-3-yl]-acetic acid methyl ester, the title compound was prepared essentially as described in Example 1.

$^1$H NMR (DMSO-d$_6$, 400 MHz): δ 1.02–1.06 (3H, m), 1.09 (18H, d, J=4.4 Hz), 1.33 (3H, s), 1.38 (6H, s), 1.80–1.87 (2H, m), 2.85 (2H, t, J=7.2 Hz), 3.67 (2H, t, J=6.8 Hz), 3.84 (2H, br), 4.41–4.45 (2H, m), 4.77 (2H, d, J=19.6 Hz), 6.53–6.62 (2H, m), 6.79 (1H, d, J=7.6 Hz), 6.73–6.78 (2H, m), 6.83 (1H, d, J=7.2 Hz), 7.65 (1H, d, J=12.4 Hz), 7.70 (1H, d, J=4.8 Hz), 10.91 (1H, s), 11.62 (1H, s)

IS-MS, m/e 695.5 (m−1)

EXAMPLE 272

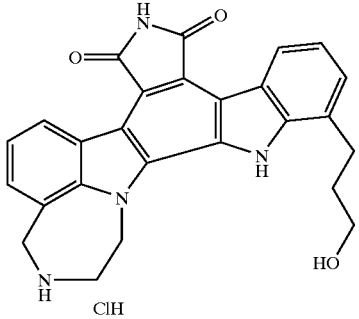

1-(2-hydroxyprop-1-yl)-11,12,13,14-tetrahydro-12H, 15H-pyrrolo[3,4-c]benzo[1,4]diazepino[9',9a,1':3,2,1]-pyrrolo[2,3-a]carbazole-5,7-dione Hydrochloride Beginning with 7-{2,5-Dioxo-4-[7-(3-triisopropylsilyloxypropyl)-1H-indol-3-yl]-2,5-dihydro-1H-pyrrol-3-yl}-3,4-dihydro-1H-[1,4]diazepino[6,7,1-hi]indole-2-carboxylic acid tert-butyl ester, the title compound was prepared essentially as described in Example 70 and 136.

$^1$H NMR (DMSO-d$_6$, 400 MHz): δ 1.96 (2H, br), 3.32 (2H, br), 3.53 (2H, br), 3.92 (2H, br), 4.80 (2H, br), 4.93 (1H, br), 4.99 (2H, br), 7.32 (1H, t, J=8.4 Hz), 7.40 (2H, d, J=7.2 Hz), 7.50 (1H, d, J=7.2 Hz), 8.94 (1H, d, J=7.6 Hz), 9.11 (1H, d, J=7.2 Hz), 9.90 (2H, br), 11.14 (1H, s), 11.63 (1H, s)

IS-MS, m/e 437.2 (m−1)

EXAMPLE 273

7-{2,5-Dioxo-4-[6-(3-triisopropylsilanyloxy-propyl)-1H-indol-3-yl]-2,5-dihydro-1H-pyrrol-3-yl}-3,4-dihydro-1H-[1,4]diazepino[6,7,1-hi]indole-2-carboxylic Acid Tert-butyl Ester Beginning with 7-Carbamoylmethyl-3,4-dihydro-1H-[1,4]diazepino[6,7,1-hi]indole-2-carboxylic acid tert-butyl ester and Oxo-[6-(4-triisopropylsilanyloxy-propyl)-1H-indol-3-yl]-acetic acid methyl ester, the title compound was prepared essentially as described in Example 1.

$^1$H NMR (DMSO-d$_6$, 400 MHz): δ 1.02 (18H, d, J=4.4 Hz), 1.03–1.07 (3H, m), 1.32 (3H, s), 1.37 (6H, s), 1.71 (2H, m), 2.59 (2H, d, J=6.8 Hz), 3.59 (2H, t, J=6.0 Hz), 3.85 (2H, s), 4.42 (2H, d, J=20.0 Hz), 4.76 (2H, d, J=19.6 Hz), 6.42–6.49 (1H, m), 6.57–6.58 (1H, m), 6.63 (2H, d, J=7.6 Hz), 6.79 (1H, d, J=7.6 Hz), 6.77–6.85 (1H, m), 7.4 (1H, d, J=4.0 Hz), 7.61–7.67 (2H, m), 10.89 (1H, s), 11.52 (1H, s)

IS-MS, m/e 696.0 (m−1)

EXAMPLE 274

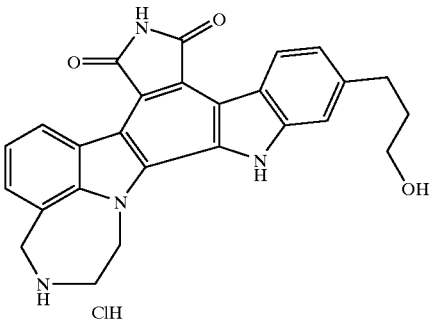

2-(3-hydroxyprop-1-yl)-11,12,13,14-tetrahydro-12H, 15H-pyrrolo[3,4-c]benzo[1,4]diazepino[9',9a',1':3,2,1]-pyrrolo[2,3-a]carbazole-5,7-dione Hydrochloride Beginning with 7-{2,5-Dioxo-4-[6-(3-triisopropylsilyl-oxypropyl)-1H-indol-3-yl]-2,5-dihydro-1H-pyrrol-3-yl}-3,4-dihydro-1H-[1,4]diazepino[6,7,1-hi]indole-2-carboxylic acid tert-butyl ester, the title compound was prepared essentially as described in Example 70 and 136.

$^1$H NMR (DMSO-d$_6$, 400 MHz): δ 1.84 (2H, br), 2.93 (2H, br), 3.49 (2H, br), 3.90 (2H, br), 4.85 (2H, br), 5.10 (2H, br), 7.21 (1H, d, J=8.0 Hz), 7.39 (1H, t, J=8.0 Hz), 7.55 (2H, d, J=6.4 Hz), 8.91 (1H, d, J=8.4 Hz), 9.07 (1H, d, J=8.4 Hz), 9.82 (2H, br), 11.16 (1H, s), 12.34 (1H, s)

IS-MS, m/e 439.4 (m+1)

EXAMPLE 275

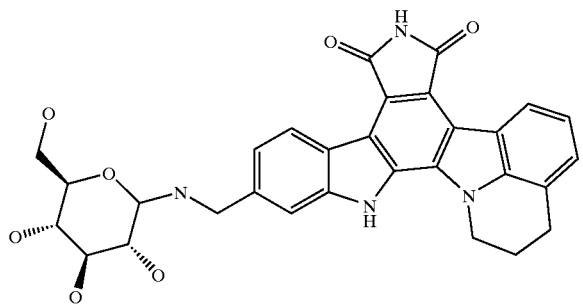

A solution of 1-amino-1-deoxy-β-D-glucose (0.18 g, 1.0 mmol) in 5 mL of N-methylpyrrolidinone was slowly added to a solution of 2-(bromomethyl)-11H, 12H, 14H-pyrrolo[3,4-c]quinolino-[8',8a',1':3,2,1]pyrrolo[2,3-a]carbazole-5,7-dione (0.10 g, 0.19 mmol) in 5 mL of N-methylpyrrolidinone. The mixture was stirred overnight at room temperature and diluted with 20 mL of water and the resulting solid was filtered, washed with more water and dried under vacuum to give 0.04 g (37%) of the desired product. IS-MS, m/e 557.1 (m+1)

EXAMPLE 276

7-[2,5-Dioxo-4-(7-triisopropylsilanyloxymethyl-1H-indol-3-yl)-2,5-dihydro-1H-pyrrol-3-yl]-3,4-dihydro-1H-[1,4]diazepino[6,7,1-hi]indole-2-carboxylic Acid Tert-butyl Ester Beginning with 7-Carbamoylmethyl-3,4-dihydro-1H-[1,4]diaze-pino[6,7,1-hi]indole-2-carboxylic acid tert-butyl ester and oxo-(7-triisopropylsilanyloxymethyl-1H-indol-3-yl)-acetic acid methyl ester, the title compound was prepared essentially as described in Example 1.

$^1$H NMR (DMSO-d$_6$, 400 MHz): δ 1.12 (18H, d, J=6.4 Hz), 1.21–1.23 (3H, m), 1.38 (3H, s), 1.41 (6H, s), 4.13 (1H, s), 4.22 (1H, s), 4.88 (2H, s), 4.97 (2H, d, J=13.6 Hz), 5.35 (2H, d, J=7.2 Hz), 7.33 (2H, t, J=7.6 Hz), 7.36–7.38 (2H, m,), 7.61–7.66 (1H, m), 9.04 (1H, d, J=7.6 Hz), 11.10 (1H, s), 11.61 (1H, s)

EXAMPLE 277

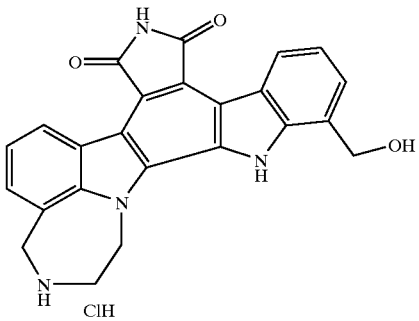

1-(2-hydroxymethyl)-11,12,13,14-tetrahydro-12H, 15H-pyrrolo[3,4-c]benzo[1,4]diazepino[9',9a',1':3,2, 1]-pyrrolo[2,3-a]carbazole-5,7-dione Hydrochloride Beginning with 7-{2,5-Dioxo-4-[7-(3-triisopropylsilanyloxy-methyl)-1H-indol-3-yl]-2,5-dihydro-1H-pyrrol-3-yl}-3,4-dihydro-1H-[1,4]diazepino[6,7,1-hi]indole-2-carboxylic acid tert-butyl ester, the title compound was prepared essentially as described in Example 70 and 136.

$^1$H NMR (DMSO-d$_6$, 400 MHz): δ 3.94 (2H, br), 4.81 (2H, br), 5.04 (2H, br), 5.47 (2H, s), 5.52 (1H, s), 7.34–7.44 (2H, m), 7.58 (1H, d, J=7.2 Hz), 7.77 (1H, d, J=6.8 Hz), 9.10 (2H, t, J=8.8 Hz), 9.79 (2H, br), 11.17 (1H, s), 11.65 (1H, s)

IS-MS, m/e 411.2 (m+1)

The ability of the compounds of Formula I to inhibit CDK4 activity is demonstrated by the following assays.

Assay of Cyclin D1-cdk4 Kinase Activity with the ING Peptide as Substrate

The cyclin D1-cdk4 kinase activity of a compound was assayed by preparing a 100 ul reaction at the following concentrations: 35 mM Hepes pH 7.0, 10 mM MgCl$_2$, 300 uM ATP, 200 uM ING peptide, 1.0 uCi of γ-$^{33}$P-ATP, 4.34 ug of cyclin D-cdk4 enzyme, 4% DMSO, and various concentrations of inhibitor. The reaction was incubated at room temperature (about 74° F.) for 60 minutes, and then terminated by the addition of 100 ul of 10% phosphoric acid. Next, the reaction was filtered through a Millipore Multiscreen-PH Plate—Catalog number MAPH NOB 10, and the plate was washed 2 times with 320 ul each of 0.5% phosphoric acid, followed by the addition of 100 ul of scintillation fluid and quantitation on a Packard Instruments, Top Count, scintillation counter. Representative examples of the results of these experiments are summarized in the following table.

TABLE II

| Compound | Kinase Activity with ING (μM) |
|---|---|
| (structure) | 0.1055 |
| (structure) | 0.1162 |

TABLE II-continued

| Compound | Kinase Activity with ING (μM) |
|---|---|
| (structure) | 0.1270 |
| (structure) | 0.0787 |
| (structure) | 0.0645 |
| (structure) | 0.2693 |
| (structure) | 0.4663 |
| (structure) | 0.1734 |
| (structure) | 0.0513 |
| (structure) | 0.0368 |
| (structure) | 0.7864 |

TABLE II-continued

| Compound | Kinase Activity with ING (μM) |
|---|---|
| 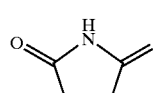 | 0.3669 |
| 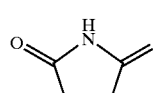 | 0.1509 |
| 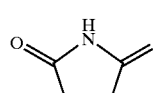 | 1.5633 |
| 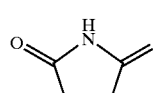 | 0.7928 |

TABLE II-continued

| Compound | Kinase Activity with ING (μM) |
|---|---|
| 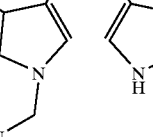 | 0.4552 |

Assay of Cyclin D1-cdk4 Kinase Activity with the Rb21 Protein as Substrate

The cyclin D1-cdk4 kinase activity of a compound was assayed by preparing a 100 ul reaction at the following concentrations: 20 mM Hepes pH 7.0, 10 mM MgCl$_2$, 30 uM ATP, 5 ug of Rb21 protein (Santa Cruz Biotech, Catalog #sc-4112), 1.0 uCi of γ-$^{33}$P-ATP, 1.09 ug of cyclin D-cdk4 enzyme, 4% DMSO, and various concentrations of inhibitor. The reaction was incubated at room temperature (about 74° F.) for 60 minutes, and then terminated by the addition of 100 ul of 25% trichloroacetic acid. Next, the reaction was filtered through a Millipore Multiscreen-FC Plate—Catalog number MAFC NOB 10, and the plate was washed 2 times with 320 ul each of 10% trichloroacetic acid, followed by the addition of 100 ul of scintillation fluid and quantitation on a Packard Instruments, Top Count, scintillation counter. Representative examples of the results of these experiments are summarized in the following table.

TABLE III

| Compound | Kinase Activity with Rb21 (μM) |
|---|---|
| 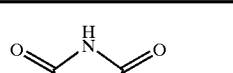 | 0.0650 |

TABLE III-continued

| Compound | Kinase Activity with Rb21 (μM) |
|---|---|
| (structure) | 0.0666 |
| (structure) | 0.0714 |
| (structure) | 0.0179 |
| (structure) | 0.0311 |
| (structure) | 0.1799 |
| (structure) | 0.2022 |
| (structure) | 0.0301 |
| (structure) | 0.0111 |

TABLE III-continued

| Compound | Kinase Activity with Rb21 (µM) |
|---|---|
| [structure] | 0.0155 |
| [structure] | 0.7086 |
| [structure] | 0.8114 |

The ability of CDK4 inhibitors to treat proliferative disorders is illustrated by the following assays.

Cell Growth Inhibition Assay

The MTT assay was used to measure growth inhibitory activity (Schultz, R. M., et. al. Oncology Res. 5, 223–228, 1993). The IC50 was determined as the concentration of drug required to inhibit cell growth by 50% over 72 h of drug exposure. Basically, 1000 HCT-116 or NCI H460 cells were added per well to 96-well flat-bottom plates in 100-ul RPMI 1640 medium containing 10% dialyzed fetal bovine serum. The plates were incubated for 24 h prior to addition of test compounds. A stock solution (10 mM) was prepared in DMSO and serially diluted in medium. Compound dilutions were added to triplicate wells, and the plates were incubated for 72 hours. The compound of. Example 52 was tested in this assay and was found to inhibit cell growth.

Cell Cycle Analysis Using Flow Cytometry

The HCT-116 and NCI H460 cell lines were seeded in 75 cm² flasks at 5×10⁵ cells/25 ml RPMI 1640 medium containing 10% dialyzed fetal bovine serum. They were incubated for 24 hours. Compound is then added at 1×IC50 and 3×IC50 (determined from above section "growth inhibition studies") and incubated for an additional 24 hours. The cells were subsequently harvested and the protocol (Robinson, J. P. and Darzynkiewicz, Z. Current Protocols in Cytometry. 1997) for staining was followed. DNA histogram analysis was performed using ModFit LT (Verity House). The coumpound of Example 52 was tested in this assay and was found to arrest cells in the G1 phase of the cell cycle.

Inhibition of Rb Phosphorylation Assay

Human HCT116 colon carcinoma cell line was purchased from American Tissue Culture Collection (Rockville, Md.) and maintained as monolayer in RPMI-1640 with L-Glutamine and 25 mM HEPES supplemented with 10% fetal bovine serum in a 37° C. incubator with a 10% $CO_2$ atmosphere. The detection of mycoplasm in cultured cells was performed using Mycoplasma Rapid Detection System (TaKaRa Shuzo Co. Ltd., Shiga, Japan) every 2–3 months and the cells were found consistently negative throughout these experiments. The Rb phosphorylation assay was done be plating 4×10⁵ cells/well in 6-well plates. After 24 hours, exponentially growing HCT116 cells were treated with compounds at 1×, 2× and 3×$IC_{50}$ (as determined by MMT assay) or DMSO in complete medium for 24 hours. At the end of the incubation period the mediumj was removed and the cells were washed twice with cold PBS containing 1 mM sodium orthovanadate ($Na_3VO_4$). Cellular protein lysates were prepared by adding freshly prepared 50 uL/well lysis buffer (50 mM HEPES pH 7.5, 1% Triton X-100, 5 mM EDTA, 50 mM NaCl, 10 mM sodim pyrophospate, 50 mM sodium fluoride, 1 mM Na3VO4, 1 mM phenylmethylsulfonyl fluoride, 10 ug/mL Aprotinin, 10 ug/mL Leupeptin, and 10 ug/mL Pepstatin). The cell lysates were collected and incubated on ice for 30 min with frequent brief vortexing. Cellular debris was removed by centrifugation at 14000×g for 10 min at 4° C. Protein concentration was determined by the Bio-Rad DC protein assay (Bio-Rad, Hercules, Calif.). To analyze extracts, equal amounts of protein (30 ug) were dissolved in 1×Laemmli sample buffer, bioled for 5 min and resolved by electrophoresis on 10% polyacrylamide gels containing SDS. The proteins were transferred to Immobilon-P membrane (Millipore, Bedford, Mass.). Membranes were incubated with 5% non-fat dried milk in TBS-T (10 mM Tris-Cl, pH 7.4, 150 mM NaCl, and 0.1% Tween-20) for 1 h at room temperature to block non-specific sites. Immunoblotting was done by incubating membranes with alpha-Phospho-Ser-780 pRb (1 ug/mL, New England Biolab, Beverly, Mass.) and alpha-actin (0.2 ug/mL) antibodies in TBS-T containing 5% non-fat dried milk for overnight at 4° C. Membranes were washed three times (15 min each) in TBS-T, and subsequently incubated for 2 hours at room temperature with horseradish peroxidase-conjugated anti-rabbit (1:2000) and anti-mouse (1:1000) antibody (Amersham) in TBS-T. Membranes were washed three times (15 min each) with TBS-T, and incubated for 5 min in SuperSignal West Pico Chemiluminescent reagents (Pierce, Rockford Ill.). Proteins were detected by capturing image of the membrane using Quantity One Software on a Fluor-S multi-Imager (Bio-Rad, Hercules, Calif.) in a linear range. Specific bands were quantified using Quantity One Software. After correcting for variable loading using actin as a control, Ser-780 phosphorylated pRb protein levels in the drug treated samples were compared with that of cells treated with vehicle (DMSO). Results are expressed as a percentage inhibition of Ser-780 pRb phosphorylation in drug treated cells versus control DMSO treated cells. The compound of Example 52 was tested in this assay and was found to inhibit Rb (retinoblastoma protein) phosphorylation.

The compounds of this invention are bioavailable through several routes of administration including, but not limited to, oral, buccal, intravenous, subcutaneous, intranasal, intraocular, transdermal, rectal and by inhalation. Because compounds of this invention are potent CDK4 inhibitors, extremely low doses are required to maintain therapeutic levels.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, buccal, rectal, intranasal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., Remington's Pharmaceutical Sciences, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
| --- | --- |
| Compound of Example 52 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Compound of Example 1 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Compound of Example 52 | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Compound of Example 52 | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Compound of Example 52 | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Compound of Example 52 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Compound of Example 52 | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
|---|---|
| Compound of Example 52 | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
|---|---|
| Compound of Example 52 | 250.0 mg |
| Isotonic saline | 1000 ml |

Formulation Example 10

A topical formulation may be prepared as follows:

| Ingredient | Quantity |
|---|---|
| Compound of Example 52 | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
| --- | --- |
| Compound of Example 52 | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 g |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:
1. A compound of Formula I where:

A and B are independently O or S;

X and Y are both hydrogen or, taken together, form a bond;

$R^1$ is hydrogen or $C_1-C_4$ alkyl;

$R^2$ is optionally up to two substituents independently selected from the group consisting of halo, cyano, $C_1-C_6$ alkyl, substituted $C_1-C_6$ alkyl, $C_1-C_6$ alkenyl, substituted $C_1-C_6$ alkenyl, $C_1-C_6$ alkoxy, aryloxy, benzyloxy, $C_1-C_6$ alkylthio and arylthio;

$R^3$ is a substituent optionally selected from the group consisting of aryl heteroaryl, —$CH_2$—NH— (1-deoxy-β-D-glucose), and —$(CH_2)_m$—Z;

$R^4$ is hydrogen, $C_1-C_4$ alkyl, —$(CH_2)_m$—Z, or 2-deoxy-α-D-ribofuranos-1-yl;

$R^5$ is optionally up to two substituents independently selected from the group consisting of halo, cyano, $C_1-C_6$ alkyl, substituted $C_1-C_6$ alkyl, $C_1-C_6$ alkenyl, substituted $C_1-C_6$ alkenyl, $C_1-C_6$ alkoxy, aryloxy, benzyloxy, $C_1-C_6$ alkylthio and arylthio;

$R^6$ is optionally up to three substituents selected from $C_1-C_4$ alkyl;

$R^7$ is a substituent optionally selected from ($C_1-C_6$ alkoxy)carbonyl or —$(CH_2)_m$—Z;

Z is halo, hydroxy, ($C_1-C_6$ alkyl)$_3$SiO—, (diphenyl)($C_1-C_6$ alkyl)SiO, carboxy, ($C_1-C_4$ alkoxy)carbonyl, or $NR^8R^9$;

$R^8$ is hydrogen, $C_1-C_6$ alkyl, or substituted $C_1-C_6$ alkyl, $C_1-C_6$ alkenyl, substituted $C_1-C_6$ alkenyl;

$R^9$ is hydrogen, $C_1-C_6$ alkyl, substituted $C_1-C_6$ alkyl, $C_1-C_6$ alkenyl, substituted $C_1-C_6$ alkenyl, $C_1-C_6$ alkanoyl, substituted $C_1-C_6$ alkanoyl, tert-butoxycarbonyl, benzyloxycarbonyl, an amino acid residue, a protected amino acid residue, β-(pyridinyl) alaninyl, aryl, heteroaryl, arylcarbonyl, or heteroarylcarbonyl; or $R^8$ and $R^9$ taken together with the nitrogen to which they are attached form a saturated heterocycle optionally substituted with one or two hydroxy, amino, or $C_1-C_6$ alkyl groups;

$Q^1$ is O, $S(O)_n$, or —$(CH_2)_{1-3}$—;

$Q^2$ is a carbon-carbon single bond, a carbon-carbon double bond, —$NR^{10}$—, or —$NR^{10}$—$CHR^{11}$—;

$Q^3$ is —$(CH_2)_{1-3}$—;

$R^{10}$ is hydrogen, ($C_1-C_6$ alkyl)sulfonyl, arylsulfonyl, hetroarylsulfonyl, $C_1-C_6$ alkyl, substituted $C_1-C_6$ alkyl, (C$_1$–C$_5$ alkyl)carbonyl, substituted (C$_1$–C$_5$ alkyl) carbonyl, an amino acid residue, a protected amino acid residue, β-(pyridinyl)alaninyl, aryl, heteroaryl, arylcarbonyl, or heteroarylcarbonyl;

R$^{11}$ is hydrogen, C$_1$–C$_6$ alkyl, or substituted C$_1$–C$_6$ alkyl, C$_1$–C$_6$ alkenyl, substituted C$_1$–C$_6$ alkenyl; or R$^{10}$ and R$^{11}$ taken together with the atoms to which they are attached form a 5- or 6-membered saturated heterocycle;

m is 0, 1, 2, 3, 4, or 5;

n is 0, 1, or 2; or a pharmaceutically acceptable salt thereof.

2. A compound of claim 1 where X and Y, taken together, form a bond.

3. A compound of claim 1 or 2 where Q$^2$ is a carbon-carbon single bond.

4. A compound of claim 1 or 2 where Q$^2$ is —NR$^{10}$—.

5. A compound of claim 4 where R$^{10}$ is hydrogen.

6. A compound of claim 1 or 2 where Q$^2$ is —NR$^{10}$—CHR$^{11}$—.

7. A compound of claim 6 where R$^{10}$ is hydrogen.

8. A pharmaceutical formulation comprising a compound of Formula I

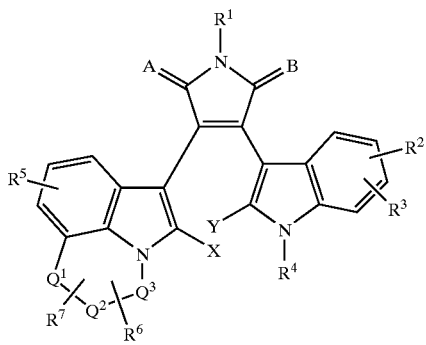

I where:

A and B are independently O or S;

X and Y are both hydrogen or, taken together, form a bond;

R$^1$ is hydrogen or C$_1$–C$_4$ alkyl;

R$^2$ is optionally up to two substituents independently selected from the group consisting of halo, cyano, C$_1$–C$_6$ alkyl, substituted C$_1$–C$_6$ alkyl, C$_1$–C$_6$ alkenyl, substituted C$_1$–C$_6$ alkenyl, C$_1$–C$_6$ alkoxy, aryloxy, benzyloxy, C$_1$–C$_6$ alkylthio and arylthio;

R$^3$ is a substituent optionally selected from the group consisting of aryl, heteroaryl, —CH$_2$—NH—(1-deoxy-β-D-glucose), and —(CH$_2$)$_m$—Z;

R$^4$ is hydrogen, C$_1$–C$_4$ alkyl, —(CH$_2$)$_m$—Z, or 2-deoxy-α-D-ribofuranos-1-yl;

R$^5$ is optionally up to two substituents independently selected from the group consisting of halo, cyano, C$_1$–C$_6$ alkyl, substituted C$_1$–C$_6$ alkyl, C$_1$–C$_6$ alkenyl, substituted C$_1$–C$_6$ alkenyl, C$_1$–C$_6$ alkoxy, aryloxy, benzyloxy, C$_1$–C$_6$ alkylthio and arylthio;

R$^6$ is optionally up to three substituents selected from C$_1$–C$_4$ alkyl;

R$^7$ is a substituent optionally selected from (C$_1$–C$_6$ alkoxy)carbonyl or —(CH$_2$)$_m$—Z;

Z is halo, hydroxy, (C$_1$–C$_6$ alkyl)$_3$SiO—, (diphenyl)(C$_1$–C$_6$ alkyl)SiO, carboxy, (C$_1$–C$_4$ alkoxy)carbonyl, or NR$^8$R$^9$;

R$^8$ is hydrogen, C$_1$–C$_6$ alkyl, or substituted C$_1$–C$_6$ alkyl, C$_1$–C$_6$ alkenyl, substituted C$_1$–C$_6$ alkenyl;

R$^9$ is hydrogen, C$_1$–C$_6$ alkyl, substituted C$_1$–C$_6$ alkyl, C$_1$–C$_6$ alkenyl, substituted C$_1$–C$_6$ alkenyl, C$_1$–C$_6$ alkanoyl, substituted C$_1$–C$_6$ alkanoyl, tert-butoxycarbonyl, benzyloxycarbonyl, an amino acid residue, a protected amino acid residue, β-(pyridinyl)alaninyl, aryl, heteroaryl, arylcarbonyl, or heteroarylcarbonyl; or R$^8$ and R$^9$ taken together with the nitrogen to which they are attached form a saturated heterocycle optionally substituted with one or two hydroxy, amino, or C$_1$–C$_6$ alkyl groups;

Q$^1$ is O, S(O)$_n$ or —(CH$_2$)$_{1-3}$—;

Q$^2$ is a carbon-carbon single bond, a carbon-carbon double bond, —NR$^{10}$— or —NR$^{10}$—CHR$^{11}$—;

Q$^3$ is —(CH$_2$)$_{1-3}$—;

R$^{10}$ is hydrogen, (C$_1$–C$_6$ alkyl)sulfonyl, arylsulfonyl, hetroarylsulfonyl, C$_1$–C$_6$ alkyl, substituted C$_1$–C$_6$ alkyl, C$_1$–C$_6$ alkenyl, substituted C$_1$–C$_6$ alkenyl, (C$_1$–C$_5$ alkyl)carbonyl, substituted (C$_1$–C$_5$ alkyl)carbonyl, an amino acid residue, a protected amino acid residue, β-(pyridinyl)alaninyl, aryl, heteroaryl, arylcarbonyl, or heteroarylcarbonyl;

R$^{11}$ is hydrogen, C$_1$–C$_6$ alkyl, or substituted C$_1$–C$_6$ alkyl, C$_1$–C$_6$ alkenyl, substituted C$_1$–C$_6$ alkenyl; or R$^{10}$ and R$^{11}$ taken together with the atoms to which they are attached form a 5- or 6-membered saturated heterocycle;

m is 0, 1, 2, 3, 4, or 5;

n is 0, 1, or 2; or a pharmaceutically acceptable salt thereof.

* * * * *